United States Patent
Farren et al.

(10) Patent No.: US 9,682,161 B2
(45) Date of Patent: Jun. 20, 2017

(54) COMPOSITIONS AND METHODS FOR UV STERILIZATION

(71) Applicant: BLUEMORPH, LLC, Oakland, CA (US)

(72) Inventors: Alexander Farren, Oakland, CA (US); Serdar Yeralan, San Francisco, CA (US)

(73) Assignee: BlueMorph, LLC, Oakland, CA (US)

( * ) Notice: Subject to any disclaimer, the term of this patent is extended or adjusted under 35 U.S.C. 154(b) by 444 days.

(21) Appl. No.: 14/091,311

(22) Filed: Nov. 26, 2013

(65) Prior Publication Data

US 2014/0161663 A1 Jun. 12, 2014

Related U.S. Application Data

(63) Continuation-in-part of application No. 13/650,028, filed on Oct. 11, 2012, now Pat. No. 9,387,268, which
(Continued)

(51) Int. Cl.
*A61L 2/00* (2006.01)
*H01J 37/20* (2006.01)
(Continued)

(52) U.S. Cl.
CPC ...... *A61L 2/10* (2013.01); *A23L 3/28* (2013.01); *A61L 9/20* (2013.01); *A61L 2202/14* (2013.01);
(Continued)

(58) Field of Classification Search
CPC ........................................................ A61L 2/10
(Continued)

(56) References Cited

U.S. PATENT DOCUMENTS 1,788,906 A 1/1931 Brown
2,194,463 A * 3/1940 Powley ............... A61L 2/00
250/453.11
(Continued)

FOREIGN PATENT DOCUMENTS

CN 2608008 Y 3/2004
CN 201481833 U 5/2010
(Continued)

OTHER PUBLICATIONS

International Search Report and Written Opinion under Patent Cooperation Treat (PCT) for PCT/US2011/38826; Sep. 12, 2011; 8 pages.
(Continued)

*Primary Examiner* — Kevin Joyner
(74) *Attorney, Agent, or Firm* — Duane Morris LLP; Siegfried J. W. Ruppert

(57) ABSTRACT

Provided herein are systems, ultraviolet (UV) devices, and methods for UV disinfection and sterilization, more specifically, systems, UV devices, and methods for UV disinfection and sterilization of a container, room, space or defined environment. The systems, UV devices, and methods are particularly useful for the UV disinfection and sterilization of a container used in the food and dairy industry and for containers used in the process of fermentation for an alcoholic beverage. Provided are also systems, UV devices, and methods for inhibiting the growth of one or more species of microorganisms present in a container, room, space or defined environment, preferably for inhibiting the growth of one or more species of microorganisms present on an interior surface of a container, room, space or defined environment.

38 Claims, 60 Drawing Sheets

Related U.S. Application Data is a continuation-in-part of application No. 13/314,007, filed on Dec. 7, 2011, which is a continuation-in-part of application No. 13/308,383, filed on Nov. 30, 2011, now abandoned, which is a continuation-in-part of application No. 13/151,196, filed on Jun. 1, 2011, now Pat. No. 9,044,521.

(60) Provisional application No. 61/350,414, filed on Jun. 2, 2010.

(51) Int. Cl.
| | |
|---|---|
| A61L 2/10 | (2006.01) |
| A23L 3/28 | (2006.01) |
| A61L 9/20 | (2006.01) |

(52) U.S. Cl.
CPC ....... A61L 2202/16 (2013.01); A61L 2202/23 (2013.01); A61L 2202/25 (2013.01); A61L 2209/212 (2013.01)

(58) Field of Classification Search
USPC ........................................ 422/24; 250/455.11
See application file for complete search history.

(56) References Cited

U.S. PATENT DOCUMENTS

| | | | |
|---|---|---|---|
| 2,499,153 | A | 2/1950 | Nicholson |
| 3,906,236 | A | 9/1975 | Callahan |
| 4,150,164 | A | 4/1979 | Gerek |
| 4,396,582 | A | 8/1983 | Kodera |
| 4,786,812 | A | 11/1988 | Humphreys |
| 4,830,968 | A | 5/1989 | Thornton et al. |
| 4,871,559 | A | 10/1989 | Dunn et al. |
| 4,877,964 | A | 10/1989 | Tanaka |
| 5,020,183 | A | 6/1991 | Grant, Jr. |
| 5,597,597 | A | 1/1997 | Newman |
| 5,744,094 | A | 4/1998 | Castberg et al. |
| 5,920,075 | A | 7/1999 | Whitehead |
| 6,074,565 | A | 6/2000 | Buckner |
| 6,110,424 | A | 8/2000 | Maiden |
| 6,299,770 | B1 | 10/2001 | Diener |
| 6,368,554 | B1 | 4/2002 | Wajsfeiner et al. |
| 6,396,068 | B1 | 5/2002 | Sweatt |
| 6,403,030 | B1 | 6/2002 | Horton, III |
| 6,517,776 | B1 | 2/2003 | Rodgers et al. |
| 6,524,529 | B1 | 2/2003 | Horton, III |
| 6,579,495 | B1 | 6/2003 | Maiden |
| 6,592,816 | B1 | 7/2003 | Ebel |
| 6,646,270 | B2 | 11/2003 | Cunningham |
| 6,665,326 | B2 | 12/2003 | Kusunose |
| 6,953,940 | B2 | 10/2005 | Leighley |
| 7,081,636 | B2* | 7/2006 | Moruzzi ............ A23L 3/28 250/432 R |
| 7,390,417 | B2 | 6/2008 | Kuhlmann |
| 7,443,903 | B2 | 10/2008 | Leonardo |
| 7,547,893 | B1* | 6/2009 | Tantillo ............ A61L 2/10 206/575 |
| 7,829,016 | B2 | 11/2010 | Deal et al. |
| 8,125,333 | B2 | 2/2012 | Ressler |
| 8,519,356 | B2 | 8/2013 | Boyle |
| 8,921,813 | B2 | 12/2014 | Palmer |
| 9,006,683 | B2 | 4/2015 | Wen |
| 9,013,116 | B2 | 4/2015 | Porter |
| 9,045,358 | B2 | 6/2015 | Greuel |
| 2002/0063954 | A1 | 5/2002 | Horton |
| 2002/0122742 | A1 | 9/2002 | Wajsfelner |
| 2002/0122743 | A1 | 9/2002 | Huang |
| 2003/0067768 | A1 | 4/2003 | Shiau |
| 2006/0011263 | A1 | 1/2006 | Till |
| 2006/0032199 | A1 | 2/2006 | Beam |
| 2006/0042205 | A1 | 3/2006 | Kalous |
| 2006/0284109 | A1 | 12/2006 | Scheir |
| 2007/0140435 | A1 | 6/2007 | Schwieker |
| 2008/0073595 | A1 | 3/2008 | Thiruppathi |
| 2008/0095661 | A1 | 4/2008 | Kohler |
| 2008/0199353 | A1 | 8/2008 | Mlodzonski |
| 2008/0206095 | A1 | 8/2008 | Duthie |
| 2008/0240978 | A1 | 10/2008 | Sorensen et al. |
| 2008/0253941 | A1* | 10/2008 | Wichers ............ A61L 2/10 422/186.3 |
| 2009/0010826 | A1 | 1/2009 | Shin |
| 2009/0148358 | A1 | 6/2009 | Wind |
| 2009/0274576 | A1 | 11/2009 | Ressler |
| 2010/0187443 | A1 | 7/2010 | Leben |
| 2010/0266445 | A1 | 10/2010 | Campagna |
| 2011/0031203 | A1 | 2/2011 | Chapman |
| 2011/0049391 | A1 | 3/2011 | Yang |
| 2011/0079590 | A1 | 4/2011 | Lin |
| 2011/0143000 | A1 | 6/2011 | Fiset |
| 2011/0165018 | A1 | 7/2011 | Lynn |
| 2011/0286883 | A1 | 11/2011 | Hecht |
| 2011/0305597 | A1 | 12/2011 | Farren |
| 2012/0121457 | A1 | 5/2012 | Farren |
| 2013/0175460 | A1 | 7/2013 | Farren |
| 2013/0323118 | A1 | 12/2013 | Krueger |

FOREIGN PATENT DOCUMENTS

| | | |
|---|---|---|
| CN | 202724291 U | 2/2013 |
| CN | 202961251 U | 6/2013 |
| CN | 203169632 U | 9/2013 |
| CN | 104340508 A | 2/2015 |
| DE | 3500487 A1 | 7/1986 |
| DE | 4407183 A1 | 9/1995 |
| DE | 29812427 U1 | 4/1999 |
| EP | 1120121 A2 | 8/2001 |
| GB | 495499 A | 11/1938 |
| GB | 556912 A | 10/1943 |
| GB | 2454642 A | 5/2009 |
| JP | H0280509 U | 6/1990 |
| JP | H1024092 A | 1/1998 |
| JP | 2001171621 A | 6/2001 |
| JP | 2001247108 A | 9/2001 |
| JP | 2015157646 A | 9/2015 |
| KR | 846075 B1 | 7/2008 |
| KR | 20100122422 A | 11/2010 |
| KR | 20110070267 A | 6/2011 |
| KR | 20150028154 A | 3/2015 |
| KR | 20150042959 A | 4/2015 |
| WO | WO90/05909 | 5/1990 |
| WO | WO 02/36437 A1 | 5/2002 |
| WO | WO2004/064875 A2 | 8/2004 |
| WO | WO2007/035907 | 3/2007 |
| WO | WO 2009/086053 A1 | 7/2009 |
| WO | WO2010/021506 A2 | 2/2010 |
| WO | WO2010/133688 A2 | 11/2010 |
| WO | WO2010/133698 A2 | 11/2010 |
| WO | WO 2011/153288 A1 | 12/2011 |
| WO | WO 2015/080768 A1 | 6/2015 |
| WO | WO2015/116833 A1 | 8/2015 |

OTHER PUBLICATIONS

International Search Report and Written Opinion under Patent Cooperation Treat (PCT) for PCT/US11/63827; Dated Apr. 18, 2012; 10 pages.

International Search Report from the International Searching Authority Issued Oct. 28, 2016 for PCT/US2016/044924.

Written Opinion from the International Searching Authority issued Oct. 28, 2016 for PCT/US2016/044924.

* cited by examiner

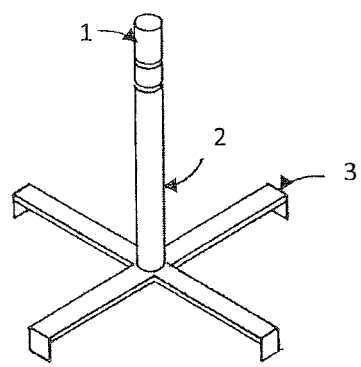
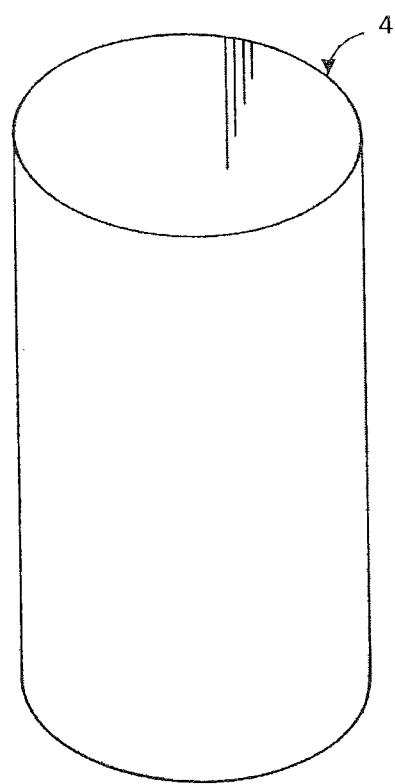
FIG. 1

| Length | Model | Description | Type* | Diameter/Base | UVC Output Watts | UV pW/cm² @1m |
|---|---|---|---|---|---|---|
| | GML370 | Hot Cathode | PL-S9W/TUV | PL-S | 2.4 | |
| 6" | GML180 | Hot Cathode | G 4T5 | T5/mini bi-pin | 0.5 | 5.4 |
| | GML170 | Hot Cathode | OZ 4T5 | T5/mini bi-pin | 0.5 | 5.4 |
| 9" | GML195 | Hot Cathode | G 6T5 | T5/mini bi-pin | 1.0 | 11 |
| | GML190 | Hot Cathode | OZ 6T5 | T5/mini bi-pin | 1.1 | 11 |
| | GML205 | Hot Cathode | G 8T5 | T5/mini bi-pin | 1.6 | 17 |
| 12" | GML125 | Slimline | G12T5½L/BP | T5/mini bi-pin | 6.0 | 66 |
| | GML075 | Slimline | G12T5½VH/BP | T5/mini bi-pin | 6.0 | 66 |
| | GML405 | High Output | GPH357T5L/HO | Four-pin | 8.5 | 92 |
| 14" | AAWHO/14 | High Output | Custom | Four-pin | 12 | 105 |
| | GML020 | Cold Cathode | 782 L 10 | T5/single-pin | 2.0/2.8 | 20/28 |
| | GML120 | Cold Cathode | 782 VH 10 | T5/single-pin | 2.0/2.8 | 20/28 |
| 16" | GML060 | Slimline | G10T5½L | T5/single-pin | 5.3 | 55 |
| | GML350 | Slimline | G10T5½L-4P | T5/four-pin | 5.3 | 55 |
| | GML070 | Slimline | G10T5½LVH | T5/single-pin | 5.3 | 55 |
| | GML430 | Hot Output | GSL406T5L/HO | Four-pin | 10.0 | 108 |
| 18" | GML210 | Hot Cathode | G15T8 | T8/medium bi-pin | 3.6 | 38 |
| | GML215 | Hot Cathode | G25T8 | T8/medium bi-pin | 5.0 | 54 |
| | GML410 | High Output | GSL406T5L/HO | Single-pin | 10.0 | 100 |
| 22" | AAWHO/22 | High Output | GPH550T5/HO/4 | Four-pin | 18 | 174 |
| | GML225MBP | High Output | CUSTOM | T5 15mm Bi-pin | 18 | 157 |
| | GML435 | High Output | GPH610T5L/HO | Four-pin | 16.2 | 175 |
| 24" | GML0224/4PNO | High Output | CUSTOM | T5 15mm Four-pin | 20 | 168 |
| | GML0244PO | High Output | CUSTOM | T5 15mm Four-pin | 20 | 168 |
| | GML025 | Cold Cathode | 782 L 20 | T5/single-pin | 3.9/5.5 | 35/52 |
| | GML290 | Cold Cathode | 782 VH 20 | T5/single-pin | 3.9/5.5 | 35/52 |
| 27" | GML325 | Slimline | GSL591 | T5/single-pin | | |
| | GML355 | Slimline | S24T5-4P | T5/four-pin | | |
| | GML415 | High Output | GPH610T5L/HO | Single-pin | 16.2 | 140 |
| 30" | GML030 | Cold Cathode | 782 L 25½ | T5/single-pin | 7.3 | 75 |
| | GML010 | Cold Cathode | 782 L 30 | T5/single-pin | 5.2/8.3 | 46/73 |
| | GML035 | Cold Cathode | 782 VH 29 | T5/mini bi-pin | 5.7/9.1 | 50/80 |
| | GML040 | Cold Cathode | 782 H 30 | T5/single-pin | 5.2/8.3 | 46/73 |
| | GML220 | Hot Cathode | G30T8 | T8/medium bi-pin | 8.3 | 85 |
| 36" | GML005 | Slimline | G36T6L | T5/single-pin | 13.8 | 120 |
| | GML100 | Slimline | G36T6L-4P | T5/four-pin | 12.7 | 110 |
| | GML090 | Slimline | G36T6VH | T5/single-pin | 13.8 | 120 |
| | GML095 | Slimline | G37T6VH | T5/single-pin | 15.2 | 124 |
| | GML420 | High Output | GSL843T5L/HO | Single-pin | 25 | 195 |
| | GML440 | High Output | GSL843T5L/HO/4 | Four-pin | 25 | 195 |
| 48" | GML425 | High Output | GSL1148T5L/HO | Single-pin | 36.1 | 250 |
| | GML445 | High Output | GSL1148T5L/HO/4 | Four-pin | 36.1 | 250 |
| | GML015 | Slimline | G64T5L | T5/single-pin | 26.7 | 190 |
| 64" | GML017 | High Output | GXO64T5L H/O | Single-pin | 46 | 370 |
| | GML140 | Slimline | G84T5VH | T5/single-pin | 26.7 | 190 |
| | GML270 | Slimline | G64T5L-4P | T5/four-pin | 26.7 | 190 |

FIG. 17

5" Parabolic Diffuser
10' Sections

7" Parabolic Diffuser
10' Sections

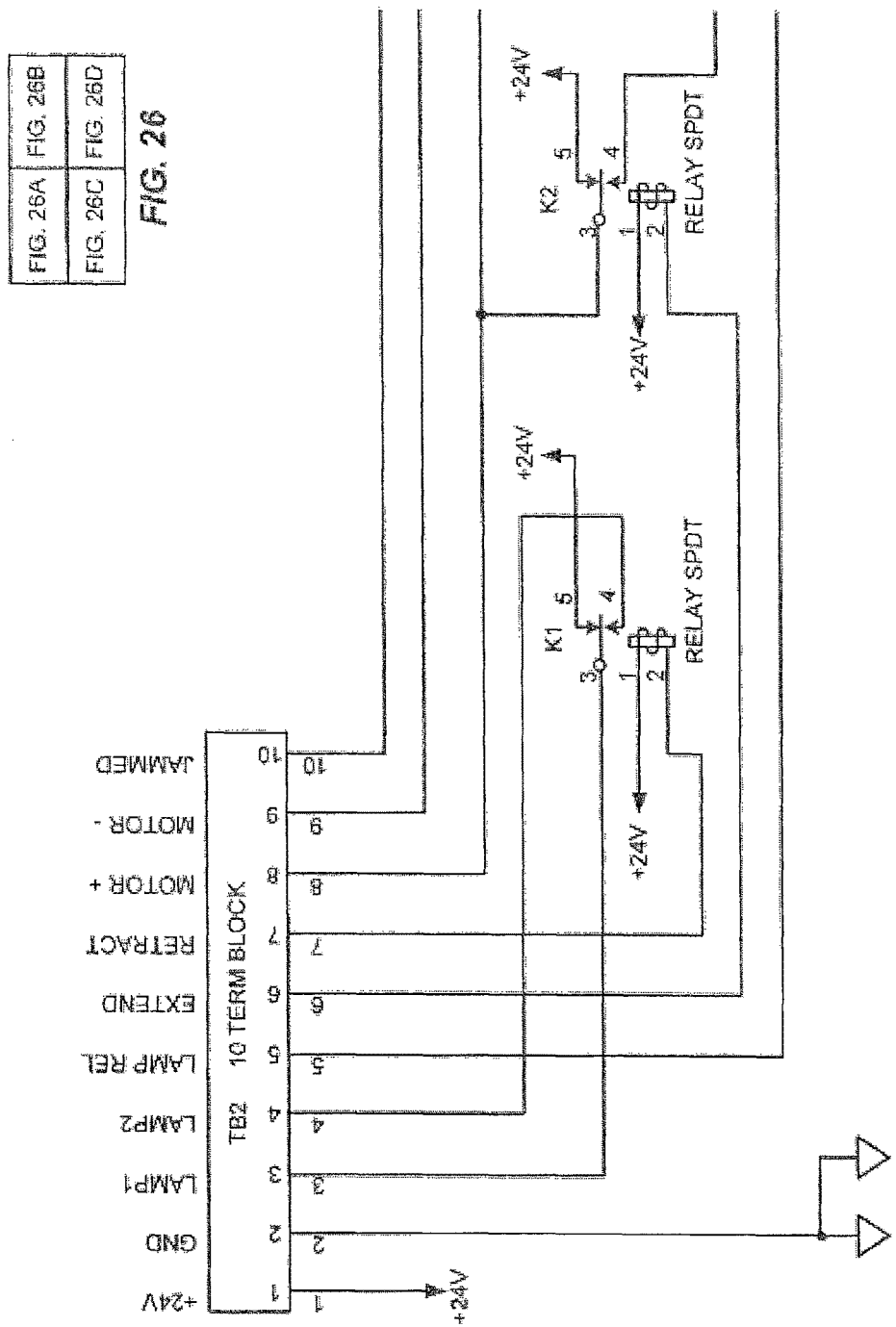

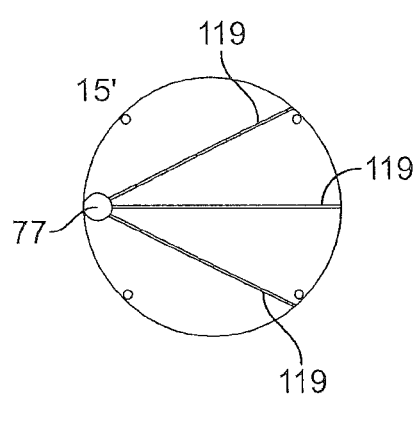
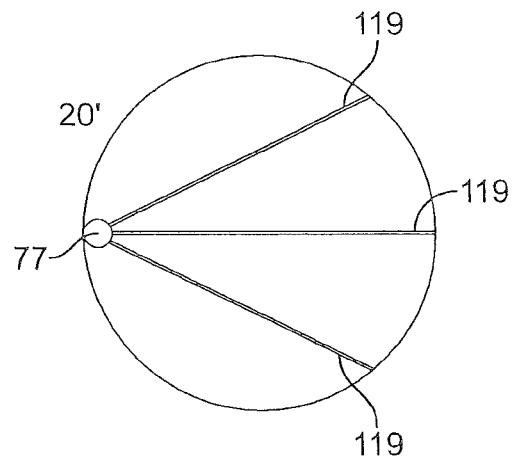
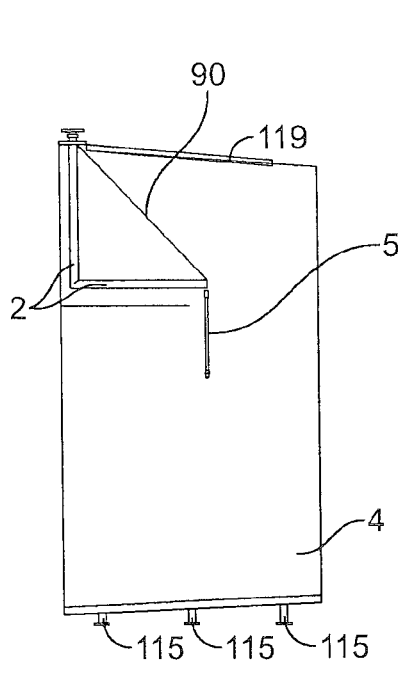
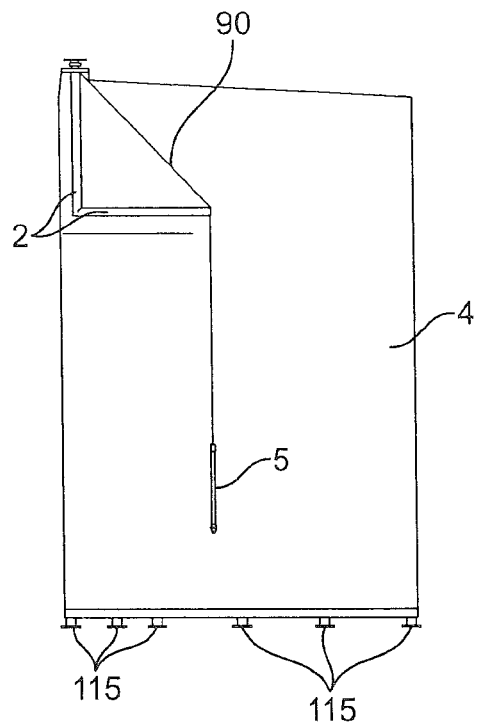
FIG. 34B            FIG. 34C

COMPOSITIONS AND METHODS FOR UV STERILIZATION

CROSS-REFERENCE TO RELATED APPLICATIONS

This patent application is a continuation-in-part application of U.S. application Ser. No. 13/650,028, filed Oct. 11, 2012, which is a continuation-in-part application of U.S. application Ser. No. 13/314,007, filed Dec. 7, 2011, which is a continuation-in-part application of U.S. application Ser. No. 13/308,383, filed Nov. 30, 2011, now abandoned, which is a continuation-in-part application of U.S. application Ser. No. 13/151,196, filed Jun. 1, 2011, which claims the benefit of U.S. provisional patent application Ser. No. 61/350,414, entitled "UV Sterilization Of Containers," filed Jun. 1, 2010, the disclosures of which are incorporated herein by reference in their entirety by reference for all purposes. U.S. application Ser. No. 13/314,007, filed Dec. 7, 2011, also claims benefit of PCT patent application Ser. No. PCT/US2011/63827, filed Dec. 7, 2011, which is (i) a continuation-in-part application of U.S. application Ser. No. 13/151,196, filed Jun. 1, 2011, and (ii) a continuation-in-part application of PCT/US 11/38826, filed Jun. 1, 2011, each (i) and (ii) claiming the benefit of U.S. provisional patent application Ser. No. 61/350,414, entitled "UV Sterilization Of Containers," filed Jun. 1, 2010, the disclosures of which are incorporated herein by reference in their entirety by reference for all purposes.

FIELD OF INVENTION

The present invention relates generally to compositions, systems and methods for ultraviolet (UV) disinfection, and more specifically, to compositions, systems and methods for UV disinfection of a container, and more particularly to compositions, systems and methods for UV disinfection of a container used in the food and dairy industry or in the process of fermentation for an alcoholic beverage. The present invention also relates to compositions, systems and methods for UV disinfection of a room, a space or a defined environment.

BACKGROUND OF THE INVENTION

It has been well established that ultraviolet (UV) light has germicidal properties. Specifically, the mechanism by which UV light kills microorganisms is by damaging the genetic material, the deoxyribonucleic acid (DNA), of the microorganisms. Wavelengths between 200-300 nm have been shown to initiate a photoreaction between adjacent pyrimidines. Pyrimidine bases, such as cytosine and thymine, have conjugated double bonds and as such absorb UV light. The photoreaction between adjacent thymine or cytosine bases proceeds at an exceedingly rapid rate (on the order of picoseconds). There are two possible products. The most common is the formation of a cyclobutane ring between the two pyrimidines (Fu et al., 1997, *Applied and Environ Microbiol* 63(4):1551-1556). The other photoproduct is a (6-4) pyrimidone. The formation of these dimers leads to "kinks" within the structure of the DNA inhibiting the formation of proper transcriptional and replicational templates. Cytosine cyclobutane photodimers are susceptible to deamination and can therefore induce point mutations, specifically the CC (two adjacent cytosines) are converted into TT (two adjacent thymines) via the SOS Response system in both eukaryotic and prokaryotic organisms (Fu et al., 2008, *FEMS Microbiol Rev* 32(6):908-26; Eller and Gilchrest; 2000, *Pigment Cell Res* 13 Suppl 8:94-7). The inactivation of specific genes via point mutations is one of the mechanisms of how UV-induced genetic damage can lead to cell death or to the inhibition of cell replication. The inability to form proper replicational and transcriptional templates coupled with the increased number of point mutations leads to the deactivation and inability to reproduce of microorganisms.

DNA, specifically has a maximum absorbency of UV light at 253.7 nm. It has been determined that approximately 26,400 microwatt-seconds/$cm^2$ are needed to deactivate 100% of the most resistant bacteria (Osburne et al., 2010, *Environ Microbiol;* doi:10.1111/j.1462-2920.2010.02203.x).

UV light is separated into 3 distinct categories: UV-A (315-400 nm), UV-B (280-315 nm), and UV-C (200-280 nm). Since DNA optimally absorbs UV light at 253.7 nm, it is UV-C lamps that are used in most prior art germicidal devices. LTV devices are used, e.g., to inactivate microorganisms in laboratory settings.

UV radiation is used for disinfection in hospitals, nurseries, operating rooms, cafeterias and to sterilize vaccines, serums, toxins, municipal waste, and drinking waters.

Current steel vessel and container sanitation protocols involve the use of a pressure wash using a hot water cycle to remove pigments, colloidal deposits, and tartrates following wine fermentations. After the hot water cycle, typically the vessels are washed with a 200 mg/L solution of hypochlorite as a sanitation cycle. This is usually followed by a rinse with citric acid. (Boulton et al., Principles and Practices of Winemaking, page 210, Springer, $1^{st}$ Edition, Jan. 15, 1996).

Sodium hypochlorite (NaOCl) is often used for disinfecting hospital wastewater in order to prevent the spread of pathogenic microorganisms, causal agents of nosocomial infectious diseases. Chlorine disinfectants in wastewater react with organic matters, giving rise to organic chlorine compounds such as AOX (halogenated organic compounds adsorbable on activated carbon), which are toxic for aquatic organisms and are persistent environmental contaminants (Bohrerova et al., 2008, *Water Research* 42(12):2975-2982). Other protocols follow the removal of pigments, colloidal deposits, and tartrates with a wash with a caustic solution containing sodium hydroxide (typically 3%) and further followed by a final wash with a citric acid solution (typically 3%) to neutralize any remaining sodium hydroxide. There are several disadvantages to using sodium hydroxide and citric acid for sterilization. The primary disadvantage is the necessary use of large amounts of water as a solvent for both solutions. Any potential water saving measure is of great value both economically and environmentally. Further, the reduction in use of extremely caustic sodium hydroxide would be an added environmental benefit.

Other methods currently used for sterilizing fermentation vessels (made from metals and/or wood) include the use of ozone. Prior to 1997, ozone could only be used for sanitation and purification of bottled drinking water in the United States, and it is widely used around the world for this purpose today. In May 1997, an expert panel assembled by the Electric Power Research Institute (EPRI) declared ozone to be Generally Recognized as Safe (GRAS) for use in food processing in the United States. Since then, wineries have embraced the use of ozone. Its use has been generally accepted and documented to be effective for barrel cleaning and sanitation, tank cleaning and sanitation, clean-in-place systems, and for general surface sanitation. Results have shown the same degree of sanitization as that achieved using caustic for a fraction of the cost and wasted water.

However, in the wine industry, ozone systems tend to be mobile (a single unit can be moved to different vessels), with multiple operators in multiple locations. This makes it important that safety features and ozone management systems be in place and that the system itself be reliable and easy to operate.

Natural levels of ozone range from 0.01 ppm to 0.15 ppm and can reach higher concentrations in urban areas. Ozone is an unstable gas and readily reacts with organic substances. It sanitizes by interacting with microbial membranes and denaturating metabolic enzymes.

Ozone is generated by irradiation of an air stream with ultraviolet (UV) light at a wavelength of 185 nm or by passing dry air or oxygen through a corona discharge (CD technology) generator. For low ozone concentrations (ca. 0.14% by weight, or 0.5 grams per hour), the less expensive UV equipment is sufficient. For more demanding situations where higher ozone concentrations (1.0% to 14% by weight) are required, CD systems are used.

The wine industry is using both CD technology and UV (different from the one described herein). Some manufacturers use multiple UV tubes to achieve a desired level of output. Several manufacturers chose to install air-cooled or water-cooled CD generators in their systems. It is really a question of how much ozone at a certain gallons per minute (gpm) is desired for an application. For clean in place (CIP), 20 gpm may be desired, necessitating a larger system, while only 10 gpm at a lower concentration may provide satisfactory barrel washing.

The Occupational Safety and Health Administration (OSHA) has set limits for ozone exposure in the workplace. These limits are for continuous eight-hour exposure of no more than 0.1 ppm, and a short-term exposure limit (STEL) of 15 minutes at 0.3 ppm, not to be exceeded more than twice per eight-hour work day. Consequently, ozone requires monitoring in the workplace if used for environmental or equipment sanitation using, e.g., ozone.

Ozone is known to have adverse physiological effects on humans (Directorate-General of Labour, the Netherlands 1992, 4(92), 62). Technically, there is no minimum threshold for ozone toxicity. Even low concentrations of ozone produce transient irritation of the lungs as well as headaches. Higher concentrations induce severe eye and upper respiratory tract irritation. Chronic exposure to ozone leads to respiratory tract disease and has been associated with reported increases in tumor growth rates. Exposure to ozone levels greater than the maximum thresholds specified by the American Conference of Governmental Industrial Hygienists (ACGIH)/Occupational Safety and Health Administration (OSHA) results in nausea, chest pain, coughing, fatigue and reduced visual acuity. Thus, while ozone provides an efficient means of sterilization, it also poses an occupational hazard to those involved in the sterilization process.

Another bactericidal chemical frequently used to sterilize fermentation vessels is chlorinated trisodium phosphate (TSP). It has been well established that chlorinated TSP is an effective germicidal agent. TSP, however, is also a severe irritant, capable of inducing contact dermatitis in addition to irritating the respiratory tract (Health Hazard Evaluation Report No. HETA-82-281-1503; HETA-82-281-1503). Also, certain microorganisms, such as *Cryptosporidium*, have developed resistance to reactive chlorine compounds. Further, evidence is mounting that organic chemical byproducts of chemical disinfection, especially byproducts of chlorination, are carcinogens and/or toxins for humans. Thus, expensive filtration devices may be required to remove the chemicals. Further, systems based on filtration require frequent replacement and/or cleaning of the filters. In addition, use of chlorinated TSP requires large quantities of water as a solvent and to extensively rinse the container following chemical sterilization. Also, chlorinated compounds are notorious for causing wine fouling. Thus, chemical disinfection is not a viable alternative when chemical purity of a fluid or alcoholic beverage in a fermentation vessel is desired or required.

Ozone sterilization was originally used to purify blood in the late 1800s. In the 1900s, ozonated water was in use for the treatment of multiple types of disease. In the first World War, ozone was used to treat wounds, gangrene and the effects of poisonous gas. Thus, throughout the time period, toxic and/or carcinogenic chemicals have been used in the sterilization of containers used for fermenting alcoholic beverages.

Using the chemical disinfection or ozone disinfection methods, there is also no established protocol for verifying the level of sterilization achieved by using those methods.

Sanitization of food-containing equipment or food-containing containers is a growing concern in the world. An increasing number of people fall ill each year by being exposed to contaminated food or food kept in contaminated containers.

Thus, there is a need in the art for non-toxic and non-carcinogenic methods, systems, and compositions useful for the sterilization of containers, and in particular, for the sterilization of containers for fermenting alcoholic beverages and containers for food and dairy products. There is also a need for providing improved UV devices, systems, and methods for the sanitization of a room, a space or defined environment. The compositions, systems, and methods provided herein meet these and other needs in the art.

BRIEF SUMMARY OF THE INVENTION

The present invention provides compositions, systems, and methods useful for the ultraviolet (UV) sterilization of containers and for the sanitization of rooms, spaces and environments.

The present invention provides a UV device. In some embodiments of a UV device of the present invention, the UV device is a UV device for UV sterilization of an interior surface of a container. In some embodiments of a UV device of the present invention, the UV device comprises a germicidal UV light source comprising a lamp, a housing the germicidal UV light source, a means for moving the germicidal UV light source inwardly into a container; and a means for attaching the UV device to an opening of a container.

In some embodiments of a UV device of the present invention, a UV device further comprises a central sleeve attached to the housing. The central sleeve may comprise one or more cavities. The one or more cavities may house one or more additional components of the UV device.

In some embodiments of a UV device of the present invention, the central sleeve comprises a first cavity. In some embodiments of a UV device of the present invention, the first cavity houses an additional component of the UV device, such as a circuit board.

In some embodiments of a UV device of the present invention, the central sleeve comprises a second cavity. In some embodiments of a UV device of the present invention, the second cavity houses an additional component of the LTV device, such as a power supply.

The present invention provides several embodiments for attaching a UV light source to the UV device. In some embodiments of a UV device of the present invention, the UV light source is attached to the central sleeve.

The present invention provides a central sleeve that has several functionalities. In some embodiments of a UV device of the present invention, the central sleeve moves downwardly within the housing and thereby releases the UV light source from the housing.

A UV device of the present invention comprises a UV light source comprising a lamp. In some embodiments of a UV device of the present invention, the lamp is selected from the group consisting of a low pressure mercury lamp, a medium pressure mercury lamp, a high pressure mercury lamp, an ultra-high pressure mercury lamp, a low pressure short arc xenon lamp, a medium pressure short arc xenon lamp, a high pressure short arc xenon lamp, an ultra-high pressure short arc xenon lamp, a low pressure long arc xenon lamp, a medium pressure long arc xenon lamp, a high pressure long arc xenon lamp, an ultra-high pressure long arc xenon lamp, a low pressure metal halide lamp, a medium pressure metal halide lamp, a high pressure metal halide lamp, an ultra-high pressure metal halide lamp, a tungsten halogen lamp, a quartz halogen lamp, a quartz iodine lamp, a sodium lamp, and an incandescent lamp.

In some embodiments of a UV device of the present invention, a UV device comprises a germicidal UV light source. In some embodiments of a UV device of the present invention, the germicidal UV light source is a UV-C light source.

The present invention provides various a means for attaching the UV device to an opening of a container. In some embodiments of a UV device of the present invention, a means for attaching the UV device to an opening of a container is a base plate permitting positioning of the UV device on top of an opening of a container.

In some embodiments of a UV device of the present invention, a UV device comprises an interface. An interface may provide one or more buttons for controlling several one or more functionalities. In some embodiments of a UV device of the present invention, an interface provides at least one functional button for a function selected from the group of functions consisting of activating the UV device, deactivating the UV device, releasing the germicidal UV light source from the housing, providing time remaining for completing the UV sterilization of the container, and providing time elapsed for UV sterilization of the container. The functionality may result in an audible or visual signal for the user of the UV device.

In some embodiments of a UV device of the present invention, a UV light source comprises a plurality of UV lamps arranged in a UV lamp cluster.

In some embodiments of a UV device of the present invention, a UV device comprises a reflector partially surrounding the UV light source.

In some embodiments of a UV device of the present invention, a UV device comprises a rangefinder.

The present invention also provides systems. In some embodiments of a system of the present invention, a system comprises a UV device and a container. The UV device of a system as described herein, can be any UV device described herein. In some embodiments of a system of the present invention, the UV device is a UV device for UV sterilization of an interior surface of a container. In some embodiments of a system of the present invention, a UV device comprises a germicidal UV light source comprising a lamp, a housing housing the germicidal UV light source, a means for moving the germicidal UV light source inwardly into a container; and a means for attaching the UV device to an opening of a container.

In some embodiments of a system of the present invention, a UV device further comprises a central sleeve attached to the housing. The central sleeve may comprise one or more cavities. The one or more cavities may house one or more additional components of the UV device.

In some embodiments of a system of the present invention, the central sleeve comprises a first cavity. In some embodiments of a system of the present invention, the first cavity houses an additional component of the UV device, such as a circuit board.

In some embodiments of a system of the present invention, the central sleeve comprises a second cavity. In some embodiments of a system of the present invention, the second cavity houses an additional component of the UV device, such as a power supply.

The present invention provides several embodiments for attaching a UV light source to the UV device. In some embodiments of a system of the present invention, the UV light source is attached to the central sleeve.

The present invention provides a central sleeve that has several functionalities. In some embodiments of a system of the present invention, the central sleeve of a UV device moves downwardly within the housing and thereby releases the UV light source from the housing.

A system of the present invention comprises a UV device comprising a UV light source comprising a lamp. In some embodiments of a system of the present invention, the lamp is selected from the group consisting of a low pressure mercury lamp, a medium pressure mercury lamp, a high pressure mercury lamp, an ultra-high pressure mercury lamp, a low pressure short arc xenon lamp, a medium pressure short arc xenon lamp, a high pressure short arc xenon lamp, an ultra-high pressure short arc xenon lamp, a low pressure long arc xenon lamp, a medium pressure long arc xenon lamp, a high pressure long arc xenon lamp, an ultra-high pressure long arc xenon lamp, a low pressure metal halide lamp, a medium pressure metal halide lamp, a high pressure metal halide lamp, an ultra-high pressure metal halide lamp, a tungsten halogen lamp, a quartz halogen lamp, a quartz iodine lamp, a sodium lamp, and an incandescent lamp.

In some embodiments of a system of the present invention, a UV device comprises a germicidal UV light source. In some embodiments of a system of the present invention, the germicidal UV light source is a UV-C light source.

In some embodiments of a system of the present invention, a container comprises an opening. The systems provided by the present invention provide various a means for attaching a UV device to an opening of a container. In some embodiments of a system of the present invention, a means for attaching the UV device to an opening of a container is a base plate permitting positioning of the UV device on top of an opening of a container.

In some embodiments of a system of the present invention, a UV device comprises an interface. An interface may provide one or more buttons for controlling several one or more functionalities. In some embodiments of a system of the present invention, an interface of a UV device provides at least one functional button for a function selected from the group of functions consisting of activating the UV device, deactivating the UV device, releasing the germicidal UV light source from the housing, providing time remaining for completing the UV sterilization of the container, and providing time elapsed for UV sterilization of the container. The functionality may result in an audible or visual signal for the user of the UV device.

In some embodiments of a system of the present invention, a UV light source comprises a plurality of UV lamps arranged in a UV lamp cluster.

In some embodiments of a system of the present invention, a UV device comprises a reflector partially surrounding the UV light source.

In some embodiments of a system of the present invention, a UV device comprises a rangefinder.

A system of the present invention may comprise various containers. In some embodiments of a system of the present invention, a container is selected from the group consisting of a container for fermenting an alcoholic beverage and a container for storing or transporting a dairy product, a liquid dairy, a liquid dairy composition or a dry dairy composition.

The present invention also provides methods for UV sterilization of an interior surface of a container. In some embodiments of a method of the present invention, the method for UV sterilization of an interior surface of a container comprises the step of movably and inwardly inserting through an opening of a container a germicidal UV light source of a UV device and activating the germicidal UV light source. Thereby the interior surface of the container is sterilized.

In some embodiments of a method of the present invention, a UV device further comprises a central sleeve attached to the housing. The central sleeve may comprise one or more cavities. The one or more cavities may house one or more additional components of the UV device.

In some embodiments of a method of the present invention, the central sleeve comprises a first cavity. In some embodiments of a method of the present invention, the first cavity houses an additional component of the UV device, such as a circuit board.

In some embodiments of a method of the present invention, the central sleeve comprises a second cavity. In some embodiments of a method of the present invention, the second cavity houses an additional component of the UV device, such as a power supply.

The present invention provides several embodiments for attaching a UV light source to the UV device. In some embodiments of a method of the present invention, the UV light source is attached to the central sleeve.

The present invention provides a central sleeve that has several functionalities. In some embodiments of a method of the present invention, the central sleeve of a UV device moves downwardly within the housing and thereby releases the UV light source from the housing.

A method of the present invention comprises a UV device comprising a UV light source comprising a lamp. In some embodiments of a method of the present invention, the lamp is selected from the group consisting of a low pressure mercury lamp, a medium pressure mercury lamp, a high pressure mercury lamp, an ultra-high pressure mercury lamp, a low pressure short arc xenon lamp, a medium pressure short arc xenon lamp, a high pressure short arc xenon lamp, an ultra-high pressure short arc xenon lamp, a low pressure long arc xenon lamp, a medium pressure long arc xenon lamp, a high pressure long arc xenon lamp, an ultra-high pressure long arc xenon lamp, a low pressure metal halide lamp, a medium pressure metal halide lamp, a high pressure metal halide lamp, an ultra-high pressure metal halide lamp, a tungsten halogen lamp, a quartz halogen lamp, a quartz iodine lamp, a sodium lamp, and an incandescent lamp.

Various germicidal UV light sources may be used in the methods of the present invention. In some embodiments, the germicidal UV light source is a UV-C light source. In some embodiments, the germicidal UV light source is a pulsed germicidal UV light source. In some embodiments of a method of the present invention, a UV device comprises a germicidal UV light source. In some embodiments of a method of the present invention, the germicidal UV light source is a UV-C light source.

In some embodiments of a method of the present invention, a container comprises an opening. The methods provided by the present invention provide various a means for attaching a UV device to an opening of a container. In some embodiments of a method of the present invention, a means for attaching the UV device to an opening of a container is a base plate permitting positioning of the UV device on top of an opening of a container.

In some embodiments of a method of the present invention, a UV device comprises an interface. An interface may provide one or more buttons for controlling several one or more functionalities. In some embodiments of a method of the present invention, an interface of a UV device provides at least one functional button for a function selected from the group of functions consisting of activating the UV device, deactivating the UV device, releasing the germicidal UV light source from the housing, providing time remaining for completing the UV sterilization of the container, and providing time elapsed for UV sterilization of the container. The functionality may result in an audible or visual signal for the user of the UV device.

In some embodiments of a method of the present invention, a UV light source comprises a plurality of UV lamps arranged in a UV lamp cluster.

In some embodiments of a method of the present invention, a UV device comprises a reflector partially surrounding the UV light source.

In some embodiments of a method of the present invention, a UV device comprises a rangefinder.

Various containers can be UV sterilized using a method of the present invention. A method of the present invention may comprise various containers. In some embodiments of a method of the present invention, a container is selected from the group consisting of a container for fermenting an alcoholic beverage and a container for storing or transporting a dairy product, a liquid dairy, a liquid dairy composition or a dry dairy composition. In some embodiments, the container is a container for fermenting an alcoholic beverage. In some embodiments, the alcoholic beverage is beer, wine. Gin, vodka, or whisky. In some embodiments, the container is a container for storing or transporting a dairy product, a liquid dairy, a liquid dairy composition or a dry dairy composition.

In some embodiments of a method of the present invention one or more species of microorganisms is/are present on an interior surface of a container. Microorganisms on the interior surface of the container can be effectively killed using a method of the present invention. In some embodiments, one or more species of microorganisms is present on the interior surface of the container and the activation of the germicidal UV light source results in inhibiting the growth of the one or more species of microorganisms. In some embodiments of a method of the present invention, the one or more species of microorganisms is selected from the group consisting of *Candida, Kloeckera, Hanseniaspora, Zygosaccharomyces, Schizosaccharomyces, Torulaspora, Brettanomyces, Saccharomycodes, Pichia, Williopsis, Pediococcus, Lactobacillus*, and *Oenococcus*.

Various microorganisms can be killed or growth inhibited using a method of the present invention. In some embodiments, the one or more species of microorganisms is selected from the group consisting of *Candida, Kloeckera, Hanseniaspora, Zygosaccharomyces, Schizosaccharomyces, Torulaspora, Brettanomyces, Saccharomycodes, Pichia, Williopsis, Pediococcus, Lactobacillus,* and *Oenococcus*. In some embodiments, the microorganism is *Lactobacillus*.

Using methods of the present invention effective UV sterilization of an interior surface of a container is achieved. In some embodiments, the growth of one or more species of microorganisms is inhibited by at least 2 log. In some embodiments, the growth of one or more species of microorganisms is inhibited by at least 3 log. In some embodiments, the growth of one or more species of microorganisms is inhibited by at least 4 log. In some embodiments, the growth of one or more species of microorganisms is inhibited by at least 5 log. In some embodiments, the growth of one or more species of microorganisms is inhibited by at least 6 log.

The present invention also provides UV devices and systems comprising a UV devices for the UV sterilization of a room, a space or a defined environment, preferably a surface within the room, space or defined environment.

The present invention provides methods for the ultraviolet (UV) sterilization of a room, a space or defined environment. In some embodiments, this method comprises the steps of selecting a room, space or defined environment in need of sanitization and exposing the room, space or defined environment to UV sterilization using a UV device described herein. For example, the UV device may comprise a housing and a germicidal UV light source comprising one or more UV lamps that are arranged in one or more UV lamp clusters. Preferably, the UV device is attached to the ceiling or wall of the room so that the room can be sanitized when the UV device is activated.

In some embodiments of a UV device, when used for sanitization of a room, one or more UV lamps are attached to the side of a room in a housing. In other embodiments, the one or more UV lamps are attached to the ceiling of the room in a housing. When in use, the UV lamps extend from the housing at varying angles. Extension of the UV lamps from the housing may be achieved and controlled by using a motor.

In some embodiments of a UV device, when used for sanitization of a room, space or defined environment, the UV device comprises a range finding device to determine the size of the room, space or defined environment. The rangefinder then provides information to preprogram an effective sanitization cycle.

In some embodiments of a UV device, when used for sanitization of a room, a multi lamp UV cluster extends from the ceiling of the room with the UV lamps extending at varying angles to optimize coverage and UV exposure of the room.

In some embodiments of a UV device, when used for sanitization of a room, a multi lamp UV cluster extends from the ceiling of the room with individual UV light coming down independently at varying angles.

In some embodiments of a UV device, when used for sanitization of a room, the UV lamp cluster and housing are permanently fixed to either the walls or ceiling of the room.

In some embodiments of a UV device, when used for sanitization of a room, the UV lamp cluster is attached via a fixture to the ceiling of a room. The fixture may be permanently attached and the UV lamp cluster and housing may be removable.

In some embodiments of the method for sanitization of a room, a space or defined environment, UV lamp clusters that are movably attached to the housing move from a closed position to an exposed position. In some embodiments, the UV lamp cluster is movably connected to the housing via a hinge and upon moving the hinge position, the UV lamp cluster moves from a closed position into an exposed position.

The room, space or defined environment that can be sterilized using a UV device is not limited. The room, space or defined environment can be, for example, a commercial kitchen, a residential kitchen, a medical facility, an acute care area, an operating room, a medical equipment storage cabinet, a clean room, a bathroom, a food production area, a nursery home, a trailer, a rail car, a grocery store display case, or a deli counter.

In some embodiments of a UV device, when used for sanitization of a room, a space or defined environment, the dimensions of the room, space or defined environment are preprogrammed into the UV device allowing the timing of sanitization to be optimized and the minimal necessary UV dose required for sanitation (approximately 3 log reduction) to be reached while minimizing power use.

In some embodiments of a UV device, when used for sanitization of a room, space or defined environment, the UV device is connected to a motion detector. This may be helpful to ensure people and/or animals are absent from the room prior to the beginning of the sanitization cycle.

In some embodiments of a UV device, when used for sanitization of a room, a space or defined environment, multiple UV lamp clusters are spread throughout the room. Based on the dimension and shape of the room, space or defined environment, the positioning of the UV lamps and angles are accounted for and this information is programmed into an algorithm allowing the timing of sanitization to be optimized and the minimal necessary UV dose required for sanitation (approximately 3 log reduction) to be reached while minimizing power use. The positioning of the UV lamps and angles can also be communicated via wireless technology. A rangefinder may analyze the shape and dimension of a room and input information into an algorithm allowing the timing of sanitization to be optimized and the minimal necessary UV dose required for sanitation (approximately 3 log reduction) to be reached while minimizing power use.

In some embodiments of a device, when used for sanitization of a room, space or defined environment, the UV bulb is attached to the bottom of a robot having wheels and follows programming allowing it to both perform an effective moving pattern on the floor covering desired areas. The robot may also have an object and wall avoiding programming and technology. The robot may move at a speed allowing an effective UV dose required for sanitization (approximately 3 log reduction) to be reached while minimizing power use.

In some embodiments of a device, the UV bulb is to the bottom of a robot crawler that uses suction allowing it to crawl vertically on walls and horizontally on ceilings. The robot crawler may follow programming allowing it to perform an effective pattern on the wall and ceiling covering desired areas. The robot crawler may move at a speed allowing an effective UV dose required for sanitization (approximately 3 log reduction) to be reached while minimizing power use.

BRIEF DESCRIPTION OF THE DRAWINGS

FIG. 1 depicts a schematic diagram of a UV device of the present invention above a container 4, here a cylindrical fermentation vessel. In the UV device shown, a singular mobile cylindrical UV lamp is retracted in a housing 2, here a protective sleeve. A motorized unit 1 is mounted on top of the protective sleeve. The housing 2 is attached to a mounting bracket 3.

FIG. 17 depicts a variety of commercially available UV lamps of different length, shape, and type useful in the present invention (American Air & Water Inc., Hilton Head Island, S.C. 29926, USA). For each UV lamp, the UV-C output is provided in watts and the UV intensity is provided in UV $\mu W/cm^2$ at 1 m. Length as indicated reflects nominal length with standard lamp holders adding 2" overall length.

Additional lamp lengths and types are available. *, Ozone is negligible unless noted as OZ for high or VH for very high ozone production.

FIG. 18 depicts the cross section of four commercially available reflectors (Hill Technical Sales Corp.) for use in the present invention. The upper two cross sections of the reflectors shown in (A) and (B) are elliptical and provide a line source of UV light. One focal point of the ellipse is located at the center of the UV lamp the other focal point is positioned approximately 1.75" or 3.5" (depending on reflector used) from the bottom edge of the reflector to the surface being irradiated. The lower two cross sections of the reflectors shown in (C) and (D) are parabolic and provide a collimated UV radiation source. The reflectors bottom edge preferably are located 4 to 5 inches from the surface being irradiated.

Figure 19A:
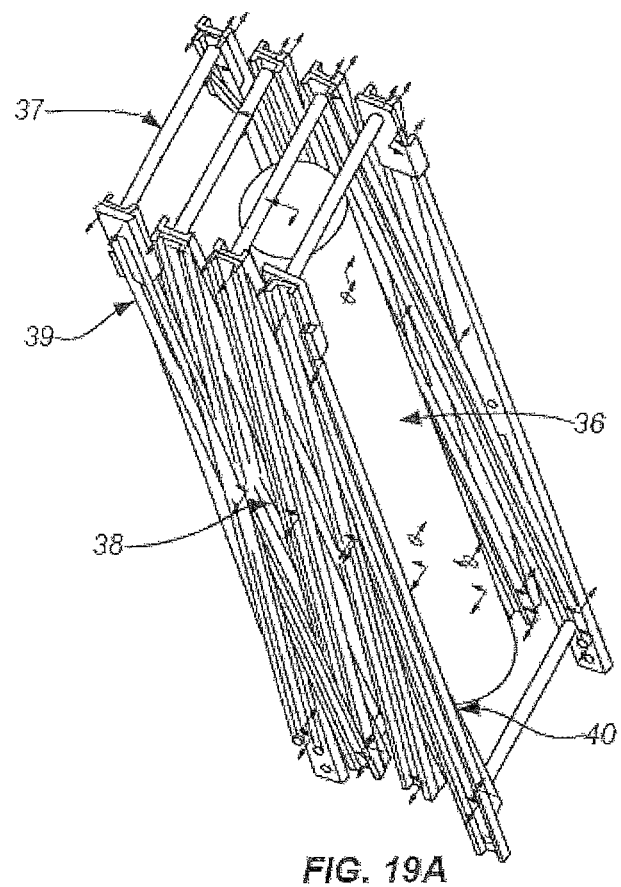

FIG. 19 depicts an embodiment of a UV device of the present invention referred to herein as linear actuator or scissor boom wherein the central post 16 is a scissor boom. Two configurations are shown: (A), scissor boom folded; (B), scissor boom extended. A UV lamp cluster housing 36 is attached to the outer end of the scissor boom. The UV lamp cluster housing houses a cluster of UV lamps (41, not shown in Figure). A linear actuator 37 pushes a scissor mechanism 38 up and down a first slide rail 39 located at the inner end (first end) of the scissor boom and allows the length of the scissor boom to be varied according to the diameter of the container into which it is inserted and/or mounted to. A second sliding rail 40, located at the outer end (second end) of the scissor boom allows the scissor boom to expand and contract in length. Once in place, the UV lamp cluster 40 (not shown in Figure) is dropped from its UV lamp cluster housing 36 and lowered down the central axis of the container. Arrows indicate pivot points. A sensor, e.g., a range-finding device (not shown in Figure) may also be attached to the second end of the scissor boom and will determine the length to which the scissor boom expands.

FIG. 20 depicts an embodiment of a UV device of the present invention referred to herein as bulb cluster assembly wherein the central post 16 is a central bar. A. closed configuration; B, open configuration. In this embodiment, the bulb cluster assembly is shown without a protective housing. In other embodiments, the UV lamps 5 are in a protective housing when not in use. Three UV lamps 5 are attached via pins 41 to an upper plate 42. When dropped out of a protective housing (not shown), a spring 43 on each UV lamp (only shown for one UV lamp in Figure) forces the UV lamps out to a 15 degree angle. A central bar 44 attaches to a lower plate 45 to the upper plate 42. As the cluster is retracted back into the protective cover, the UV lamps are forced back into a vertical position and are held in place by the lower plate 45.

FIGS. 21-25 depict several views of an exemplary embodiment of a UV device of the present invention comprising a telescopic arm as a means for moving a UV light source, here shown as a UV lamp cluster, into a desired or predetermined position. The UV device is shown schematically in various configurations: in its folded position (FIG. 21), in its load position (FIG. 22), in its payout position (FIG. 23), in its horizontal position (FIG. 24), and in its UV lamp down position (FIG. 25). Individual parts of this UV device are shown in detail in some of FIGS. 21-25, however, because of providing different overall views of this UV device, not all details or individual parts will be apparent in each of FIGS. 21-25.

Figure 21A:
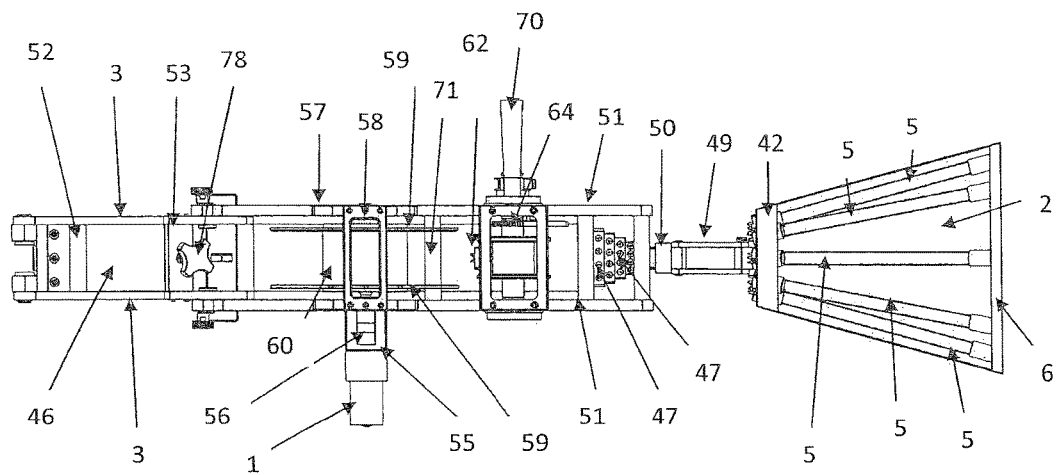

FIG. 21A shows a schematic top view of the UV device having a telescopic arm in its folded position. UV lamps 5 are clustered in a UV lamp cluster and are within a housing 2, here a UV mesh cage, which allows UV light to pass through. The UV lamps 5 are attached to a frame 6 and an upper plate 42. The upper plate 42 is connected to a UV lamp pivot arm 49 allowing the UV lamp cluster to be positioned in a desired position. The UV lamp pivot arm 49 is attached to a UV lamp stop block 50. A mounting bracket 3, also referred to as hanger, is used to attach the UV device to a container (not shown). The mounting bracket 3 is attached to a pulley mount arm 51, to which also other parts of the UV device can be attached, such as the motorized unit 1 (also referred to as motor) and a winch 48. The mounting bracket (hanger) 3 comprises one or more hanger support bars 52, a clamp post 53 and a tightening screw 78 for firmly attaching the UV device to a container. A motorized unit 1 (also referred to as motor) is connected to a reel assembly 54, which is mounted to the pulley mount arm 51. A motorized unit 1 or gravity extends the telescoping arm 46 consisting of multiple telescoping units 47 shown here as slided into each other, from the folded and load position (FIG. 22) into the payout position (FIG. 23). As shown schematically in this embodiment, the motor 1 is connected to a reel assembly 54 (shown in greater detail in FIGS. 21 E-G). The motor 1 connects to the reel assembly 54 via a reel assembly motor unit 55 and a motor coupler 56. As shown in this embodiment, the reel assembly 54 comprises a reel assembly idler post 57 for mounting the reel assembly 54 to the pulley mount bar 51, a reel assembly top plate 58, one or more reel assembly flanges 59, a reel assembly hub 60, and a reel assembly drive post 61. A winch 48 mounted on the pulley mount arm 51 moves the telescoping arm 46 and the telescoping units 47 from a payout position (FIG. 23) into a horizontal position (FIG. 24). As shown in this embodiment, the winch 48 comprises a winch pulley guide 62, a winch guide pulley shaft 63, a winch shaft 64, a winch hub 65, a winch top plate 66, one or more winch flanges 67, a winch ratchet retainer 68, a pawl 69, and a crank or handle 70. The outer telescoping unit 47 of the telescopic arm 46 is attached to the bottom part of the pulley mount arm 51 by one or more cross member support bars 71 and a cross bar stop plate 72. One end of the outer telescopic unit 47 is connected to a telescopic arm pivot 73 allowing the telescoping arm to be moved from the loaded (FIG. 22) or layout position (FIG. 23) into a horizontal position (FIG. 24) and back into the loaded or payout position.

Figure 21B:
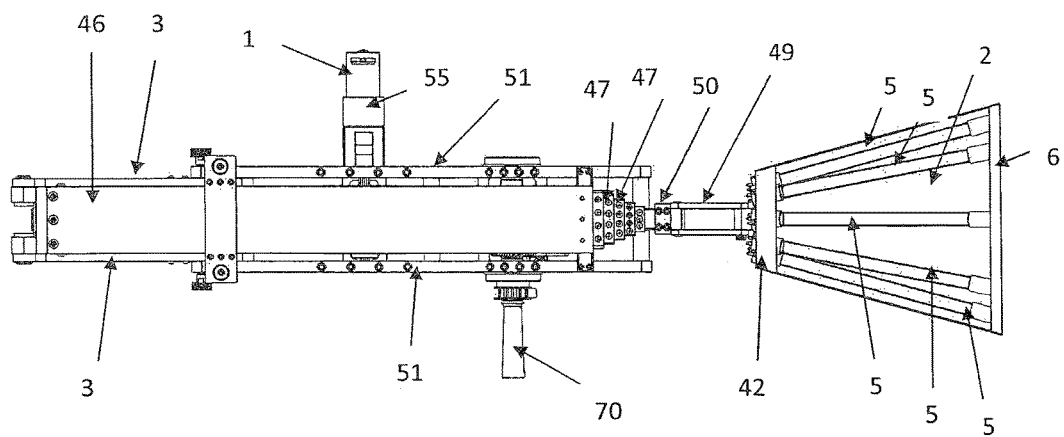

FIG. 21B shows a schematic bottom view of a UV device having a telescopic arm in its folded position. Individual parts are shown and numbered as described in FIG. 21A. A lifting eye 74 having a lifting eye base 75 and a lifting eye side support 76 (better shown e.g., in FIGS. 21E, F) is attached to the outer telescoping unit 47 and to the pulley mount arm 51.

Figure 21C:
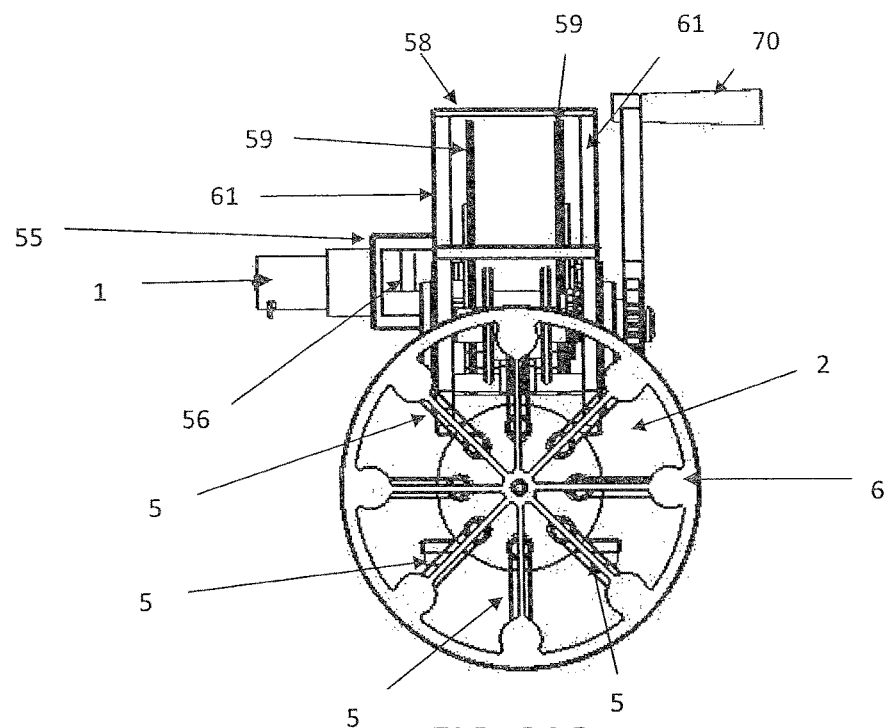

FIG. 21C shows a schematic front view of a UV device having a telescopic arm in its folded position. Individual parts are shown and numbered as described in FIGS. 21A, B.

Figure 21D:
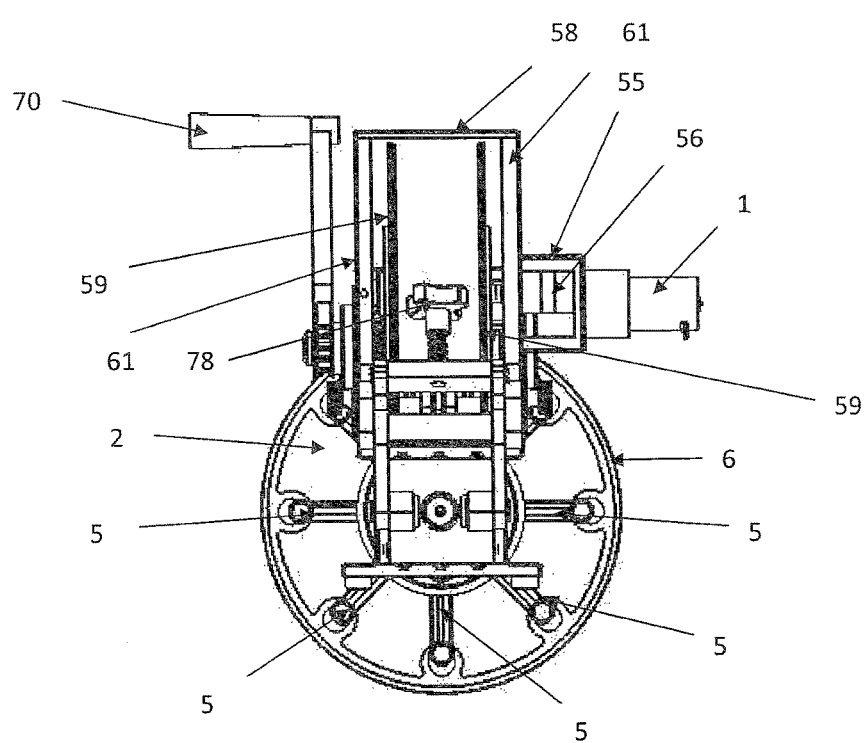

FIG. 21D shows a schematic back view of a UV device having a telescopic arm in its folded position. Individual parts are shown and numbered as described in FIGS. 21A-C A cable 7 functions as a lamp holder and for vertically extending the position of the UV light source (here a UV lamp cluster) towards the bottom of a container (not shown). The cable 7 attaches the UV light source through the inner telescoping unit 47 to the reel assembly 54.

Figure 21E:
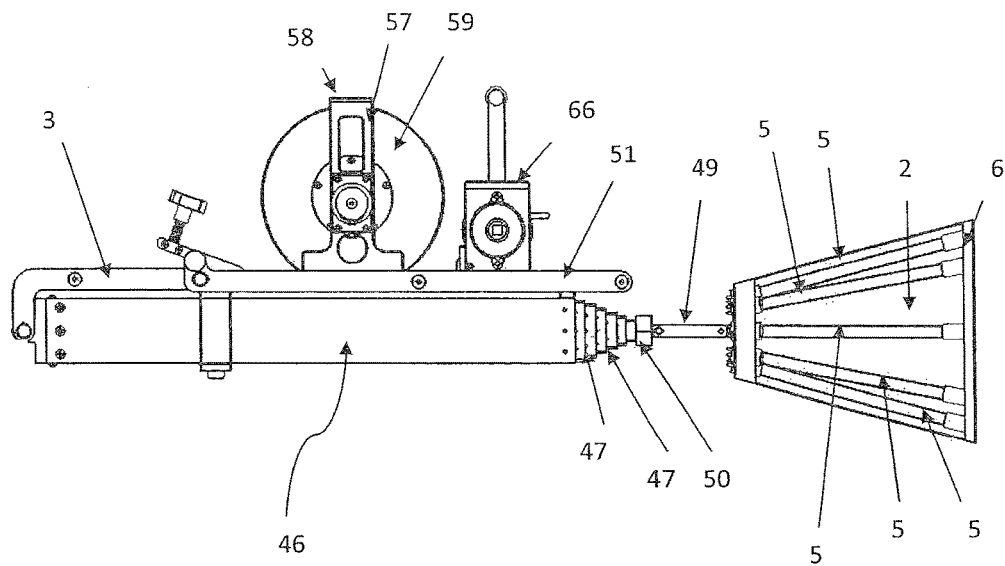

FIG. 21E shows a schematic first side view of a UV device having a telescopic arm in its folded position. Individual parts are shown and numbered as described in FIGS. 21A-D.

Figure 21F:
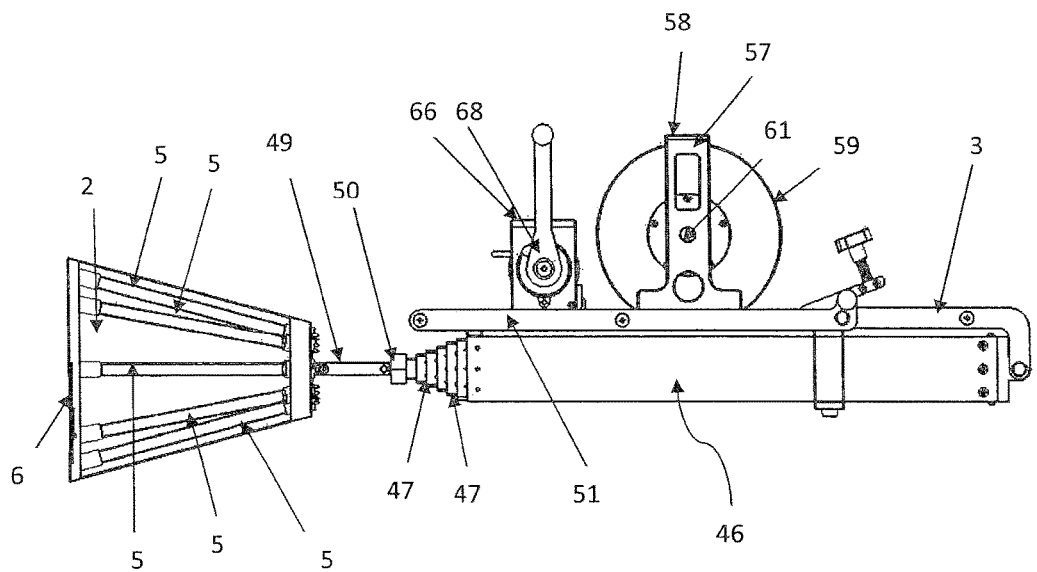

FIG. 21F shows a schematic second side view of a UV device having a telescopic arm in its folded position. Individual parts are shown and numbered as described in FIGS. 21A-E.

Figure 21G:
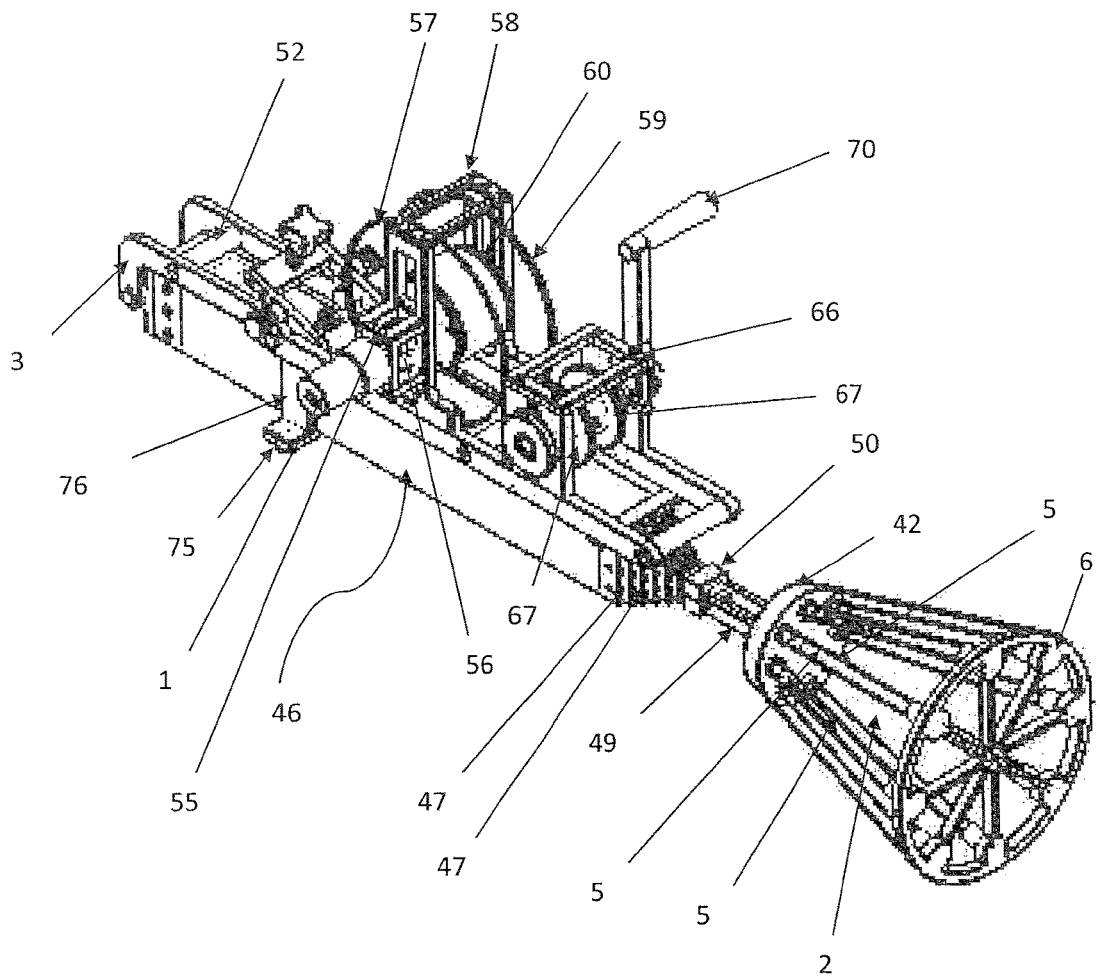

FIG. 21G shows a schematic isometric view of a UV device having a telescopic arm in its folded position. Individual parts are shown and numbered as described in FIGS. 21A-F.

Figure 22A:
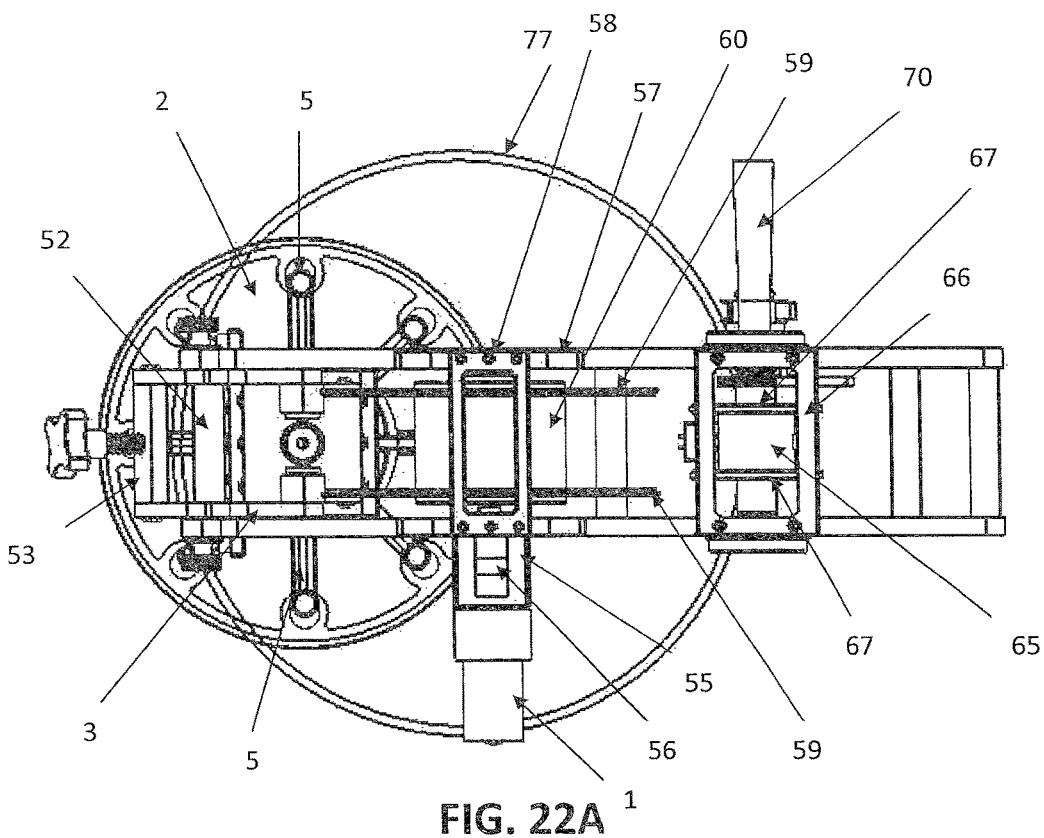

FIG. 22A shows a schematic top view of a UV device having a telescopic arm in its load position. Individual parts are shown and numbered as described in FIGS. 21A-F. A manhole or port 77 provides for access to the container from the top of the container and allows, e.g., for pressure washing devices to be attached and for attaching of a UV device of the present invention.

Figure 22B:
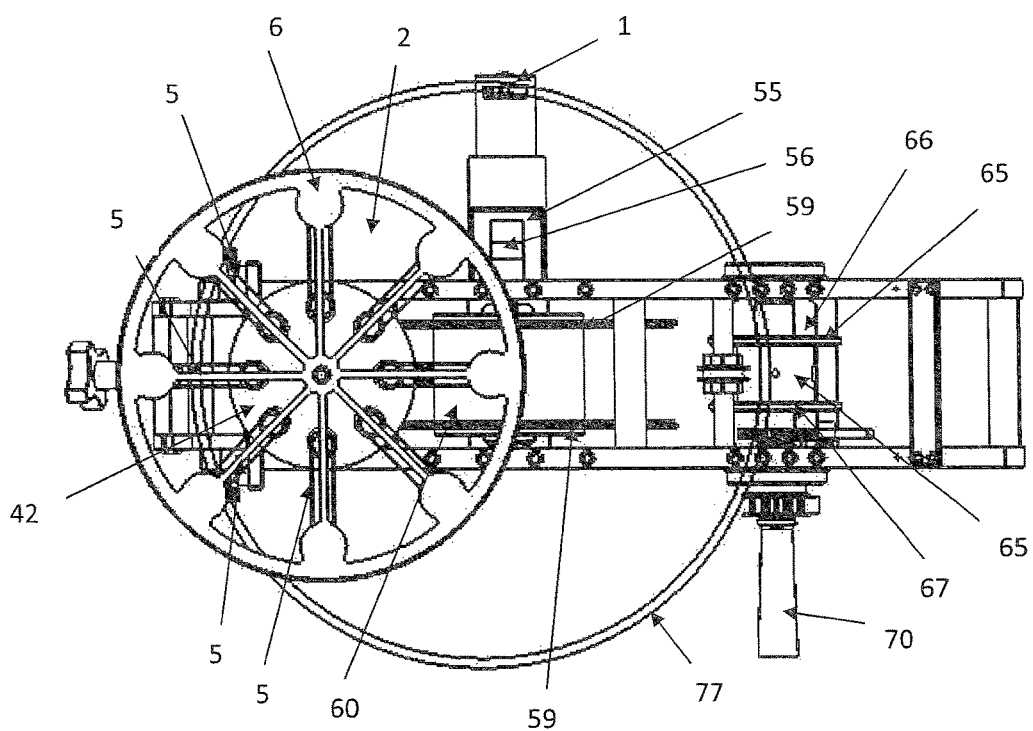

FIG. 22B shows a schematic bottom view of a UV device having a telescopic arm in its load position. Individual parts are shown and numbered as described in FIGS. 21A-F.

Figure 22C:
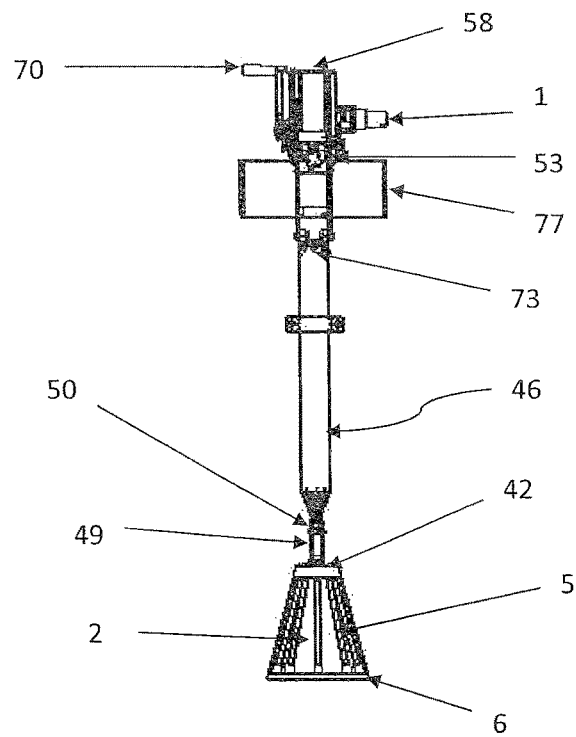

FIG. 22C shows a schematic front view of a UV device having a telescopic arm in its load position. Individual parts are shown and numbered as described in FIGS. 21A-F.

Figure 22D:
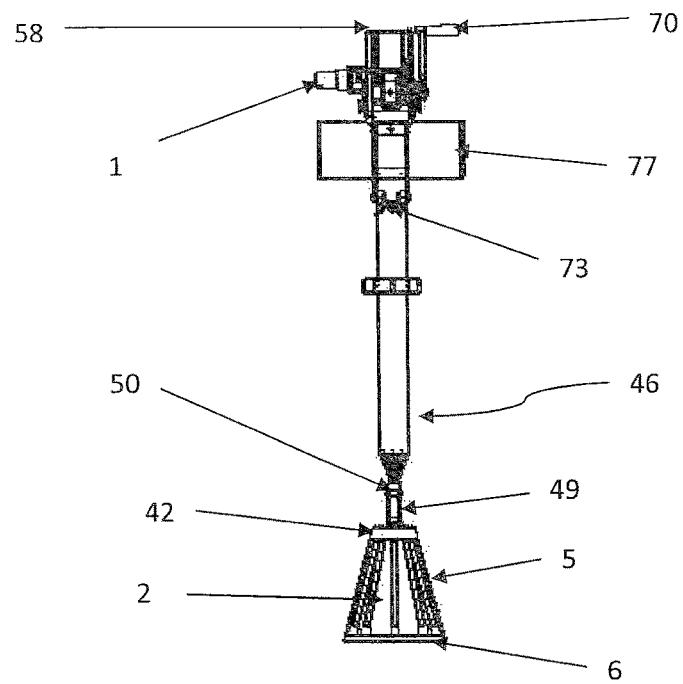

FIG. 22D shows a schematic back view of a UV device having a telescopic arm in its load position. Individual parts are shown and numbered as described in FIGS. 21A-F.

Figure 22E:
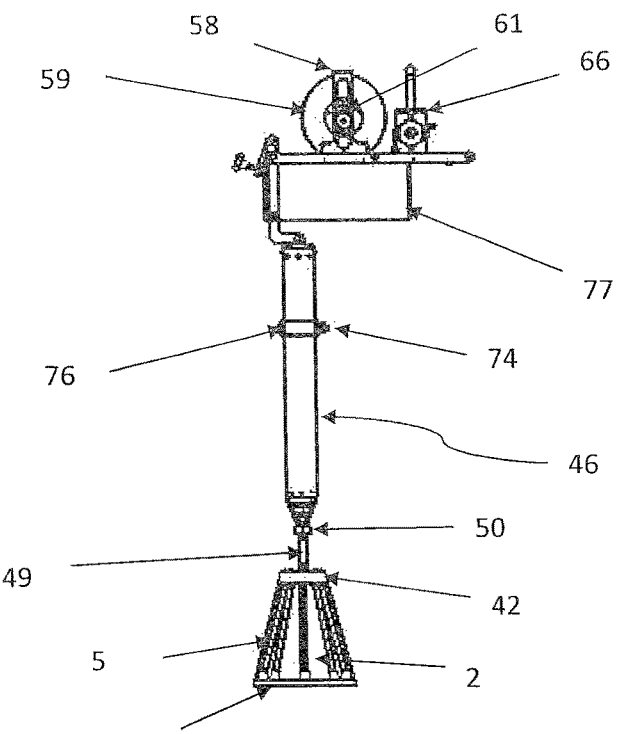

FIG. 22E shows a schematic first side view of a UV device having a telescopic arm in its load position. Individual parts are shown and numbered as described in FIGS. 21A-F.

Figure 22F:
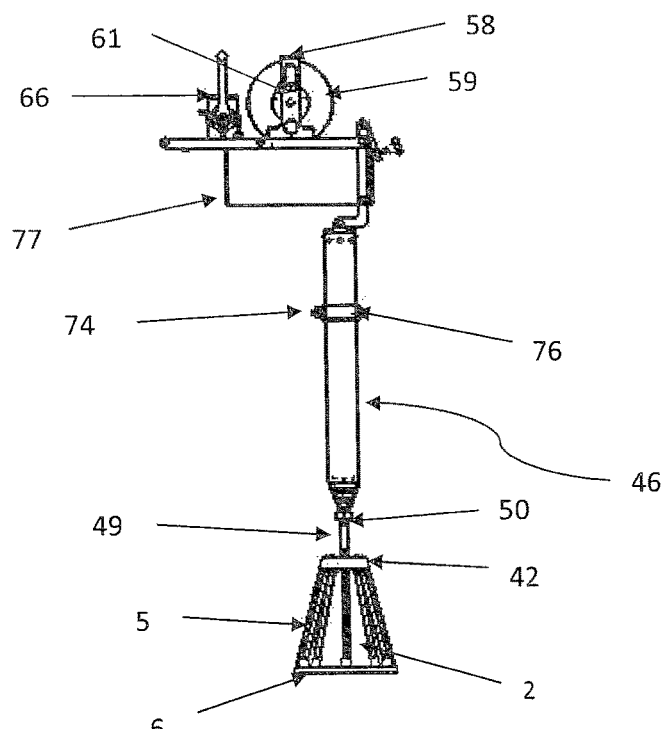

FIG. 22F shows a schematic second side view of a UV device having a telescopic arm in its load position. Individual parts are shown and numbered as described in FIGS. 21A-F.

Figure 22G:
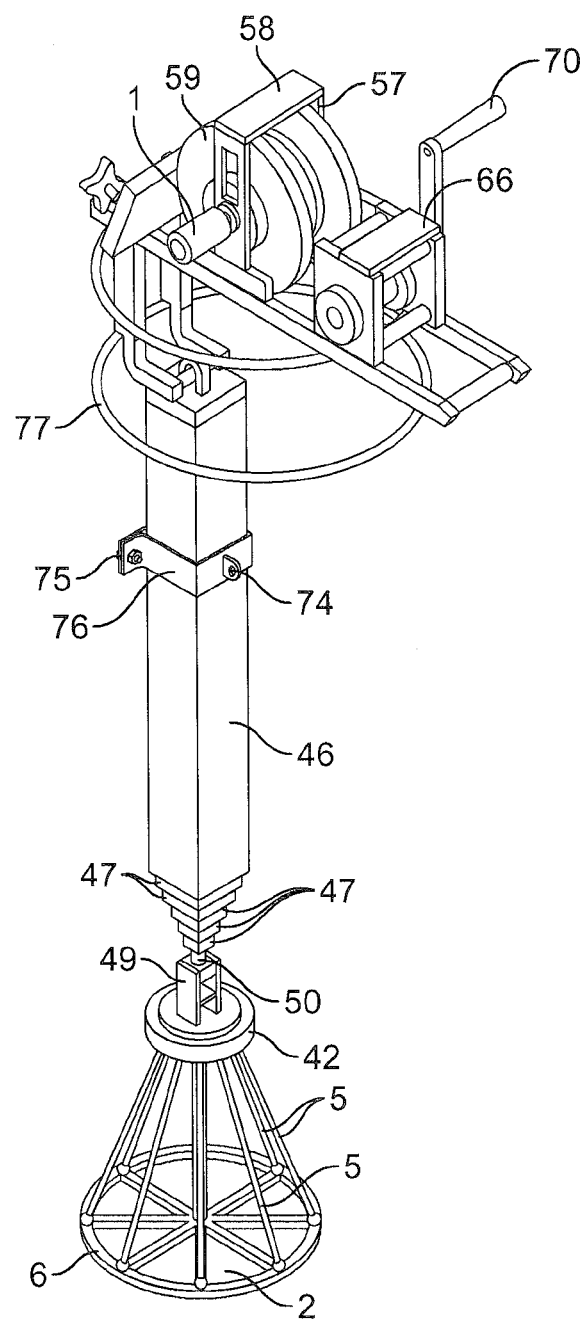

FIG. 22G shows a schematic isometric view of a UV device having a telescopic arm in its load position. Individual parts are shown and numbered as described in FIGS. 21A-F.

Figure 23A:
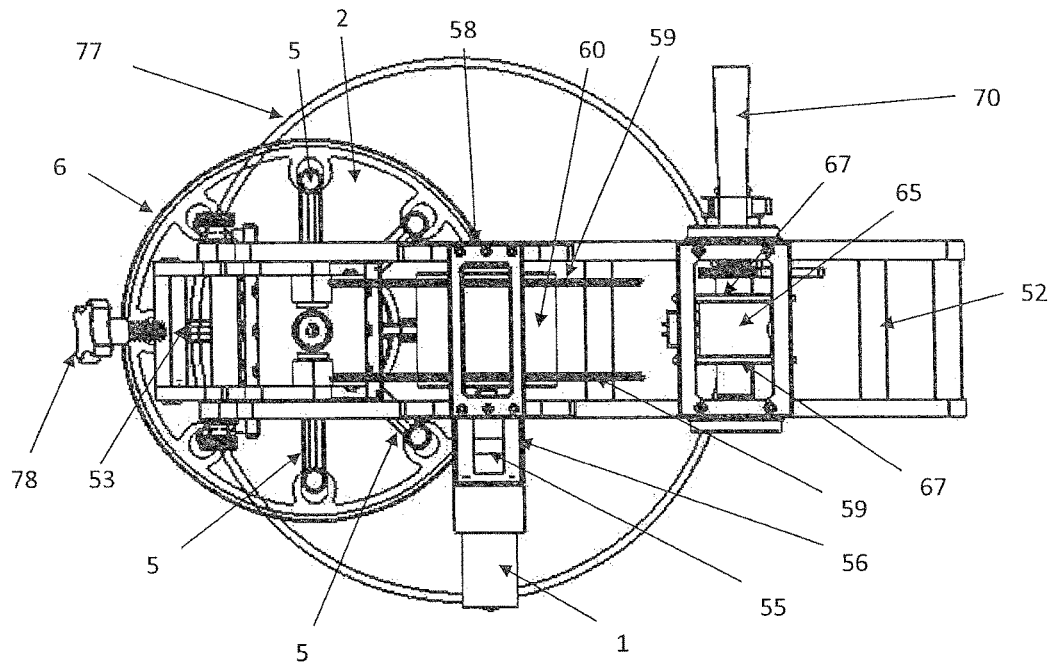

FIG. 23A shows a schematic top view of a UV device having a telescopic arm in its payout position. Individual parts are shown and numbered as described in FIGS. 21A-F.

Figure 23B:
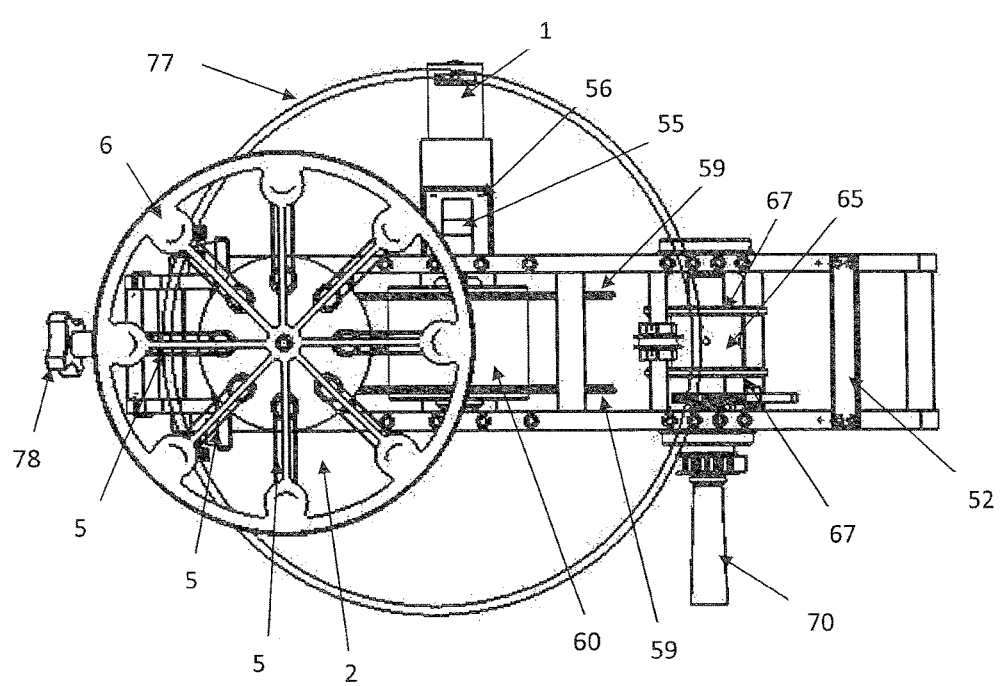

FIG. 23B shows a schematic bottom view of a UV device having a telescopic arm in its payout position. Individual parts are shown and numbered as described in FIGS. 21A-F.

Figure 23C:
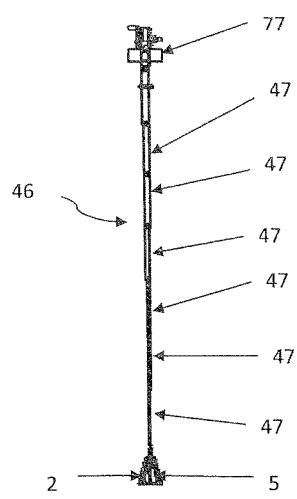

FIG. 23C shows a schematic front view of a UV device having a telescopic arm in its payout position. Individual parts are shown and numbered as described in FIGS. 21A-F.

Figure 23D:
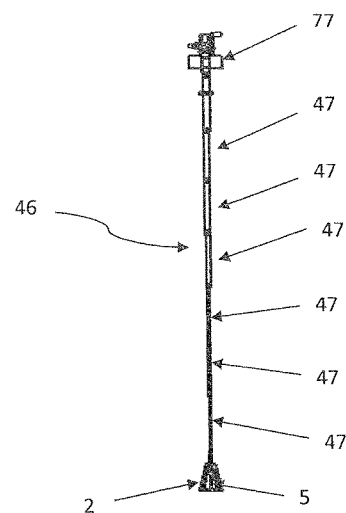

FIG. 23D shows a schematic back view of a UV device having a telescopic arm in its payout position. Individual parts are shown and numbered as described in FIGS. 21A-F.

Figure 23E:
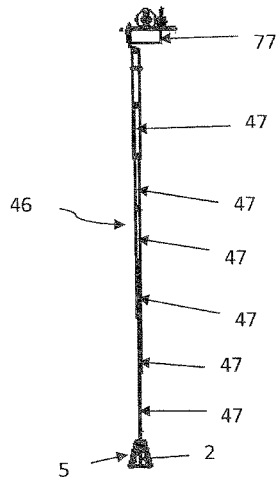

FIG. 23E shows a schematic first side view of a UV device having a telescopic arm in its payout position. Individual parts are shown and numbered as described in FIGS. 21A-F.

Figure 23F:
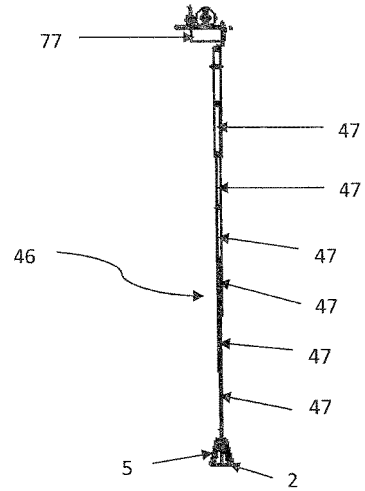

FIG. 23F shows a schematic second side view of a UV device having a telescopic arm in its payout position. Individual parts are shown and numbered as described in FIGS. 21A-F.

Figure 23G:
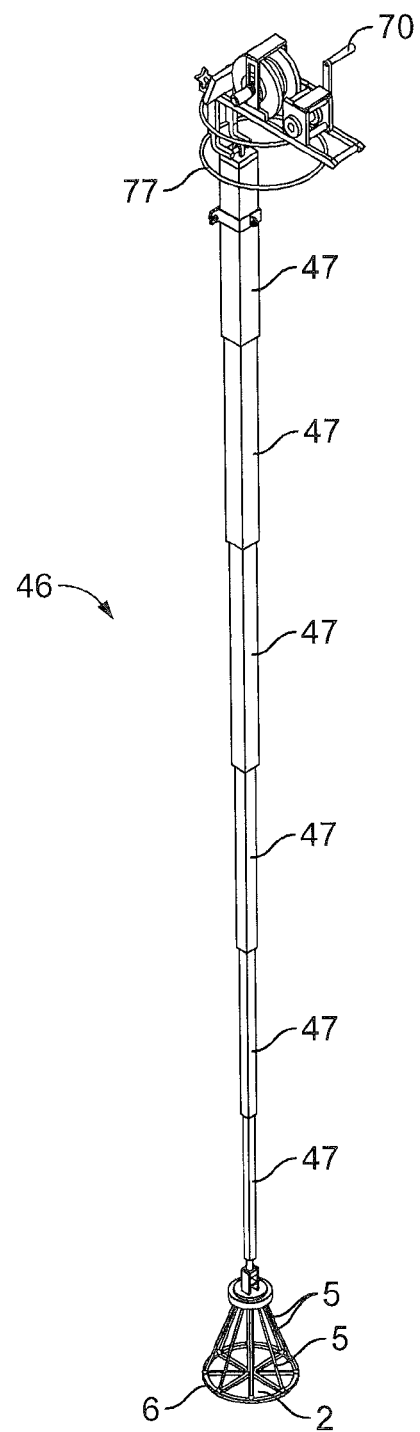

FIG. 23G shows a schematic isometric view of a UV device having a telescopic arm in its payout position. Individual parts are shown and numbered as described in FIGS. 21A-F.

Figure 24A:
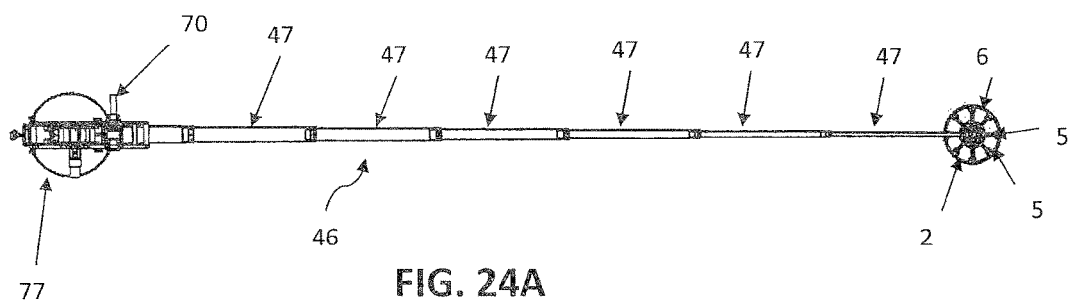

FIG. 24A shows a schematic front view of a UV device having a telescopic arm in its horizontal position. Individual parts are shown and numbered as described in FIGS. 21A-F.

Figure 24B:
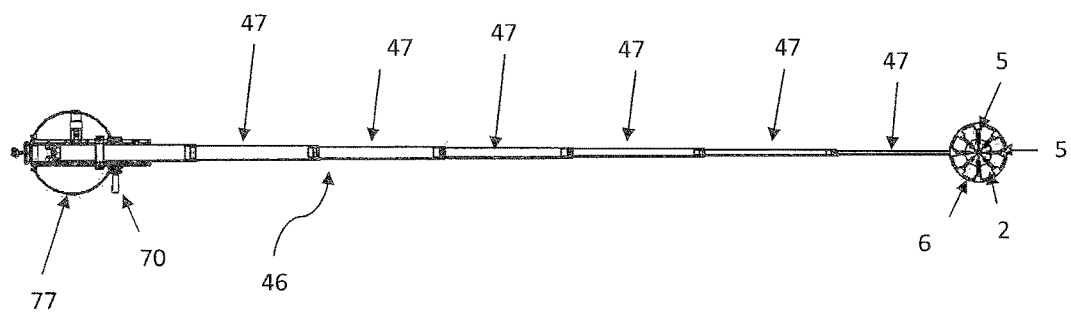

FIG. 24B shows a schematic back view of a UV device having a telescopic arm in its horizontal position. Individual parts are shown and numbered as described in FIGS. 21A-F.

Figure 24C:
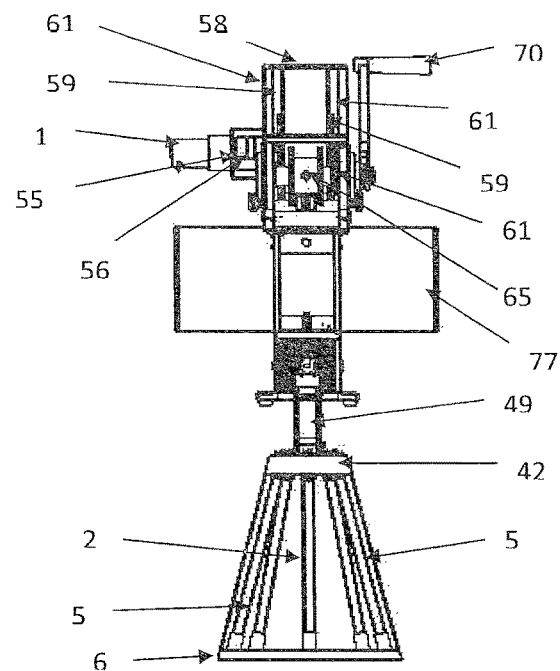

FIG. 24C shows a schematic top view of a UV device having a telescopic arm in its horizontal position. Individual parts are shown and numbered as described in FIGS. 21A-F.

Figure 24D:
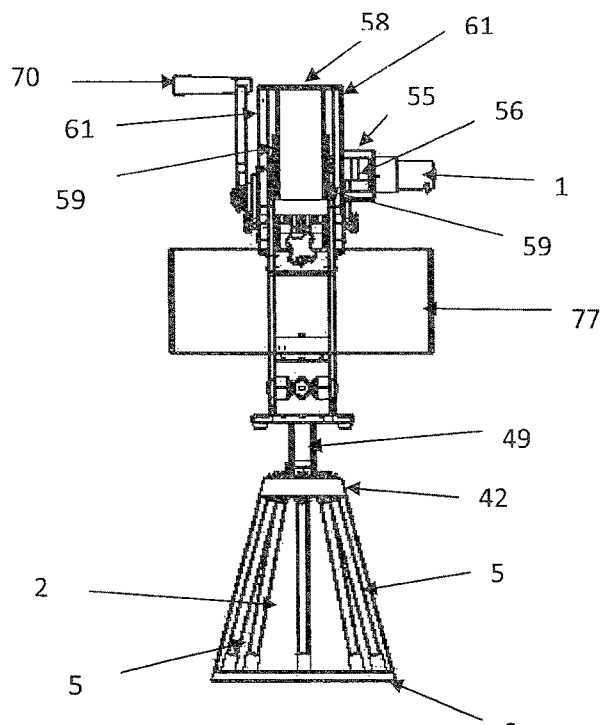

FIG. 24D shows a schematic bottom view of a UV device having a telescopic arm in its horizontal position. Individual parts are shown and numbered as described in FIGS. 21A-F.

Figure 24E:
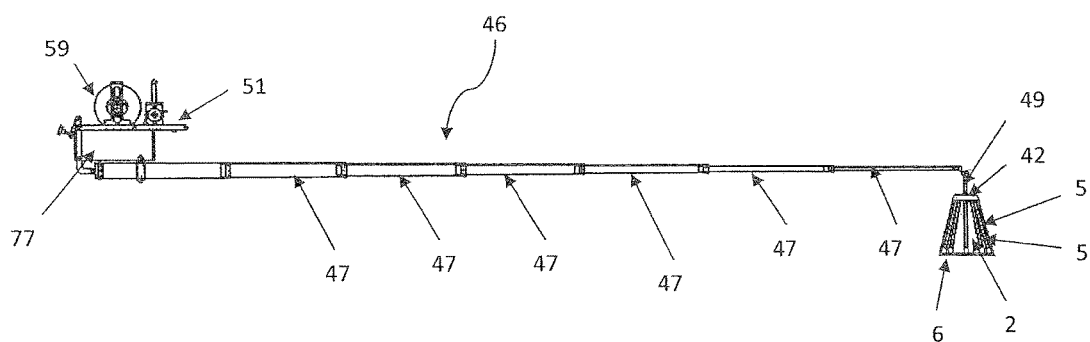

FIG. 24E shows a schematic first side view of a UV device having a telescopic arm in its horizontal position. Individual parts are shown and numbered as described in FIGS. 21A-F.

Figure 24F:
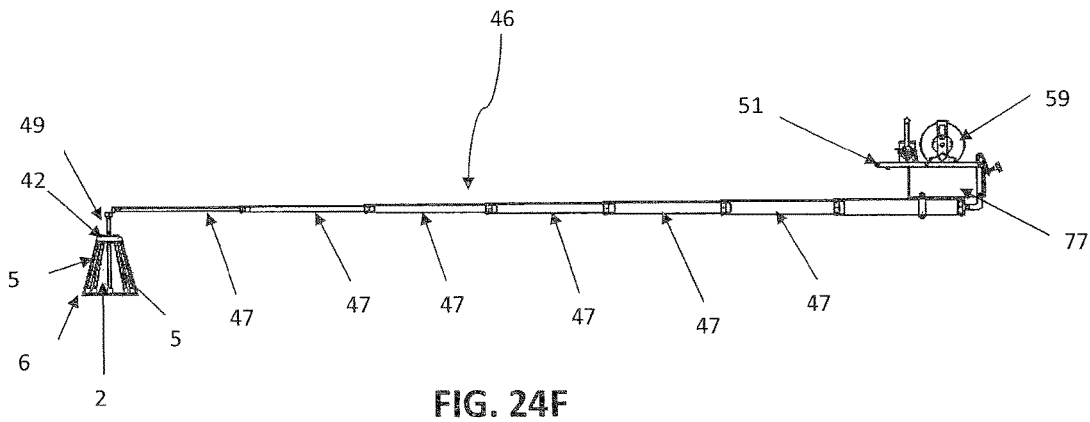

FIG. 24F shows a schematic second side view of a UV device having a telescopic arm in its horizontal position. Individual parts are shown and numbered as described in FIGS. 21A-F.

Figure 24G:
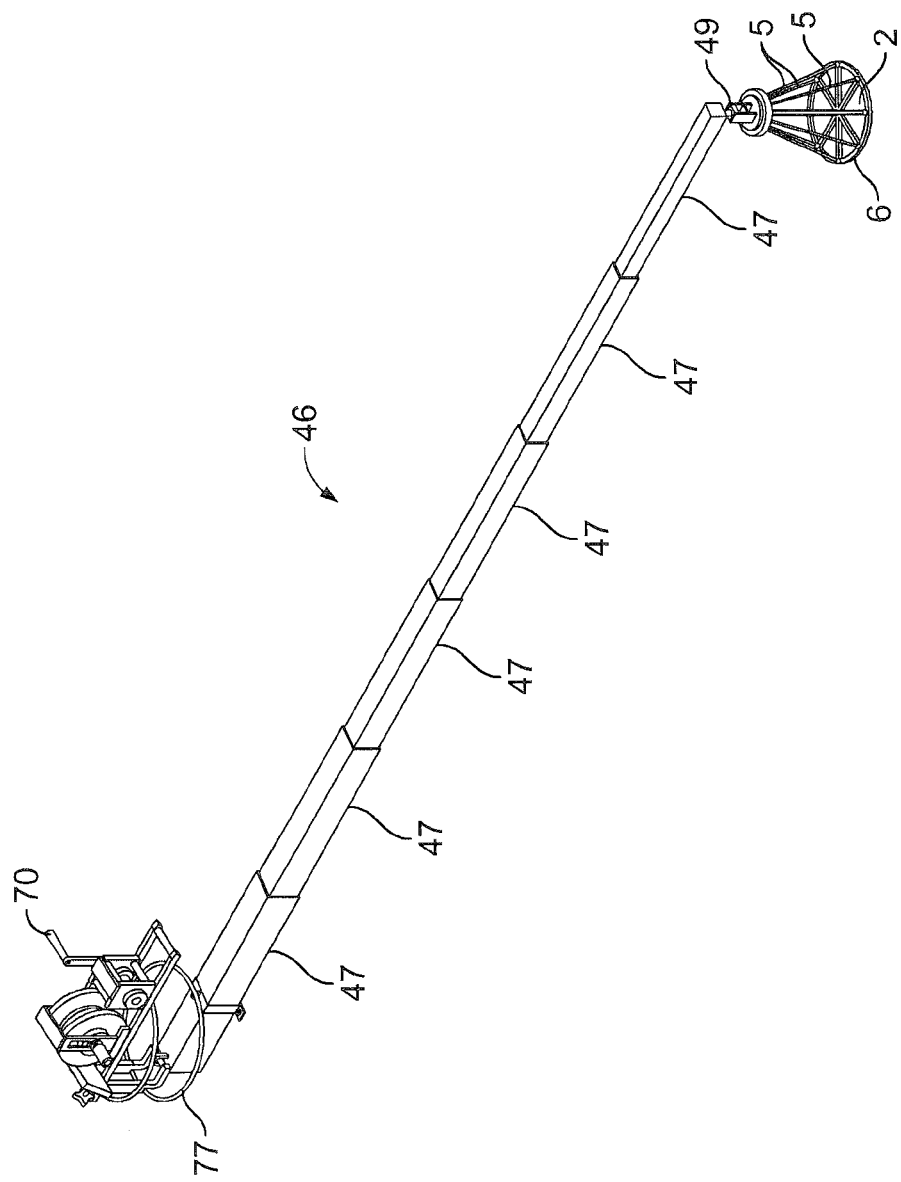

FIG. 24G shows a schematic isometric view of a UV device having a telescopic arm in its horizontal position. Individual parts are shown and numbered as described in FIGS. 21A-F.

Figure 25A:
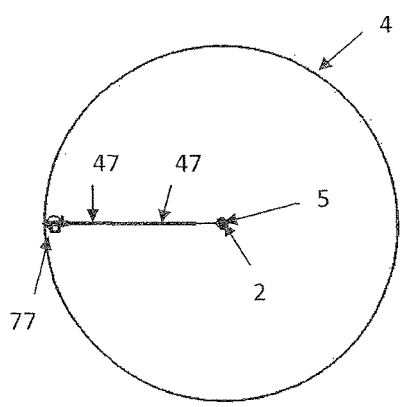
Figure 25C:
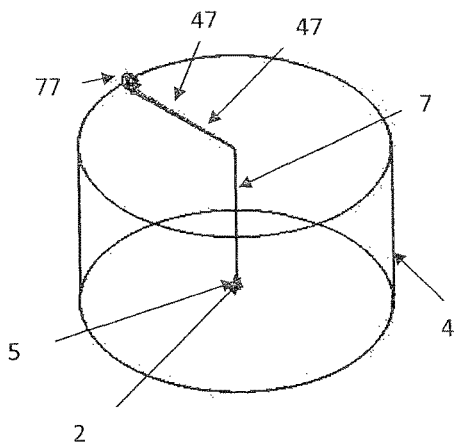
Figure 25B:
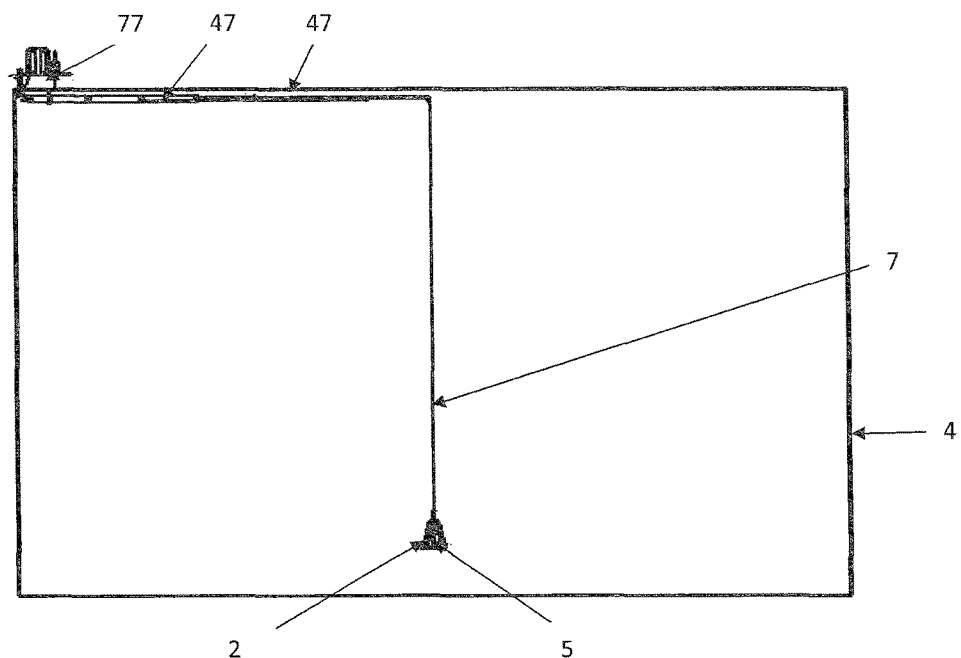

FIG. 25A shows a schematic top view of a UV device having a telescopic arm in its UV lamp down position. FIG. 25B shows a schematic side view of a UV device having a telescopic arm in its UV lamp down position. FIG. 25C shows a schematic isometric view of a UV device having a telescopic arm in its UV lamp down position. Individual parts are shown and numbered as described in FIGS. 21A-F.

Figure 26B:
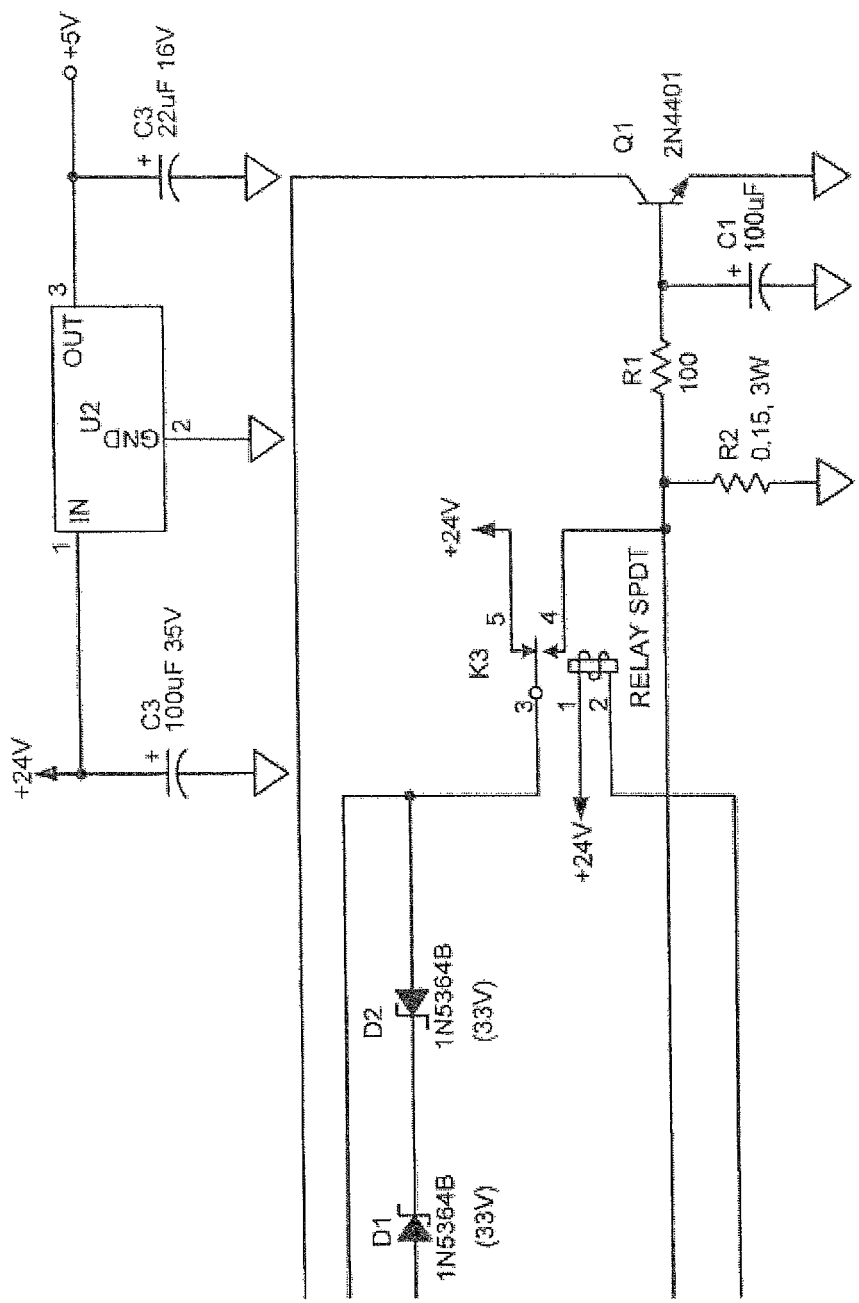
Figure 26C:
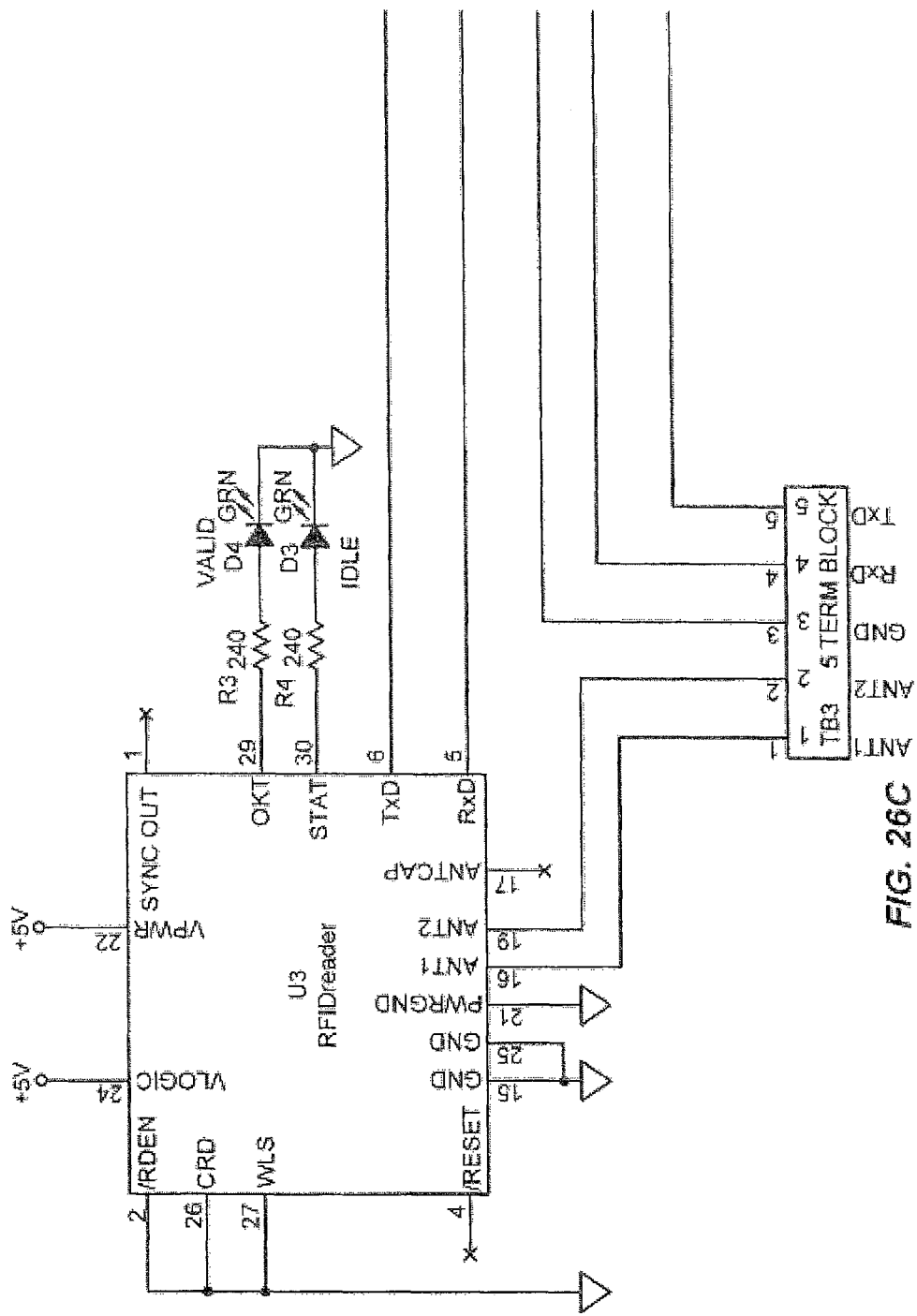
Figure 26D:
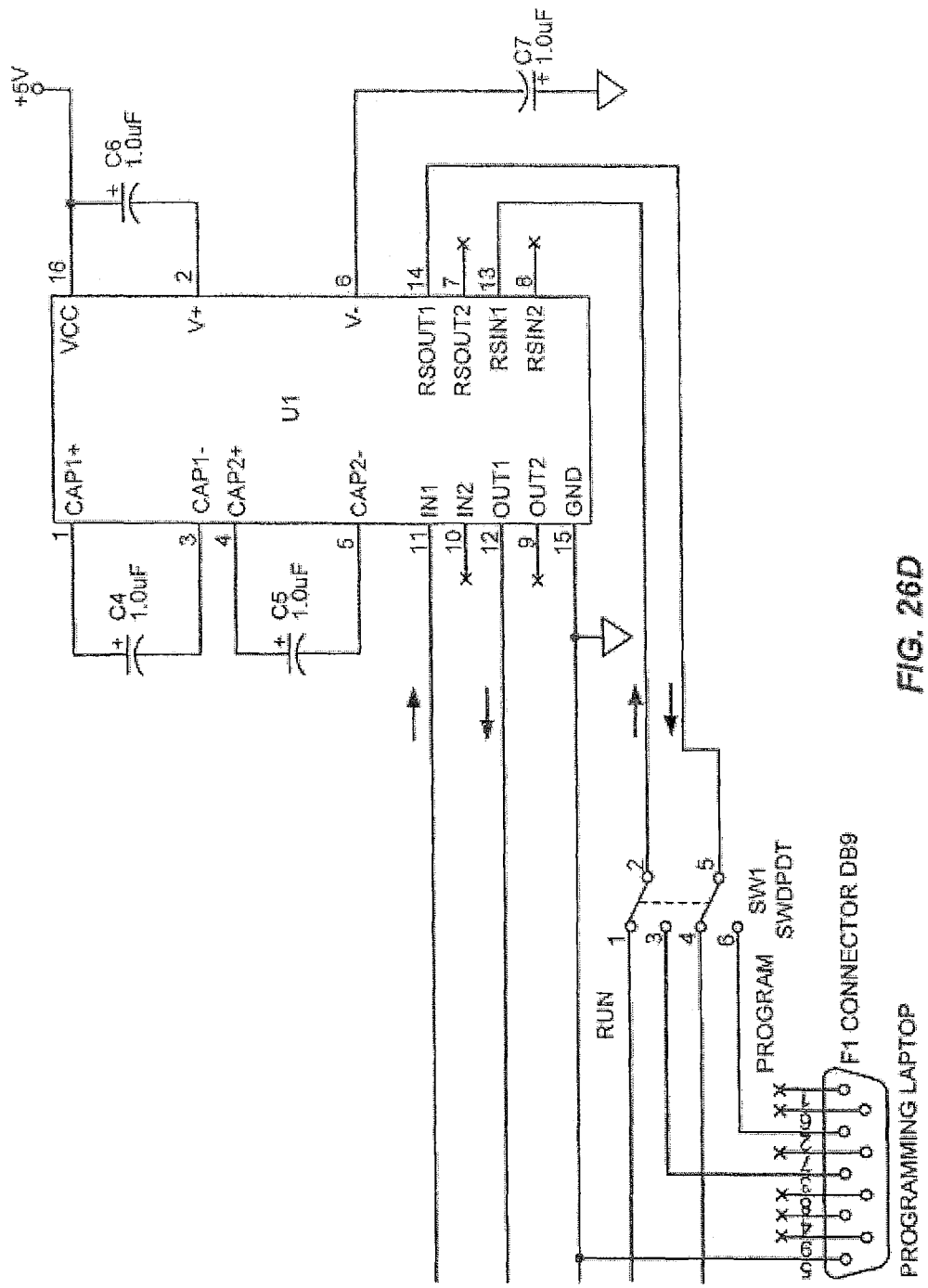

FIG. 26 consists of FIG. 26A, FIG. 26B, FIG. 26C and FIG. 26D arranged as shown and schematically shows a circuit board used in an embodiment of the present invention. The circuit board will be attached to a UV device and communicate with the RFID chip mounted to the container. Once information is retrieved from the RFID chip, this circuit board will control movement, the length of which the telescopic arm descends (i.e., the length to which the telescoping units 47 move the UV light source into a vertical downwards position) and the rate of descent based on tank dimensions stored in the RFID chip. As one of ordinary skill in the art will appreciate, the exemplary circuit board shown, comprises a TI module (part number shown) and a serial port. Also shown on the board are relays to control a motor and the positioning of the UV light source. In some embodiments is also a 5 VDC regulator to power the electronics. In the circuit board shown, the RFID tag part number is also shown.

Figure 27A:
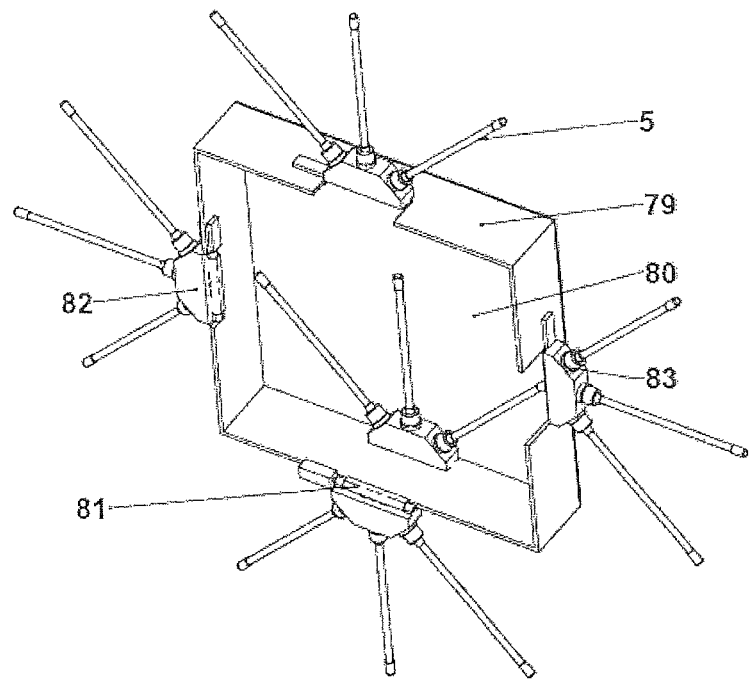
Figure 27B:
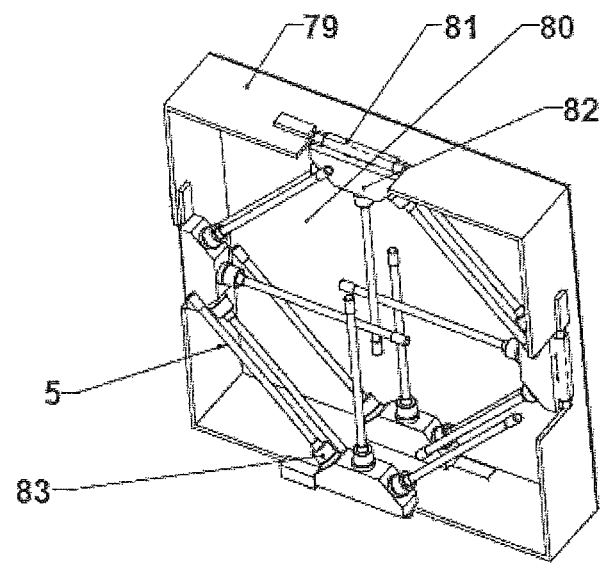
Figure 27C:
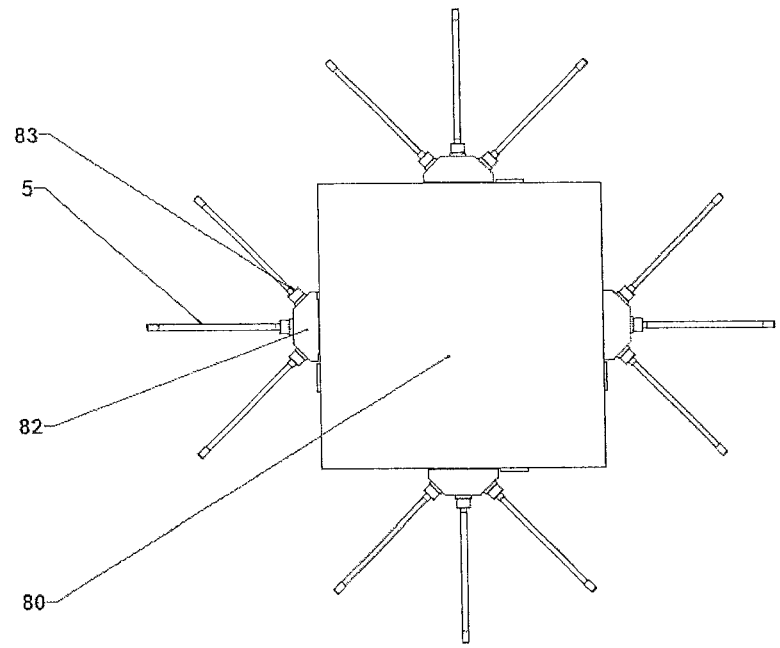
Figure 27D:
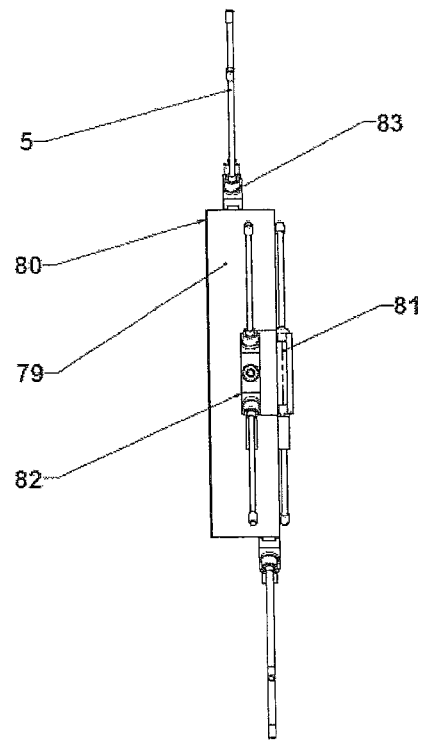
Figure 27E:
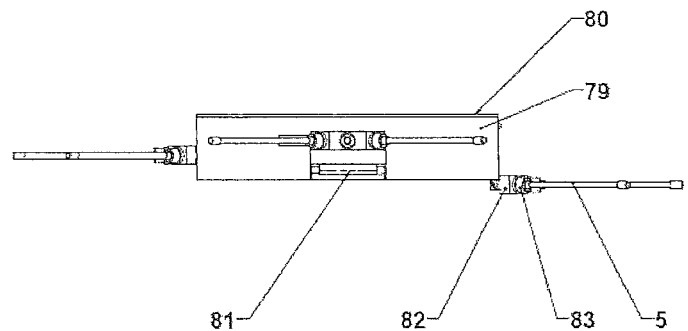
Figure 27F:
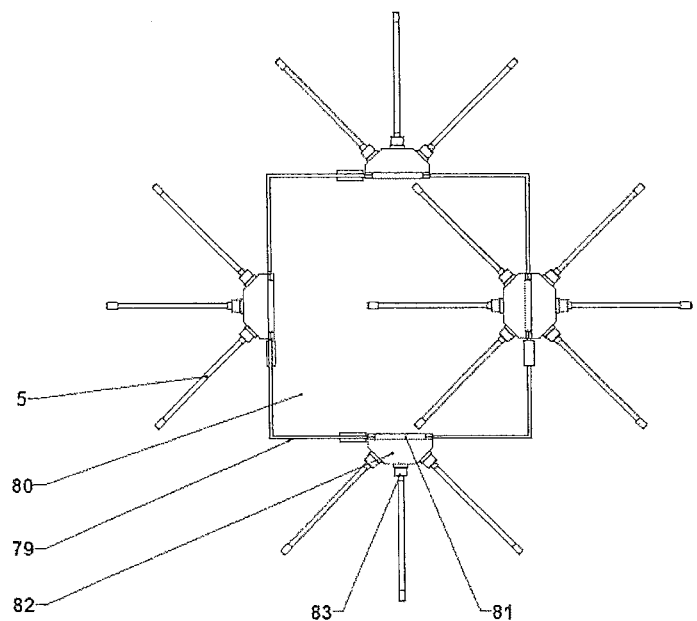
Figure 27G:
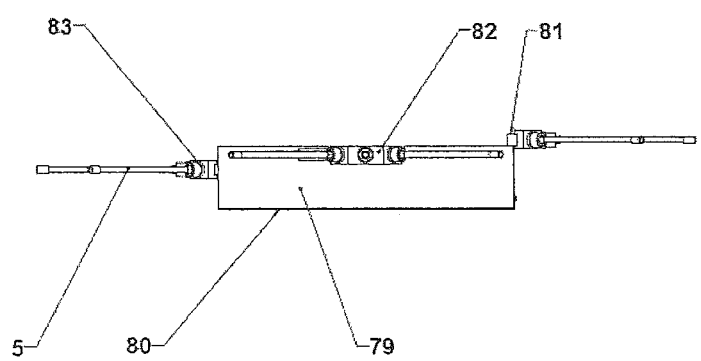

FIGS. 27A through 27G schematically show a UV device mountable to the ceiling or wall of a room. In this particular embodiment, UV lamps are arranged in UV lamp clusters. More specifically, five UV lamp clusters are shown, one stationary UV lamp cluster and four retrievable UV lamp clusters each comprising three UV lamps 5. The UV device shown may be referred to as UV light box. In the embodiment shown, the UV device comprises (i) UV lamps, 5, (ii) a light box, 79, comprising a back wall, 80, (iii) a hinge or UV lamp module swing, 81, (iv) a UV lamp holder, and (v) a UV lamp head connector, 83, for connecting the UV lamps. FIG. 27A shows a perspective view of the UV light box with the UV lamps in an exposed position. FIG. 27B shows a bottom view of the UV light box with the UV lamps in a closed position. FIG. 27C shows a back view of the UV light box with the UV lamps in an exposed position. FIG. 27D shows a side view of the UV light box with the UV lamps in an exposed position. FIG. 27E shows a top view of the UV light box with the UV lamps in an exposed position. FIG. 27F shows a front view of the UV light box with the UV lamps in an exposed position. FIG. 27G shows a bottom view of the UV light box with the UV lamps in an exposed position.

FIGS. 28A through 28H schematically depict details of an embodiment of a UV device of the present invention.

Figure 28A:
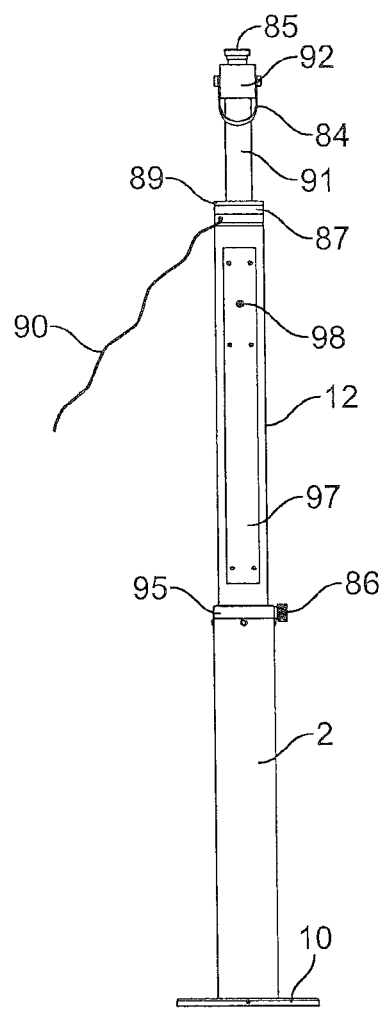

FIG. 28A schematically depicts a front view of an embodiment of a UV device of the present invention, wherein the UV light source is retracted in a housing. Housing 2, base plate 10, central sleeve 12, hanging hook 84, on/off/reset button 85, central sleeve tightening knob 86, translucent plastic ring 87, metal disc 89, power cord 90, handle 91, handle cap 92, metal sleeve attachment ring 95, power supply access plate 97, optical switch 98. In this embodiment, the power supply access plate is attached to the central sleeve by six screws.

Figure 28B:
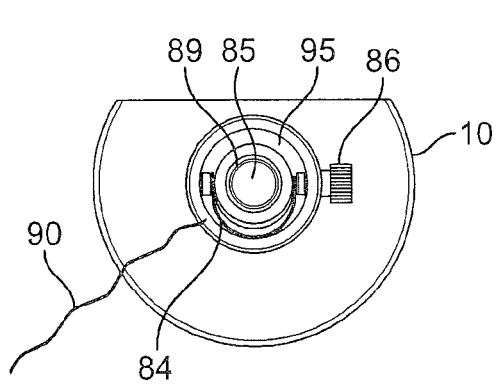

FIG. 28B schematically depicts a top view of an embodiment of a UV device of the present invention, wherein the UV light source is retracted in a housing. Base plate 10, hanging hook 84, on/off/reset button 85, central sleeve tightening knob 86, power cord 90, metal sleeve attachment ring 95.

Figure 28C:
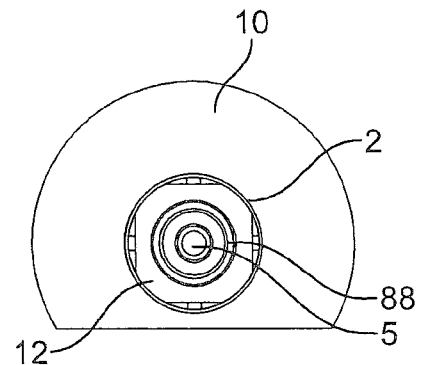

FIG. 28C schematically depicts a bottom view of an embodiment of a UV device of the present invention, wherein the UV light source is retracted in a housing. Housing 2, UV lamp 5, base plate 10, central sleeve 12, stopping plate 88.

Figure 28D:
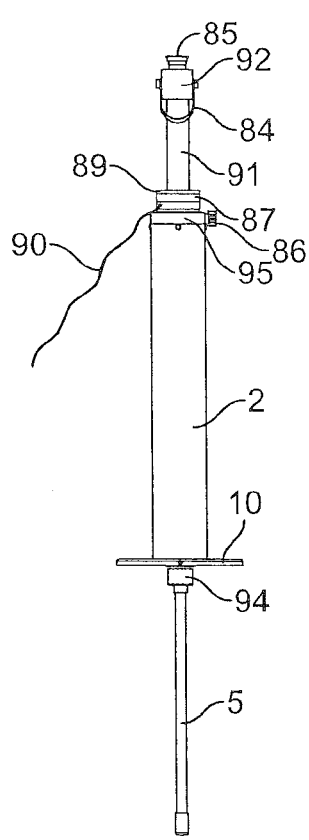

FIG. 28D schematically depicts a front view of an embodiment of a UV device of the present invention, wherein the UV light source is released from a housing. Housing 2, UV lamp 5, base plate 10, central sleeve 12, hanging hook 84, on/off/reset button 85, central sleeve tightening knob 86, translucent plastic ring 87, metal disc 89, power cord 90, handle 91, handle cap 92, UV lamp socket/adaptor 94, metal sleeve attachment ring 95, power supply access plate 97, optical switch 98. In this embodiment, the power supply access plate is attached to the central sleeve by six screws.

Figure 28E:
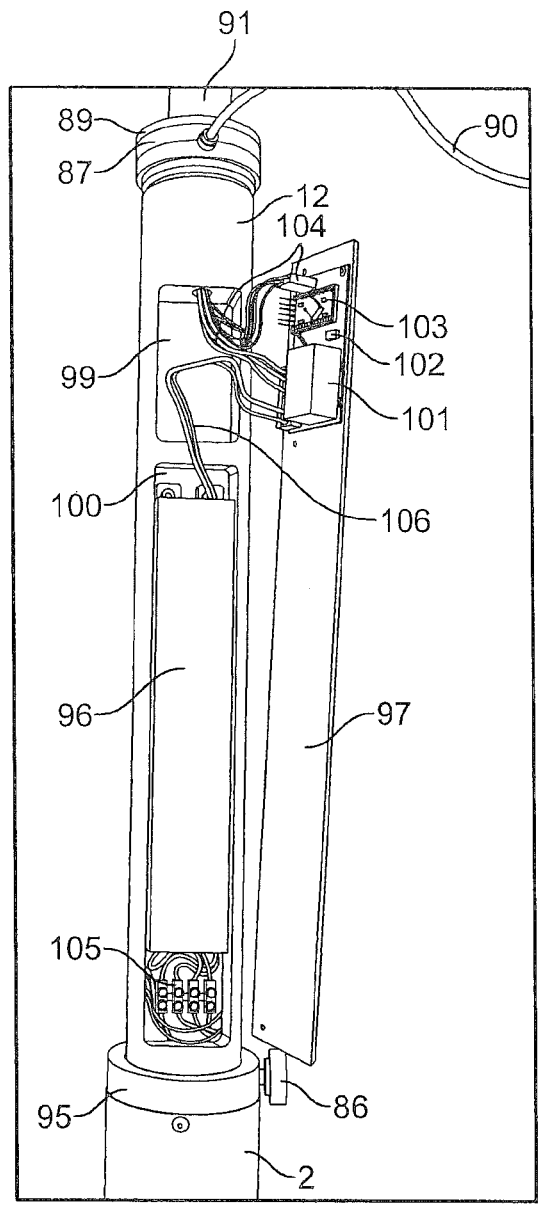

FIG. 28E schematically depicts a detail of an embodiment of a UV device of the present invention, wherein a cover of a central sleeve (power supply access plate 97) is opened to show inner compartments of the central sleeve 12 harboring, among others, a circuit board 103 and a ballast/power supply 96. Housing 2, central sleeve 12, central sleeve tightening knob 86, translucent plastic ring 87, metal disc 89, power cord 90, handle 91, handle cap 92, metal sleeve attachment ring 95, power supply 96, power supply access plate 97, optical switch 98, circuit board cavity 99, power supply cavity 100, AC to DC power converter 101, electronic component 102, circuit board (micro controller) 103, connector and wires (to e.g., LED, optical switch, acoustic speaker) 104, connector and wires to UV light source (e.g., UV lamp 5) 105, connector and wires to power supply 106.

Figure 28F:
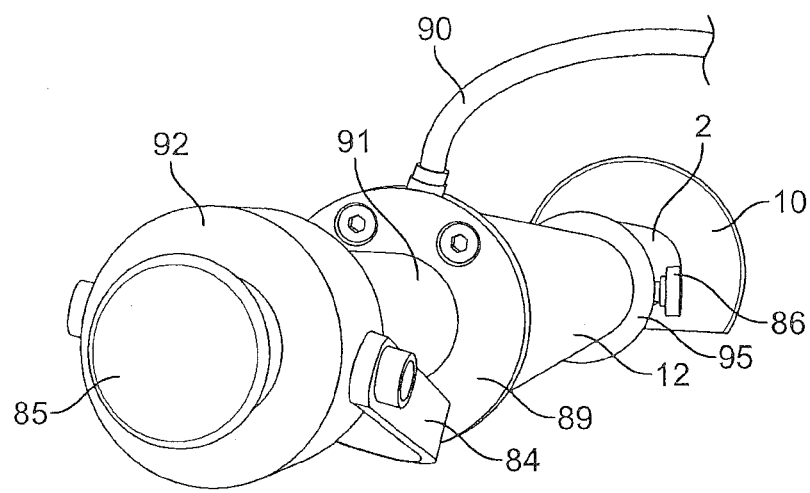

FIG. 28F schematically depicts an upper side view of a detail of an embodiment of a UV device of the present invention, wherein the UV light source is retracted in a housing. Housing 2, base plate 10, central sleeve 12, hanging hook 84, on/off/reset button 85, central sleeve tightening knob 86, metal disc 89, power cord 90, handle 91, handle cap 92, metal sleeve attachment ring 95.

Figure 28G:
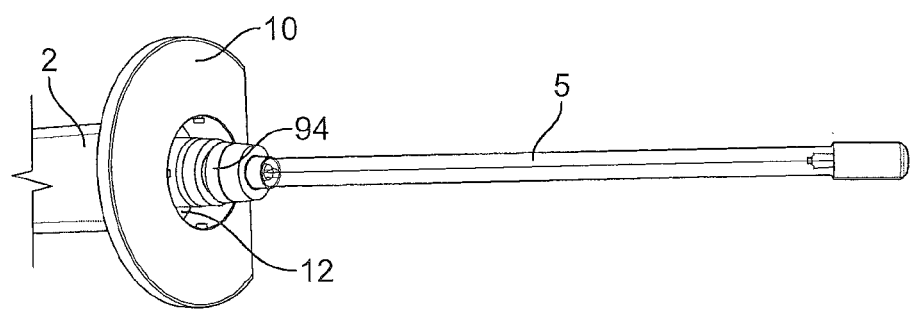

FIG. 28G schematically depicts a side view of an embodiment of a UV device of the present invention, wherein the UV light source is released from a housing. Housing 2, UV lamp 5, base plate 10, central sleeve 12, UV lamp socket/adaptor 94.

Figure 28H:
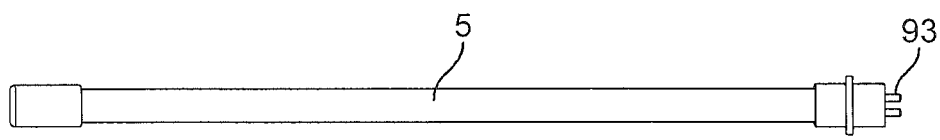

FIG. 28H schematically depicts a UV light source, here a longitudinal UV light bulb. UV lamp 5, pins for UV lamp 93.

Figure 29A:
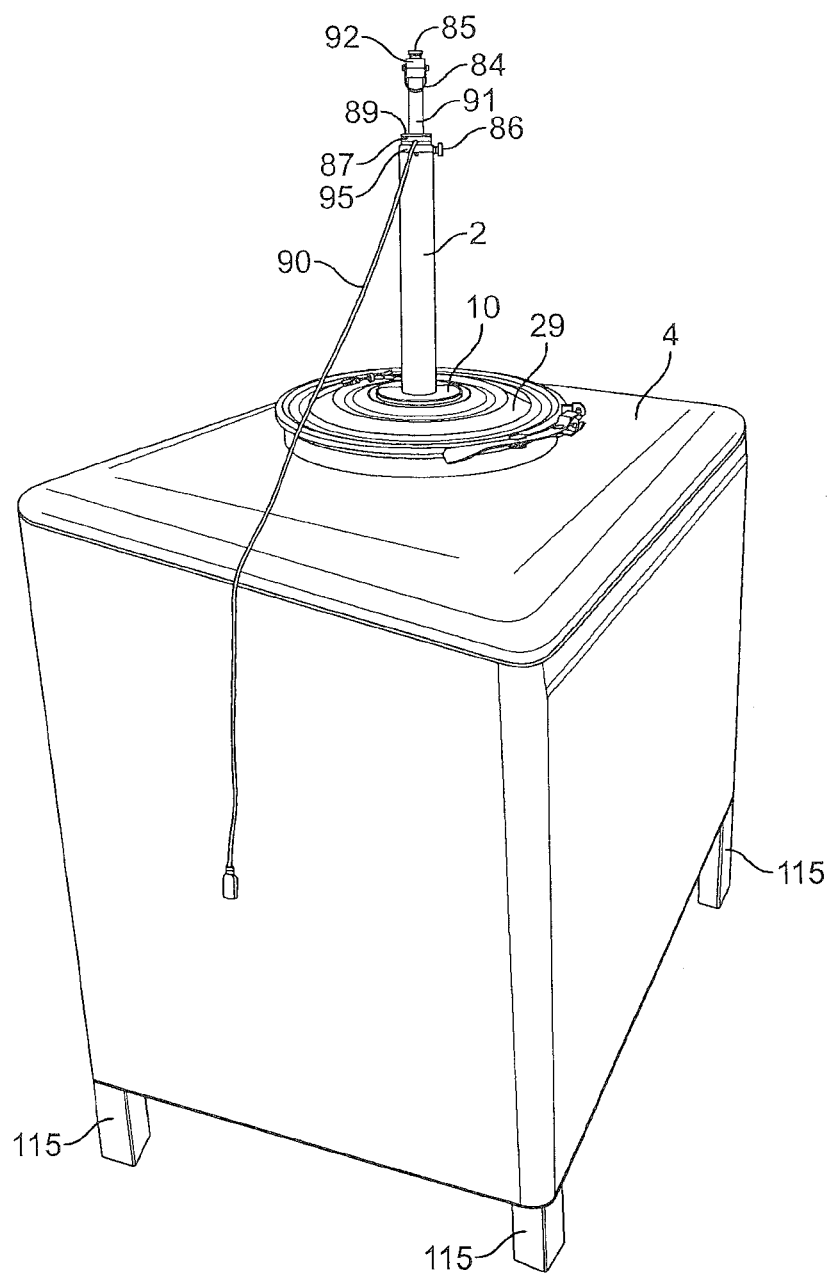

FIG. 29A schematically depicts an embodiment of a UV device of the present invention positioned on top of a container 4 having a lid 29, wherein the central sleeve 12 of the UV device shown in FIGS. 28A, D-G has been moved downwardly through an opening in the lid 29 into the container 4. Housing 2, container 4, base plate 10, lid 29, hanging hook 84, on/off/reset button 85, central sleeve tightening knob 86, translucent plastic ring 87, metal disc 89, power cord 90, handle 91, handle cap 92, metal sleeve attachment ring 95, container support stand 115.

Figure 29B:
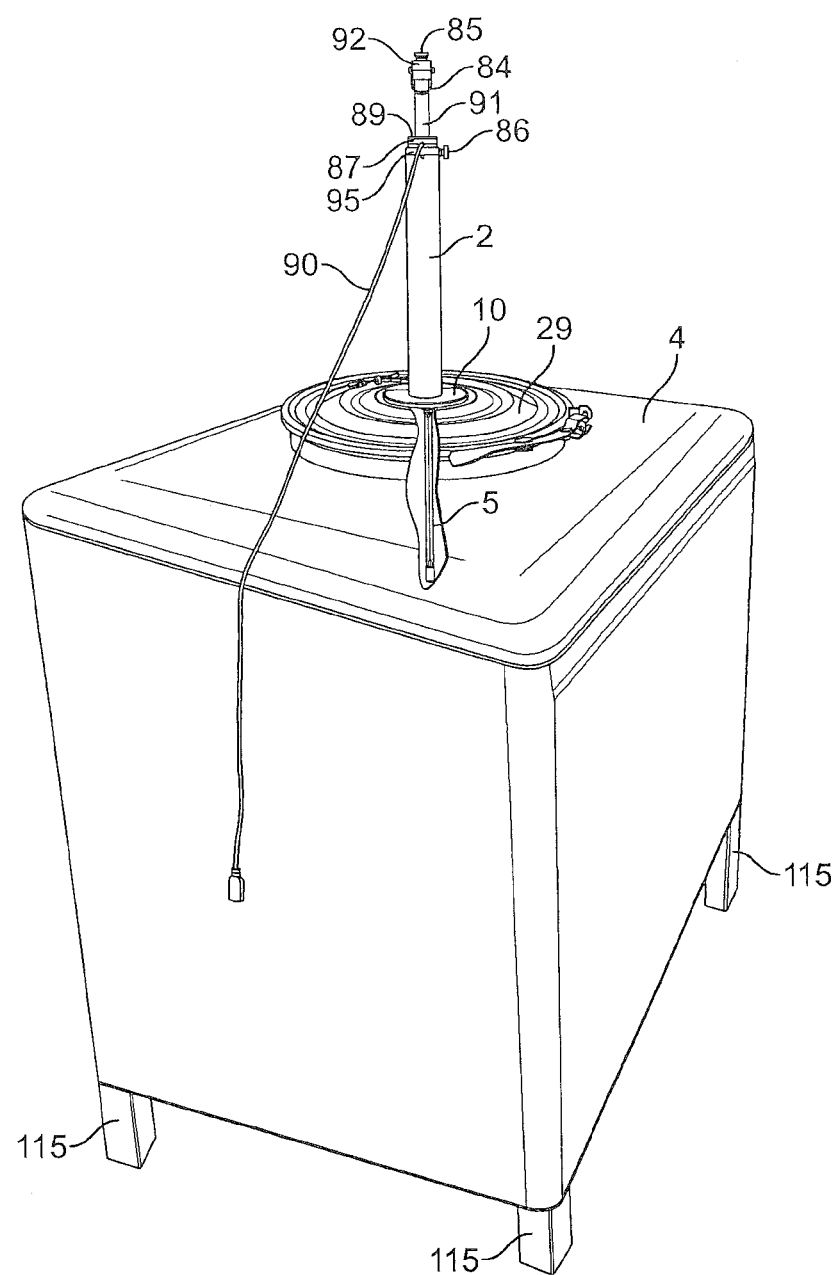

FIG. 29B schematically depicts an embodiment of a UV device of the present invention positioned on top of a container 4 having a lid 29, wherein the central sleeve 12 of the UV device shown in FIGS. 28A, D-G has been moved downwardly through an opening in the lid 29 into the container 4 and wherein the UV light source has been released from the housing 2. Housing 2, container 4, UV lamp 5, base plate 10, lid 29, hanging hook 84, on/off/reset button 85, central sleeve tightening knob 86, translucent plastic ring 87, metal disc 89, power cord 90, handle 91, handle cap 92, metal sleeve attachment ring 95, container support stand 115.

Figure 30:
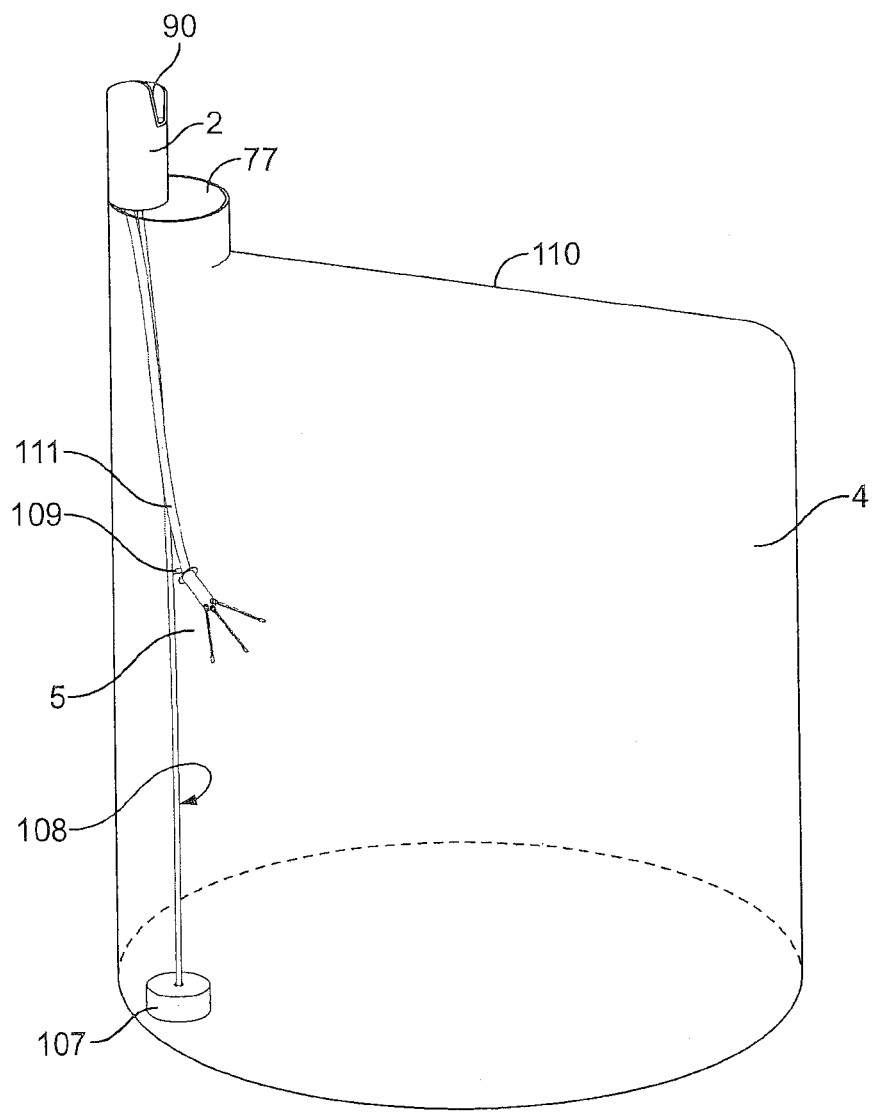

FIG. 30 schematically depicts a UV device of the present invention attached to the top of a container and wherein the UV light source has been inserted through an opening of the container 4 downwardly into the container 4. The UV device shown here comprises a plurality of UV lamps 5 arranged in a UV lamp cluster. Housing 2, container 4, UV lamp(s) 5, manhole or port 77, power cord 90, anchor 107, anchor line 108, anchor connector 109, angled top of container 110, UV lamp cluster line 111.

Figure 31A:
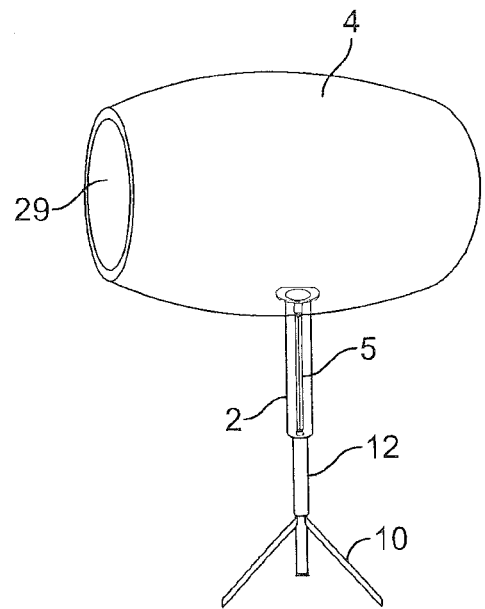
Figure 31B:
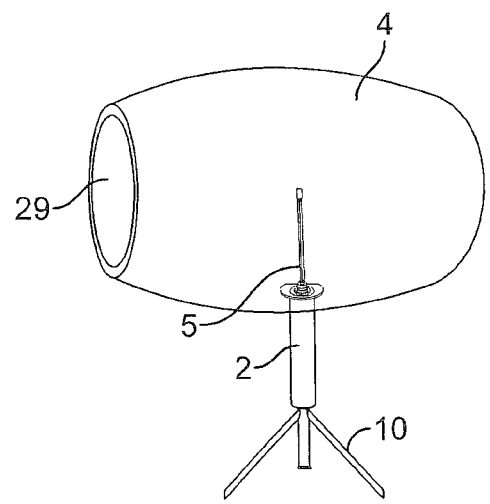

FIGS. 31A and 31B schematically depict the insertion of a UV light source into a container 4 by inserting the UV light source through an opening at the side of the container 4. In FIG. 31A, the UV lamp 5 is shown in the housing 2. In FIG. 31B the UV lamp 5 is released from the housing 2, The housing 2 slides back on a central sleeve 12. While the UV light source is inserted through a n opening at a side of a container, the container itself may be positioned to reside on its side so that the UV light source can be moved inwardly into the container from a bottom position. In such configuration, as shown in FIGS. 31A and 31B, the movement of the UV light source within the container is upwardly. Alternatively, a container having an opening on a side wall, may be positioned so that the opening resides on top of the container and the UV light source is inserted into the container and moves downwardly into the container. Housing 2, container 4, UV lamp 5, base plate 10 (here a tripod-like support stand), central sleeve 12, lid 29.

Figure 32:
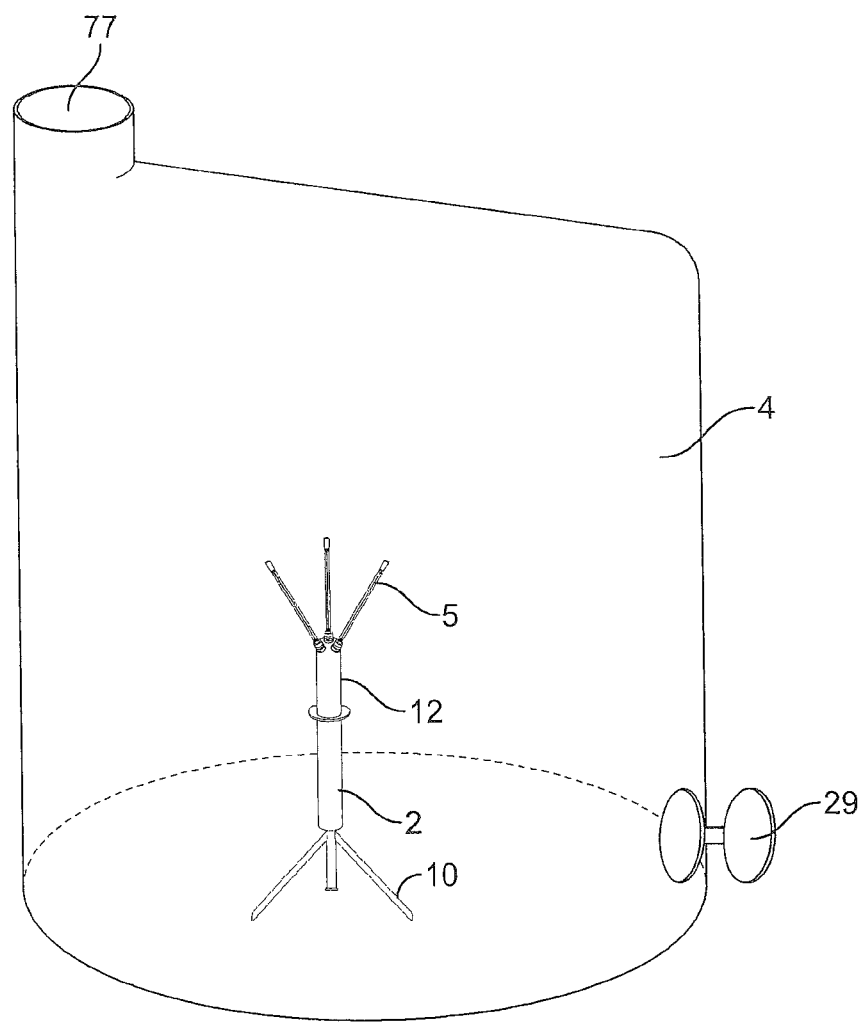

FIG. 32 schematically depicts a UV light source positioned at the bottom of a container 4. The UV light source has been inserted into the container 4 through an opening at the side of the container. Housing 2, container 4, UV lamp 5, base plate 10 (here a tripod-like support stand), central sleeve 12, lid 29, manhole or port 77, In this embodiment, the UV light source comprises a plurality of UV lamps 5 arranged in a UV lamp cluster.

Figure 33:
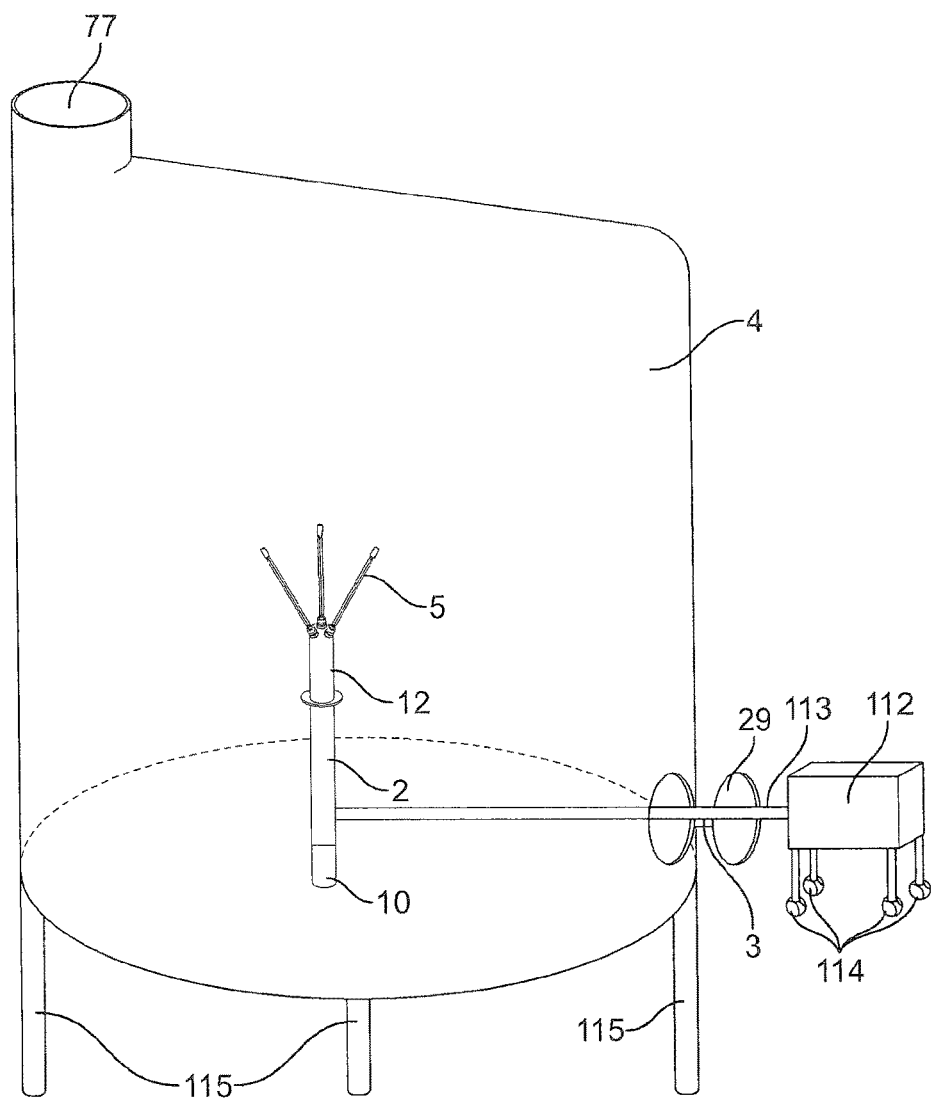

FIG. 33 schematically depicts a UV light source attached to a movable object having wheels. Housing 2, container 4, UV lamp 5, base plate 10 (here a simple support stand), central sleeve 12, lid 29, manhole or port 77, movable object 112, horizontal arm 113, wheels 114, support stand for container 115. In this embodiment, the UV light source comprises a plurality of UV lamps 5 arranged in a UV lamp cluster.

Figure 34A:
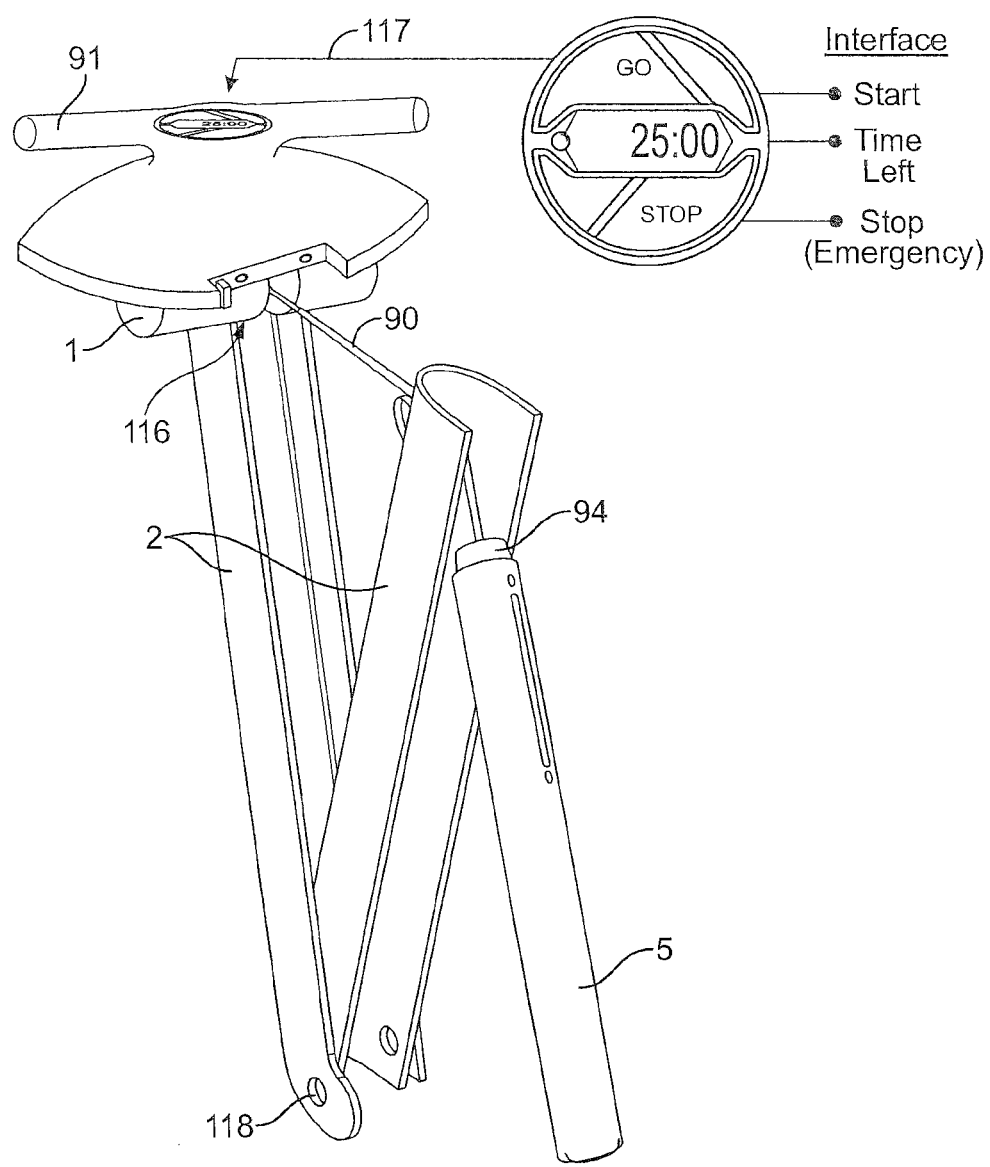

FIG. 34A schematically depicts an embodiment of a UV device of the present invention, wherein a UV light source is released from a housing 2 via a motorized unit 1 and by gravity. Shown to the right is an enlargement of the interface 117 showing buttons for activating (Start) and deactivating (Stop) the UV device. An optional timer shows the time remaining for completing a sterilization cycle. Motorized unit 1, housing 2, UV lamp 5, power cord 90, handle 91, UV lamp socket/adaptor 94, twist lock 116, interface 117, pivot point 118 within housing 2.

FIGS. 34B and 34C schematically depict an attachment of the UV device of FIG. 34A at the top of a closed container 4 and the insertion of the central sleeve 12, housing 2 and UV lamp 5 into the container 4. Housing 2, container 4, UV lamp 5, power cord 90, container support stand 115. FIG. 34B, upper, schematically depicts a top view of a 15 feet (15') container showing a manhole or port 77 through which the UV device can be inserted. Lines 119 radiating from the manhole or port 77 are steel support structures on top of the container. FIG. 34B, lower, shows the housing 2 being extended into a 90 degree angle position with respect to the central sleeve 12 FIG. 34C, upper, schematically depicts a top view of a 20 feet (20') container showing a manhole or port 77 through which the UV device can be inserted. Lines 119 radiating from the manhole or port 77 are steel support structures on top of the container. FIG. 34C, lower, shows the lowering of the UV lamp 5 downwardly into the container 4. The distance of lowering the UV lamp 5 towards the bottom of the container (inwardly and downwardly movement) can be calculated to stop short of the bottom of the shortest container and will be sufficient for the tallest container as long as the distance to the bottom of the container is smaller than the distance to the furthest wall of the container (FIG. 34B). In a taller wider container, the UV light irradiation might stop short of reaching an outer wall, but still sufficient to illuminate the bottom of the container more than the walls (FIG. 34C). The UV device can be configured so that the UV light source (UV lamp 5) can be centered within the container.

Figure 35B:
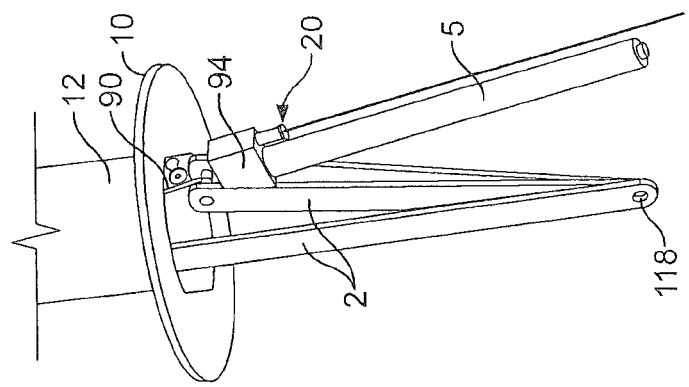
Figure 35A:
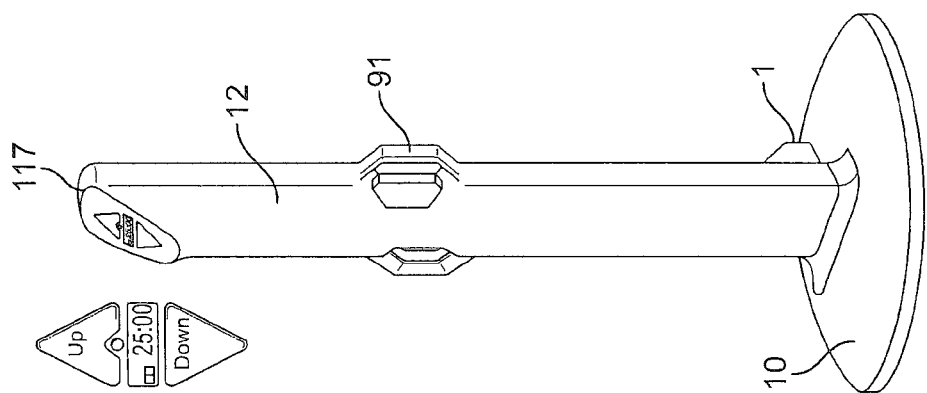
Figure 36A:
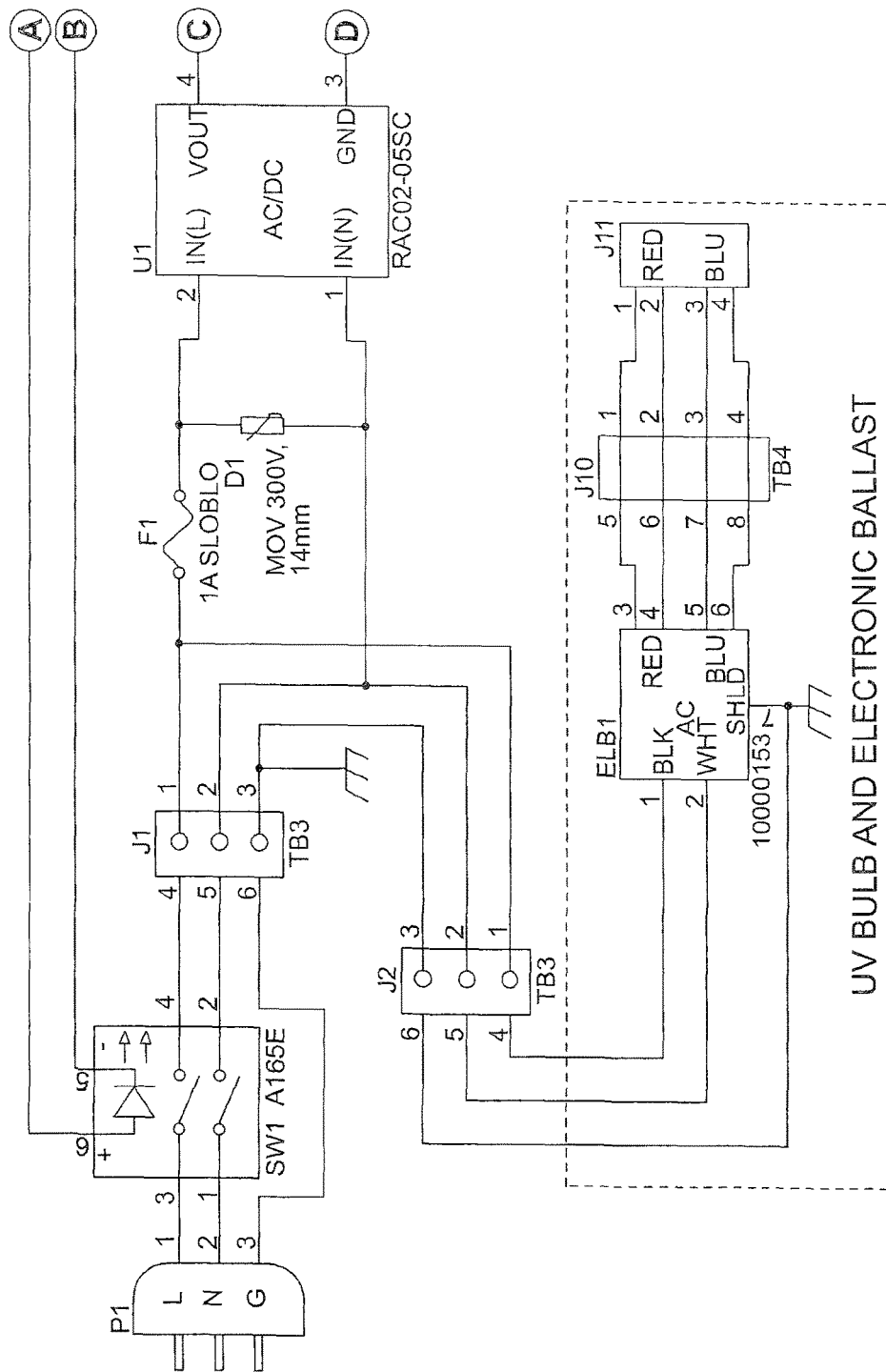
Figure 36B:
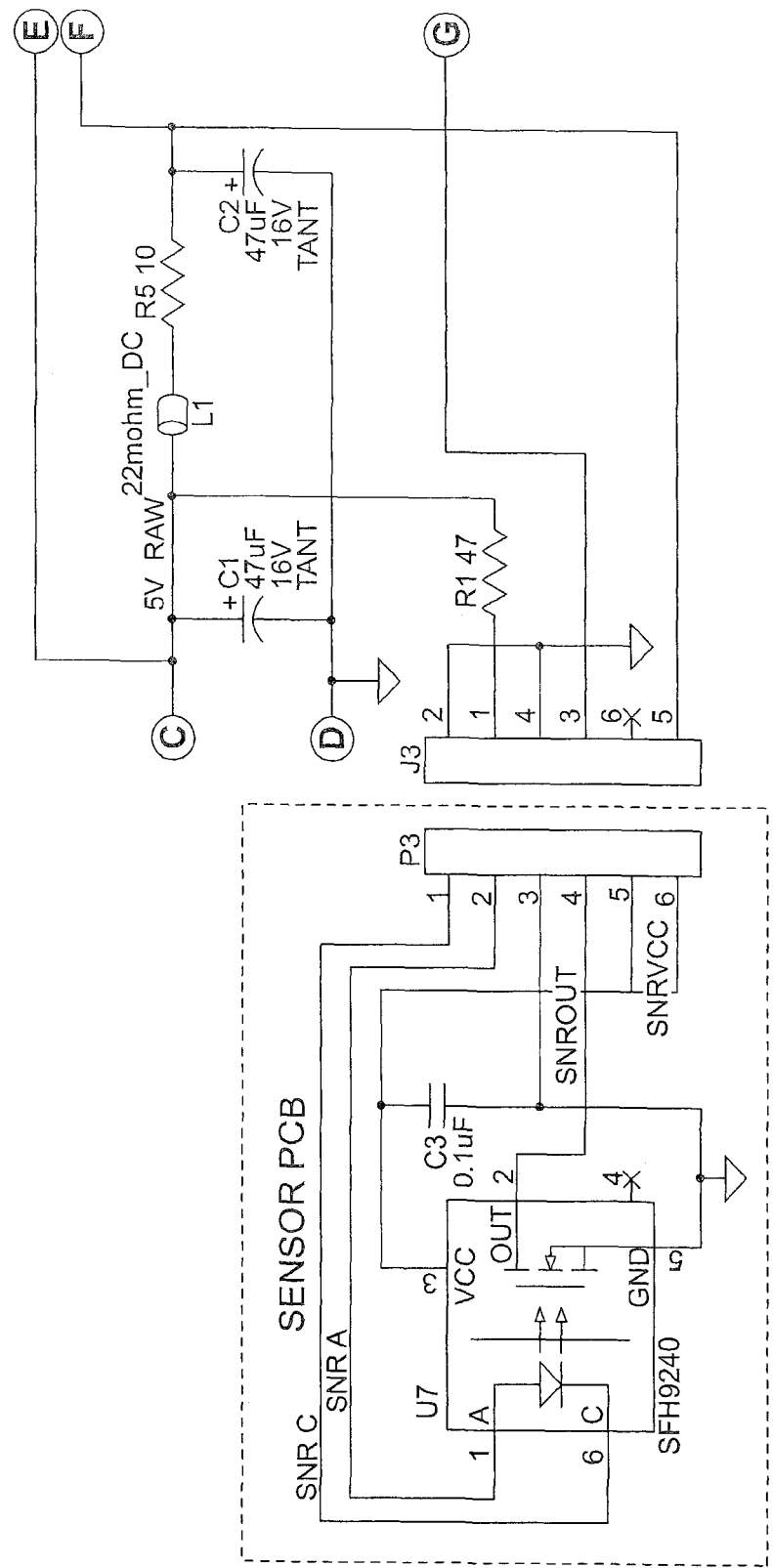
Figure 36C:
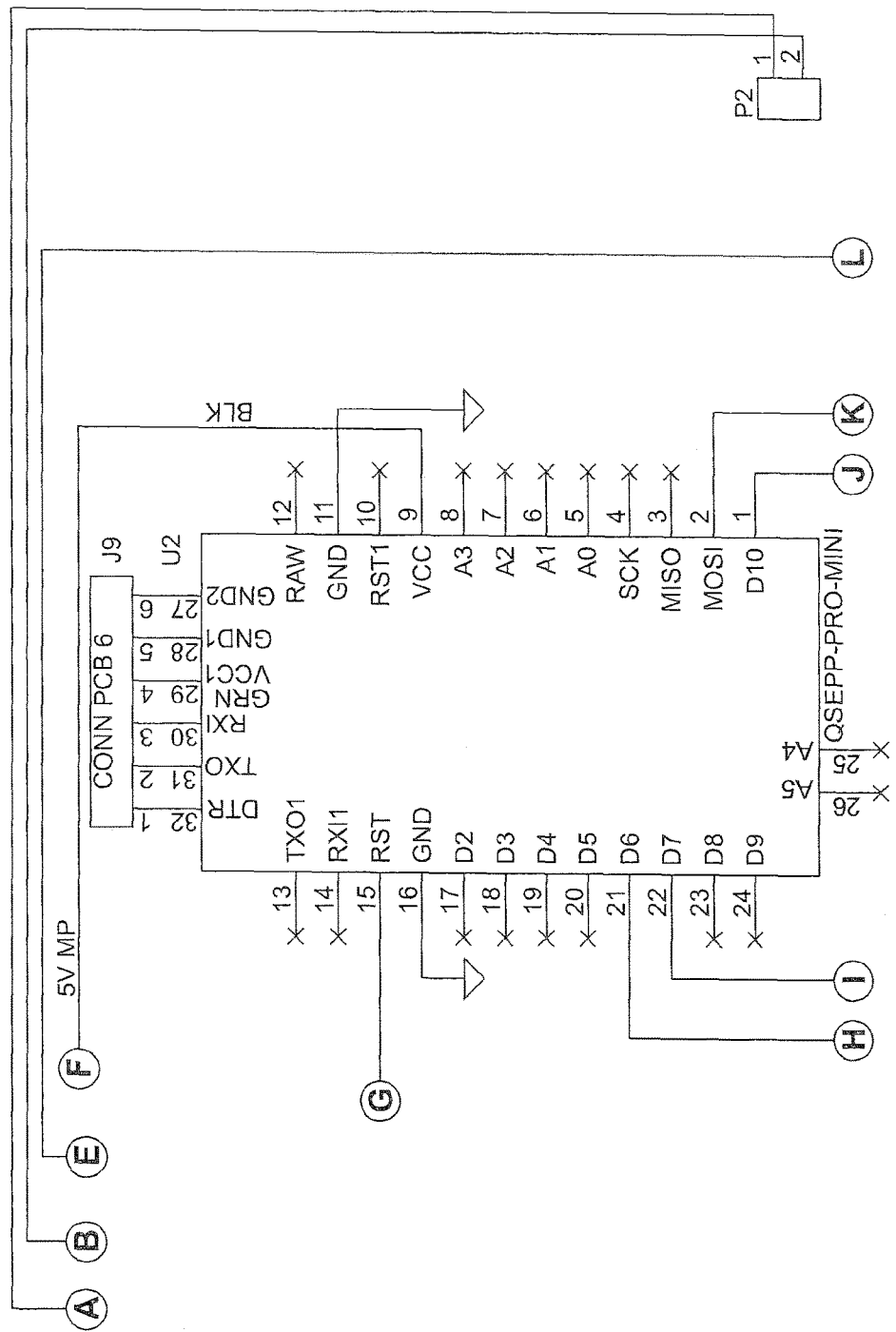
Figure 36D:
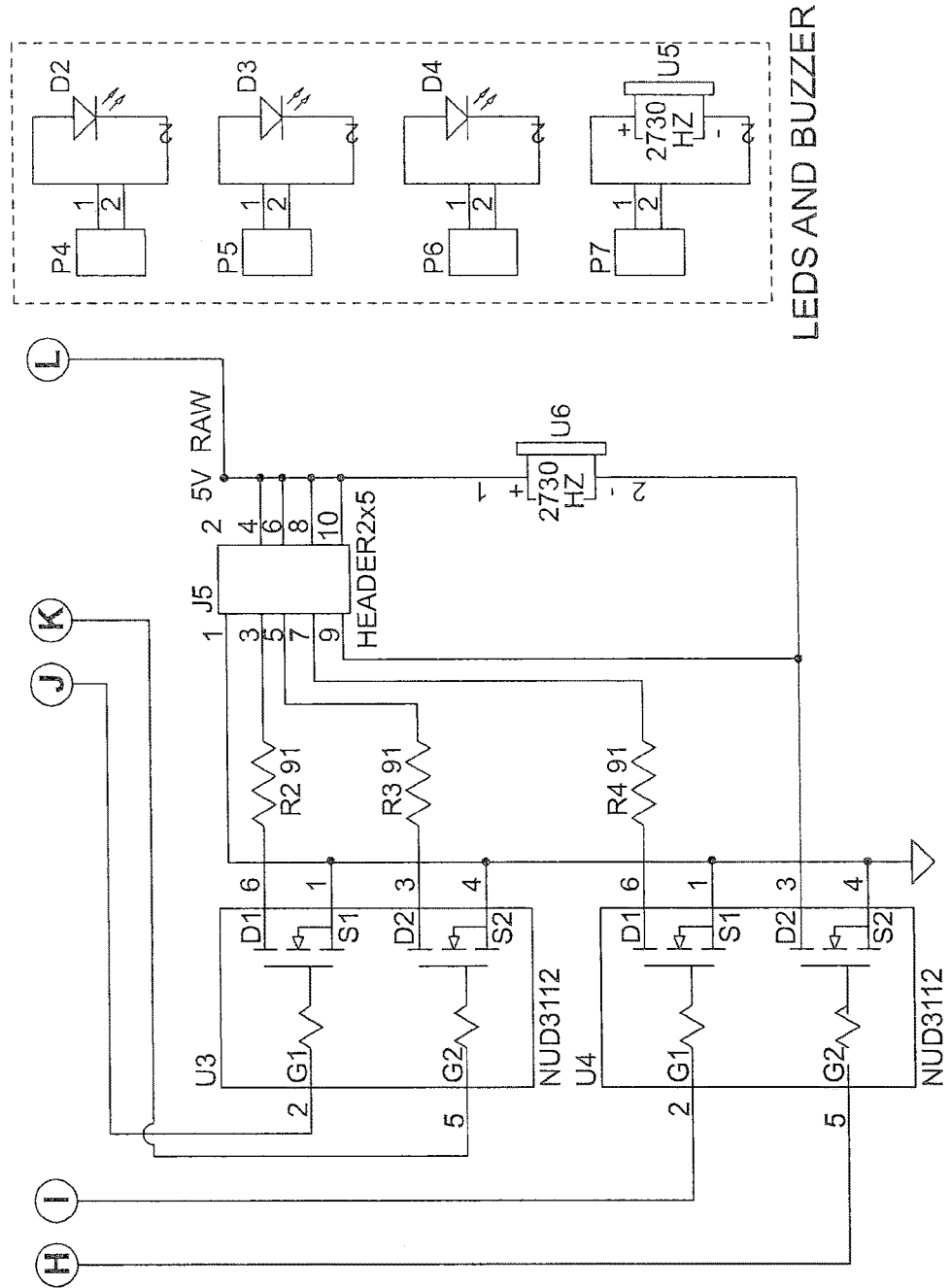

FIGS. 35A and 35B schematically depict an embodiment of a UV device of the present invention. FIG. 35A depicts a UV light source completely retracted into the central sleeve 12 of a UV device standing in an upright position on its base plate 10. Motorized unit 1, central sleeve 12, handle 91, interface 117. An enlargement of the interface 117 showing buttons for up and down movement of the UV lamp and a timer is shown in the upper left part of FIG. 35A.

FIG. 35B schematically depicts the release of the housing 2 and UV lamp 5 from the central sleeve 12 by gravity and a motorized unit 1. Attached to the socket 94 into which the UV lamp 5 is inserted is a guide or range finding device 20 (here schematically a laser depth guide). The broken arrow indicates that the housing 2 can be positioned in an angle ranging from about 0 degree to about 90 degrees with respect to the central sleeve 12. Housing 2, UV lamp 5, central sleeve 12, guide or range-finding device 20, UV lamp socket/adaptor 94, pivot point 118 within housing 2.

FIGS. 36A-D schematically shows a circuit board used in an embodiment of the present invention, UV device UV55.

Figure 37A:
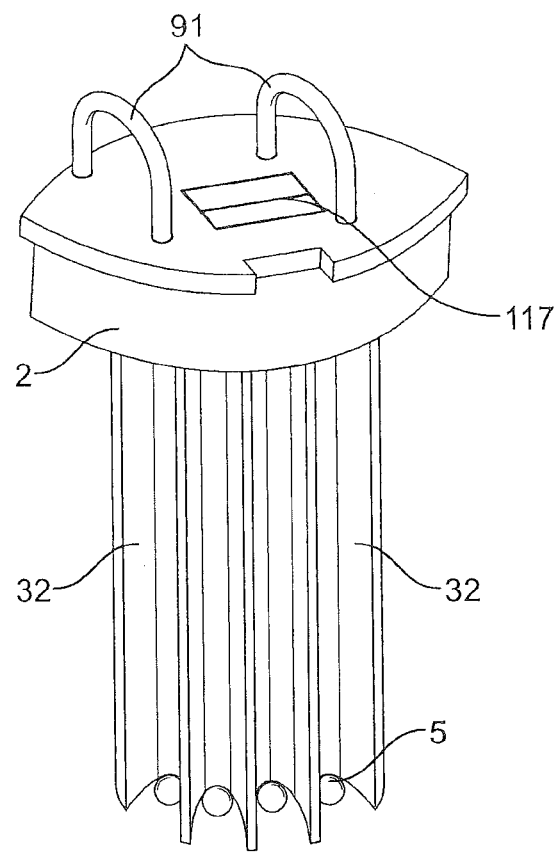
Figures 37B, 37C:
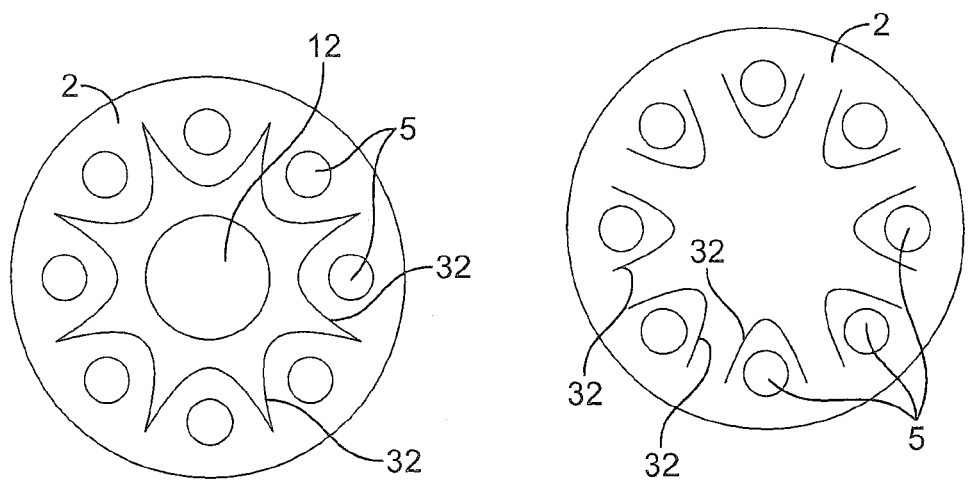

FIGS. 37A (side view), 37B and 37C (both bottom views) schematically depict a non-limiting UV device embodiment of the present invention wherein UV lamps 5 are arranged in a UV lamp cluster and wherein each UV lamp 5 is surrounded by a reflector 32. FIG. 37B schematically depicts an embodiment wherein the reflectors 32 form a contiguous surrounding attached to a central sleeve 12. FIG. 37C schematically depicts an embodiment wherein the reflectors 32 and UV lamps 5 are attached to the housing 2. Reflectors 32 partially surround a UV lamp 5. Housing 2, UV lamp(s) 5, central sleeve 12, handle 91, interface 117, reflector(s) 32.

DETAILED DESCRIPTION OF THE INVENTION

I. Definitions

Throughout the present specification and the accompanying claims the words "comprise" and "include" and variations thereof, such as "comprises," "comprising," "includes," and "including" are to be interpreted inclusively. That is, these words are intended to convey the possible inclusion of other elements or integers not specifically recited, where the context allows. No language in the specification should be construed as indicating any non-claimed element essential to the practice of the invention.

The terms "a" and "an" and "the" and similar referents used in the context of describing the invention (especially in the context of the following claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, each individual value is incorporated into the specification as if it were individually recited herein. Ranges may be expressed herein as from "about" (or "approximate") one particular value, and/or to "about" (or "approximate") another particular value. When such a range is expressed, another embodiment includes from the one particular value and/or to the other particular value. Similarly, when values are expressed as approximations, by use of the antecedent "about" or "approximate" it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that is "less than or equal to the value" or "greater than or equal to the value" possible ranges between these values are also disclosed, as appropriately understood by the skilled artisan. For example, if the value "10" is disclosed, the "less than or equal to 10" as well as "greater than or equal to 10" is also disclosed.

All methods described herein can be performed in any suitable order unless otherwise indicated herein or otherwise clearly contradicted by context. The use of any and all examples, or exemplary language (e.g., "such as" or "e.g.," or "for example") provided herein is intended merely to better illuminate the invention and does not pose a limitation on the scope of the invention otherwise claimed.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

The headings used herein are for organizational purposes only and are not meant to be used to limit the scope of the description or the claims, which can be had by reference to the specification as a whole. Accordingly, the terms defined immediately below are more fully defined by reference to the specification in its entirety.

Illustrations are for the purpose of describing a preferred embodiment of the invention and are not intended to limit the invention thereto.

The abbreviations used herein have their conventional meaning within the mechanical, chemical, and biological arts.

As used herein, the term "about" refers to a range of values of plus or minus 10% of a specified value. For example, the phrase "about 200" includes plus or minus 10% of 200, or from 180 to 220, unless clearly contradicted by context.

As used herein, the terms "amount effective" or "effective amount" mean an amount, which produces a desired effect, such as a biological effect. In particular, an effective amount of a UV dosage is an amount, which inhibits the growth of a microorganism by at least 90% (by at least 1 log reduction), by at least 99% (by at least 2 log reduction), by at least 99.9% (by at least 3 log reduction), by at least 99.99% (by at least 4 log reduction), by at least 99.999% (at least 5 log reduction), or by at least 99.9999% (at least 6 log reduction).

As used herein, the terms "attach to" or "attached to" or grammatical equivalents thereof mean to fasten on, fasten together, affix to, mount to, mount on, connect to, to join, to position onto, position into, place onto, or place into. "Attachment" means the act of attaching or the condition of being attached. Attachment can be direct or indirectly. For example a part A may be attached directly to part B. Alternatively, part A may be attached indirectly to part B through first attaching part A to part C and then attaching part C to part B. More than one intermediary part can be used to attach part A to part B. Attaching can be permanent, temporarily, or for a prolonged time. For example, a UV device of the present invention may be attached to a container temporarily for the time necessary to perform a method of the invention. Alternatively, a UV device of the present invention may be attached to a container or to an object or structure in a room, a space or defined environment for a prolonged time, e.g., also when a method of the present invention is not performed. Also, a UV device of the present invention may be attached permanently to a container or to an object or structure in a room, a space or defined environment.

The terms "container," "vessel," or "tank" are used interchangeably herein.

As used herein, the terms "germicidal lamp" or "germicidal UV lamp" refer to a type of lamp, which produces ultraviolet (UV) light. Short-wave UV light disrupts DNA base pairing causing thymine-thymine dimers leading to death of bacteria and other microorganisms on exposed surfaces.

As used herein, the terms "inhibiting the growth of a microorganism," "inhibiting the growth of a population of microorganisms," "inhibiting the growth of one or more species of microorganisms" or grammatical equivalents thereof refer to inhibiting the replication of one or more microorganisms and may include destruction of the microorganism(s). Assays for determining inhibiting the growth of a microorganism are known in the art and are described herein.

As used herein, the terms "microorganism" or "microbe" comprise a diverse group of microscopic organisms, including, but not limited to, bacteria, fungi, viruses, archaea, and protists.

The terms "optional" or "optionally" as used throughout the specification means that the subsequently described event or circumstance may but need not occur, and that the description includes instances where the event or circumstance occurs and instances in which it does not. The terms also refer to a subsequently described composition that may but need not be present, and that the description includes instances where the composition is present and instances in which the composition is not present.

As used herein, the terms "sterile" or "sterilization" and grammatical equivalents thereof refer to an environment or an object, which is free or which is made free of detectable living cells, viable spores, viruses, and other microorganisms. Sometimes the process of sterilization is also referred herein to as "disinfection" or "sanitization."

As used herein, the term "radiation" or grammatical equivalents refer to energy, which may be selectively applied, including energy having a wavelength of between $10^{-14}$ and $10^4$ meters including, for example, electron beam radiation, gamma radiation, x-ray radiation, light such as ultraviolet (UV) light, visible light, and infrared light, microwave radiation, and radio waves. A preferred radiation is UV light radiation. "Irradiation" refers to the application of radiation to a surface.

As used herein the term "ultraviolet" and the abbreviation "UV" refer to electromagnetic radiation with wavelengths shorter than the wavelengths of visible light and longer than those of X-rays. The UV part of the light spectrum is situated beyond the visible spectrum at its violet end.

As used herein, the abbreviation "UV-A" refers to ultraviolet light in the range of 315-400 nanometers (nm).

As used herein, the abbreviation "UV-B" refers to ultraviolet light in the range of 280-315 nanometers (nm).

As used herein, the abbreviation "UV-C" refers to ultraviolet light in the range of 200-280 nanometers (nm).

As used herein, the term "UV dose" refers to an amount of UV irradiation absorbed by an exposed population of microbes, typically in units of $mJ/cm^2$ ($mJ/cm^2$=1,000 $\mu W/cm^2$ per second).

As used herein, the terms "UV intensity" or "UV irradiance" refer to the irradiance field of a UV germicidal irradiation system (such as a UV light source described herein), i.e., the total radiant energy incident on a surface from all directions. It is measured in $\mu W/cm^2$ at 1m. The UV intensity greatly depends on the distance from the UV emitter and the transmittance of the medium.

As used herein, the terms "ultraviolet radiation" or "UV radiation" refer to radiation having a wave-length or wavelengths between from 160 to 400 nm. If a range is specified, a narrower range of radiation is meant within the 160 to 400 nm range. The range specified, unless otherwise indicated, means radiation having a wavelength or wavelengths within this specified range.

In the following description it is to understood that terms such as "forward," "rearward," "front," "back," "right," "left," "upward," "downward," "horizontal," "vertical," "longitudinal," "lateral," and the like are words of convenience and are not to be construed as limiting terms.

The present invention generally relates to compositions, systems and methods for ultraviolet (UV) sterilization, and more specifically, to compositions, systems and methods for UV sterilization of a container, and more particularly to compositions, systems and methods for UV sterilization of a container used in the process of fermentation for an alcoholic beverage. A system as described herein comprises a UV device and a container.

II. UV Devices

Figure 2:
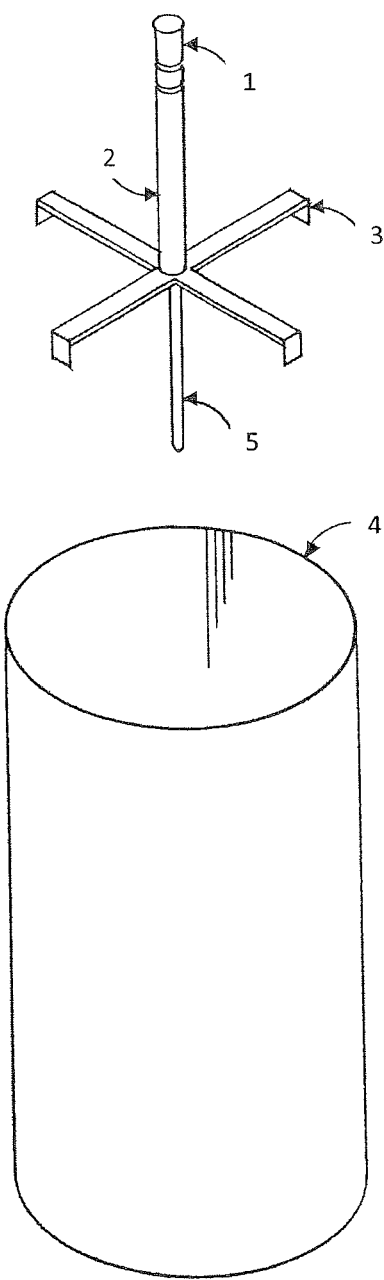
FIG. 2 depicts a schematic diagram of a UV device of the present invention above a container 4, here a cylindrical fermentation vessel. In this embodiment, the UV lamp 5 is being lowered from within a housing 2, here a protective sleeve. The UV lamp 5 can be suspended above the container 4 via a mounting bracket 3. The UV lamp 5 can be raised and lowered by a motorized unit 1 mounted on top of the housing 2.
Figure 3:
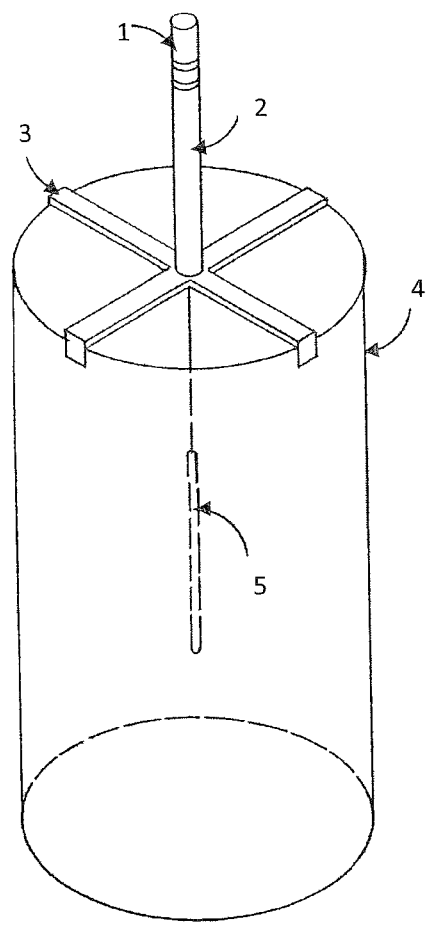
FIG. 3 depicts a schematic diagram of a UV device of the present invention placed on a container 4, here a cylindrical fermentation vessel. In this embodiment, the UV lamp 5 is being lowered into the interior of the container 4. The UV device is supported by a mounting bracket 3. The UV lamp is being lowered from a housing 2, here a protective sleeve, by a motorized unit 1 mounted on top of the housing 2.
Figure 4:
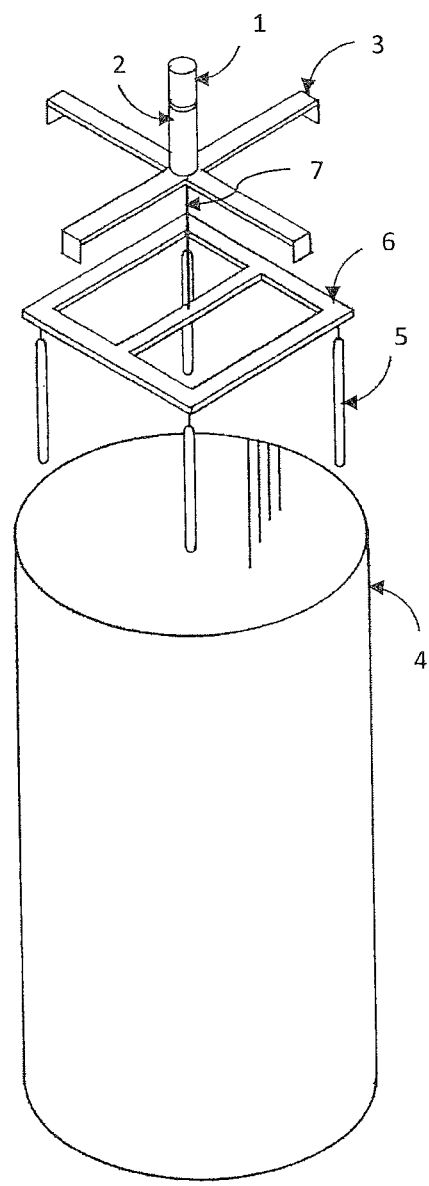
FIG. 4 depicts a schematic diagram of a UV device of the present invention comprising four UV lamps 5 mounted on a frame 6, which can be attached to a motorized unit 1 by a rigid rod or flexible cable 7. In this embodiment, four UV lamps were chosen as an example to demonstrate that the use of more than one UV lamp 5 in various un-clustered positions is encompassed by the present invention. In this embodiment, the UV lamps 5 are being lowered into the interior of the container 4, here a cylindrical fermentation vessel. The UV device is supported by a mounting bracket 3. The cable or rigid rod 7 supporting the frame 6 is lowered from within a housing 2, here a protective sleeve, by a motorized unit 1 mounted on top of the housing 2.
Figure 5:
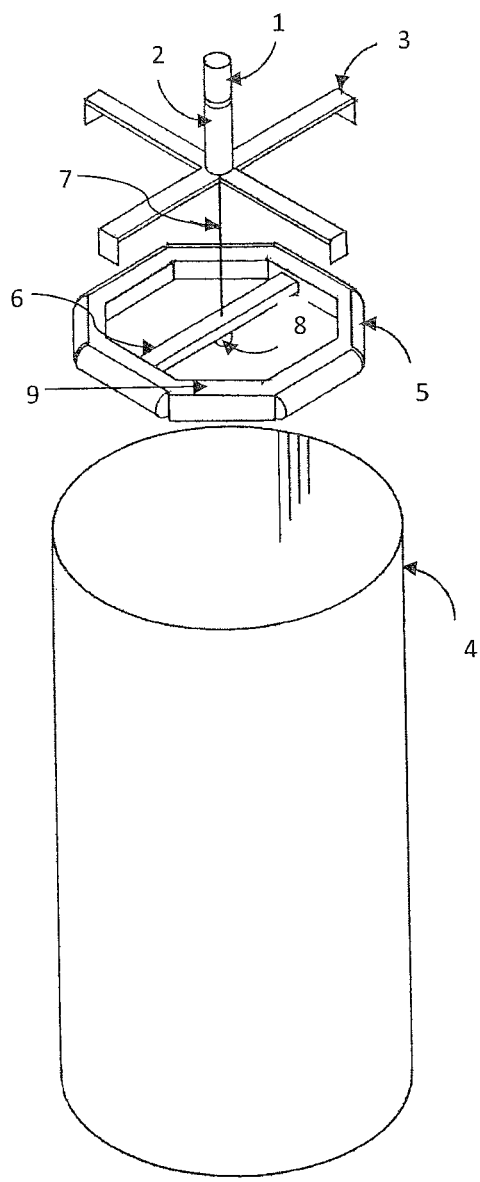
FIG. 5 depicts a schematic diagram of a UV device of the present invention showing a different configuration of UV lamps 5. In this embodiment, eight UV lamps 5 are mounted on an octagonal bracket 9, which can be attached to a motorized unit 1 by a rigid rod or flexible cable 7. In this figure, the UV lamps 5 are being lowered into the interior of the container 4, here a cylindrical fermentation vessel. The UV device is supported by a mounting bracket 3. The cable or rigid rod 7 attached to a connecting plate 6 is lowered from within a housing 2, here a protective sleeve, by a motorized unit 1 mounted on top of the housing 2. An additional UV lamp 8 may optionally be placed at the bottom of the connecting plate 6. The UV lamp 8 will be attached to a position on the connecting plate 6 such that the lower surface of the container 4 will receive sufficient UV radiation to kill or inhibit the growth of all desired microorganisms by the end of the sterilization cycle. In another embodiment, a reflective lid is positioned horizontally between the octagonal bracket 9 and the UV lamp 8 may be fixed to the surface of the octagonal bracket 9 to increase the intensity of UV light directed at the lower surface and pointing downwards to ensure the bottom surface of the container 4 is exposed to sufficient UV radiation.
Figure 6:
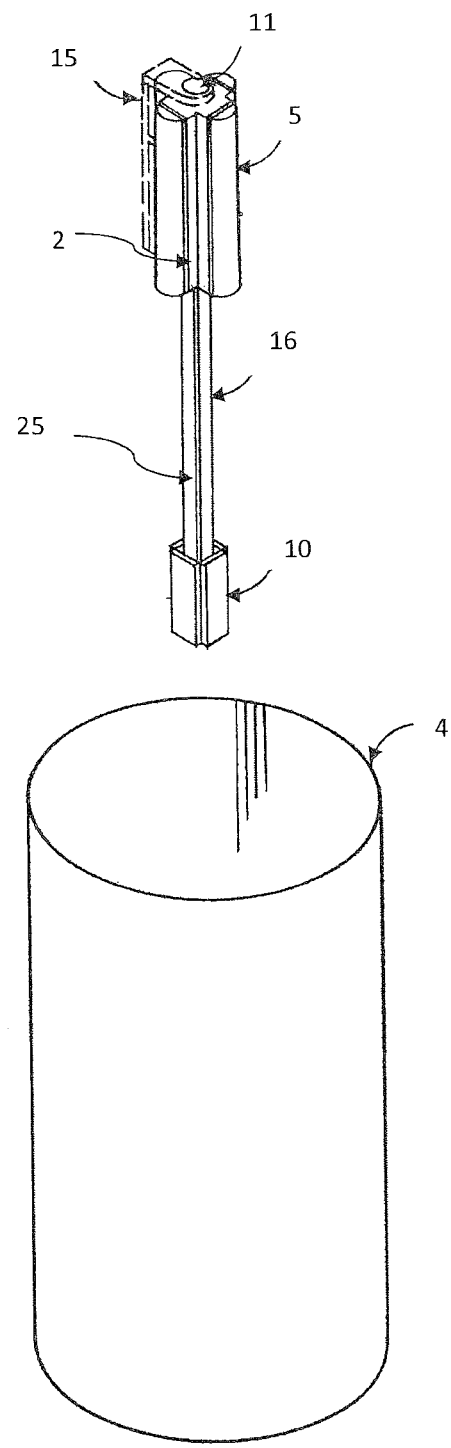
FIG. 6 depicts a schematic diagram of a UV device of the present invention showing a different configuration of UV lamps 5. The UV device is supported by a folding base plate 10, which is attached to a central post 16 having a track 25. The device is inserted through the top opening of a container 4, here a cylindrical fermentation vessel. The intensity of the UV radiation is monitored by a UV detector 11, which optionally is attached to an adjustable bracket 15 allowing the detector 11 to be placed as close to the inner surface of the container 4 as possible. The UV lamps 5 are optionally covered in this configuration by an acrylic covering that does not absorb UV-C light. The lamps 5 are supported by a housing 2, which as shown in FIG. 7 may fold open. The position and angle of the lamps 5 may be adjusted as depicted in FIG. 7.
Figure 7:
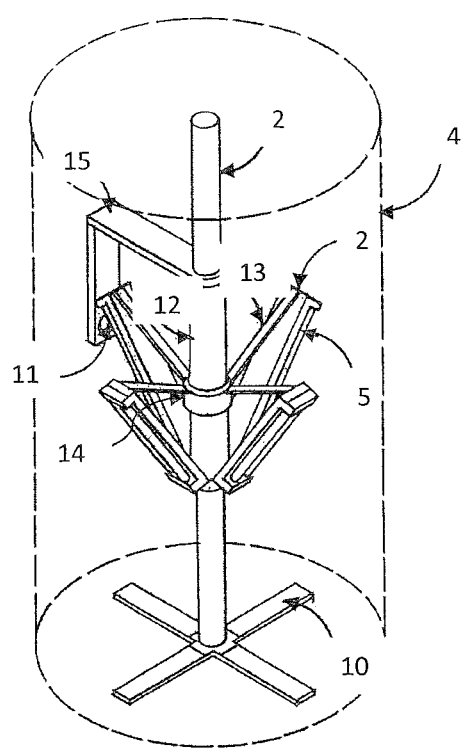
FIG. 7 depicts a schematic diagram of a UV device of the present invention showing a different configuration of UV lamps 5. The UV device is supported by a folding base plate 10. The UV device is inserted through the top opening of a container 4, here a cylindrical fermentation vessel. The UV lamps 5 are held in housings 2, which fold open. The housings 2 are attached to a central sleeve 12 via connecting rods 13. The position of the central sleeve 12 may be adjusted to adjust the angle that the UV lamps 5 protrude from the central axis. In this embodiment, the central sleeve 12 is mounted in turn on another centrally mounted motorized sleeve 14, which can move the entire UV device up and down within the container 4. The intensity of the UV radiation is monitored by a UV detector 11, which is attached to an adjustable bracket 15 allowing the detector 11 to be placed as close to the inner surface of the container as possible. The angling of the lamps 5 also ensures the base of the container is irradiated with UV.
Figure 8:
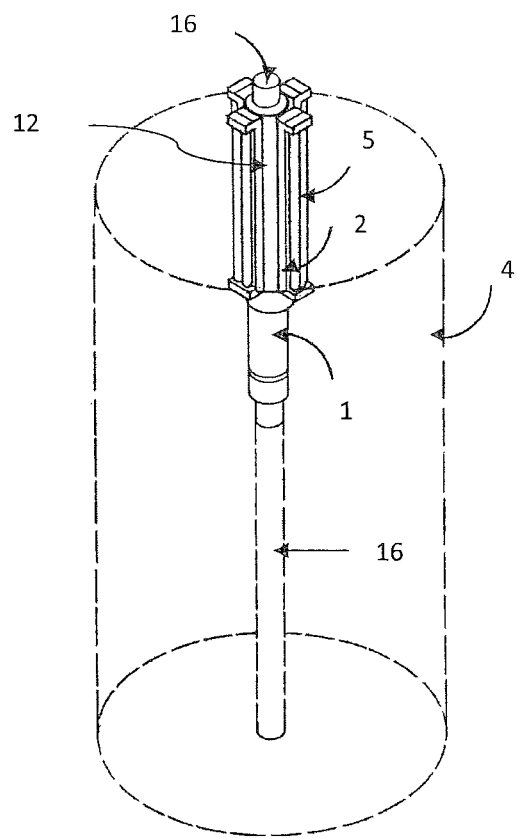
FIG. 8 depicts a schematic diagram of a UV device of the present invention showing a different configuration of UV lamps 5. In this embodiment, four UV lamps 5 mounted in housings 2 are mounted to a central sleeve 12, which can be moved up and down within the container 4, here a cylindrical fermentation vessel, on a central post 16, via a motorized unit 1 attached to the central sleeve 12. The lamp housings 2 are affixed to two parallelogramming arms (not shown in this Figure, shown in FIG. 9), which can move in a circular motion and adjust the position of the UV lamps 5 and their proximity to the inner surface of container 4 of varying diameter.
Figure 9:
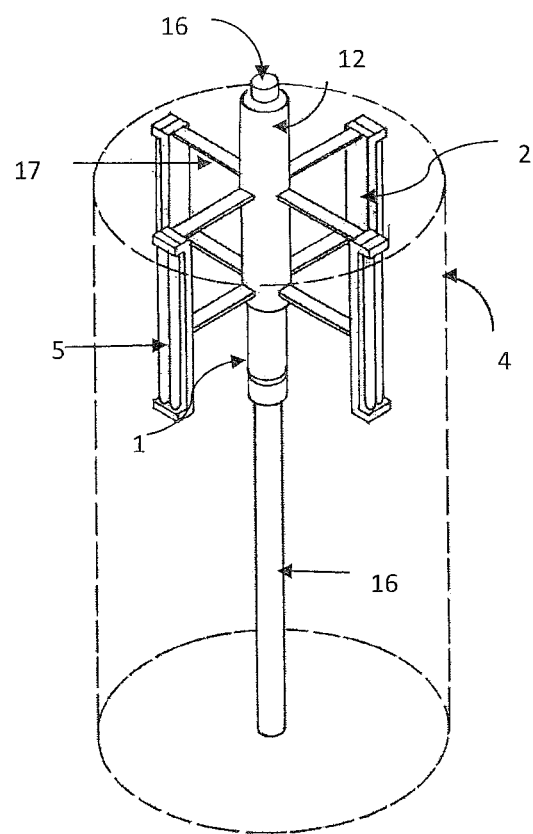
FIG. 9 depicts a schematic diagram of a UV device of the present invention showing a different position of UV lamps 5 (same as FIG. 8, but with UV lamps 5 extended). In this embodiment, four UV lamps 5 mounted in housings 2 are mounted to a central sleeve 12, which can be moved up and down within the container 4, here a cylindrical fermentation vessel on a central post 16, via a motorized unit 1 attached to the central sleeve 12. The lamp housings 2 are affixed to two parallelogramming arms 17, which can move in a circular motion and adjust the position of the UV lamps 5 and their proximity to the inner surface of containers 4 of varying diameter. In this figure the parallelogramming arms 17 are shown fully extended. Arms 17 may also not be fully extended, i.e., form they an angle between 0 and 90 degrees and be positioned within the closed position (shown in FIG. 8) and the open position (shown in FIG. 9).
Figure 10:
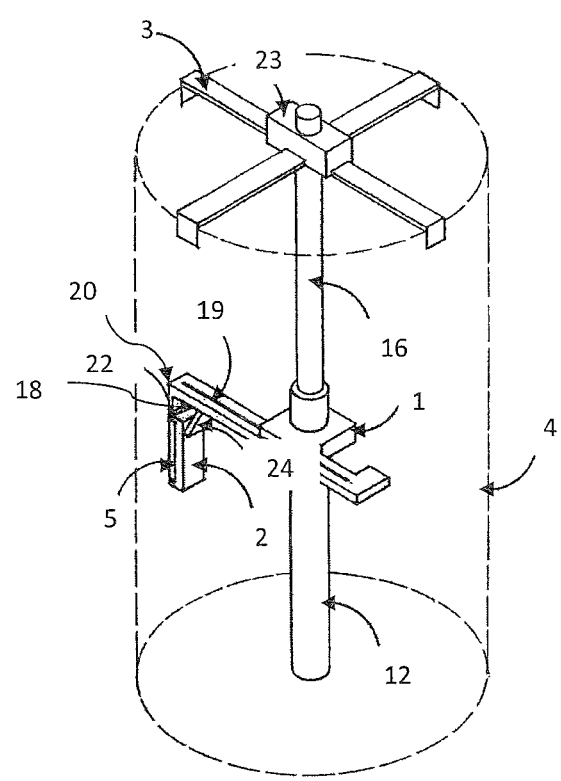
FIG. 10 depicts a schematic diagram of a UV device of the present invention showing a different configuration using a pulsed UV lamp 5. In this embodiment, the pulsed UV lamp 5 is shown within a housing 2, which contains a fan cooling system (not shown) in order to maintain the lamp temperature within an optimal range. The entire UV device is supported by a bracket 3, mounted on top of the container 4, here a cylindrical fermentation vessel. The assembly holding the UV lamp 5 is attached via an arm 18, with a track 19, that allows the position of the UV light to be adjusted horizontally via a motorized unit 1. The positioning of the UV pulsed lamp 5 can be optimized by a range-finding device 20 (also referred to as a guide) mounted at position 22. The motorized unit 1 can also move up and down a central sleeve 12, adjusting the position vertically. Central sleeve 12 also moves up and down on central post 16, and can telescope up covering central post 16 in order to decrease the overall size of the device facilitating transport. Motor unit 23 mounted at the top of the central post 16 spins the central post 16 enabling the pulsed UV lamp 5 to irradiate the entire surface of the container 4 (by moving vertically and rotating). Adjusting bracket 24 can adjust the position of the pulsed UV lamp 5 from vertical to horizontal (shown in FIG. 11) by moving along a track 19 at the bottom of arm 18.
Figure 11:
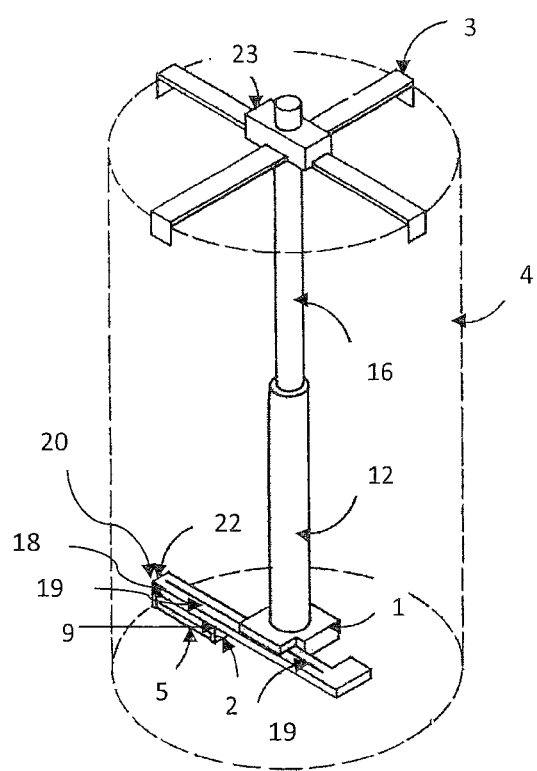
FIG. 11 depicts a schematic diagram of a UV device of the present invention showing a different position using a pulsed UV lamp 5 (same as embodiment as FIG. 10, but with UV lamps 5 in horizontal position). In this embodiment, the pulsed UV lamp 5 is shown within a housing 2, which contains a fan cooling system (not shown) in order to maintain the lamp temperature within an optimal range. The UV device is supported by a bracket 3 placed or mounted on top of a container 4, here a cylindrical fermentation vessel. The assembly holding the UV lamp 5 is attached via an arm 18, with a track 19, that allows the position of the UV light to be adjusted horizontally via a motorized unit 1. The positioning of the UV pulsed lamp 5 can be optimized by range-finding device 20 mounted at position 22. The motorized unit 1 can also move up and down a central sleeve 12 adjusting the position vertically. Central sleeve 12 also moves up and down on central post 16 and can telescope up covering central post 16 in order to decrease the overall size of the device facilitating transport. Motor unit 23 mounted at the top of the central post 16 spins the central post 16 enabling the pulsed UV lamp 5 to irradiate the entire surface of the container 4 (by moving vertically and rotating). Adjusting bracket 24 (hidden) can adjust the position of the pulsed UV lamp 5 from vertical to horizontal (shown in FIG. 12) by moving along a track 19 at the bottom of arm 18. In the embodiment shown, the UV lamp 5 is held horizontally allowing the of the vessel to be bottom surface of the vessel to be irradiated with pulsed UV light.
Figure 12:
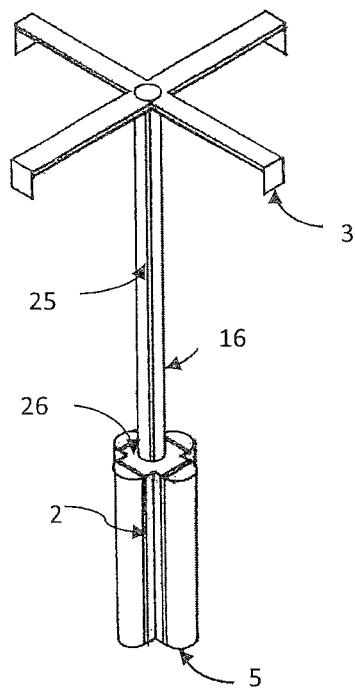
FIG. 12 depicts a schematic diagram of a UV device of the present invention showing a different configuration using four clustered UV lamps 5. In this embodiment, the UV lamps 5 are mounted to a housing 2 (the housing may or may not have reflectors of various cross sections e.g. parabolic, elliptical, or circular). The UV device is supported to the top of a container (not shown) by a four-armed bracket 3. The clustered UV lamps 5 can move up and down a central post 16 along a track 25. This is accomplished by a motorized unit (not shown here) located between the clustered UV lamps 5 in position 26. The bracket 3 can be used to attach the UV device to a container. Alternatively, the bracket 3 can also function as a base plate or stand similar to base plate 10 as shown, e.g., in FIG. 7 In such configuration, the UV device may be positioned on a surface of a container, e.g., on an interior bottom surface of a container (e.g., see FIG. 7) or on an upper exterior surface of a container (e.g., see FIG. 25, 29).
Figure 13:
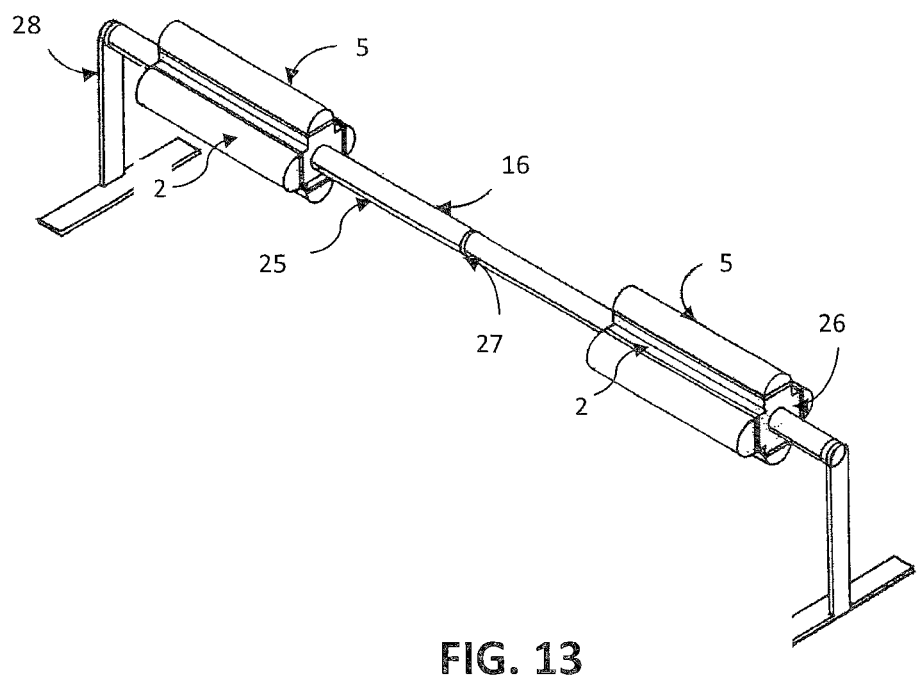
FIG. 13 depicts a schematic diagram of a UV device of the present invention showing a different configuration using two sets of four clustered UV lamps 5. In this embodiment, the UV lamps 5 are mounted to a housing 2 (the housing may or may not have reflectors of various cross sections e.g., parabolic, elliptical, or circular). This embodiment is preferred for use within a horizontal container. The UV device is supported to the top of a container (not shown) by a horizontal stand 28 The clustered UV lamps 5 can move horizontally along a central post 16 along a track 25. This is accomplished by a motorized unit located between the clustered lamps in position 26. The central post 16 is telescoping allowing one half to slide into the other at position 27. This allows the length of the UV device to be adjusted to the length of the container. Two clusters of UV lamps 5 are shown to demonstrate that more than one cluster of UV lamps 5 can be used.
Figure 14:
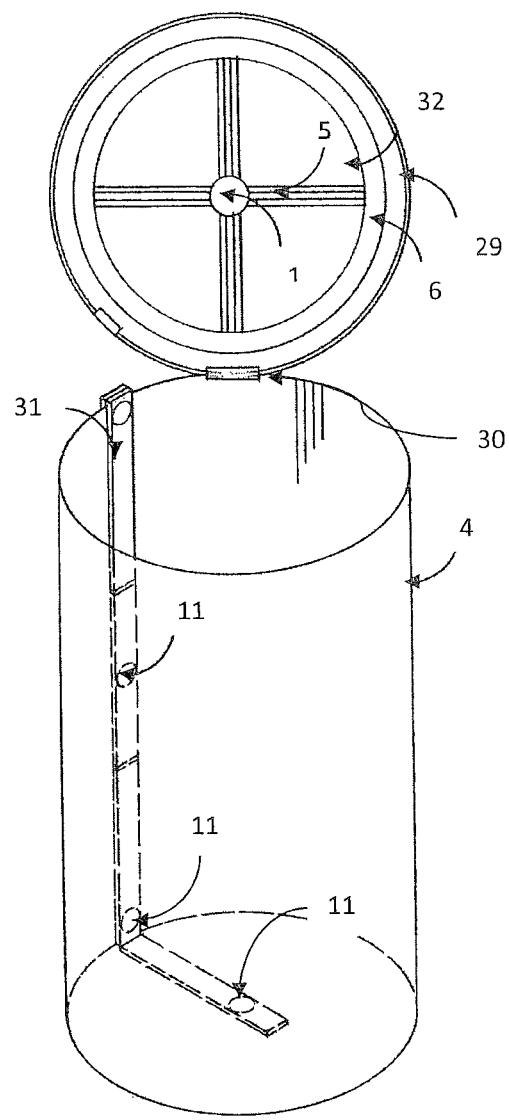
FIG. 14 depicts a schematic diagram of a UV device of the present invention showing a different configuration of UV lamps 5. In this embodiment, the UV lamps 5 are mounted on a lid 29, such as a hinged lid 30, to a container 4, here a cylindrical fermentation vessel. A removable bracket 31 providing support for a system comprising one or more UV detectors 11 is mounted along the inner surface of the container 4. These UV detectors 11 ensure sufficient intensity of UV radiation required to kill or inhibit growth of unwanted microorganisms has reached all interior surfaces of the container 4. In this embodiment, the UV lamps 5 are mounted to frame 6 and lowered via a cable 7 (not shown, shown in FIG. 15) attached to a motorized unit 1. A reflector 32 may optionally be mounted to the lower surface of the lid 29.
Figure 15:
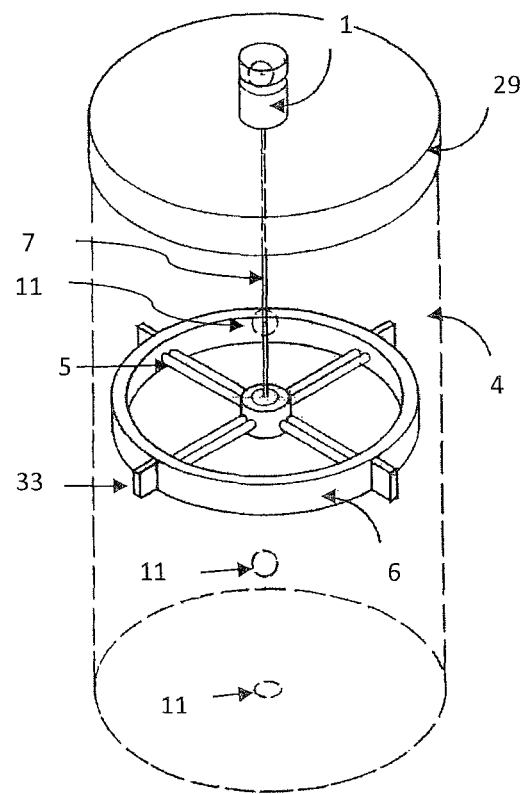
FIG. 15 depicts a schematic diagram of a UV device of the present invention showing a different position of UV lamps 5 (same embodiment as FIG. 14 but now with the frame 6 and UV lamps 5 lowered). A removable bracket 31 (not shown here, shown in FIG. 14) providing support for a system comprising one or more UV detectors 11 (shown in FIG. 14) is mounted along the inner surface of the container 4. These UV detectors 11 ensure sufficient intensity of UV radiation required to kill or inhibit growth of unwanted microorganisms has reached all surfaces of the container 4. In this embodiment, the UV lamp assembly is guided down the container 4 by nylon blocks 33 attached to frame 6. The lowering of the UV lamp assembly occurs via a motorized unit 1, to which the UV lamp assembly is attached via a cable 7. The lowering of the UV lamp assembly is optional. It can remain at the top of the vessel situated just below the lid 29. In some embodiments, the motorized unit moves the UV lamp assembly in a circular manner.
Figure 16:
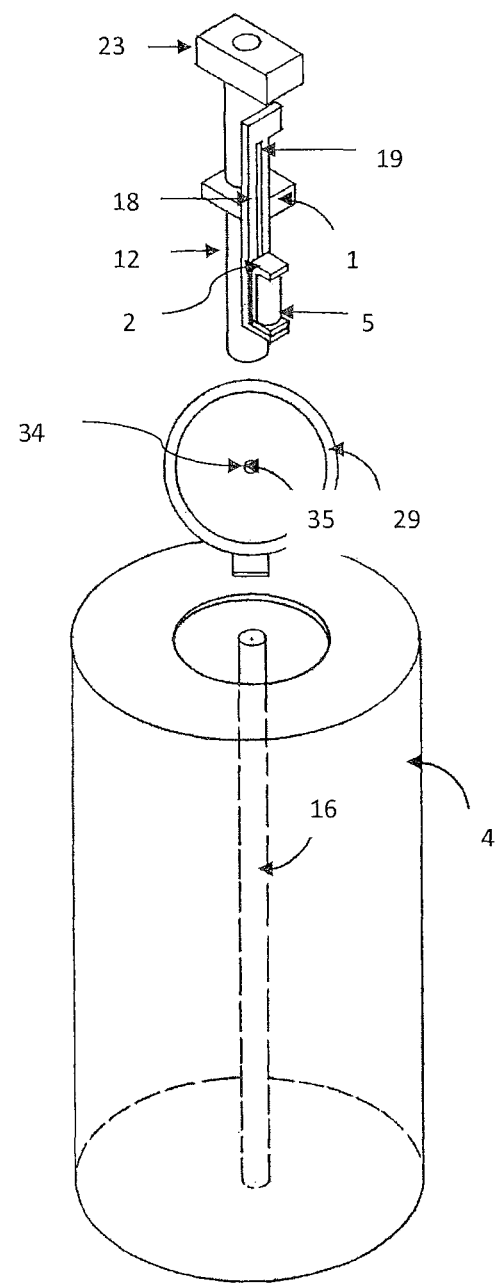
FIG. 16 depicts a schematic diagram of a UV device of the present invention showing a different configuration of a pulsed UV lamp 5. The pulsed UV lamp 5 is shown within a housing 2, which contains a fan cooling system (not shown) in order to maintain the lamp temperature within an optimal range. The assembly holding the UV lamp 5 (e.g., a pulsed UV lamp) attached via an arm 18 with a track 19 that allows the position of the UV lamp 5 to be adjusted horizontally via a motorized unit 1. The motorized unit 1 can also move up and down a central sleeve 12 adjusting the position vertically. Central sleeve 12 also moves up and down on central post 16 that can be a permanent integral component of the container 4, here a cylindrical fermentation vessel. Motor unit 23 mounted at the top of the central sleeve 12 spins the central sleeve 12 enabling the pulsed UV lamp 5 to irradiate the entire surface of the container (by moving vertically and rotating). The assembly holding the UV lamp 5 is attached via an arm 18 with a track 19 that allows the position of the UV lamp 5 to be adjusted horizontally via a motorized unit 1. A post or boss 34 at position 35 further enhances the stability of central post 16 once the UV device is mounted and lid 29 is closed.
Figure 18A:
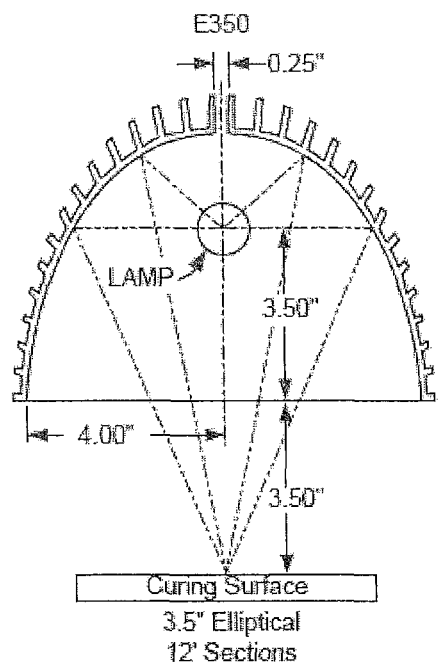
Figure 18B:
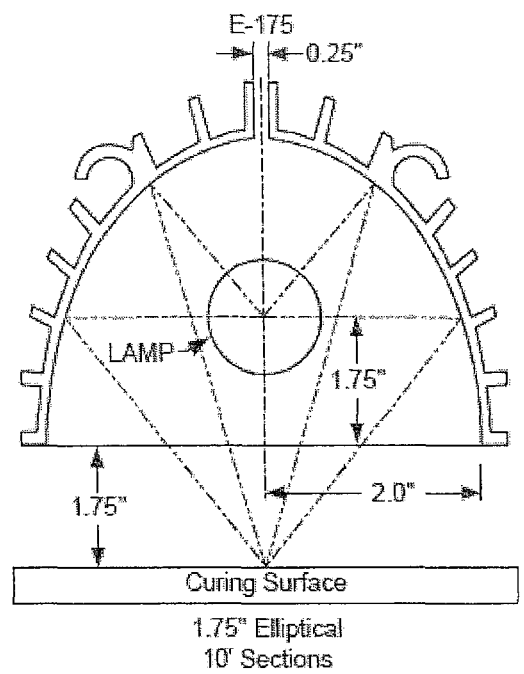
Figure 18C:
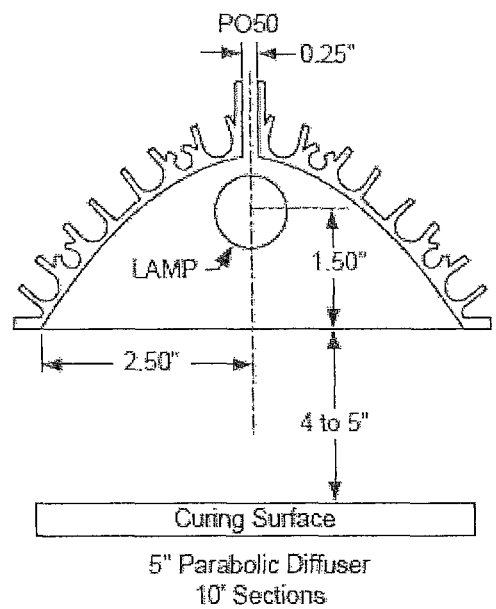
Figure 18D:
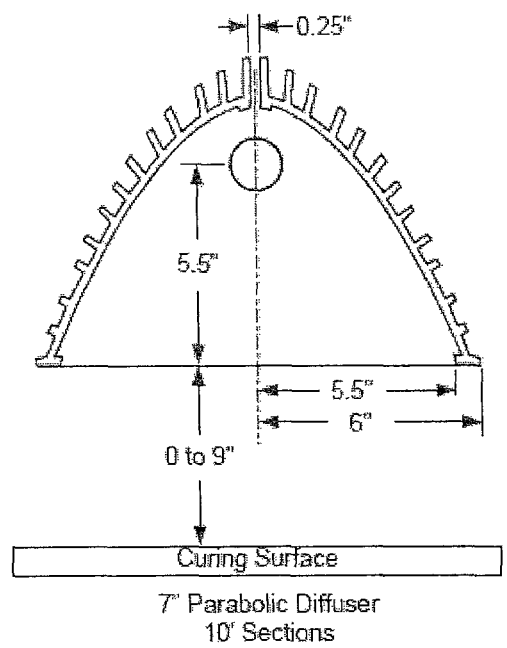

The present invention describes a variety of UV devices. In some embodiments of the present invention, a UV device is a UV device as depicted in FIG. 1, 2 or 3. In some embodiments of the present invention, a UV device is a UV device as depicted in FIG. 4. In some embodiments of the present invention, a UV device is a UV device as depicted in FIG. 5. In some embodiments of the present invention, a UV device is a UV device as depicted in FIG. 4. In some embodiments of the present invention, a UV device is a UV device as depicted in FIG. 6 or 7. In some embodiments of the present invention, a UV device is a UV device as depicted in FIG. 8 or 9. In some embodiments of the present invention, a UV device is a UV device as depicted in FIG. 10. In some embodiments of the present invention, a UV device is a UV device as depicted in FIG. 11. In some embodiments of the present invention, a UV device is a UV device as depicted in FIG. 12. In some embodiments of the present invention, a UV device is a UV device as depicted in FIG. 13. In some embodiments of the present invention, a UV device is a UV device as depicted in FIG. 14 or 15. In some embodiments of the present invention, a UV device is a UV device as depicted in FIG. 16. In some embodiments of the present invention, a UV device is a UV device as depicted in FIG. 19. In some embodiments of the present invention, a UV device is a UV device as depicted in FIG. 20. In some embodiments of the present invention, a UV device is a UV device as depicted in FIGS. 21-25. In some embodiments of the present invention, a UV device is a UV device as depicted in FIG. 27. In some embodiments of the present invention, a UV device is a UV device as depicted in FIG. 28. In some embodiments of the present invention, a UV device is a UV device as depicted in FIG. 29. In some embodiments of the present invention, a UV device is a UV device as depicted in FIG. 30. In some embodiments of the present invention, a UV device is a UV device as depicted in FIG. 31. In some embodiments of the present invention, a UV device is a UV device as depicted in FIG. 32. In some embodiments of the present invention, a UV device is a UV device as depicted in FIG. 33. In some embodiments of the present invention, a UV device is a UV device as depicted in FIG. 34. In some embodiments of the present invention, a UV device is a UV device as depicted in FIG. 35. In some embodiments of the present invention, a UV device is a UV device as depicted in FIG. 37.

UV light sources of the present invention include pulsed UV light sources and continuous wavelength mode UV light sources. In some embodiments of the present invention, a UV light source is a pulsed UV light source. In some embodiments of the present invention, a UV light source is a continuous wavelength mode UV light source.

A UV device comprises a UV light source, also referred to as UV lamp.

In some embodiments of the present invention, a UV light source comprises a lamp selected from the group consisting of a low pressure mercury lamp, a medium pressure mercury lamp, a high pressure mercury lamp, an ultra-high pressure mercury lamp, a low pressure short arc xenon lamp, a medium pressure short arc xenon lamp, a high pressure short arc xenon lamp, an ultra-high pressure short arc xenon lamp, a low pressure long arc xenon lamp, a medium pressure long arc xenon lamp, a high pressure long arc xenon lamp, an ultra-high pressure long arc xenon lamp, a low pressure metal halide lamp, a medium pressure metal halide lamp, a high pressure metal halide lamp, an ultra-high pressure metal halide lamp, a tungsten halogen lamp, a quartz halogen lamp, a quartz iodine lamp, a sodium lamp, and an incandescent lamp.

Notably, any number of UV lamps including low pressure, medium pressure, high pressure, and ultra-high pressure lamps, which are made of various materials, e.g., most commonly mercury (Hg) can be used with the system configuration according to the present invention and in the methods described herein.

In some embodiments, a UV light source of the present invention comprises a low pressure mercury lamp. In some embodiments, a UV light source of the present invention comprises a medium pressure mercury lamp. In some embodiments, a UV light source of the present invention comprises a high pressure mercury lamp. In some embodiments, a UV light source of the present invention comprises an ultra-high pressure mercury lamp. Such mercury lamps are known in the art and are commercially available, e.g., Steril Aire Model SE series UVC Emitters™.

In some embodiments, a UV light source of the present invention comprises a low pressure short arc xenon lamp. In some embodiments, a UV light source of the present invention comprises a medium pressure short arc xenon lamp. In some embodiments, a UV light source of the present invention comprises a high pressure short arc xenon lamp. In some embodiments, a UV light source of the present invention comprises an ultra-high pressure short arc xenon lamp. Short arc xenon lamps are known in the art and are commercially available, e.g., Ushio #5000371-UXL-75XE Xenon Short Arc Lamp.

In some embodiments, a UV light source of the present invention comprises a low pressure long arc xenon lamp. In some embodiments, a UV light source of the present invention comprises a medium pressure long arc xenon lamp. In some embodiments, a UV light source of the present invention comprises a high pressure long arc xenon lamp. In some embodiments, a UV light source of the present invention comprises an ultra-high pressure long arc xenon lamp. Long arc xenon lamps are known in the art and are commercially available, e.g., Lumi-Max XLA1500W Long Arc Xenon Lamp.

In some embodiments, a UV light source of the present invention comprises a low pressure metal halide lamp. In some embodiments, a UV light source of the present invention comprises a medium pressure metal halide lamp. In some embodiments, a UV light source of the present invention comprises a high pressure metal halide lamp. In some embodiments, a UV light source of the present invention comprises an ultra-high pressure metal halide lamp. Metal halide lamps are known in the art and are commercially available, e.g., Venture Lighting product number 32519, open rated 175 watt probe start lamp.

In some embodiments, a UV light source of the present invention comprises a halogen lamp. A halogen lamp includes, but is not limited to a tungsten halogen lamp, a quartz halogen lamp and a quartz iodine lamp. Halogen lamps are known in the art and are commercially available, e.g., General Electric model 16751.

In some embodiments, a UV light source of the present invention comprises a sodium lamp. A sodium lamp includes, but is not limited to a high pressure sodium lamp. Sodium lamps are known in the art and are commercially available, e.g., General Electric ED18, 400 W, high pressure sodium lamp.

In some embodiments, a UV light source of the present invention comprises an incandescent lamp. An incandescent lamp includes, but is not limited to an electric light filament lamp. Incandescent lamps are known in the art and are commercially available, e.g., Philips 60-Watt Household Incandescent Light Bulb.

In some embodiments, a UV light source of the present invention comprises a light emitting diode (LED) or a solid state light emitting device, including, but not limited to a semiconductor laser. LEDs are known in the art and are commercially available, e.g., Model L-A3W Energy Efficient UV 110V LED Spot light from Battery Junction.

Additionally, spectral calibration lamps, electrodeless lamps, and the like can be used.

A. Germicidal UV Light Source

Ultraviolet (UV) light is classified into three wavelength ranges: UV-C, from about 200 nanometers (nm) to about 280 nm; UV-B, from about 280 nm to about 315 nm; and UV-A, from about 315 nm to about 400 nm. Generally, UV light, and in particular, UV-C light is "germicidal," i.e., it deactivates the DNA of microorganism, such as bacteria, viruses and other pathogens and thus, destroys their ability to multiply and cause disease, effectively resulting in sterilization of the microorganisms. While susceptibility to UV light varies, exposure to UV energy for about 20 to about 34 milliwatt-seconds/cm$^2$ is adequate to deactivate approximately 99 percent of the pathogens. In some embodiments of the present invention, a UV light source is a germicidal UV light source. A UV light source, also referred to herein as UV lamp, is indicated in the drawings and respective legends as 5.

In some embodiments of a UV device of the present invention, the UV light source is a germicidal UV light source. In some embodiments of a UV device of the present invention, the UV light source is a UV-C light source. In some embodiments of a UV device of the present invention, the UV light source is a UV-B light source. In some embodiments of a UV device of the present invention, the UV light source is a UV-A light source.

In some embodiments of a UV device of the present invention, a UV light source comprises one UV lamp. In some embodiments of a UV device of the present invention, a UV light source comprises one or more UV lamps. If a UV light source comprises more than one UV lamp, e.g., two, three, four, five, six, seven, eight or more UV lamps, it is also referred to as a "UV lamp cluster," "UV cluster" "UV lamp assembly" or "UV assembly."

1. Pulsed Germicidal UV Light Source

In some embodiments of the present invention, a germicidal UV light source is a pulsed germicidal UV light source. Pulsed UV light is composed of a wide spectrum of light ranging from the UV region to the infrared (Wang and MacGregor, 2005, *Water Research* 39(13):2921-25). A large portion of the spectrum lies below 400 nm and as such has germicidal properties. Pulsed UV light has proven equally if not more effective (same sterilization levels achieved more rapidly) at sterilizing surfaces when compared with traditional germicidal UV-C lights (Bohrerova et al., 2008, *Water Research* 42(12):2975-2982). In a pulsed UV system, UV-light is pulsed several times per second, each pulse lasting between 100 ns (nanosecond) and 2 ms (millisecond). An additional advantage of a pulsed UV light system is that it obviates the need for the toxic heavy metal mercury, which is used in traditional germicidal UV lamps. A pulsed UV system requires less power than a mercury UV lamp and as such, is more economical.

The peak intensity of a pulsed UV lamp is typically one to two orders of magnitude higher than that of a mercury UV lamp of similar wattage. These high peak energies are achieved by storing energy in the high voltage storage capacitor and releasing this energy in a very short burst through the flash lamp. Pulse widths of 10 μs (microsecond) to 300 μs are common in today's industrial flashlamp systems. Peak energy levels range from 300 kilowatts to over a megawatt. (Kent Kipling Xenon Corporation Wilmington, Mass.). Sterilization is achieved because the intensity of the light produced by the pulsed lamp is greater than that of conventional UV-C lamps Further, pulsed UV achieves sterilization via the rupture and disintegration of micro-organisms caused by overheating following absorption UV photons emitted in the light pulse (Wekhof et al., "Pulsed UV Disintegration (PUVD): a new sterilization mechanism for packaging and broad medical-hospital applications." The First International Conference on Ultraviolet Technologies. Jun. 14-16, 2001; Washington, D.C., USA).

2. Low Pressure UV Lamp

In some embodiments of the present invention, a germicidal UV light source is a low pressure UV lamp. Low-pressure UV lamps are very similar to a fluorescent lamp, with a wavelength of 253.7 nm. Low pressure lamps are most effective, because they emit most of the radiant energy in the germicidal wavelength of 253.7 nm also known as the UV-C part of the spectrum. This is why low pressure lamps are mostly used in germicidal UV applications. The most common form of germicidal lamp looks similar to an ordinary fluorescent lamp but the tube contains no fluorescent phosphor. In addition, rather than being made of ordinary borosilicate glass, the tube is made of fused quartz. These two changes combine to allow the 253.7 nm UV light produced by the mercury arc to pass out of the lamp unmodified (whereas, in common fluorescent lamps, it causes the phosphor to fluoresce, producing visible light). Germicidal lamps still produce a small amount of visible light due to other mercury radiation bands. In some embodiments, a low pressure UV lamp looks like an incandescent lamp but with the envelope containing a few droplets of mercury. In this design, the incandescent filament heats the mercury, producing a vapor which eventually allows an arc to be struck, short circuiting the incandescent filament. Some low pressure lamps are shown in FIG. 17. Each of those low pressure UV lamp can be used in the present invention.

3. Medium and High Pressure UV Lamps

In some embodiments of the present invention, a germicidal UV light source is a medium-pressure UV lamp. Medium-pressure UV lamps are much more similar to high-intensity discharge (HID) lamps than fluorescent lamps. Medium-pressure UV lamps radiate a broad-band UV-C radiation, rather than a single line. They are widely used in industrial water treatment, because they are very intense radiation sources. They are as efficient as low-pressure lamps. A medium-pressure lamps typically produces very bright bluish white light. In some embodiments of the present invention, a germicidal UV light source is a high pressure UV lamp.

4. Dimension Of Germicidal UV Light Source

Different sized and shaped UV light sources may be used to practice a method of the present invention, largely depending on the shape of the container and the desired duration of the sterilization cycle. In some embodiments, a longer and more powerful UV lamp will provide for shorter duration cycles.

In some embodiments of the present invention, the UV light source is a UV-C lamp of 64" in length with an output of 190 microwatts/cm$^2$ at 254 nm (American Air and Water®, Hilton Head Island, S.C. 29926, USA). Other useful UV-C lamps for use in the systems and methods of the present invention are shown in FIG. 17.

In some embodiments of the present invention, a germicidal UV lamp is a hot cathode germicidal UV lamp, examples of which are shown in FIG. 17.

In some embodiments of the present invention, a germicidal UV lamp is a slimline germicidal UV lamp, examples of which are shown in FIG. 17.

In some embodiments of the present invention, a germicidal UV lamp is a high output germicidal UV lamp, examples of which are shown in FIG. 17.

In some embodiments of the present invention, a germicidal UV lamp is a cold cathode germicidal UV lamp, examples of which are shown in FIG. 17.

In some embodiments of the present invention, a germicidal UV lamp is an 18" single ended low pressure mercury lamp, e.g., as made commercially available by Steril-Aire.

5. Power Output and UV Intensity of Germicidal UV Light Sources

UV disinfection is a photochemical process. The effectiveness of UV-C is directly related to intensity and exposure time. Environmental factors, such as, air flow, humidity, airborne mechanical particles and distance of microorganism to the UV light source can also affect the performance of a UV device. While those environmental factors when present make it somewhat difficult to calculate the effective UV dosage required to kill or to inhibit the growth of a microorganism of interest, it has been shown that UV light will kill or inhibit the growth of any microorganism given enough UV dosage.

For UV disinfection and sterilization, the microorganisms present in a container or on a surface of a room, a space or defined environment are exposed to a lethal dose of UV energy. UV dose is measured as the product of UV light intensity times the exposure time within the UV lamp array. The microorganisms are exposed for a sufficient period of time to a germicidal UV light source in order for the UV rays to penetrate the cellular membrane and breaking down the microorganisms' genetic material. The following tables provide the approximate required intensities to kill or growth inhibit ("Kill Factor") either 90% or 100% of microorganisms (American Water & Air® Inc., Hilton Head Island, S.C. 29926, USA):

Table 1 provides the approximate required intensities to kill or growth inhibit ("Kill Factor") either 90% or 99% of mold spores (American Water & Air® Inc., Hilton Head Island, S.C. 29926, USA):

| | Energy Dosage of UV Radiation (UV Dose) in µWs/cm² Needed for Kill Factor | |
|---|---|---|
| Mold Spores | 90% (1 log Reduction) | 99%* (2 log Reduction) |
| *Aspergillius flavus* | 60,000 | 99,000 |
| *Aspergillius glaucus* | 44,000 | 88,000 |
| *Aspergillius niger* | 132,000 | 330,000 |
| *Mucor racemosus* A | 17,000 | 35,200 |
| *Mucor racemosus* B | 17,000 | 35,200 |
| *Oospora lactis* | 5,000 | 11,000 |
| *Penicillium expansum* | 13,000 | 22,000 |
| *Penicillium roqueforti* | 13,000 | 26,400 |
| *Penicillium digitatum* | 44,000 | 88,000 |
| *Rhisopus nigricans* | 111,000 | 220,000 |

*it is noted that American Ultraviolet Company (Lebanon, IN, USA) states that the energy dosage of UV radiation (UV Dose) shown above to kill 99% of the indicated mold spores, is sufficient to achieve a 100% kill factor of the indicated mold spores.

Table 2 provides the approximate required intensities to kill or growth inhibit ("Kill Factor") either 90% or 99% of bacteria (American Water & Air® Inc., Hilton Head Island, S.C. 29926, USA):

| | Energy Dosage of UV Radiation (UV Dose) in µWs/cm² Needed for Kill Factor | |
|---|---|---|
| Bacteria | 90% (1 log Reduction) | 99%* (2 log Reduction) |
| *Bacillus anthracis* - Anthrax | 4,520 | 8,700 |
| *Bacillus anthracis* spores - Anthrax spores | 24,320 | 46,200 |
| *Bacillus magaterium* sp. (spores) | 2,730 | 5,200 |
| *Bacillus magaterium* sp. (veg.) | 1,300 | 2,500 |
| *Bacillus paratyphusus* | 3,200 | 6,100 |
| *Bacillus subtilis* spores | 11,600 | 22,000 |
| *Bacillus subtilis* | 5,800 | 11,000 |
| *Clostridium tetani* | 13,000 | 22,000 |
| *Corynebacterium diphtheriae* | 3,370 | 6,510 |
| *Ebertelia typhosa* | 2,140 | 4,100 |
| *Escherichia coli* | 3,000 | 6,600 |
| *Leptospiracanicola* - infectious Jaundice | 3,150 | 6,000 |
| *Microccocus candidus* | 6,050 | 12,300 |
| *Microccocus sphaeroides* | 1,000 | 15,400 |
| *Mycobacterium tuberculosis* | 6,200 | 10,000 |
| *Neisseria catarrhalis* | 4,400 | 8,500 |
| *Phytomonas tumefaciens* | 4,400 | 8,000 |
| *Proteus vulgaris* | 3,000 | 6,600 |
| *Pseudomonas aeruginosa* | 5,500 | 10,500 |
| *Pseudomonas fluorescens* | 3,500 | 6,600 |
| *Salmonella enteritidis* | 4,000 | 7,600 |
| *Salmonela paratyphi* - Enteric fever | 3,200 | 6,100 |
| *Salmonella typhosa* - Typhoid fever | 2,150 | 4,100 |
| *Salmonella typhimurium* | 8,000 | 15,200 |
| *Sarcina lutea* | 19,700 | 26,400 |
| *Serratia marcescens* | 2,420 | 6,160 |
| *Shigella dyseteriae* - Dysentery | 2,200 | 4,200 |
| *Shigella flexneri* - Dysentery | 1,700 | 3,400 |
| *Shigella paradysenteriae* | 1,680 | 3,400 |
| *Spirillum rubrum* | 4,400 | 6,160 |
| *Staphylococcus albus* | 1,840 | 5,720 |
| *Staphylococcus aerius* | 2,600 | 6,600 |
| *Staphylococcus hemolyticus* | 2,160 | 5,500 |
| *Staphylococcus lactis* | 6,150 | 8,800 |
| *Streptococcus viridans* | 2,000 | 3,800 |
| *Vibrio comma* - Cholera | 3,375 | 6,500 |

*it is noted that American Ultraviolet Company (Lebanon, IN, USA) states that the energy dosage of UV radiation (UV Dose) shown above to kill 99% of the indicated microorganisms, is sufficient to achieve a 100% kill factor of the indicated microorganism.

Table 3 provides the approximate required intensities to kill or growth inhibit ("Kill Factor") either 90% or 99% of protozoa (American Water & Air® Inc., Hilton Head Island, S.C. 29926, USA):

| | Energy Dosage of UV Radiation (UV Dose) in µWs/cm² Needed for Kill Factor | |
|---|---|---|
| Protozoa | 90% (1 log Reduction) | 99%* (2 log Reduction) |
| *Chlorella vulgaris* (Algae) | 13,000 | 22,000 |
| Nematode Eggs | 45,000 | 92,000 |
| Paramecium | 11,000 | 20,000 |

*it is noted that American Ultraviolet Company (Lebanon, IN, USA) states that the energy dosage of UV radiation (UV Dose) shown above to kill 99% of the indicated protozoa, is sufficient to achieve a 100% kill factor of the indicated protozoa.

Table 4 provides the approximate required intensities to kill or growth inhibit ("Kill Factor") either 90% or 99% of viruses (American Water & Air® Inc., Hilton Head Island, S.C. 29926, USA):

| | Energy Dosage of UV Radiation (UV Dose) in µWs/cm² Needed for Kill Factor | |
|---|---|---|
| Virus | 90% (1 log Reduction) | 99%* (2 log Reduction) |
| Bacteriophage - *E. Coli* | 2,600 | 6,600 |
| Infectious Hepatitis | 5,800 | 8,000 |
| Influenza | 3,400 | 6,600 |
| Poliovirus - Poliomyelitis | 3,150 | 6,600 |
| Tobacco mosaic | 240,000 | 440,000 |

*it is noted that American Ultraviolet Company (Lebanon, IN, USA) states that the energy dosage of UV radiation (UV Dose) shown above to kill 99% of the indicated viruses, is sufficient to achieve a 100% kill factor of the indicated viruses.

Table 5 provides the approximate required intensities to kill or growth inhibit ("Kill Factor") either 90% or 99% of yeast (American Water & Air® Inc., Hilton Head Island, S.C. 29926, USA):

| | Energy Dosage of UV Radiation (UV Dose) in µWs/cm² Needed for Kill Factor | |
|---|---|---|
| Yeast | 90% (1 log Reduction) | 99% (2 log Reduction) |
| Brewers yeast | 3,300 | 6,600 |
| Common yeast cake | 6,000 | 13,200 |
| *Saccharomyces carevisiae* | 6,000 | 13,200 |
| *Saccharomyces ellipsoideus* | 6,000 | 13,200 |
| *Saccharomyces* spores | 8,000 | 17,600 |

*it is noted that American Ultraviolet Company (Lebanon, IN, USA) states that the energy dosage of UV radiation (UV Dose) shown above to kill 99% of the indicated yeast, is sufficient to achieve a 100% kill factor of the indicated yeast.

By way of example, using a germicidal UV lamp with 190 microwatts/cm² output at 254 nm, it would take approximately about 1 minute and 26 seconds to kill or growth inhibit ("Kill Factor") 100% of *Saccharomyces* sp. (which requires 17,600 microwatt/cm²) at a distance of 36" and 3 minutes 41 seconds at a distance of 60".

In some embodiments a UV lamp within a UV device has a polymer coating. The polymer coating will prevent small glass pieces from falling into a container in case of accidental shattering during use of a UV device in a method of the present invention.

B. Detector

The present invention describes a variety of UV devices. In some embodiments of the present invention, a UV device comprises a detector. In the drawings, showing exemplary embodiments, detectors are shown by 11. The use of a detector ensures that in addition to the algorithm (taking into account vessel size and shape, size and shape of a room, a space or defined environment, lamp intensity, distance of lamp or lamps from surfaces to be sterilized) a required or predetermined UV light intensity is achieved. Further, a detector ensures that all areas known to specifically accumulate microorganisms also receive the required or predetermined dose of UV radiation.

The use of a detector solves a significant problem existing using the chemical and ozone disinfection methods. When those methods are used, there is no established protocol for verifying the level of sterilization achieved. In contrast thereto, methods of the present invention comprising the use of a detector offers a unique, quick, and reliable means of providing verifiable levels of the sterilization achieved. As described herein, once set at a predetermined UV dose, the detector will shut of the UV lamp when this predetermined amount of UV radiation has been attained.

In some embodiments of the present invention, a UV light source is connected to one or more UV detectors. In some embodiments of the present invention, a germicidal light source is connected to one or more UV detectors. As shown in the exemplary UV devices in FIGS. 6, 7, 14, and 15, one or more detectors may be mounted to a different position within the UV assembly or onto a removable bracket.

A variety of commercially available detectors can be used. UV-C detectors commercially available include, e.g., a PMA2122 germicidal UV detector (Solar Light Company, Inc., Glenside, Pa. 19038, USA). Detectors, such as the PMA2122 Germicidal UV detector, provide fast and accurate irradiance measurements of the effective germicidal radiation. A UV producing lamp is monitored to insure that the microorganisms, such as bacteria, are receiving a desired dose of germicidal UV radiation. Using a detector, the UV lamps can also be monitored to get maximum life out of the lamp before replacement. A germicidal UV detector can also be used to insure that the proper lamp has been installed after replacement.

In some embodiments of the present invention, a germicidal light source is connected electrically to one or more UV detectors. In some embodiments, a UV detector is connected by wire to a radiation meter, which in turn can communicate via the wire with a UV lamp and instruct it to turn off, e.g., when a desired radiation level has been attained.

In some embodiments of the present invention, a germicidal light source is connected to one or more UV detectors via a signal.

In some embodiments, a detector is placed at a location within a container where microorganisms, which negatively impact production and flavor of an alcoholic beverage, a dairy product, a liquid dairy, a liquid dairy composition, or a dry dairy composition, are known to accumulate. In some embodiments, a detector is placed within a room, a space or defined environment.

In some embodiments of the present invention, the one or more UV detectors are placed in conjunction with a UV light source, preferably, a germicidal UV light source, so that the one or more detectors ensure that a desired UV intensity has been attained and/or maintained. In some embodiments, a detector is placed strategically in corners or on uneven surfaces of containers such as weld seams where microorganisms may accumulate.

In some embodiments, a detector is arranged so that it is both furthest away from the UV lamp and closest to the most uneven interior surface of a container (e.g., weld seam or a corner), a room, a space or defined environment. The purpose of the detector is to ensure that the required or predetermined UV dose is attained at a given interior location of a container, room, space or defined environment in order to achieve the desired log reduction of microorganisms. By placing a detector or more than one detector (i.e., at least two detectors) in one or more positions in the interior of the container or within a room, a space or defined environment to be sanitized, it will be ensured that the even surfaces and those closer to the UV lamp will receive more than sufficient UV radiation to achieve the desired log reduction of microorganisms and that the more problematic interior surfaces of a container (e.g., weld seams and corners) or uneven surfaces in a room, a space or defined environment will receive the required or predetermined UV dose.

In some embodiments of the present invention, a UV light source communicates back and forth with a detector so that the UV light source is shut off when a desired specified germicidal level of UV radiation has been attained. As will be appreciated by one of skill in the art, a desired specified germicidal level is dependent on the log reduction or percentage reduction of microorganisms desired. If sterilization is required, a six log reduction in microorganisms may be specified. In the interest of saving time and electricity, however, a five log reduction or a four-log reduction may be desired. Once the desired UV intensity has been attained, the detector will cause the UV light source to shut off.

One of skill in the art using a detector in combination with a UV device to sterilize a container, a room, a space or defined environment according to a method of the present invention would not need to know the diameter of the container or dimension of a room, a space or defined environment as the detector would automatically detect the appropriate UV dose necessary to achieve a predetermined sterilization rate (log reduction value).

The use of a detector, however, is optional. Detectors are not required to practice methods of the present invention provided that the timing of the sterilization cycle has been calculated correctly. Detectors can be used as a redundant system if the shape of the container and/or lamp does allow the skilled artisan to apply a simple programmable calculation of the sterilization cycle duration.

C. Housing

In some embodiments of the present invention, a UV device comprises a housing. Various housings for UV lamps are shown in the exemplary UV devices in FIGS. 1-13, 16, 21-25, 28-35, and 37 by 2. In some embodiments of the present invention, a germicidal UV light source is residing in a housing. In some embodiments of the present invention, a germicidal UV light source is positioned within a housing. In some embodiments of the present invention, the housing surrounds or encloses the germicidal UV light source. An exemplary surrounding or enclosure of a UV light source by a housing is shown in FIGS. 1-3, 7, 9, 21, 22, 23, 24, 25, 28, 29, 31, 34, 35, and 37. The surrounding or enclosure may be complete or partial. An exemplary complete surrounding or enclosure of a UV light source by a housing is shown in FIGS. 1-3, 21, 22, 23, 24, 25, 28, 29, and 31. An exemplary partial surrounding or enclosure of a UV light source by a housing is shown in FIGS. 7, 9, 34, 35, and 37. The housing is designed to protect the UV light source from damage during transport or when it is retracted from a container according to a method of the present invention. A UV light source can also be directly or indirectly attached to a housing.

The housing can be of a variety of materials. It can be made from a polymer (e.g., plastic) or metal depending on the desired weight. In some embodiments, a housing is made of DuPont Teflon®FEP (Fluorinated Ethylene Propylene).

The housing can have various shapes and forms. In some embodiments of the present invention, the housing is a mesh cage allowing the UV light to pass through. An exemplary mesh cage housing is shown in FIGS. 21-25. When using housings that allow passing through of the UV light, the UV light source does not need to be released from the housing to practice a method of the invention.

In some embodiments of the present invention, the housing is a housing which does not allow the UV light to pass through or which only allows the UV light to pass through partly. When using such a housing in the methods of the present invention, the UV light source is being released from a housing. Upon release of the germicidal UV light source from the housing, the germicidal UV light source may be stationary or mobile. The housing can be of any shape. The shape of the housing is largely depending on the size and shape of the UV light source (e.g., see FIGS. 1-13, 16, 21-25, and 27). FIGS. 21-25 show a UV lamp cluster (comprising 8 UV lamps) arranged at an angle and a correspondingly shaped housing. FIG. 27 shows five UV lamp clusters each comprising three UV lamps arranged at an angle and in a square or rectangular housing.

In some embodiments a single longitudinal UV lamp is used as a UV light source. In those embodiments, the housing may surround or enclose the UV lamp either completely or partially. In some embodiments, a housing comprises two arms, a first arm and a second arm, e.g., as schematically shown in FIGS. 34 and 35. The first arm may be positioned in a fixed position, while the second arm may be movably attached to the first arm. In some embodiments the second arm can reside completely or partially within the first arm. The movable attachment of the second arm to the first arm may be through a pivot point. In some embodiments, a UV lamp is attached to such housing through an opening in the second arm and further connected to a part of the UV device through a rope, string, or a power cord. In a configuration wherein the second arm resides within the first arm, the UV lamp would then reside within the second arm. The rope, string or power cord could also prevent the second arm of the housing from moving downwardly. Upon lowering the rope, string, or power cord, the UV lamp along with the second arm will be release from the first arm of the housing. The rope, string or power cord can be lowered to the point whereupon the second and first arm form a 90 degree angle (e.g., see FIG. 34B). Thereby the UV light source can be moved into almost any position within the confines of a container (FIG. 34B). As one of ordinary skill in the art will appreciate, such positioning depends on the length of the first arm, the length of the second arm and the angle formed between the first and second arm. The inventions contemplates various lengths of the first and second arms depending on the diameter and height of a container which should be sterilized. For example, if the diameter of a container is about 5 meters, then a second arm having a length of about 2.5 meters could position a UV device approximately in the middle of the container when the UV device is attached to an outer part on top of the container (see FIGS. 34B, 34C). The height positioning of a UV light source within a container can then be controlled conveniently by the extent to which the rope, string or power cord is further lowered (compare FIG. 34B to FIG. 34C). Lowering of the UV lamp can be achieved as described herein by use of a motorized unit (e.g., see FIGS. 34 and 35).

D. Guides, Range-Finding Devices, and Circuit Boards

In some embodiments of the present invention where the UV lamp is mobile, a UV device comprises a range-finding device or guide, such as a laser range finder. A range-finding device may be placed or aligned at some point along the longitudinal axis of the UV device in order to prevent the UV lamp(s) or UV device from contacting either the top or bottom surface of the container (depending on the embodiment the device may be suspended from the top of the container or supported from below by a mount). If the embodiment uses lateral movement to position the UV lamp(s) closer to the internal surface the container or to a predetermined position in a room, a space or defined environment, the rangefinder may be aligned in the same orientation ensuring that the UV lamp(s) is positioned at the desired distance depending on the internal diameter of the container or dimension of the room, space or defined environment. In some embodiments where the UV lamp is mobile, a range-finding device is used in conjunction with the system to guarantee that the UV lamp(s) is in correct distance from the interior surface of a container to be sterilized or the surface, walls or ceilings of a room, a space or defined environment to be sterilized as well as preventing the UV lamp from impacting the interior surfaces of the container, room, space or defined environment. Range-finding devices or guides are indicated by 20 in exemplary UV devices herein, e.g., in FIGS. 11, 12 and 35.

In some embodiments of the present invention, a range-finding device 20 is a radiofrequency identifier (RFID), which is used to position a UV light source to a desired or predetermined position within a container. An RFID receives information about the dimensions of a container to be sterilized, such as depth and radius of the container. An RFID may be attached to a UV device of the present invention. In some embodiments, an RFID is attached to the container to be sterilized.

For example, as described herein, an RFID determines the depth of moving a UV light source from its load position into its payout position. FIG. 35 schematically depicts a laser depth guide attached in proximity of a UV lamp.

FIG. 26 schematically shows a circuit board used in an embodiment of the present invention. FIG. 36 schematically shows a circuit board used in UV device UV55 described further herein. FIG. 28E schematically depicts the positioning of a circuit board 103 within a circuit board cavity 99 within a central sleeve 12.

E. Means for Attaching a UV Device

The UV devices described herein can be used to practice the methods described herein. A UV device of the present invention can be attached movably, adjustably, temporarily, or permanently to a container, surface of an object, floor, ceiling or wall of a room, a space or defined environment by using various attachment means, such as fasteners, screws, mounting tabs, etc. In some embodiments of the present invention, a UV device is positioned on top of a container 4, as e.g., schematically depicted in FIGS. 1-5, 10, 11, 25, 29. In some embodiments of the present invention, a UV device is positioned on the bottom of a container 4, as e.g., schematically depicted in FIGS. 6-9, 32, 33. In some embodiments of the present invention, a UV device is attached to a lid 29 of a container 4, as e.g., schematically depicted in FIGS. 14 and 15. In some embodiments of the present invention, a UV device is attached to a wall or ceiling, as e.g., schematically depicted in FIG. 27.

The UV devices described herein can be attached temporarily to a container, e.g., for the time required to perform a method described herein. The LTV devices described herein can also be attached to a container for a prolonged time, e.g., for the time required to perform a method described herein and an extended period of time before or after practicing the method. The UV devices described herein can also be attached permanently to a container.

In some embodiments of a UV device of the present invention, a UV device comprises a means for attaching the UV device to a container. This invention provides various means for attaching the UV device to a container, including, but not limited to a bracket, a hanger, and the like.

The means for attaching the UV device to a container essentially serves to attach the UV device on an outer perimeter of the opening of the container so that the LTV light source and other parts of the UV device necessary to perform a method of the present invention can be movably inserted through the opening of the container into the interior part of the container. In some embodiments of the present invention, the means for attaching the UV device to a container is a bracket, also referred to as mounting bracket. In some embodiments of the present invention, a housing is affixed to a bracket. In some embodiments, the bracket supports the housing in the desired position and allows the UV lamp to project and descend from the housing into the desired positions for the "sterilization cycle." In some embodiments, the bracket supports the housing centrally. In some embodiments, the bracket supports the housing asymmetrically. The bracket may be in the form of a base, tripod or stand if the device is to be supported from the bottom of the fermentation vessel. The arms of the bracket may be adjustable to accommodate containers of various diameters and dimensions. Exemplary bracket embodiments 3 are depicted in the exemplary UV devices shown in FIGS. 1-5, 10-12, and 33.

In some embodiments of the present invention, a means for attaching the UV device to a container is a hanger as shown, e.g., in FIGS. 21-25. A hanger may comprise one or more of the following: a clamp post 53, a hanger support bar 52, and a tightening screw 78. A preferred configuration of those parts is shown in FIGS. 21-24. A hanger can have any shape or size as long as it can be used to attached the UV device to the container to be sterilized, for example, FIGS. 21-24 schematically show an L-shaped hanger.

In some embodiments, the hanger is attached to a pulley mount arm 51 (FIGS. 21-24). In some embodiments, the hanger is attached to a telescopic arm pivot 73 (FIGS. 21-24).

In some embodiments of the present invention, the housing enclosing the UV lamp is attached to a UV impermissible lid or cover that is placed on top of the opening of a container so that the UV lamp can be moved downwards into the container through the housing (movement similarly as shown in FIGS. 1-3). In one embodiment, as the UV lamp is retracted, the impermissible lid descends via gravity. A person standing close by will not be exposed to UV irradiation but rather be shielded from irradiation because of the UV impermissible lid or cover.

FIG. 27 shows a UV device that can be mounted to a surface, wall, floor or ceiling of a room, a space or defined environment. Preferably the device shown in FIG. 27 is mounted to the ceiling of a room.

F. Optical Components

To increase the UV intensity over a reduced area, to focus the UV intensity, or to control the UV intensity, in some embodiments of the present invention, a UV device of the present invention comprises an optical component. Optical components include, but are not limited to, a reflector, a shutter, a lens, a splitter, a mirror, and the like. The optical component may be of any shape. In some embodiments of the present invention, a UV device comprises a reflector. A reflector can have a variety of configurations. In some embodiments, the reflector is a parabolic reflector. In some embodiments, the reflector is an elliptical reflector. In some embodiments, the reflector is a circular reflector. Exemplary embodiments comprising a reflector are depicted in the exemplary UV devices shown in FIGS. 12-14 and 37.

Reflectors are generally provided by the manufacturer of UV light sources. For example, reflectors of circular, elliptical and parabolic cross sections can be purchased from Hill Technical Sales Corp (Arlington Heights, Ill., USA). Exemplary reflectors are schematically shown in FIG. 18.

UV devices comprising a reflector are schematically shown in FIGS. 14 and 37. However, as one of ordinary skill in the art will appreciate, a reflector can be configured into other UV devices described herein. In the exemplary UV device schematically shown in FIG. 37, the UV device comprises a UV lamp cluster having eight UV lamps arranged in a circular arrangement, wherein each reflector partially surrounds a UV lamp. Other suitable UV lamp clusters are described herein. UV lamps and reflectors may be attached to a housing as schematically depicted in FIG. 37C. In some embodiments, reflectors individually and partially surrounding a UV lamp may form a continuous reflecting wall as schematically depicted in FIG. 37B. Such a reflecting wall may be connected to a central sleeve.

The UV device schematically shown in FIG. 37 can be inserted through an opening of a container, e.g., an opening located on top of a container so that the reflectors and UV lamps move inwardly into the container and the housing rests on the opening of the lid while the sterilization cycle is being performed. In some embodiments, the UV lamp cluster of such device is arranged so that it can be moved through the opening of the container, while the diameter of the housing of the UV device is larger than the diameter of the opening of the container so that the UV device can be positioned on top of the container opening. In some embodiments, both the housing and the UV lamp cluster can be moved through an opening of a container. In such embodiment, the housing is attached to a cover (or plate) which has a larger diameter than the housing and the UV lamp cluster and the housing is attached to the cover (or plate) through a cable, which can be extended so that both the housing and UV lamp cluster can move further downwards into the container upon release of the cable. The cover then remains positioned on top of the container opening. The cover (or plate) can have various shapes, such as round, oval, square, rectangular, hexagonal, etc. A handle attached to such cover (or plate) conveniently allows the user to place the UV device onto an opening of a container.

In some embodiments of the present invention, the UV device schematically shown in FIG. 37 is inserted inwardly into a container from an opening located at the bottom or side of a container (e.g., see FIGS. 31-33).

G. Additional Components of a UV Device

FIGS. 1-37 show exemplary embodiments of exemplary UV devices of the present invention and uses thereof. Those figures also show additional components of UV devices of the present invention, their positioning and how those components are connected to a container, a UV lamp, a UV detector, a frame, a bracket, a housing, and a range-finding device, which are described in detail above. As one of ordinary skill in the art will appreciate individual components described herein can be combined in various ways in a UV device for a use described herein.

In some embodiments of the present invention, a UV device comprises a motorized unit (indicated by 1 in the figures). In some embodiments of the present invention, a UV device comprises a second motor unit (indicated by 23 in the figures; different from the motorized unit "1"). A motorized unit can provide various functions, including, but not limited to positioning a UV lamp within a container. A motorized unit may move a UV lamp within a container to a horizontal position, a vertical position or combination of both. As one of ordinary skill in the art will appreciate the moving of a UV lamp within a container depends on parameters, such as size and power of a UV lamp, diameter and height of a container and areas within the container a practitioner desires to sterilize as described herein.

In some embodiments of the present invention, a UV device comprises a cable or rigid rod (indicated by 7 in the figures). A cable or rigid rod is also useful for the positioning of a UV lamp within a container. For example, as schematically depicted in FIGS. 4 and 5, a cable 7 is used to lower the UV lamps 5 of the UV devices shown inwardly into the container 4. In some embodiments, a cable 7 is a power cord 90 as, e.g., schematically shown in FIGS. 34 and 35.

In some embodiments of the present invention, a UV device comprises a base plate (indicated by 10 in the figures). A base plate can have many different shapes and configurations as schematically depicted in the figures herein. A function of a base plate is to allow the UV device be positioned onto or into a container or allow the UV device be attached to a container (although attachment of a UV device to a container can also be done by other means as described herein). Exemplary embodiments of base plates are schematically depicted in FIGS. 6, 7, 28, 29, 31-33, and 35. The base plate 10 of the UV device embodiments shown in those figures allows the UV device to stand upright on a surface, e.g., within a container (see, FIGS. 7, 32, 33), on top of a container (see FIGS. 28 and 29) or on a floor and the container is slided onto the UV device (see FIG. 31). The base plate 10 of the UV device shown in FIGS. 28 and 29, is partially circular and has a straight part allowing the UV device to be positioned vertically on a surface (e.g., when servicing it) without rolling away. The base plate 10 of the exemplary UV device embodiments depicted in FIGS. 31 and 32 has a tripod-like configuration. The base plate 10 of the exemplary UV device embodiment depicted in FIG. 35 is round. It can be oval, rectangular, hexagonal, etc. as well.

In some embodiments of the present invention, a UV device comprises a central sleeve (indicated by 12 in the figures). A central sleeve can have various configurations and shapes. Typically, the central sleeve 12 is round. A central sleeve can have various configurations and can be connected to other components of a UV device in various ways. For example, as shown in FIG. 7, a central sleeve 12 is connected to a housing 2. In some embodiments, a central sleeve 12 can slide over a housing 2. As depicted exemplary in FIG. 8, more than one housing 2 can be attached to a central sleeve 12. Attachment of the housings 2 to the central sleeve can be direct or indirect. For example, as depicted in FIG. 9, the housings 2 are attached to a central sleeve 12 via parallelogramming arms 17. Various components of a UV device can be attached directly or indirectly to a central sleeve 12 as shown in figures. For example, as depicted in FIGS. 28 and 29, a central sleeve 12 is movably attached to a housing 2. In some embodiments of the present invention (see e.g., FIGS. 28, 29, 37), a UV lamp 5 is attached to a central sleeve 12. The attachment of a UV lamp 5 to a central sleeve 12 may be achieved via pins 93 and a UV lamp socket or adaptor 94. The device depicted in FIGS. 28 and 29, referred to as UV55, is described in more detail below.

In some embodiments of the present invention, a UV device comprises one or more connecting rods (indicated by 13 in the figures).

In some embodiments of the present invention, a UV device comprises a motorized sleeve (indicated by 14 in the figures), In some embodiments of the present invention, a UV device comprises an adjustable bracket (indicated by 15 in the figures).

In some embodiments of the present invention, a UV device comprises a central post (indicated by 16 in the figures). In some embodiments of the present invention, the central post 16 is a scissor boom. In some embodiments of the present invention, the central post 16 is a central bar 44. In some embodiments of the present invention the central post 16 is surrounded by a central sleeve 12.

In some embodiments of the present invention, a UV device comprises parallelogramming arms (indicated by 17 in the figures).

In some embodiments of the present invention, a UV device comprises an arm (indicated by 18 in the figures; distinguished from "17").

In some embodiments of the present invention, a LTV device comprises a track on the arm (indicated by 19 in the figures).

In some embodiments of the present invention, a UV device comprises an "adjustable bracket" or "mounting frame" (indicated by 24 in the figures).

In some embodiments of the present invention, a UV device comprises a track on a central post (indicated by 25 in the figures).

In some embodiments of the present invention, a UV device comprises a removable bracket (indicated by 31 in the figures).

In some embodiments of the present invention, a LTV device comprises a reflector (indicated by 32 in the figures).

In some embodiments of the present invention, a UV device comprises one or more nylon blocks (indicated by 33 in the figures).

In some embodiments of the present invention, a UV device comprises a post or boss (indicated by 34 in the figures).

In some embodiments of the present invention, a UV device comprises a hanging hook (indicated by 84 in the figures). A hanging hook provides a convenient way of storing a UV device when not in use, by e.g., hanging it on hook. A hanging hook can be attached to a UV device at various locations. Form, shape, positioning and function of an exemplary hanging hook 84 are described in detail in the UV device embodiment UV55 (see FIGS. 28 and 29 and below).

In some embodiments of the present invention, a UV device comprises an on/off or reset button (indicated by 85 in the figures). As one of ordinary skill in the art an on/off or reset button provides for the activation of the UV device. An on/off or reset button can be attached to a UV device at various locations. Form, shape, positioning and function of an exemplary on/off or reset button 85 are described in detail in the UV device embodiment UV55 (see FIGS. 28 and 29 and below).

In some embodiments of the present invention, a UV device comprises a central sleeve tightening knob (indicated by 86 in the figures). A central sleeve tightening knob, for example, allows the precise sliding of a central sleeve 12 into a housing 2 or onto a housing 2. Typically, a central sleeve tightening knob is tightened by a person to maintain a central sleeve in a predetermined position. It is loosened by a person to allow the central sleeve to be moved from a first position to a second position. In the exemplary UV device embodiment UV55 (see below) and others, movement of the central sleeve can be upwardly or downwardly. A central sleeve tightening knob can be attached to a UV device at various locations. Form, shape, positioning and function of an exemplary central sleeve tightening knob 86 are described in detail in the UV device embodiment UV55 (see FIGS. 28 and 29 and below).

In some embodiments of the present invention, a UV device comprises a translucent plastic ring (indicated by 87 in the figures). In some embodiments of the present invention, a plurality of LED lights are located behind the translucent plastic ring. Upon activation of the LED light, the light can be seen through the translucent plastic ring. The appearance of a light signal may indicate to a user of the UV device the time of use of the UV device to perform the sterilization of a container, the termination of a sterilization cycle, etc. A translucent plastic ring can be attached to a UV device at various locations. Form, shape, positioning and function of an exemplary translucent plastic ring 87 are described in detail in the UV device embodiment UV55 (see FIGS. 28 and 29 and below).

In some embodiments of the present invention, a UV device comprises a stopping plate (indicated by 88 in the figures). A stopping plate can be attached to a UV device at various locations. Form, shape, positioning and function of an exemplary stopping plate 88 are described in detail in the UV device embodiment UV55 (see FIGS. 28 and 29 and below).

In some embodiments of the present invention, a UV device comprises a metal disc (indicated by 89 in the figures). A metal disc can be attached to a UV device at various locations. Form, shape, positioning and function of an exemplary metal disc 89 are described in detail in the UV device embodiment UV55 (see FIGS. 28 and 29 and below).

In some embodiments of the present invention, a UV device comprises a power cord (indicated by 90 in the figures). A power cord can be attached to a UV device at various locations. Form, shape, positioning and function of an exemplary power cord 90 are described in detail in the UV device embodiment UV55 (see FIGS. 28 and 29 and below).

In some embodiments of the present invention, a UV device comprises a handle (indicated by 91 in the figures). A handle provides for the convenient transport of a UV device by a user. A handle can be part of a central sleeve 12, such as an extension of a central sleeve 12. The handle may be of a different thickness than the central sleeve. The handle and the central sleeve can be made of the same material. A preferred material is a plastic. A preferred plastic is Delrin. A handle can be attached to a UV device at various locations. Form, shape, positioning and function of an exemplary handle 91 are described in detail in the UV device embodiment UV55 (see FIGS. 28 and 29 and below) and in FIG. 37.

In some embodiments of the present invention, a UV device comprises a handle cap (indicated by 92 in the figures). A handle cap is attached to a handle 91. In some embodiments of the present invention, a handle cap houses an acoustic speaker. Thus, in some embodiments of the present invention, a UV device comprises an acoustic speaker. A handle cap can be attached to a UV device at various locations. Form, shape, positioning and function of an exemplary handle cap 92 are described in detail in the UV device embodiment UV55 (see FIGS. 28 and 29 and below).

In some embodiments of the present invention, a UV device comprises one or more pins for attaching a UV lamp 5 to a UV lamp socket or adaptor 94 (indicated by 93 in the figures). Pins can be attached to a UV lamp 5 at various locations, preferably at an end of a UV lamp 5. Form, shape, positioning and function of exemplary pins 93 are described in detail in the UV device embodiment UV55 (see FIGS. 28 and 29 and below).

In some embodiments of the present invention, a UV device comprises one or more UV lamp sockets or adaptors (indicated by 94 in the figures). A UV lamp socket or adaptor 94 attaches a UV lamp 5 to a UV device, preferably through pins 93. A UV lamp socket or adaptor can be attached to a UV device at various locations. Typically, each UV lamp 5 is attached to a UV lamp socket or adaptor 94. Form, shape, positioning and function of an exemplary UV lamp socket or adaptor 94 are described in detail in the UV device embodiment UV55 (see FIGS. 28 and 29 and below).

In some embodiments of the present invention, a UV device comprises a metal sleeve attachment ring (indicated by 95 in the figures). A metal sleeve attachment ring can be attached to a UV device at various locations. For example, it can be attached to a housing 2. Form, shape, positioning and function of an exemplary metal sleeve attachment ring 95 are described in detail in the UV device embodiment UV55 (see FIGS. 28 and 29 and below).

In some embodiments of the present invention, a UV device comprises a power supply of UV lamp ballast (indicated by 96 in the figures). A power supply 96 can be attached to a UV device at various locations. Preferably, a power supply is not visible from the outside of a UV device and housed in an inner compartment or cavity within the UV device. A preferred cavity for housing a power supply 96 is a power supply cavity 100. Typically, the power supply cavity is covered by a power supply access plate 97 so that the power supply is not visible from the outside. Form, shape, positioning and function of an exemplary power supply 96 are described in detail in the UV device embodiment UV55 (see FIGS. 28 and 29 and below).

In some embodiments of the present invention, a UV device comprises a power supply access plate (indicated by 97 in the figures). A power supply access plate 97 can be attached to a UV device at various locations. A power supply access plate covers a power supply, which is housed in an inner compartment or cavity within the UV device. A power supply cavity access plate may be screwed to a UV device with one or more screws. Form, shape, positioning and function of an exemplary power supply access plate 97 are described in detail in the UV device embodiment UV55 (see FIGS. 28 and 29 and below).

In some embodiments of the present invention, a UV device comprises an optical switch (indicated by 98 in the figures). An optical switch, also referred to as cycle time count reset sensor, can be attached to a UV device at various locations. Form, shape, positioning and function of an exemplary optical switch 98 are described in detail in the UV device embodiment UV55 (see FIGS. 28 and 29 and below).

As described herein, in some embodiments of the present invention, a UV device comprises a circuit board (indicated by 103 in the figures; see also FIG. 26). A circuit board 103 can be attached to a UV device at various locations. Preferably, a circuit board is not visible from the outside of a UV device and housed in an inner compartment or cavity within the UV device. A preferred cavity for housing a circuit board 103 is a circuit board cavity 99. Typically, the circuit board cavity is covered by a plate. Conveniently, a power supply access plate 97 may also cover the circuit board so that the circuit board is not visible from the outside. Form, shape, positioning and function of an exemplary circuit board 103 and circuit board cavity 99 are described in detail in the UV device embodiment UV55 (see FIGS. 28 and 29 and below).

In some embodiments of the present invention, a UV device comprises an AC to DC power converter (indicated by 101 in the figures). An AC to DC power converter can be attached to a UV device at various locations. Form, shape, positioning and function of an exemplary AC to DC power converter 101 are described in detail in the UV device embodiment UV55 (see FIGS. 28 and 29 and below).

In some embodiments of the present invention, a UV device comprises an electronic component (indicated by 102 in the figures). An AC to DC power converter can be attached to a UV device at various locations. Form, shape, positioning and function of an exemplary electronic component 102 are described in detail in the UV device embodiment UV55 (see FIGS. 28 and 29 and below).

In some embodiments of the present invention, a UV device comprises one or more connectors or wires (indicated by 104 in the figures) to connect to e.g., an LED, an optical switch, or an acoustic speaker. Connectors and wires 104 can be attached to a UV device at various locations. Form, shape, positioning and function of an exemplary connectors and wires 104 are described in detail in the UV device embodiment UV55 (see FIGS. 28 and 29 and below).

In some embodiments of the present invention, a UV device comprises one or more connectors or wires (indicated by 105 in the figures) to connect to a UV light source, such as a UV lamp 5. Connectors and wires 105 can be attached to a UV device at various locations. Form, shape, positioning and function of an exemplary connectors and wires 105 are described in detail in the UV device embodiment UV55 (see FIGS. 28 and 29 and below).

In some embodiments of the present invention, a UV device comprises one or more connectors or wires (indicated by 106 in the figures) to connect to the power supply 96. Connectors and wires 106 can be attached to a UV device at various locations. Form, shape, positioning and function of an exemplary connectors and wires 106 are described in detail in the UV device embodiment UV55 (see FIGS. 28 and 29 and below).

In some embodiments of the present invention, a UV device comprises an anchor (indicated by 107 in the figures). An anchor 107 can be attached to a UV device at various locations. Form, shape, positioning and function of an exemplary anchor 107 are described in detail in the UV device embodiment depicted in FIG. 30 and below.

In some embodiments of the present invention, a UV device comprises an anchor line (indicated by 108 in the figures). An anchor line 108 can be attached to a UV device at various locations. Form, shape, positioning and function of an exemplary anchor line 108 are described in detail in the UV device embodiment depicted in FIG. 30 and below.

In some embodiments of the present invention, a UV device comprises an anchor connector (indicated by 109 in the figures). An anchor connector 109 can be attached to a UV device at various locations. Form, shape, positioning and function of an exemplary anchor connector 109 are described in detail in the UV device embodiment depicted in FIG. 30 and below.

In some embodiments of the present invention, a container comprises manhole or port (indicated by 77 in the figures). A manhole or port 77 can be attached to a container at various locations, preferably at a position close to the periphery of the upper part of the container.

In some embodiments of the present invention, a UV device comprises a UV lamp cluster line (indicated by 111 in the figures). A UV lamp cluster line 111 can be attached to a UV device at various locations. Form, shape, positioning and function of an exemplary UV lamp cluster line 111 are described in detail in the UV device embodiment depicted in FIG. 30 and below.

In some embodiments of the present invention, a UV device comprises a twist lock (indicated by 116 in the figures). A twist lock 116 can be attached to a UV device at various locations. Form, shape, positioning and function of an exemplary twist lock 116 are described in detail in the UV device embodiment depicted in FIG. 34 and below.

In some embodiments of the present invention, a UV device comprises an interface (indicated by 117 in the figures). An interface, e.g., permits a user to activate a UV device, by e.g., pushing a start button. An interface, e.g., permits a user to inactivate a UV device, by e.g., pushing a stop button. An interface, e.g., permits a user to set the time it takes to perform a sterilization cycle. An interface, e.g., permits a user to read the time remaining to complete a sterilization cycle. An interface 117 can be attached to a UV device at various locations. Form, shape, positioning and function of an exemplary interface 117 are described in detail in the UV device embodiment depicted in FIG. 34 and below.

Some UV devices of the present invention comprise an easily accessible control box with an on-off switch to activate and shut off (deactivate) the UV lamps. Further, UV devices comprise circuitry for activating and shutting off (deactivating) the UV lamps. The control box may include a lamp indicator light to show whether power is being sent to the UV device.

H. Positioning of a UV Light Source

As will be appreciated by one of ordinary skill in the art, the positioning of a UV light source at a desired or predetermined position for the UV sterilization of a container will be determined by e.g., the shape and volume (dimension) of the vessel, steel type used, and the shape, size and power output of the UV light source. Given the guidance provided herein, one of ordinary kill in the art will be able to properly position one or more UV lamps to achieve the desired killing or growth inhibition of one or more microorganisms using a method of the invention.

In some embodiments of the present invention, a UV light source is suspended from a removable lid of a container of various dimensions.

In other embodiments of the present invention, a UV light source is suspended from a fixed or hinged lid of a container of various dimensions.

In some embodiments of the present invention, the UV device is portable. A portable UV device can be transported between different vessels, vats and facilities.

In some embodiments of the present invention, e.g., when a UV device is used to sterilize a rather large container, the UV light source may be moved within the container from a first position to a second position and from a second position to a third position. This is demonstrated, for example in FIGS. 21 to 25, showing a UV device in various positions and configurations, e.g., folded position (FIG. 21), load position (FIG. 22), payout position or first vertical downwards position (FIG. 23), horizontal position (FIG. 24), and lamp down position or second vertical downwards position (FIG. 25). For example, as shown in FIG. 25 (and others) the UV light source is positioned in the approximate middle of a container to practice a method of the invention.

As will be appreciated by one of ordinary skill in the art, the positioning of a UV light source at a desired or predetermined position for the UV sterilization of a room, a space or defined environment will be determined by, e.g., the shape and dimension of the room, space or defined environment to be sanitized, and the shape, size and power output of the UV light source. Given the guidance provided herein, one of ordinary kill in the art will be able to properly position one or more UV lamps to achieve the desired killing or growth inhibition of one or more microorganisms using a method of the invention.

In some embodiments of the present invention, a UV light source is suspended from a the ceiling of a room of various dimensions. In other embodiments of the present invention, a UV light source is suspended from a fixed or hinged connecting part within a housing of various dimensions. An exemplary embodiment is shown in FIG. 27.

In some embodiments of the present invention, the UV device is portable. A portable UV device can be transported between different rooms, spaces and defined environments.

In some embodiments of the present invention, e.g., when a UV device is used to sterilize a rather large room, space or defined environment, the UV light source may be moved within the room, space or defined environment from a first position to a second position and from a second position to a third position.

I. Multiple UV Lamps

For use in the methods of the present invention, UV light sources, also referred to herein as UV lamps, can be configured in a variety of ways in a UV device. The configuration of one or more UV lamps within a UV device is referred to herein also as a UV lamp assembly or UV lamp cluster. In some embodiments of the present invention more than one UV lamp is used for the sterilization of a container, a room, a space or defined environment. Multiple UV lamps can be clustered together or spaced apart either symmetrically or asymmetrically in order to achieve the desired reduction in microorganisms in a timely and efficient manner For example, FIGS. 2 and 3 depict embodiments of the present invention where the UV assembly consists of a single UV lamp. FIG. 4 depicts an embodiment of the present invention showing a UV lamp assembly having four UV lamps. FIG. 5 depicts an embodiment of the present invention showing a UV lamp assembly having eight UV lamps arranged in an octagonal configuration. In addition, as depicted in FIG. 5, an additional UV lamp may be attached to a support plate. Those UV lamps are typically mounted to a frame 6, as shown, e.g., in FIGS. 4, 5, 14, 15 and 21-25. FIGS. 21-25 depict an embodiment of the present invention showing eight UV lamps attached to a frame 3 and an upper plate 42. Alternatively, those UV lamps are attached to or enclosed in a housing 2, as shown, e.g., in FIGS. 2, 3, 6-13, 16, and 21-25. When more than one UV lamp is used in an UV assembly or in a method of the present invention, each UV lamp may be the same or different.

In some embodiments of the present invention a UV device comprises more than one UV lamp. In some embodiments, at least two UV lamps are clustered together. In some embodiments, at least three UV lamps are clustered together. In some embodiments, at least four UV lamps are clustered together. In some embodiments, four UV lamps are clustered together. In some embodiments, five UV lamps are clustered together. In some embodiments, six UV lamps are clustered together. In some embodiments, seven UV lamps are clustered together. In some embodiments, eight UV lamps are clustered together. The clustering of the lamps may be at perpendicular angles as shown in FIG. 4 or at any other angle. The more than one UV lamps in a UV lamp cluster can be positioned to each other at various angles ranging from about 5 to about 45 degree, preferably from about 10 to about 30 degree, more preferably from about 15 to about 20 degree. In some embodiments of the present invention, the more than two UV lamps are positioned to each other in an about 5 degree angle. In some embodiments of the present invention, the more than two UV lamps are positioned to each other in an about 10 degree angle. In some embodiments of the present invention, the more than two UV lamps are positioned to each other in an about 15 degree angle. In some embodiments of the present invention, the more than two UV lamps are positioned to each other in an about 20 degree angle. In some embodiments of the present invention, the more than two UV lamps are positioned to each other in an about 25 degree angle.

In some embodiments, more than one UV lamp is attached to a bracket. In some embodiments, at least two UV lamps are attached to a bracket. In some embodiments, at least three UV lamps are attached to a bracket. In some embodiments, at least four UV lamps are attached to a bracket. In some embodiments, four UV lamps are attached to a bracket. In some embodiments, five UV lamps are attached to a bracket. In some embodiments, six UV lamps are attached to a bracket. In some embodiments, seven UV lamps are attached to a bracket. In some embodiments, eight UV lamps are attached to a bracket. The UV lamps may be attached to a means for attaching the UV device to a container, e.g., a bracket as shown in FIGS. 1-5, and 10-15, which typically, but not always, comprises mounting the UV lamp to a housing or frame and mounting the housing or frame to the bracket. Other embodiments for attaching a UV light source, such as a UV lamp cluster, to a means for attaching the UV device to a container, are shown in FIGS. 21-25.

In some embodiments, more than one UV lamp is attached to a frame. In some embodiments, at least two UV lamps are attached to a frame. In some embodiments, at least three UV lamps are attached to a frame. In some embodiments, at least four UV lamps are attached to a frame. Four UV lamps may be attached to a frame as shown exemplary in FIGS. 4-9, 12, and 15. In some embodiments, at least five UV lamps are attached to a frame. In some embodiments, at least six UV lamps are attached to a frame. In some embodiments, at least seven UV lamps are attached to a frame. In some embodiments, at least eight UV lamps are attached to a frame. Eight UV lamps may be attached to a frame as shown exemplary in FIGS. 5, 13, and 21-25. In the embodiments shown in FIGS. 21-25, the UV lamps are also attached to an upper plate 42.

In some embodiments, more than one UV lamp is attached to a housing. In some embodiments, at least two UV lamps are attached to a housing. In some embodiments, at least three UV lamps are attached to a housing. In some embodiments, at least four UV lamps are attached to a housing. In some embodiments, at least five UV lamps are attached to a housing. In some embodiments, at least six UV lamps are attached to a housing. In some embodiments, at least seven UV lamps are attached to a housing. In some embodiments, at least eight UV lamps are attached to a housing. FIG. 27 depicts an embodiment of the present invention where a UV assemble comprises 15 UV lamps, arranged in five UV lamp clusters each having three UV lamps and of which one UV lamp cluster is stationary and four UV lamp clusters are movable. In this embodiment, a light box 79, comprising a back wall 80 for mounting to the ceiling of a room is considered an equivalent of a housing 2. FIG. 27 depicts a UV device mountable to a ceiling or wall of a room, a space or defined environment.

J. UV Lamp Cluster

In some embodiments of the present invention, a UV lamp is configured into a UV lamp cluster. Increasing the number of UV lamps increases the intensity of UV light emitted throughout the tank or container. For packaging purposes, multiple short UV lamps are preferable to fewer long UV lamps. The increased UV intensity decreases the time necessary for sterilization or sanitization.

Exemplary UV lamp clusters of a UV device are shown in FIGS. 2-25, 27, 30, 32, 33, and 37. While FIG. 20 shows that the UV lamps are not in a housing, in some embodiments UV lamps may be in a protective housing (e.g., FIGS. 21-25, and 27, 28-35, and 37). UV lamps assembled into a UV lamp cluster may be spring loaded. As they emerge from the housing, they spring out to a relatively optimal angle of 15 degrees. Other preferred angles are 10 degrees, 11 degrees, 12 degrees, 13 degrees, 14 degrees, 16 degrees, 17 degrees, 18 degrees, 19 degrees, and 20 degrees. These angles are preferred as they allow for good UV coverage on both horizontal and vertical surfaces of a container.

In some embodiments of the present invention, UV lamp clusters can move out of a housing due to being attached via a hinge mechanism, i.e., wherein the UV device comprises, for example, a hinge or a UV lamp module swing 81, allowing the so attached UV lamps/UV lamp cluster to move from a closed position (e.g., when not in use) into an exposed position (i.e., for sanitization). An exemplary embodiment of such a UV device is shown in FIG. 27.

In some embodiments, a UV lamp cluster is lowered into a container on a rope.

K. Scissor Boom

In some embodiments of a UV device of the present invention, the UV device comprises one or more means for moving a UV light source to a predetermined position, typically to a predetermined position within a container, a room, a space or defined environment. A means for moving the UV light source can be a means for moving the UV light source to vertical downwards position in a container, room, space or defined environment. Another means for moving the UV light source can be a means for moving the UV light source to a horizontal position in a container, a room, a space or defined environment. In some embodiments of the present invention, a UV device comprises more than one means for moving a UV light source to a predetermined position within a container, a room, a space or defined environment. For example, a UV device may comprise a means for moving the UV light source to a first vertical downwards position within a container, a room, a space or defined environment. The UV device may also comprise a means for moving the UV light source from the first vertical position to a horizontal position within a container, a room, a space or defined environment. The UV device may also comprise a means for moving the UV light source from the horizontal position to a second vertical downwards position within a container, a room, a space or defined environment.

In some embodiments of the present invention, a UV device comprises a means for moving a UV light source to a predetermined position within a container, a room, a space or defined environment and is referred to as a scissor boom.

A scissor boom comprises a first end and a second end. The first end is also referred to as inner end, and the second end is also referred to as outer end.

In some embodiments, the scissor boom comprises at least one scissor unit between its first end and second end. In some embodiments, the scissor boom comprises at least two scissor units between its first end and second end. In some embodiments, the scissor boom comprises at least three scissor units between its first end and second end. In some embodiments, the scissor boom comprises at least four scissor units between its first end and second end. In some embodiments, the scissor boom comprises at least five scissor units between its first end and second end. In some embodiments, the scissor boom comprises at least ten scissor units between its first end and second end. A scissor unit can be made from any material. A preferred scissor bracket is a metal bracket. In some embodiments, a metal bracket is an aluminum bracket. Aluminum brackets are particularly preferred based on low cost and low weight. Preferred are also carbon fiber brackets. The scissor units are connected to each other by pivots. The pivots allow the horizontal extension of the scissor boom units.

The dimensions of a scissor boom for use in the methods of the present invention are not limited. A scissor boom may have various dimensions and may extend for several feet. A non-limiting scissor boom constructed by the Applicant measures about 10" by 10" by 50" in its retracted position and can extend over 15 feet.

In some embodiments of the present invention, an actuator unit is mounted to the first end of the scissor boom. An exemplary, non-limiting, embodiment of a linear actuator 37 is shown in FIG. 19. An actuator of the present invention operates by conversion of a rotary motion into a linear motion. An actuator extends the scissor boom and the extent of the expansion is determined by a sensor.

In some embodiments, a UV lamp 5 is mounted to the second end of the scissor boom. In some embodiments of this UV device, the UV lamp 5 is housed in a housing (e.g., FIG. 19). In some embodiments, a UV lamp cluster 41 (i.e., more than one UV lamp) is mounted to the second end of the scissor boom. In some embodiments of the present invention, a UV lamp cluster comprises at least two germicidal UV light sources. In some embodiments of the present invention, a UV lamp cluster comprises at least three germicidal UV light sources. In some embodiments of the present invention, a UV lamp cluster comprises at least four germicidal UV light sources. In some embodiments of the present invention, a UV lamp cluster comprises at least five germicidal UV light sources. In some embodiments of the present invention, a UV lamp cluster comprises two germicidal UV light sources. In some embodiments of the present invention, a UV lamp cluster comprises three germicidal UV light sources. In some embodiments of the present invention, a UV lamp cluster comprises four germicidal UV light sources. In some embodiments of the present invention, a UV lamp cluster comprises five germicidal UV light sources.

In some embodiments of this UV device, the UV lamp cluster 41 is housed in a UV lamp cluster housing 36 (FIG. 19). In some embodiments, the first end of the scissor boom is attached to an additional bracket mounted to a container (e.g., an adjusting bracket 24 as shown in FIG. 10) so that the scissor boom can be moved up and down via sliding rails 39 located at the inner end of the scissor boom (FIG. 19).

A scissor boom of the present invention can move (a) horizontally from an interior position of a container (i.e., from its folded position, FIG. 19A) towards the inner wall of the container (i.e., into its extended position, FIG. 19B) via slide rail 40, (b) vertically along sliding rails 39 in an up and down movement, and (c) in a circular motion when the scissor boom is fixed at a desired vertical position in the container and in its extended position. In the embodiments where the UV lamp(s) are within a housing, upon reaching the desired position, the UV lamp(s) are released and the housing is removed.

L. UV Lamp Cluster Assembly Combined with Scissor Boom

In some embodiments, a UV device of the present invention comprises a UV lamp cluster and a scissor boom. In some embodiments, a UV lamp cluster comprise three UV lamps. In some embodiments, a UV lamp cluster comprise four UV lamps. In some embodiments, a UV lamp cluster comprise five UV lamps. The function of the scissor boom mechanism is to move the UV lamps horizontally across the top of a container and position the UV lamps to the central axis of the container. A linear actuator (37 in FIG. 19) pushes the scissor mechanism up and down a slide rail (39 in FIG. 19) allowing the length of the scissor to be varied according to the diameter of the container. Slide rails (40 in FIG. 19) on the second side of the scissor boom allow the system to expand and contract in length. Once in place, the UV lamp cluster is dropped from its housing, if present (36, in FIG. 19), and lowered down the central axis of the container.

Figure 19B:
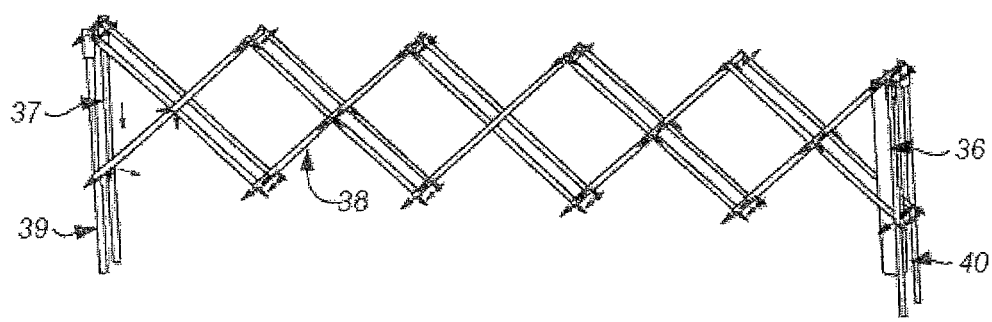
Figure 20A:
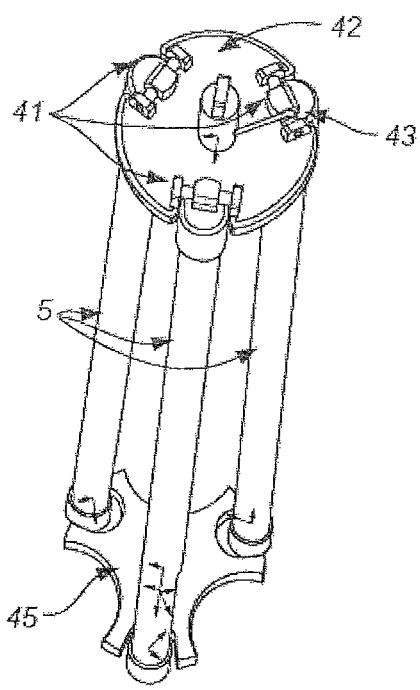
Figure 20B:
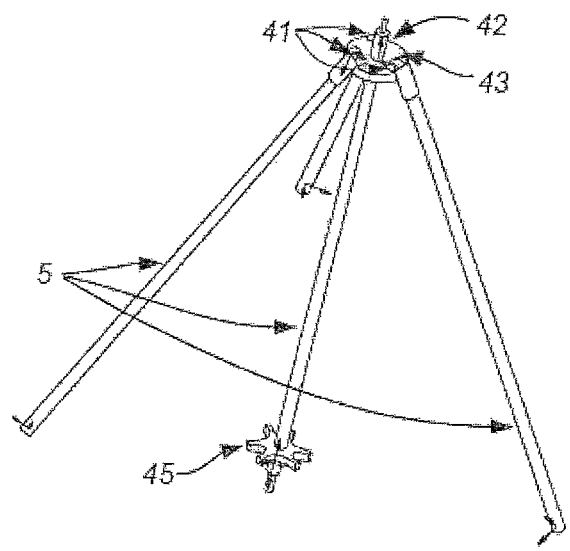

The UV lamp cluster may be housed in a protective housing 36 (FIG. 19) and can be attached to a winch at the second end of a scissor mechanism. Once the linear actuator extends the scissor boom to the central position in the tank, the winch drops the UV lamp cluster from the protective cover. As this occurs, the UV lamps will spring out into a tripod configuration in case three UV lamps were clustered (FIG. 20B). An algorithm based on the diameter and depth of the tank will determine the speed at which the winch lowers and raises the tripod configuration. These distances may be determined either by ultrasonic or laser range finders. As the winch retracts the lamp back into the protective housing, the lamps are forced back into a vertical position and secured in that position by the lower plate (FIG. 20A). The scissor arm is then retracted and the system can be removed from the tank.

The entire UV device unit can be mounted to the port of a tank via either a molding attached to the slide rails. This molding or bracket can be made from a variety of materials, including various polymers, aluminum or other metals or carbon fiber. Preferably, it will be made for the lightest and most cost effective material. The standard access port on most modern tanks is offset to one side of the tank and is 18" in diameter.

M. UV Device with Telescoping Arm

In some embodiments of a UV device of the present invention, a UV device comprises a means for moving a UV light source to a predetermined position within a container, a room, a space or defined environment and is referred to herein as a UV device with telescoping arm. In some embodiments of a UV device of the present invention, a UV device comprises a UV light source that is attached to a telescopic arm 46. In some embodiments, the telescopic arm 46 corresponds to a central sleeve 12 (as shown exemplary in FIGS. 7-11), comprising two or more movable units, referred to herein as telescoping units 47. Exemplary embodiments of a UV device comprising a telescopic arm 46 are shown in various configurations in FIGS. 21-25.

FIGS. 21-25 depict several views of an exemplary embodiment of a UV device of the present invention comprising a telescopic arm as a means for moving a UV light source or a UV lamp cluster to a desired position within a container, a room, a space or defined environment. The UV device is shown schematically in various configurations: in its folded position (FIG. 21), in its load position (FIG. 22), in its payout position (FIG. 23), in its horizontal position (FIG. 24), and in its UV lamp down position (FIG. 25). While FIGS. 21-25 show a UV device comprising a telescopic arm and a UV lamp cluster having eight UV lamps, any number of UV lamps can be attached to a UV device having a telescopic arm 46.

The telescopic arm 46 comprises two or more telescoping units 47. The number of telescoping units is not important for practicing the methods of the present invention as long as the telescoping units 47 can be used to move the UV light source to a desired position within a container (e.g., see FIGS. 21-25), a room, a space or defined environment. In some embodiments, the telescopic arm 46 comprises two or more telescoping units 47. In some embodiments, the telescopic arm 46 comprises two telescoping units 47. In some embodiments, the telescopic arm 46 comprises three telescoping units 47. In some embodiments, the telescopic arm 46 comprises four telescoping units 47. In some embodiments, the telescopic arm 46 comprises five telescoping units 47. In some embodiments, the telescopic arm 46 comprises six telescoping units 47. An example of a telescopic arm 46 comprising six telescoping units 47 is shown in FIGS. 21-25. In some embodiments, the telescopic arm 46 comprises seven telescoping units 47. In some embodiments, the telescopic arm 46 comprises eight telescoping units 47. In some embodiments, the telescopic arm 46 comprises nine telescoping units 47. In some embodiments, the telescopic arm 46 comprises ten telescoping units 47. In some embodiments, the telescopic arm 46 comprises more than ten telescoping units 47.

The form of the telescoping units 47 is not important for practicing the methods of the present invention as long as the telescoping units 47 can be used to move the UV light source to a desired (also referred to as predetermined) position within a container, a room, a space or defined environment. The telescoping units 47 can be of any form. For example, in some embodiments, the telescoping units 47 are square. In some embodiments, the telescoping units 47 are rectangular. In some embodiments, the telescoping units 47 are round. In some embodiments, the telescoping units 47 are oval. In one embodiment of a UV device of the present invention, exemplified in FIGS. 21-25, the telescoping units 47 are square.

The dimensions of the telescoping units 47 are not important for practicing the methods of the present invention as long as the telescoping units 47 can be used to move the UV light source to a desired position within a container, a room, a space or defined environment. The telescoping units 47 may have various dimensions. Typically a telescoping unit 47 having the smallest diameter, $D_1$, is surrounded by a telescoping unit 47 having a larger diameter, $D_2$, which in turn is surrounded by a telescoping unit 47 having a larger diameter, $D_3$, which in turn is surrounded by a telescoping unit 47 having a larger diameter, $D_4$, and so on. An exemplary embodiment thereof, showing six telescoping units 47 of different diameters, is shown in FIGS. 21-25. In the embodiment shown schematically in FIGS. 21-25 and produced by the inventor, the diameter $D_1$ of the inner telescoping unit 47 is about 20×20 mm, the diameter $D_2$ of the next larger telescoping unit 47 is about 30×30 mm, the diameter $D_3$ of the next larger telescoping unit 47 is about 40×40 mm, the diameter $D_4$ of the next larger telescoping unit 47 is about 50×50 mm, the diameter $D_5$ of the next larger telescoping unit 47 is about 60×60 mm, and the diameter $D_6$ of the next larger telescoping unit 47 is about 70×70 mm. In the embodiment shown schematically in FIGS. 21-25 and produced by the inventor, the length of the telescoping unit 47 is about 3 feet each. Each telescoping unit 47 may, however, be of a different length, i.e., longer or shorter than 3 feet.

Each telescoping unit 47 has two ends, a first end and a second end, with which they are connected to another telescoping unit 47 or to a UV light source with respect to the inner telescoping unit 47 or to a means for attaching the UV device to a container, such as a hanger with respect to the outer telescoping unit 47 (see FIGS. 21-25). Thus, in some embodiments of the present invention, as exemplified in FIGS. 21-25, the UV light source is connected to a first end of the inner telescoping unit 47. More specifically with respect to the embodiment shown in FIGS. 21-25, the UV light source is connected to the inner telescoping unit 47 having a diameter $D_1$, the second end of the inner (or smallest in diameter) telescoping unit 47 having a diameter $D_1$ is connected to the first end of a telescoping unit 47 having a diameter $D_2$, the second end of the telescoping unit 47 having a diameter $D_2$ is connected to the first end of a telescoping unit 47 having a diameter $D_3$, the second end of the telescoping unit 47 having a diameter $D_3$ is connected to the first end of a telescoping unit 47 having a diameter $D_4$, the second end of the telescoping unit 47 having a diameter $D_4$ is connected to the first end of a telescoping unit 47 having a diameter $D_5$, and the second end of the telescoping unit 47 having a diameter $D_5$ is connected to the first end of a telescoping unit 47 having a diameter $D_6$.

The most outer (or largest in diameter) telescoping unit 47 is attached to a telescopic arm pivot 73, which in turn is attached to the means for attaching the UV device to a container 4, such as hanger as exemplified in FIGS. 21-25. The telescopic pivot arm 73 allows the UV device to be moved from a vertical position to a horizontal position and vice versa so that the UV light source can be positioned at a desired position within a container (see FIGS. 21-25), a room, a space or defined environment.

While the embodiment of the UV device having a telescopic arm shown in FIGS. 21-25 shows the telescopic unit 47 having the smallest diameter as the inner telescoping unit 47 and attached to the UV light source, in some embodiments it is the telescopic unit 47 having the largest diameter which is attached to the UV light source. In this embodiment, the telescopic unit 47 having the smallest diameter is attached to the telescopic arm pivot.

The telescopic (used herein interchangeably with the term "telescoping") arm 46 and the telescoping units 47 can be of any material as long as the material is strong enough allowing the moving of the UV light source to a desired position as described herein. A preferred material is metal.

In the exemplary embodiment shown in FIGS. 21-25, UV lamps 5 are clustered in a UV lamp cluster and are enclosed within a housing 2, such as a UV mesh cage, which allows the UV light to pass through. In some embodiments, the UV lamps 5 are attached to a frame 6, and to an upper plate 42. The upper plate 42 is connected to a UV lamp pivot arm 49 allowing the UV lamp cluster to be positioned in a desired position and orientation. In a preferred orientation, as shown e.g., in FIGS. 24 and 25, the UV light source points towards the bottom of a container.

In some embodiments, the UV lamp pivot arm 49 is attached to a UV lamp stop block 50. The UV lamp stop block 50 stops the UV light source from being retracted too high into the telescoping arm 46.

In some embodiments, a means for attaching the UV device to a container, i.e., referred to as hanger in FIGS. 21-25, is used to attach the UV device to a container, a room, a space or defined environment. The hanger can be attached to a pulley mount arm 51, to which also other parts of the UV device can be attached, such as the motorized unit 1 (also referred to as motor) and a winch 48. In some embodiments, the hanger comprises one or more hanger support bars 52 and a clamp post 53 for firmly attaching the UV device to a container, a room, a space or defined environment.

In some embodiments of the present invention the means for moving the UV light source to a desired position within a container, a room, a space or defined environment is the telescopic arm 46. The telescoping units 47 of the telescopic arm 46 can be moved either manually, by gravity, or with a motorized unit 1 (also referred to as motor). In some embodiments, the motorized unit 1 is attached to a reel assembly 54 and also permits moving the UV light source from a horizontal position to a vertical downwards position within the container (as described further herein) a room, a space or defined environment.

In some embodiments, the reel assembly 54 is attached to a pulley mount arm 51. In some embodiments, the reel assembly comprises one or more of the following: a reel assembly motor mount 55, a reel assembly idler post 57 for mounting the reel assembly 54 to the pulley mount bar 51, a reel assembly top plate 58, one or more reel assembly flanges 59, a reel assembly hub 60, and a reel assembly drive post 61. A preferred configuration of those parts is shown in FIGS. 21-25.

The motorized unit 1 or gravity or a winch (manually) extends the telescoping arm 46 comprising of multiple telescoping units 47 from a folded position (FIG. 21) and load position (FIG. 22) into the payout position (FIG. 23). In some embodiments, the motor 1 is connected to a reel assembly 54 (shown in greater detail in FIGS. 21 E-G). In some embodiments, the motor 1 connects to the reel assembly 54 via a reel assembly motor unit 55 and a motor coupler 56.

In some embodiments of a UV device of the present invention, a UV device comprises a means for moving a UV light source from a vertical downwards position (also referred sometimes as first vertical downwards position) into a horizontal position. In some embodiments the means for moving the UV light source from the vertical downwards position into the horizontal position is a winch 48. In other embodiments, the means for moving the UV light source from the vertical position into the horizontal position is a motorized unit or a motor. A winch 48 may be operated manually by hand.

In some embodiments, a winch 48 is attached to the pulley mount arm 51 and moves the telescoping arm 46 and the telescoping units 47 from the payout position (FIG. 23; also referred to as first vertical downward position) into a horizontal position (FIG. 24). In some embodiments, a winch 48 comprises one or more of the following: a winch pulley guide 62, a winch guide pulley shaft 63, a winch shaft 64, a winch hub 65, a winch top plate 66, one or more winch flanges 67, a winch ratchet retainer 68, a pawl 69, and a crank or handle 70. A preferred configuration of those parts is shown in FIGS. 21-25. A winch guide pulley shaft 63 allows the winch pulley guide 62 to rotate and reduce friction. In some embodiments, the winch shaft 64 allows the winch hub 65 to spin and wind and unwind a cable 7. Cable 7 typically wraps around winch hub 65. A winch top plate 66 adds structural integrity to the winch assembly 48. A winch ratchet retainer 68 keeps the ratchet from slipping off. In some embodiments, cable 7 connects the winch 48, more specifically, the winch hub 65 with the UV light source so that the UV light source can be moved e.g., from the horizontal position (FIG. 24) towards the bottom of the container, i.e., to a vertical position, more specifically, to a second vertical downwards position. The length of the cable 7 is sufficient to allow the UV light source to be moved from the horizontal position to a position close to the bottom of the container, i.e., into a second vertical downwards position and back into its horizontal position (see FIG. 25).

In some embodiments, the outer telescoping unit 47 of the telescopic arm 46 is attached to the bottom part of the pulley mount arm 51 by one or more cross member support bars 71 and a cross bar stop plate 72. One end of the outer telescopic unit 47 is connected to a telescopic arm pivot 73 allowing the telescoping arm to be moved from the loaded (FIG. 22) or layout position (FIG. 23) into a horizontal position (FIG. 24).

In some embodiments, a UV device having a telescopic arm comprises one or more of the following: a lifting eye 74 having a lifting eye base 75 and a lifting eye side support 76 (e.g., FIGS. 21E, F). In some embodiments, the lifting eye 74 is attached to the outer telescoping unit 47 and to the pulley mount arm 51. The lifting eye 74 allows carrying and transporting the UV device when not in use.

1. Load Position of a UV Device Having a Telescopic Arm

Generally, the positioning of a UV light source described herein into a desired or predetermined position can be done manually, by gravity, or by using a motor.

Unless permanently attached to a container, when practicing a method of the present invention, a UV device will be attached to a container 4 In FIG. 22, the attachment is schematically shown for a UV device having a telescopic arm 46 and referred to as load position. In the load position some parts of the UV device, such as the telescopic arm 46 and the UV light source 5 are movably inserted through an opening at the container, such as a manhole or port 77 so that the telescopic arm pivot 73 is below the manhole 77.

2. Payout Position of a UV Device Having a Telescopic Arm (First Vertical Position)

Once attached to a container 4 and released from its load configuration (see, FIG. 22), the telescoping units 47 of the telescopic arm 46 can movably position the UV light source 5 (e.g., a UV lamp cluster) to any desired position within a container and for practicing the methods of the present invention. In some embodiments for practicing methods of the present invention, the UV lamp cluster is moved from its released or load configuration vertically downwards towards the bottom of the container. This vertical extension of the telescoping units 47 (units that can be moved into each other) is shown schematically in FIG. 22. One or more interior telescoping units 47 move outwards of the telescoping arm 46 into a vertical downwards position.

When practicing the invention using a UV device of the present having a telescopic arm 46, the UV device is moved from its load position into its payout position. A UV device of the present invention in its payout position is schematically shown in FIG. 23. As described herein, a means for moving the UV light source to a first vertical downwards position moves the UV source into that position. In some embodiments, the means for moving the UV light source to the first vertical downwards position is the telescopic arm 46 having telescoping units 47. In some embodiments, the means for moving the UV light source to a first vertical downwards position is gravity.

The extent of the downward movement of the UV light source is determined by a premounted radiofrequency identification chip (RFID chip) which contains information about the dimensions of the container and relays that information to a circuit board on the UV device. The extent of the first downward movement of the UV light source is determined mainly by the diameter of the container and typically is about one half of the diameter of the container. For example, if the container has a diameter of 20 feet, the extent of the first downward movement of the UV light source is about 10 feet. This will guarantee that upon moving the UV light source into the horizontal position (see below), the UV light source will be positioned in the approximate center of the container.

3. Horizontal Position of a UV Device Having a Telescopic Arm

When practicing the invention using a UV device of the present having a telescopic arm 46, the UV device (and as such, the UV light source) is moved from its payout position (i.e., first vertical downwards position) into its horizontal position. The invention contemplates various means for moving the UV light source from the first vertical downwards position to a horizontal position. A UV device of the present invention in its horizontal position is schematically shown in FIG. 24. As described herein, a means for moving the UV light source from the first vertical downwards position to a horizontal position is a winch. In some embodiments, the means for moving the UV light source from the first vertical downwards position to a horizontal position is a motorized unit, Upon activating the means for moving the UV light source from the first vertical downwards position to the horizontal position, the UV device pivots at the telescopic arm pivot 73 and the telescopic arm 46 and its telescopic units 47 move from the first vertical downwards position to the horizontal position. After positioning the UV device in its horizontal position, the UV light source faces downwards into the container and ideally is positioned within the approximate center of the container to be sterilized (see FIG. 25).

The UV light source may be activated at any time while practicing a method of the present invention. In some embodiments, when the UV light source is positioned in its horizontal position within the container, the UV light source is activated.

4. Lamp Down Position of a UV Device Having a Telescopic Arm (Second Vertical Position)

When practicing the invention using a UV device of the present having a telescopic arm 46, the UV device is moved from its horizontal position to its lamp down position, also referred to herein as second vertical downwards position. The invention contemplates various means for moving the UV light source from the horizontal downwards position to the lamp down position. A UV device of the present invention in its second vertical downwards position is schematically shown in FIG. 25. In some embodiments, the means for moving the UV light source from the horizontal position to the second vertical downwards position is a motorized unit or a motor. In other embodiments, the means for moving the UV light source from the horizontal position to the second vertical downwards position is gravity. In some embodiments, the means for moving the UV light source from the horizontal position to the second vertical downwards position is a winch.

When the UV light source is moved towards the second vertical downwards position, a cable 7 connecting the UV light source 5 with the reel assembly 54, and the reel assembly hub 60 rolls off from the reel assembly hub 60 and moves the UV light source 5 downwards towards the bottom of the container. In some embodiments, the time for the downwards movement of the UV light source is controlled by a radiofrequency identification chip (RFID chip) or tag, which contain information about the UV lamps used and dimensions of the container and relays that information to a circuit board on the UV device and/or to the motor if a motor is being used for moving the UV light source into its second vertical downwards position.

As one of ordinary skill in the art will appreciate, the larger the radius of the container is (i.e., the distance of the UV light source to the interior wall of the container), the slower the speed will be with which the UV light source is moved from its horizontal position into its second vertical downwards position. Accordingly, the larger the radius of the container is, the longer the descent will be with which the UV light source is moved from its horizontal position into its second vertical downwards position. The speed of the downwards movement or the descent of the UV light source is adjusted to guarantee that the growth of one or more microorganism located on an interior surface of the container is inhibited as described herein. In some non-limiting examples, the speed with which the UV light source is moved from its horizontal position into its second downwards vertical position is 12 inches per minute.

Once the method of the invention has been practiced, the UV device is moved from its lamp-down position (second vertical downwards position) into its horizontal position, then into its payout position (first vertical downwards position) and then into its load position. At that time, the UV device can be detached from the container or can remain attached to the container until the next use.

While moving into its second vertical downwards position, the UV light source remains activated to perform a method of the present invention, i.e., the UV sterilization of an interior surface of a container.

5. Additional Vertical Movements

In some embodiments of the present invention, a scissor boom comprises a UV lamp and a means for vertically moving the UV lamp from an upper position within a container to a lower position of the container. The same means for moving the UV lamp from the upper position within a container, room, space or defined environment to the lower position of the container, room, space or defined environment can be used to move the UV lamp from the lower position within the container, room, space or defined environment to an upper position of the container, room, space or defined environment.

In some embodiments of the present invention, a means for moving a UV lamp from an upper position within a container, room, space or defined environment to a lower position within a container, room, space or defined environment and/or from a lower position within a container, room, space or defined environment to an upper position within a container, room, space or defined environment is by using an actuator. Thus, in some embodiments, a scissor boom comprises an actuator. An exemplary scissor boom is shown in FIG. 19. A preferred means for effectuating the vertical movement of the scissor boom is an actuator.

An actuator is a mechanical device for moving a UV lamp to a desired position within a container. In some embodiments, the actuator is a linear actuator. An actuator of the present invention actuates up and down (or in a lateral direction) and moves a cross bar with it effectively extending and retracting a scissor mechanism (FIG. 19).

In some embodiments, the linear actuator is mounted to a bracket.

In some embodiments, the linear actuator 37 is a DC linear actuator. In some embodiments, the linear actuator 37 is an AC linear actuator.

The force of the actuator can vary significantly, however, will be sufficient to move a UV lamp to a desired position within a container. In some embodiments, the force of an actuator is at least 100 lbs. In some embodiments, the force of an actuator is at least 200 lbs. In some embodiments, the force of an actuator is at least 300 lbs. In some embodiments, the force of an actuator is at least 500 lbs. In some embodiments, the force of an actuator is at least 750 lbs. In some embodiments, the force of an actuator is at least 1,000 lbs. In some embodiments, the force of an actuator is at least 1,200 lbs.

6. Additional Horizontal Movements

In some embodiments of the present invention, a scissor boom comprises a UV lamp and a means for horizontally moving the UV lamp from an inner position of a container to an outer position of the container. The same means for moving the UV lamp from the inner position of the container to the outer position of the container can be used to move the UV lamp from the outer position of the container to an inner position of the container.

Effectuating a horizontal movement of a scissor boom, i.e., extending a scissor boom from its folded position to its extended position can be done manually or via a motorized unit. Manual extension of a scissor boom to a desired position can be done when the distance between the UV lamp(s) and the inner wall of the container is constant, i.e., in a container with straight walls and where the interior diameter throughout the height of a container will be constant.

Some containers, such as wooden wine barrels, however, often do not have straight walls. In those containers, the interior diameter of a container varies. The diameter typically is smallest at the top and bottom of the container and the greatest at the middle of the container. For those containers a controllable motorized extension and retraction of the scissor boom is preferred.

Thus, in some embodiments extending a scissor boom to a desired position is performed by a motorized unit, also referred to as a motor unit. In some embodiments of the present invention, a scissor boom comprises a motor unit for effectuating the horizontal movement of a UV lamp mounted to a second end of the scissor boom to an inner wall of a container. The motor unit then essentially expands the scissor units of the scissor boom so that the UV lamp(s) mounted at the opposite end (outer end) of the scissor boom than the motor unit can be positioned at a desired position within a container. Upon activation of the scissor mechanism, the one or more UV lamps attached to the outer end of the scissor boom move from its (their) folded position (FIG. 19A) towards an extended position (FIG. 19B). This movement is horizontally towards the inner wall of a container (and backwards to its folded position). In its extended position, the UV lamps of the scissor boom are close to the inner wall of the container so that when activated (switched on), the desired effect on the microorganisms present on the wall of the container will be achieved (as described herein).

In some embodiments, the motorized unit is attached to the first end of scissor boom. In some embodiments, a sensor is attached to the scissor boom. The sensor can be attached to the second end of the scissor boom, e.g., in close proximity to a UV lamp. In some embodiments, the sensor, such as a laser range finder described herein, is attached to sliding rail 40. The sensor measures the distance from the UV lamp(s) to the wall of the container. The sensor is connected to the motorized unit for extending and retracting the scissor boom. The sensor effectively guarantees that the UV lamp(s) are positioned in the same distance to the inner wall of the container. In case where the sensor senses that the UV lamp(s) is too far away from the inner wall of the container, it sends a signal to the motor unit, which then extends the scissor mechanism accordingly allowing the UV lamp(s) to be moved closer to the inner wall of the container until a desired position is achieved. Likewise, should the sensor sens that the UV lamp(s) are too close to the inner wall of the container, it sends a signal to the motor unit, which then retracts the scissor mechanism accordingly allowing the UV lamp(s) to move further away from the inner wall of the container until a desired position is achieved. Thus, the sensor is connected to the motor unit.

A preferred means for effectuating the horizontal movement of the scissor boom is an actuator.

7. Circular Movement

In some embodiments of the present invention, a scissor boom comprises a UV lamp and a means for circular moving one or more UV lamp(s) from one position within a container, room, space or defined environment to another position of the container, room, space or defined environment. A motorized unit (motor unit) can be used to effectuate the circular movement of the one or more UV lamp(s). Preferably, a sensor is attached to the second end of the scissor boom and sends signals to a second motorized unit (motor unit) for extending and/or retracting the scissor mechanisms to adjust for the respective distance between the UV lamp(s) and the inner wall of the container, room, space or defined environment.

A scissor boom can be mounted at its first end to an inner wall of a container, room, space or defined environment or to a (removable) bracket as shown e.g., in FIG. 10 for a container. When mounted to an inner wall of a container at a first position or a bracket, the circular motion of the scissor boom is somewhat limited. The UV lamp(s) will, for example, not cover, and thus, not efficiently sterilize, the wall part of the inner container to which the scissor boom is mounted, i.e., the first position. Microorganisms present at around the first position may not be growth inhibited to the extent desired. This limitation can easily be overcome by mounting the scissor boom to the opposite position of its first mounting position, i.e., into a second position, and repeat the UV sterilization process.

To overcome the need for repositioning the scissor boom and to permit a complete circular rotation, in some embodiments of the present invention, a scissor boom is mounted to a central post, which can be positioned in the center of a container. In this embodiment, the circular motion of the scissor boom is such that it allows to cover 360° of the container, room, space or defined environment i.e., the complete inner walls of the container, room, space or defined environment. The central post may reach to the bottom of the container and/or may be connected to a lid of the container or, alternatively to a bracket resting on top of the container for stabilization and desired positioning.

In some embodiments of the present invention, the circular movement of a scissor boom (when extended) is done manually by pivoting the UV device. The UV device may be set in a position upon installation in the center of a container, room, space or defined environment that will allow the scissor boom to extend from the center of the container, room, space or defined environment to the outer region of the container, room, space or defined environment. Alternatively, the UV device may be set in a position upon installation at a wall of a container, room, space or defined environment that will allow the scissor boom to extend from the wall of the container, room, space or defined environment to the outer region of the container, room, space or defined environment.

The speed of the circular motion of the scissor boom is adjusted to obtain a desired effect, i.e., the growth inhibition of microorganisms present on the inner wall of the container, or in a desired area in the room, space or defined environment.

N. UV55

In some embodiments of the present invention, a UV device embodiment is a UV55 device. A UV55 device is schematically depicted in FIGS. 28 and 29 and explained in detail below and herein.

UV device UV55 comprises an 18" single ended low pressure mercury lamp 5 supplied by Steril-Aire (FIG. 28H). The UV lamp 5 is attached to the base of a cylindrical plastic (Delrin) central sleeve 12 by a UV lamp socket or adaptor 94 (FIG. 28G) The UV lamp pins 93 plug into the UV lamp socket or adaptor 94 (FIGS. 28 G, H) The UV lamp socket or adaptor 94 is attached to a cylindrical central sleeve 12 (FIG. 28G).

The cylindrical central sleeve 12 comprises two cavities, a circuit board cavity 99 and a power supply cavity 100 (FIG. 28E). A power supply 96 resides within the power supply cavity 100 (FIG. 28E). Within the power supply cavity 100 also reside a connector and wires 105 from the power supply 96 to the UV lamp 5 (FIG. 28E).

Within the circuit board cavity 99 reside an AC to DC power converter 101, electronic components 102, a circuit board 103 as well as a connector and wires 104 from on/off/reset switch 85 and optical switch 98 (FIG. 28E)

Also within the aforementioned cavities 99 and 100 are connector and wires 106 connecting the power supply 96 and the AC to DC power converter 101 (FIG. 28E)

Cavities 99 and 100 can be accessed through a power supply access plate 97, which is screwed by a plurality of screws to the central sleeve 12 to cover the cavities 99 and 100 and protect the power supply 96, circuit board 103 and other components residing within the cavities 99 and 100 (FIGS. 28A, E).

The top of the UV device embodiment UV55 comprises a hanging hook 84, and an on/off/reset button 85 (FIGS. 28A, B, D, F). The on/off/reset button 85 activates and terminates the UV device. The hanging hook 84 is attached to a handle cap 92, which forms the top part of a handle 91 (FIGS. 28A, B, D, F). Handle 91 is a narrower extension of the central sleeve 12 (FIGS. 28A, B, D, F).

At the lower end of handle 91 is a metal disc 89 protecting a translucent blue plastic ring 87, which may or may not comprise a plurality of LED lights inside (FIGS. 28A, B, D-F). Partially protruding from the translucent blue plastic ring 87 is an entrance for an external power cord 90 (FIGS. 28A, B, D-F).

A stainless steel housing 2 slides over the cylindrical sleeve 12 however does not extend beyond the plastic blue translucent ring 87 (FIGS. 28A, C, D-G). When the unit is not mounted on the lid 29 of a container 4 (such as a keg, a drum, a barrel, a porta tank, etc.) the stainless steel housing 2 is extended to cover the length of the UV lamp 5 so that none of it is exposed or visible from the outside when the UV device stands on its base plate 10 (FIG. 28A).

A stopping plate 88 is mounted at the bottom of the central sleeve 12 to prevent the steel housing 2 from sliding off (FIG. 28C).

A plastic (Delrin) base plate 10 is attached to the bottom of the stainless steel housing 2. This provides a stable platform for the unit to stand upright when not in use.

The UV55 device comprises a central sleeve tightening knob 86 on the side of the stainless steel housing 2. It locks the housing 2 into a position on the central sleeve 12 at a predetermined position selected by a user. It is tightened by screwing clockwise and loosened by unscrewing counter clockwise. When central sleeve tightening knob 86 is tightened on the stainless steel housing 2 in the fully extended position (housing 2 positioned at the bottom part of central sleeve 12; see FIG. 28A), the UV device can be stood upright on the plastic base plate 10. When the central sleeve tightening knob 86 is loosened, the UV device can be mounted over any 2-3" lid opening 29 and the plastic cylindrical sleeve 12 descends through the steel housing 2 (see FIGS. 28D, 29). Since the UV lamp 5 is attached to the bottom of the central sleeve 12 it will then be residing within the container 4 (FIG. 29).

As the stainless steel housing 2 passes over the optical switch 98 within the plastic sleeve 12 it starts a timer controlled by the circuit board 103. As the timer sequence begins, acoustic and visual signals are generated. The acoustic signal is made audible by an acoustic speaker residing in the handle cap 91. The optical switch does, however, not start or stop the activation of the UV device. The visual signal leads to the intermittent blinking of a plurality of LED lights residing behind the translucent plastic ring 87. The blinking of the LED lights indicates how much time has elapsed, i.e., the time a sterilization cycle has been activated.

O. Additional UV Devices

In some embodiments of the present invention, a UV device is UV device depicted in FIG. 30. This UV device embodiment comprises a housing 2, a UV lamp cluster line 111 attached to a UV lamp cluster. This UV device embodiment further comprises an anchor connector 109 connecting the housing 2 to an anchor 107. An anchor line 108 connects the anchor 107 with the housing 2. The anchor 107 serves to stabilize the lamp cluster as it moves upwardly and downwardly throughout a container 4. The UV device depicted schematically in FIG. 30 may comprise any additional component described herein.

In some embodiments of the present invention, a UV device is UV device depicted in FIG. 31. This embodiment describes a UV device similar to the UV device UV55 described above, however, inverted. The UV lamp 5 is inserted into an opening of a container 4 from the bottom of the container (FIG. 31A). The base plate 10, here a support stand, is attached to the central sleeve 12. A housing 2 slides over the central sleeve 12. In this embodiment, the housing 2 is spring loaded such that, as soon as UV lamp 5 is movably inserted into the container 4 (a barrel is shown in FIG. 31), the housing 2 retracts to cover the central sleeve 12 (FIG. 31B). As the unit is removed from the container 4, a spring forces the housing 2 to slide over the UV lamp 5. The UV device depicted schematically in FIG. 31 may comprise any additional component described herein.

In some embodiments of the present invention, a UV device is UV device depicted in FIG. 32. This embodiment describes a UV device that is placed in the center of a container 4 and mounted a top of a base plate 10, here, a tripod-like support stand. The support stand supports a housing 2 and a central sleeve 12 within the housing 2 that moves upwardly and downwardly. In some embodiments, this UV device comprises a UV lamp 5. In some embodiments, this UV device comprises a UV lamp cluster. The UV device depicted schematically in FIG. 32 may comprise any additional component described herein.

In some embodiments of the present invention, a UV device is UV device depicted in FIG. 33. This embodiment describes a UV device comprising a telescoping horizontal arm 113 that enters the container 4 through an opening on the side of the container 4. As described herein, instead of a single telescoping horizontal arm 13, which can be of various length (depending on the size of the container into which the UV device is being inserted), the UV device may also have one more of the telescoping arms 47, the form and function of which has been described herein. Users are protected from UV exposure by a bracket 3 fitting over the opening. A vertical housing 2 is attached to a central sleeve 12, which can be moved upwardly and downwardly in a vertical axis. In some embodiments, this UV device comprises a UV lamp 5 attached to the central sleeve 12. In some embodiments, this UV device comprises a UV lamp cluster attached to the central sleeve 12. The UV device depicted schematically in FIG. 33 may comprise any additional component described herein. The entire UV device can be transported on a movable object 112 comprising wheels 114. The wheels are attached to supports attached to the object 112. As an non-limiting example, four supports are schematically depicted in FIG. 33. In some embodiments, the length of the supports is adjustable so that the same movable object 112 can be used to introduce a UV device in to containers having an opening a different positions. The Horizontal arm 113 may be rotatably attached to the object 112 so that it can turn the UV device once inserted into the container into different angle positions and also move it upwardly, downwardly, and horizontally into any desired position.

In some embodiments of the present invention, a UV device is UV device depicted in FIG. 34A. This embodiment describes a UV device that is placed in top of a container 4 as schematically shown in FIGS. 34B, 34C. The UV device comprises a housing 2 having two arms, a first arm and a second arm (both indicated by 2 in FIG. 34A). The first arm may be in a fixed, non-movable position, whereas the second arm may be movably attached to the first arm. The two arms are connected to each other through a pivot point 118. This connection allows the two arms to provide various angles between them. When not in use, the second arm resides within the first arm. The second arm comprises an opening through which a power cord 90 (FIG. 34A) or any other rope or string 7 may be guided which may be attached to a UV lamp 5. As schematically depicted in FIG. 34A, a LTV lamp 5 resides within the second arm, which partially surrounds the UV lamp 5 (when not in use and the power cord 90 is completely retracted) and which releases the UV lamp 5 upon the twist lock 116 releasing the power cord 90. The release of the power cord 90 (or string or rope 7) is controlled by a twist lock 116. As one of skill will appreciate upon releasing the power cord 90 (or string or rope 7), the two arms of the housing 2 separate from each other. Approaching an about 90 degree angle between the two arms of the housing 2, the UV lamp will be positioned furthest away from the fixed arm of the housing 2 (schematically shown in FIGS. 34B, 34C). In some embodiments, this UV device comprises a power cord 90 connected to the UV lamp 5 and a string or rope 7 attached to the second arm of the housing 2 and the twist look 116. In this embodiment movement and positioning of the UV lamp 5 within a container can be controlled in two ways. First, upon release of the rope or string 7 from a twist look 116, the second arm moves from a vertical position to an angle position (between about 0 degree and 90 degree) without releasing the power cord 90 and the UV lamp 5. The extent to which the rope or string is being released determines, as one of ordinary skill in the art will appreciate, the positioning of the UV lamp 5 within the diameter of the container 4. The second movement controls the vertical positioning of the UV lamp 5 within the container 4 as is shown schematically in FIG. 35. Upon release of the power cord 90 from the twist look 116 (which can be the same or a different twist look releasing string or rope 7) the UV lamp 5 moves downwardly in the container 4 towards the bottom of the container 4. As described herein, when sterilizing a wide container (i.e., a container having a large diameter), the arms of the housing 2 may be chosen to have a length permitting the positioning of the UV lamp 5 within the center of the container 4. In some embodiments, this UV device comprises a UV lamp 5. In some embodiments, this UV device comprises a UV lamp cluster. The UV device depicted schematically in FIG. 34 may comprise any additional component described herein.

In some embodiments of the present invention, a UV device is UV device depicted in FIG. 35. This embodiment describes a UV device with similar functions as the UV device shown in FIG. 34A. In the UV device schematically depicted in FIG. 35, a central sleeve 12 slides movably over the housing 2. The housing 2, similarly to that of FIG. 34 comprises two arms. The two arms are attached to each other by a pivot point 118. In this embodiment, the first arm may be attached to the UV device so that it is rotatable permitting the positioning of the UV lamp 5 (upon lowering the second arm as, e.g., described herein) into various horizontal positions (see also FIGS. 8-11, 15)

In some embodiments, this UV device comprises a UV lamp 5. In some embodiments, this UV device comprises a UV lamp cluster. The UV device depicted schematically in FIG. 32 may comprise any additional component described herein.

III. Containers

In some embodiments, a UV device, preferably a UV light source, more preferably a germicidal UV light source, is introduced into a container. In some embodiments, a container is exposed to UV radiation. A container accepts a UV light source for the purpose of sterilization of the interior of the container, including any and all objects, fluids, materials, and surfaces contained within the interior of the container. In some embodiments, the objects, fluids, materials, and surfaces within the interior of the container are contained within the container temporarily. In other embodiments, they are contained within the container permanently.

The present invention provides a variety of containers. Containers, include, but are not limited to a vat, a silo, a tub, a basket, a case, a box, a barrel, a storage bin, a barrel, a keg, a tank (e.g., a Porta tank), a container for biological fluids, a beverage container, and an aquarium.

A container for biological fluid includes, but is not limited, to a container for blood, a container for blood products, a container for a fermentation product, a container for a cell culture product, or a container for a biotechnology product. In some embodiments, a fermentation product is an alcoholic beverage. In some embodiments, a fermentation product is wine.

A beverage container includes, but is not limited, to a beverage container for water, milk, coffee, tea, juice, an alcoholic beverage, or a carbonated beverage. An alcoholic beverage includes, but is not limited to beer, wine, gin, vodka, or whisky. A preferred alcoholic beverage is wine. Thus, a preferred container is a container for the fermentation of wine.

A container also includes any container for storing, transporting or selling a dairy product, a liquid dairy, a liquid dairy composition or a dry dairy composition. A "liquid dairy composition" is any source of milk or milk ingredient. In exemplary embodiments, the milk is from sheep, goats, or cows. Liquid dairy compositions include without limitations, for example, liquid milk, liquid skim milk, liquid non-fat milk, liquid low fat milk, liquid whole milk, liquid half & half, liquid light cream, liquid light whipping cream, liquid heavy cream, liquid lactose free milk, liquid reduced lactose milk, liquid sodium free milk, liquid reduced sodium milk, liquid dairy fortified with nutrients, such as vitamins A, D, E, K, or calcium, liquid high protein dairy, liquid whey protein concentrate, liquid whey protein isolate, etc. Milk concentrates and milk protein concentrates are particularly contemplated liquid dairy compositions. The term "milk concentrate" means any liquid or dried dairy-based concentrate comprising milk, skim milk, or milk proteins. Dry dairy components include without limitation, for example, whole dry milk, non-fat dry milk, low fat milk powder, whole milk powder, dry whey solids, de-mineralized whey powders, individual whey protein, casein dairy powders, individual casein powders, anhydrous milk fat, dried cream, lactose free dairy powder, dry lactose derivatives, reduced sodium dairy powder, etc. Also included are calorie-free dairy, cholesterol free dairy, low calorie dairy, low cholesterol dairy, light dairy, etc. Also included are combinations of any of the above liquid or dry dairy components in any ratio.

Containers of various sizes, shapes, heights, and diameters can be used in the methods of the present invention as long as they have at least one opening through which a UV device or a UV lamp can be introduced.

Containers of various refractive indexes can be used in the methods of the present invention.

Containers of various reflective nature can be used in the methods of the present invention. As indicated in the following table, different materials reflect different percentages of UV light (254 nm). One of skill in the art will appreciate the contribution of the reflectance of a material will have for achieving a desired UV intensity useful for UV disinfection and sterilization (see Table 6).

TABLE 6

Reflective Factors On Various Surfaces At 254 Nm Wavelength. The values are obtained at normal incidence. The percentage reflectances increases rapidly at angles greater than 75%. (American Ultraviolet Company, Lebanon, IN 46052, USA)

| Material | % Reflectance |
| --- | --- |
| Aluminum, etched | 88 |
| Aluminum, foil | 73 |
| Aluminum, polished commercial | 73 |
| Chromium | 45 |
| Glass | 4 |
| Nickel | 38 |
| Silver | 22 |
| Stainless steel | 20-30 |
| Tri-plated steel | 28 |
| Water paints | 10-30 |
| White cotton | 30 |
| White oil paint | 5-10 |
| White paper | 25 |
| White porcelain | 5 |
| White wall plaster | 40-60 |

In some embodiments of the present invention, the interior surface of a container is UV reflective.

In some embodiments of the present invention, the interior surface of a container is stainless steel.

Typically, a container for use in a method of the present invention is a closed container with one or more openings at the top. In some embodiments, this opening is referred to as manhole and is shown in FIGS. 22-25. The manhole or port 77 provides access to the container from the top of the container and further allows, e.g., for the attachment of various pressure washing devices. The manhole or port also allows the positioning of a UV device, e.g., of a UV device having a telescopic arm for practicing a method of the invention. As shown in FIGS. 22-25, part of the UV device rests on top of the manhole or port 77 when the UV device is used for the UV sterilization of the container. In some embodiments, the pulley mount arm rests on the top of the manhole.

In some embodiments, the means for attaching the UV device to a container, attaches the UV device to the manhole or port 77. This attachment is typically done using a hanger, more specifically, using the clamp post 53.

In some embodiments of the present invention, a container comprises a lid (indicated by 29 in the figures). In some embodiments of the present invention, a container comprises a hinged lid (indicated by 30 in the figures). The lid itself may have one or more openings through which a UV device or parts thereof (such as a UV light source) may be inserted inwardly into the container. In some embodiments of the present invention, a container comprises one or more support stands (indicated by 115 in the figures).

A. Fermentation Container

In some embodiments of the present invention, a container is a container used in zymurgy or the production of an alcoholic beverage. A UV device of the present invention may be used in any large scale commercial steel vessel involved in the fermentation and production of an alcoholic beverage. The term "alcoholic beverage" is used to include the alcoholic beverage prescribed in Liquor Tax Law Chapter 1, Section 2.

A fermentation container may be of various size, shape, height, and can be used in a method of the present invention as long as it has at least one opening through which a UV device or UV lamp can be introduced.

A fermentation container may be made of a variety of materials, including stainless steel, wood, plastic, concrete, a polymer, or glass. A preferred fermentation container is made of wood.

IV. Systems

In another aspect of the present invention, systems comprising a UV device described herein, are provided. In some embodiments of the present invention, a system comprises a UV device. A UV device may include one or more components as described herein, e.g., a germicidal UV light source, a detector, a housing, a range-finding device, a bracket, an optical component, and/or a motorized unit. In some embodiments of the present invention, a system comprises a UV device and a container. In other embodiments of the present invention, a system comprises a UV device and a room, a space or defined environment.

In some embodiments of the present invention, a system is for use in a method for ultraviolet (UV) sterilization of an interior surface of a container. In other embodiments of the present invention, a system is for use in a method for ultraviolet (UV) sterilization of a room, a space or defined environment.

In some embodiments of the present invention, a system is for use in a method for inhibiting the growth of one or more species of microorganisms present in a container, preferably for inhibiting the growth of one or more species of microorganisms present on an interior surface of a container. In other embodiments of the present invention, a system is for use in a method for inhibiting the growth of one or more species of microorganisms present in a room, a space or defined environment, preferably for inhibiting the growth of one or more species of microorganisms present on a surface of a room, a space or defined environment.

V. Methods

In another aspect of the present invention, methods of using a UV device described herein, are provided. In some embodiments, a method of using a UV device is a method for ultraviolet (UV) sterilization of an interior surface of a container. In some embodiments, the method for UV sterilization of an interior surface of a container comprises the steps of (a) providing a container having an opening, (b) movably inserting through the opening of the container a first germicidal UV light source and (c) activating the germicidal UV light.

In some embodiments, as described herein, the method further comprises the step of (d) moving the germicidal UV light source to a first vertical downwards position within the container.

In some embodiments, as described herein, the method further comprises the step of (e) moving the germicidal UV light source from the first vertical downwards position to a horizontal position within the container.

In some embodiments, as described herein, the method further comprises the step of (f) moving the germicidal UV light source from the horizontal position to a second vertical downwards position within the container.

In some embodiments, as described herein, the method further comprises the steps of attaching a UV device comprising the germicidal UV light source to the container.

In some embodiments, a method of using a UV device is a method for inhibiting the growth of one or more microorganisms present on an interior surface of a container. In some embodiments, the method for inhibiting the growth of one or more microorganisms present on an interior surface of a container comprises the steps of (a) providing a container having an opening, (b) movably inserting through the opening of the container a first germicidal UV light source and (c) activating the germicidal UV light.

In some embodiments, as described herein, the method further comprises the step of (d) moving the germicidal UV light source to a first vertical downwards position within the container.

In some embodiments, as described herein, the method further comprises the step of (e) moving the germicidal UV light source from the first vertical downwards position to a horizontal position within the container.

In some embodiments, as described herein, the method further comprises the step of (f) moving the germicidal UV light source from the horizontal position to a second vertical downwards position within the container.

In some embodiments, as described herein, the method further comprises the steps of attaching a UV device comprising the germicidal UV light source to the container.

A. Providing a Container

In some embodiments, the method for UV sterilization of an interior surface of a container comprises the step of providing a container having an opening. In some embodiments, the method for inhibiting the growth of one or more microorganisms present on an interior surface of a container comprises the step of providing a container having an opening. Containers useful for practicing methods of the present invention are described herein.

B. Attaching a UV Device to a Container

In some embodiments, the method for UV sterilization of an interior surface of a container comprises the step of attaching a UV device to a container. In some embodiments, the method for inhibiting the growth of one or more microorganisms present on an interior surface of a container comprises the step of attaching a UV device to a container. Attaching a UV device temporarily, for a prolonged time, or permanently to a container are described herein.

C. Inserting a UV Light Source into a Container

In some embodiments, the method for UV sterilization of an interior surface of a container comprises the step of inserting a germicidal UV light source through an opening of the container. In some embodiments, the method for inhibiting the growth of one or more microorganisms present on an interior surface of a container comprises the step of inserting a germicidal UV light source through an opening of the container. The opening of the container may be on top of the container as illustrated in FIGS. 1-3, 29, or a manhole or port as illustrated in FIGS. 22-25, 30, and 34.

Alternatively, an opening of the container may also be at the bottom of a container or at a side of a container as illustrated in FIGS. 31-33. One of skill in the art reading the instant specification will appreciate that a UV light source can be inserted into a container through an opening on the top, through an opening at the bottom, or through an opening at a side. As described herein, a UV light source, once movably inserted into a container can be moved at any desired or predetermined position. One of ordinary skill in the art will appreciate that the methods described herein for positioning a UV light source within a container can be easily modified to account for the point of where the UV light source is being movably inserted into a container. Those would be considered design choices in view of the disclosure provided herewith.

In some embodiments, once the UV light is inserted into a container, it remains in a stationary position for the time of the sterilization process. In some other embodiments, once the UV light is inserted into a container, it is mobile. In some embodiments, a UV lamp moves longitudinally within the container. In some embodiments, a UV lamp moves laterally. In some embodiments, a UV lamp rotates on its own axis or about an axis. In some embodiments, a combination of movements of some or all movements is used to achieve the desired result of positioning a UV light source at a desired or predetermined position within a container. The movement of the UV lamp is achieved through use of a motorized unit, a hydraulic system, or a combination thereof.

Mobility of the UV light source may depend on the size and shape of the container and on the size, shape, and intensity of the UV lamp(s). The use of a mobile UV light source will depend on the desired sterilization rate. If, for example, a faster rate is desired, the UV lamp preferably is positioned closer to the inner surface of the container to be sterilized. Thus, in this embodiment, a means by which the UV light source is positioned in closer proximity to the inner surface is recommended. Similarly, in some embodiments, the positioning of the UV lamp is altered to avoid an obstruction, such as an internally mounted thermometer or the like. As one of skill in the art will appreciate, the longitudinal movement of a UV lamp depends on the height of the vessel. Further, the lateral movement of a UV lamp depends on the diameter of the container. In embodiments where a rotating UV lamp is used, the rate of rotation will depend on the type of UV lamp used (continuous UVC vs. pulsed UV) and on the intensity of the UV lamp.

D. Activating a UV Light Source

In some embodiments, the method for UV sterilization of an interior surface of a container comprises the step of activating a germicidal UV light source. In some embodiments, the method for inhibiting the growth of one or more microorganisms present on an interior surface of a container comprises the step of activating a germicidal UV light source. Thereby a necessary or predetermined dose of radiation will be delivered. Activating of the UV light source initiates the process of sterilization, disinfection and growth inhibition of the one or more microorganisms by providing a UV dose for effective sterilization of microorganisms, disinfection of the interior surface of a container, and for the growth inhibition of the one or more microorganisms.

In some embodiments, the method for UV sterilization of an interior surface of a container comprises the step of manually activating a germicidal UV light source.

In some embodiments of the present invention, a UV device comprises an interface for activating the UV device, for inactivating the UV device, for making a user aware of the time elapsed in a sterilization cycle and/or making a user aware of the time remaining for completion of a sterilization cycle. Some interface function may be connected to a visual or audible alert.

In some embodiments, activation of the UV light source occurs at a predetermined time and may be controlled by an RFID communicating with a circuit board attached to the UV device (e.g., FIGS. 26 and 36). In some embodiments, the information retrieved from the RFID is used by the circuit board to determine the length of extension of the telescopic arm (e.g., moving the UV light source into a first vertical downwards position; payout position, e.g., see FIG. 23) and the length of descent of the UV light source from its horizontal position into the second vertical downwards position (e.g., see FIG. 25).

In some embodiments, activation of the UV light source occurs for a predetermined time. Preferably the duration of the activation of the UV light source is provided for a time sufficient to cause an at least about 1 log reduction of microorganisms on the interior surface of a container, an at least about 2 log reduction of one or more microorganisms on the interior surface of a container, an at least about 3 log reduction of one or more microorganisms on the interior surface of a container, an at least about 4 log reduction of one or more microorganisms on the interior surface of a container, an at least about 5 log reduction of one or more microorganisms on the interior surface of a container, or an at least about 6 log reduction of one or more microorganisms on the interior surface of a container.

By inserting the UV light source into the interior of a container and by activating the UV light source, the interior surface of the container is exposed to a UV light dose.

Once the desired UV intensity has been applied to the interior surface of a container, the UV light source may be deactivated. In some embodiments, deactivation is performed by a timer, which can be set to different times depending on the desired log reduction of the desired microorganisms (see calculations of killing rates in Example B). Deactivation can also be performed by a UV detector, which would automatically shut off the UV lamp(s) when the desired UV intensity has been attained. In some embodiments of the present invention, deactivation may also be controlled by a RFID. In some embodiments of the present invention, deactivation, upon completing a sterilization cycle, is controlled by a circuit board attached to the UV device. Again, the desired UV intensity will depend on the desired log reduction of the desired microorganisms. For example, using a lamp with an output of 190 microwatts/cm$^2$ at 254 nm (at a distance of 1 meter), placed within a fermentation vessel 60" from the interior surface, if a 2 log reduction of *Shigella dysentery* is desired, 4,200 microwatt seconds/$cm^2$ would be required. Once the UV detector has detected that 4,200 microwatt seconds/$cm^2$ have been attained it would automatically shut off the UV lamp. Thus, in some embodiments, the method for UV sterilization of an interior surface of a container comprises the step deactivating a germicidal UV light source. As described herein, deactivation may occur automatically by using a preset UV detector. Alternatively, deactivation is performed manually.

In some embodiments, the process of sterilizing the interior of a container comprises the step of subjecting the interior of the container to UV radiation.

While typically a single exposure of an interior surface of a container by a necessary or predetermined UV dose is sufficient to achieve a desired log reduction of microorganisms, in some embodiments, the interior surface of the container is exposed multiple times to UV radiation.

Short-wave UV light is harmful to humans. In addition to causing sunburn and (over time) skin cancer, UV light can produce extremely painful inflammation of the cornea of the eye, which may lead to temporary or permanent vision impairment. It can also damage the retina of the eye. For this reason, the light produced by a germicidal lamp must be carefully shielded against both direct viewing and reflections and dispersed light that might be viewed. Thus, in some embodiments of the present invention, the methods of sterilization a container and methods for inhibiting the growth of one or more microorganisms present on an interior surface of a container comprise the step of covering a container with a lid, top, or cover. The lid, top or cover essentially does not allow the UV light to penetrate and thus, protects humans from the harmful UV light.

E. Releasing a Germicidal UV Light Source from a Housing

In some embodiments, the method for UV sterilization of an interior surface of a container comprises the step of releasing a germicidal UV light source from a housing. In some embodiments, the method for inhibiting the growth of one or more microorganisms present on an interior surface of a container comprises the step of releasing a germicidal UV light source from a housing. Thereby a germicidal UV light source, e.g., a UV lamp, is released from a housing. In some embodiments, the releasing of the germicidal UV light source from the housing is accomplished by a motorized unit. The motorized unit (exemplary shown in FIGS. 1-3) is connected to a rope or wire 7, which is connected to a UV lamp 5 and thus, can move the UV lamp 5 in an downward direction for use and moves the UV lamp 5 in an upward direction after use.

In some embodiments, upon release from the housing, the germicidal UV light source moves longitudinally into the container to a predetermined position. An example of such a longitudinally movement is depicted in FIG. 3. In some embodiments, upon release from the housing, the germicidal UV light source moves laterally in the container to a predetermined position. An example of such a lateral movement is depicted in FIG. 7. In some embodiments, upon release from the housing, the germicidal UV light source rotates in the container. Examples of such a rotational movement are depicted in FIGS. 9-11.

Still another embodiment for releasing a germicidal UV light source from a housing is shown in FIG. 27. In this embodiment, a hinge or UV lamp module swing 81, is used to move the UV light source from a closed position into an exposed (released) position.

F. Placing a UV Device on an Upper Perimeter of a Container

In some embodiments, the method for UV sterilization of an interior surface of a container comprises the step of placing UV device comprising a bracket to which the germicidal UV light source is attached on the upper perimeter of a container. In some embodiments, the method for inhibiting the growth of one or more microorganisms present on an interior surface of a container comprises the step of placing a UV device comprising a bracket to which the germicidal UV light source is attached on the upper perimeter of a container. Thereby the UV device comprising the UV light source is firmly positioned on the upper perimeter of the container is restricted from moving downwards due to the brackets. An exemplary placing of a bracket to which the germicidal UV light source is attached on the upper perimeter of a container is shown in FIGS. 3, 10, and 11. While the bracket is firmly placed on the upper perimeter of a container, as shown in FIGS. 3, 10, and 11 other parts of the UV device can be moved downwards into the container.

In some embodiments, the method for UV sterilization of an interior surface of a container comprises the step of placing UV device comprising a housing to which the germicidal UV light source is attached (either directly or indirectly) on the upper perimeter of a container. In some embodiments, the method for inhibiting the growth of one or more microorganisms present on an interior surface of a container comprises the step of placing a UV device comprising a housing to which the germicidal UV light source is attached (either direcly or indirectly) on the upper perimeter of a container. Thereby the UV device comprising the UV light source is firmly positioned on the upper perimeter of the container and is restricted from moving downwards, e.g., by comprising a base plate (e.g., FIGS. 28, 29). An exemplary placing of a housing and base plate to which the germicidal UV light source is attached on the upper perimeter of a container is shown in FIGS. 28 and 29. While the base plate is firmly placed on the upper perimeter of a container, as shown in FIG. 29 other parts of the UV device, such as the UV light source can be moved downwards into the container.

In some embodiments of the present invention, a subject method comprises the step of positioning a UV device on top of an opening of a container. This step is schematically depicted, e.g., in FIGS. 1-3, 10, 11, 29, and 30.

G. Movably Inserting Through an Opening of a Container a Second Germicidal UV Light Source In some embodiments, the method for UV sterilization of an interior surface of a container comprises the step of movably inserting through the opening of a container a second germicidal UV light source. In some embodiments, the method for inhibiting the growth of one or more microorganisms present on an interior surface of a container comprises the step of movably inserting through the opening of a container a second germicidal UV light source. The second germicidal UV light source can be inserted similarly as the first germicidal light source or different. Insertion of the second germicidal UV light source can be simultaneously with the first germicidal light source or subsequently. In some embodiments, the second germicidal light source differs from the first germicidal light source in dimension and/or intensity.

H. Moving a Germicidal UV Light Source to a First Vertical Downwards Position within a Container In some embodiments, the method for UV sterilization of an interior surface of a container comprises the step of moving a germicidal UV light source to a first vertical downwards position within the container. In some embodiments, the method for inhibiting the growth of one or more microorganisms present on an interior surface of a container comprises the step of moving a germicidal UV light source to a first vertical downwards position within the container. Moving a germicidal UV light source to a first vertical downwards position within a container is described herein.

I. Moving a Germicidal UV Light Source from a First Vertical Downwards Position to a Horizontal Position within a Container In some embodiments, the method for UV sterilization of an interior surface of a container comprises the step of moving a germicidal UV light source from a first vertical downwards position to a horizontal position within the container. In some embodiments, the method for inhibiting the growth of one or more microorganisms present on an interior surface of a container comprises the step of moving a germicidal UV light source from a first vertical downwards position to a horizontal position within the container. Moving a germicidal UV light source from a first vertical downwards position to a horizontal position within a container is described herein.

J. Moving a Germicidal UV Light Source from a Horizontal Position to a Second Vertical Downwards Position within a Container In some embodiments, the method for UV sterilization of an interior surface of a container comprises the step of moving a germicidal UV light source from a horizontal position to a second vertical downwards position within the container. In some embodiments, the method for inhibiting the growth of one or more microorganisms present on an interior surface of a container comprises the step of moving a germicidal UV light source from a horizontal position to a second vertical downwards position within the container. Moving a germicidal UV light source from a horizontal position to a second vertical downwards position within a container is described herein.

K. Inhibiting Growth of Microorganisms

In some embodiments of the present invention, a germicidal light source is used to inhibit the growth of a microorganism or inhibit the growth of one or more microorganisms. The terms "inhibiting the growth of microorganisms," "growth arresting microorganisms," "reducing microorganisms," "killing microorganisms," or grammatically equivalents are used interchangeably herein.

In some embodiments of the present invention, a microorganism is a yeast species. The following provides a non-exhaustive list of yeast species that are typically found in a fermentation container, and more specifically on an interior surface of a fermentation container. Yeast species that have been investigated for wine and beer production include those from the *Candida, Kloeckera, Hanseniaspora, Zygosaccharomyces, Schizosaccharomyces, Torulaspora, Brettanomyces, Pichia, Hansenula, Metschnikowia, Torulespora, Debaryomyces, Saccharrmycodes* (species *ludwigii*), and *Williopsis* genera. Cultured yeast species include *Saccharomyces cerevisiae* and *Saccharomyces bayanus*. The growth of non-*Saccharomyces* yeast in wine production is also being investigated and can be inhibited. Thus, in some embodiments, it is particularly desirable to inhibit the growth of a yeast species using a method of the present invention. For example, 17,600 µWs/cm$^2$ is necessary for a 2 log killing of *Sacchahhmycodes* and 6,600 µWs/cm$^2$ for a 2 log killing of Brewer's yeast. UV intensities required for sterilization for unknown microorganism species can be determined by one of skill in the art using methods known in the art and described herein.

Some of the microorganisms found in a fermentation container, more specifically, on an interior surface of a fermentation container, are pathogenic. In some embodiments of the present invention, a microorganism is a pathogenic microorganism. Those microorganisms include, but are not limited to, *Escherichia coli, Corynebacterium diphtheria, Salmonella paratyphi* (causing enteric fever), *Salmonella typhosa* (causing typhoid fever), *Shigella dysenteriae* (causing dysentery), *Shigella flexerni* (causing dysentery), *Staphylococcus albus, Staphylococcus aureus, Streptococcus hemolyticus, Streptococcus lactis, Streptococcus viridians* and *Vibrio comma* (causing cholera). Thus, in some embodiments, it is particularly desirable to inhibit the growth of a pathogenic microorganism using a method of the present invention.

Other microorganisms found in a fermentation container, more specifically on an interior surface of a fermentation container, are detrimental in the production of a fermented beverage. Those microorganisms include, but are not limited to, *Brettanomyces (Dekkera)*, lactic acid bacteria, *Pediococcus, Lactobacillus*, and *Oenococcus. Brettanomyces* species include *B. abstinens, B. anomalus, B. bruxellensis, B. claussenii, B. custersianus, B. custersii, B. intermedius, B. lambicus*, and *B. naardensis*. The genus *Dekkera* (the perfect form of *Brettanomyces*, meaning it can sporulate), includes the species *D. bruxellensis* and *D. intermedius*. Thus, in some embodiments, it is particularly desirable to inhibit the growth of a microorganism, which is detrimental in the production of a fermented beverage, using a method of the present invention.

Other microorganisms found in a fermentation container, more specifically on an interior surface of a fermentation container, that are detrimental in the production of a fermented beverage are bacterial microorganisms. Bacteria genus include, but are not limited to, *Acetobacter, Lactobacillus, Pediococcus*, and *Leuconostoc. Acetobacter* species include, e.g., *A. aceti, A. hansennii, A. liquefaciens*, and *A. pasteurienus. Lactobacillus* species (ML bacteria, spoilage) include, e.g., *L. fructivorans* and others. *Pediococcus* species (ML bacteria, spoilage) include, e.g., *P. damnosus* and others. *Leuconostoc* species (ML bacteria) include, e.g., L. o and others. Thus, in some embodiments, it is particularly desirable to inhibit the growth of a bacterial microorganism using a method of the present invention.

1. Duration of Sterilization

The duration of sterilization, i.e., the time of activating a UV light source, determines the percentage of how many microorganisms are growth arrested or killed. As one of skill in the art will appreciate, the duration of a sterilization cycle is based on the power output of the UV lamp and the distance of the UV lamp from the walls and surfaces of the container to be sterilized.

In some embodiments, the duration of sterilization is performed for a time to ensure that at least 90% of the microorganisms present on the surface of a container are growth arrested or killed. One of skill in art will appreciate that a 90% growth arrest of microorganisms corresponds to a 1 log reduction.

In some embodiments, the duration of sterilization is performed for a time to ensure that at least 99% of the microorganisms present on the surface of a container are growth arrested or killed. One of skill in art will appreciate that a 99% growth arrest of microorganisms corresponds to a 2 log reduction.

In some embodiments, the duration of sterilization is performed for a time to ensure that at least 99.9% of the microorganisms present on the surface of a container are growth arrested or killed. One of skill in art will appreciate that a 99.9% growth arrest of microorganisms corresponds to a 3 log reduction.

In some embodiments, the duration of sterilization is performed for a time to ensure that at least 99.99% of the microorganisms present on the surface of a container are growth arrested or killed. One of skill in art will appreciate that a 99.99% growth arrest of microorganisms corresponds to a 4 log reduction.

In some embodiments, the duration of sterilization is performed for a time to ensure that at least 99.999% of the microorganisms present on the surface of a container are growth arrested or killed. One of skill in art will appreciate that a 99.999% growth arrest of microorganisms corresponds to a 5 log reduction.

In some embodiments, the duration of sterilization is performed for a time to ensure that at least 99.9999% of the microorganisms present on the surface of a container are growth arrested or killed. One of skill in art will appreciate that a 99.9999% growth arrest of microorganisms corresponds to a 6 log reduction.

Examples 6 and 7, in particular, provide useful times and guidance for sanitization of various containers.

2. Extinction Depths at 254 nm Wavelength

When practicing methods of the present invention, the extinction depths of the UV light source at 254 nm wavelength in various liquids needs to be taken into consideration, unless the surface of the container to be sterilized is completely dry. The application of UV light to sterilize a surface following a pressure wash would have to take into account the extinction depth of UV light at 254 nm in the remaining tap water. However, the depth of tap water the UV light must penetrate is minimal and would be equivalent to that of a film of water or at most interspersed water droplets. In some instances, the effect of depth of tap water on the duration of sterilization and kill rate will have to be tested using methods described herein and available in the art. This is due to the fact that following pressure washing of a container (e.g., a fermentation vessel), the remaining layer of water covering the container may not be homogeneous. Maximum depths of water drops can be used to calculate extra time needed for the sterilization cycle. Although the extinction coefficient could theoretically be used to calculate this, it would not take into account the reflection and scattering caused by uneven surfaces of the water film and water droplets, as such empirical data would be more useful for determining how to adjust sterilization timing. The following table provides guidance:

TABLE 7

Extinction Depths at 254 nm Wavelength (relationship to clear water) (American Ultraviolet Company, Lebanon, IN 46052, USA)

| Liquid | Extinction Depth |
| --- | --- |
| Apple juice | 1.0 |
| Beer | <1.3 |
| Liquid sugar | 1.0 |
| Milk - whole, raw | <0.1 |
| Vinegar | <5.0 |
| Water - concrete cistern | <75 |
| Water - distilled | 3,000 |
| Water - tap or mains | 125-180 |
| Wine | <2.5 |

L. Assessing Microbial Concentration

Microbial concentration on interior surfaces of containers may be assessed before and after performing a method of the present invention, such as the UV disinfection and UV sterilization methods described herein. A lower microbial concentration on interior surfaces of containers after a method of the present invention, e.g., performing a UV disinfection or UV sterilization method evidences the effectiveness of the method used. Methods for assessing microbial concentration are known in the art. Exemplary methods are described herein.

Preferred embodiments of this invention are described herein, including the best mode known to the inventor for carrying out the invention. Of course, variations on those preferred embodiments will become apparent to those of ordinary skill in the art upon reading the foregoing description. The inventor expects skilled artisans to employ such variations as appropriate, and the inventor intends for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

As can be appreciated from the disclosure above, the present invention has a wide variety of applications. While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention. The invention is further illustrated by the following examples, which are only illustrative and are not intended to limit the definition and scope of the invention in any way.

M. Sanitization of a Room, a Space or Defined Environment

In some embodiments, a UV device, preferably a UV light source, more preferably a germicidal UV light source, is used to sanitize a room, a space or a defined environment. The terms "sanitization" or "sanitation" and "UV sterilization" and grammatical equivalents thereof are used interchangeably herein. The meaning of a room is not limited to an enclosed room having walls, a ceiling, a floor or other barriers, but rather includes spaces open to at least on side and any defined environment. As exemplified herein, in some embodiments, a room, a space or defined environment is selected from the group consisting of a commercial kitchen, a medical facility, an acute care area, an operating room, a medical equipment storage cabinet, a clean room, a bathroom, a food production area, a nursery home, a trailer, a rail car, a grocery store display case, and a deli counter.

Thus, the present invention provides methods for sanitization (UV sterilization) of a room, a space or defined environment. In some embodiments of this method, the method comprises the step of providing a room, a space or defined environment in need of sanitization and exposing the room, space or defined environment to ultraviolet (UV) sterilization using a UV device. In some embodiments of this method, the method comprises the step of selecting a room, a space or defined environment in need of sanitization and exposing the room, space or defined environment to ultraviolet (UV) sterilization using a UV device. Suitable UV devices are described herein. Some embodiments of the method for sanitizing a room comprise the step of attaching a UV device to a wall of the room. Some embodiments of the method for sanitizing a room comprise the step of attaching a UV device to a ceiling of the room. Some embodiments of the method for sanitizing a space or defined environment comprise the step of attaching a LTV device to an object or structure present in the space or defined environment. Objects or structures to which a UV device can be attached include, but are not limited to, a conveyer belt, a hood, a cabinet, a display case. A UV device can also be superimposed over or attached to a preexisting light fixture.

Some embodiments of the method for sanitizing a room, a space or defined environment comprise the step of moving a UV light source from a closed position to an exposed position.

Some embodiments of the method for sanitizing a room, a space or defined environment comprise the step of activating the UV light source.

In some embodiment of a UV device being used for the sanitization of a room, a space or defined environment, a portable UV device may be used. In some embodiments, an RFID tag is mounted to the doorway of a room, a space or defined environment intended to be sanitized. In some embodiments, an RFID tag reader is mounted to the UV device, such that when the UV device is brought into the room, space or defined environment, the tag is read. Information on the tag includes, but is not limited to, dimension and type of the room, space or defined environment, and desired log reduction. This information is uploaded into the UV device and a sanitization cycle is preprogrammed.

As one of ordinary skill in the art will appreciate some embodiments of the method for sanitizing a room, a space or defined environment comprise steps described herein for the sanitization (UV sterilization) of a container or surface of a container. Those steps are described in detail herein and one of ordinary skill in the art can easily adapt those steps for the use in the method for sanitizing a room, a space or defined environment.

In some embodiments, a room, a space or a defined environment is exposed to UV radiation. It is to be understood that the invention can be applied to any defined environment. For example, an environment may be defined by solid surfaces or barriers, such as a wall or product packaging.

A room accepts a UV light source for the purpose of sterilization of the wall, ceiling or floor, including any and all objects, fluids, materials, and surfaces contained within the room. In some embodiments, the objects, fluids, materials, and surfaces within the room are contained within the room temporarily. In other embodiments, they are contained within the room permanently.

The present invention provides for the sanitization of a variety of rooms, spaces or defined environments. Rooms, spaces or defined environments include, but are not limited to a commercial kitchen, an operating room, a clean room (ISO 1-ISO 9), a food production area, a nursery home. An exemplary application of a UV device described herein would be for sanitizing a sensitive area of a medical facility, such as an acute care area or an operating room. Other areas in a medical facility that can be sanitized using a UV device described herein include a waiting room, a bathroom, and a medical equipment storage cabinet.

A UV device described herein may also be configured into a food processing equipment so that food is treated as it moves through the equipment, for example on a conveyor belt, automatic cutters and slicers and inspection areas. The product may be tumbled to promote uniform treatment. The UV device may also be configured to be placed in containers, trailers, and rail cars or as a component to a refrigeration system of such containers, trailers, and rail cars to sanitize the air therein while providing the beneficial preservative effects of ozone to any products stored therein.

Other exemplary applications of a UV device described herein include the provision or incorporation of the UV device into grocery store display cases, such as deli counters and meat, fish and poultry display cases and floral display cases, both refrigerated and non-refrigerated.

Still other examples of areas that can be sanitized with a UV device described herein include parcels, packages, and envelopes, also when moving on a conveyor belt. The parcels, packages, and envelopes may be tumbled or turned to promote uniform treatment.

In some embodiments of a UV device, when used for sanitization of a room, one or more UV lamps are attached to the ceiling of the room in a housing. One embodiment of such UV device is shown in FIG. 27. The housing may be referred to as a box, UV light box or box-like housing. In some embodiments of the UV device, the UV device comprises UV lamps arranged in one or more UV lamp clusters, each comprising two, three, or more UV lamps. As shown in FIG. 27, the UV lamp clusters can either be stationary or retrievable. The UV device may also have combinations of stationary and retrievable UV lamp clusters, For example, FIG. 27 shows a UV device having one stationary UV lamp cluster and four retrievable UV lamp clusters. Thus, in one embodiment of the invention, a UV device is a UV device mountable to the ceiling or wall of a room, a space or defined environment and comprises at least one stationary UV lamp cluster and at least one retrievable UV lamp cluster. In other embodiments, all UV lamp clusters are retrievable. In still other embodiments, all UV lamp clusters are stationary.

As one of ordinary skill in the art will appreciate, a UV device mountable to a ceiling or wall may have different configurations with respect to height, width and length dimensions as the one shown in FIG. 27.

When the UV lamp clusters comprising the UV lamps 5 are in a closed, locked or folded position, they may be folded completely within a box-like housing 79 as shown in FIG. 27B. This can be easily achieved by positioning UV lamp holders 82 at slightly different height positions on the sides of the box-like housing 79 as shown in FIG. 27. A hinge or UV lamp module swing 81 serves to move the UV lamp holder into a desired position, for example from a closed, locked, or folded position into a position where the UV lamps are exposed (FIG. 27). Optionally, the UV lamp clusters may be covered temporarily with a removable lid, cover, or panel when in the closed, locked or folded position. The interior surface of box-like housing 79 may be covered with a reflective interior surface so to enhance the sanitization process.

In some embodiments of a UV device mountable to a ceiling or wall of a room, space or environment, the UV lamps or UV lamp clusters are fully enclosed in a housing when not in use. Prior to use of the UV lamps or UV lamp clusters for sanitization, the UV lamps or UV lamp clusters are moved from an enclosed position to an exposed position through one or more openings in the housing. The opening of the housing may also be covered by a flap door/hinge mechanism so that the UV lamps are not visible when the UV device is not in use.

In some embodiments, the UV lamp clusters extend from the box-like housing at varying angles.

A motor may be used to move the hinge or UV lamp module swing 81 and arrest them in a desired fixed angle position. Thus, the position of the UV lamps is adjustable vertically and horizontally in relation to the housing to optimize sanitization. Adjustments may be made hydraulically, pneumatically, electronically, mechanically, or by other equivalent means.

In some embodiments of a UV device, when used for sanitization of a room, one or more UV lamps are attached to the side of a room in a housing. The housing can be similar to the one shown in FIG. 27, however, may have different configurations with respect to height, width and length dimensions. When in use, the UV lamps may extend from the housing at varying angles. When not in use, the UV lamps may be retracted into a closed, locked, or folded position. Positioning the UV lamps into a desired position can be done by using a motor.

A UV device described herein may be configured for general room sanitization applications where the UV device, or components thereof, may be placed on a moving part, either permanently or temporarily during the sanitization procedure.

In some embodiments of a UV device, when used for sanitization of a room, area or defined environment, the UV device comprises a range finding device to determine the size of the room, space or defined environment to be sanitized. The range-finder then provides information to preprogram an effective sanitization cycle.

In some embodiments of a UV device, when used for sanitization of a room, a space or defined environment, a multi bulb UV cluster extends from the ceiling with the UV lamps extending at varying angles to optimize coverage and UV exposure of the room, space or defined environment.

In some embodiments of a UV device, when used for sanitization of a room, a space or defined environment, a multi lamp UV cluster extends from the ceiling with individual UV light coming down independently at varying angles.

In some embodiments of a UV device, when used for sanitization of a room, a space or defined environment, the UV lamp cluster and housing are permanently fixed to either the walls, floors, or ceiling of the room, space or defined environment.

In some embodiments of a UV device, when used for sanitization of a room, a space or defined environment, the UV lamp cluster is attached via a fixture to the ceiling of the room, space or defined environment. The fixture may be permanently attached and the UV bulb cluster and housing may be removable.

In some embodiments of a UV device, when used for sanitization of a room, a space or defined environment, the dimensions of the room, space or defined environment are preprogrammed into the UV device allowing the timing of sanitization to be optimized and the minimal necessary UV dose required for sanitation to be reached while minimizing power use. Preferred is an approximately 3 log reduction of microorganism determined as described herein.

In some embodiments of a UV device, when used for sanitization of a room, a space or defined environment, the UV device is linked to a motion detector. This may be helpful to ensure people and/or animals are absent from the room, space or environment prior to the beginning of the sanitization cycle. It will also be helpful for shutting off and deactivating the UV sterilization process if a person enters a room, a space or defined environment while a UV sterilization process is ongoing.

In some embodiments of a UV device, when used for sanitization of a room, a space or defined environment, multiple UV lamp clusters are spread throughout the room, space or defined environment. Based on the dimension and shape of the room, space or defined environment, the positioning of the UV lamps and angles are accounted for and this information is programmed into an algorithm allowing the timing of sanitization to be optimized and the minimal necessary UV dose required for sanitation to be reached while minimizing power use. Preferred is an approximately 3 log reduction of microorganism determined as described herein. The positioning of the UV lamps and angles can also be communicated via wireless technology. In some embodiments, a rangefinder may analyze the shape and dimension of the room, space or defined environment and input information into an algorithm allowing the timing of sanitization to be optimized and the minimal necessary UV dose required for sanitation to be reached while minimizing power use. Preferred is an approximately 3 log reduction of microorganisms determined as described herein.

In some embodiments of a device, when used for sanitization of a room, a space or defined environment, the UV bulb is attached to the bottom of a robot having wheels and follows programming allowing it to both perform an effective moving pattern on the floor covering desired areas. The robot may also have an object and wall avoiding programming and technology. The robot may move at a speed allowing an effective UV dose required for sanitization to be reached while minimizing power use. Preferred is an approximately 3 log reduction of microorganisms determined as described herein.

In some embodiments of a UV device, the UV bulb is attached to the bottom of a robot crawler that uses suction allowing it to crawl vertically on walls and horizontally on ceilings of a room, space or environment. The robot crawler may follow programming allowing it to perform an effective pattern on the wall and ceiling covering desired areas. The robot crawler may move at a speed allowing an effective UV dose required for sanitization to be reached while minimizing power use. Preferred is an approximately 3 log reduction of microorganisms determined as described herein.

It is also understood that for the methods described herein, individual steps may be performed by more than one person or more than one entity. Thus, not every step of a method described herein must be performed by the same person or entity.

VI. Examples

The below examples are meant to illustrate specific embodiments of the methods and compositions described herein and should not be construed as limiting the scope of the invention in any way.

Example 1

Assessing Microbial Concentration i. Inoculation of a Container

The following is an exemplary method for assessing microbial concentration in a tank after UV disinfection according to a method described herein and after using the standard sodium hydroxide and citric acid procedure or hypochlorite and citric acid (Emmanuel et al., 2004, *Environmental International*, 30(7): 891-900).

Four tanks (wine fermentation vessels; stainless steel) are provided. Two tanks have a 36" radius and two tanks have a 60" radius and a height of 120". The tanks are pressure washed with water and inoculated with spoilage yeast, cultured yeast, and pathogenic microorganisms (see Table 8).

TABLE 8

Exemplary Inoculating Containers (Tanks) With Microorganism

| Spoilage Yeast | Cultured Yeast | Pathogenic Microorganisms |
|---|---|---|
| *Brettanomyces abstinens* | *Saccharomyces cerevisiae* | *Salmonella* spp |
| *Brettanomyces anomalus* | *Saccharomyces bayanus* | *Clostridium botulinum* |
| *Brettanomyces bruxellensis* | | *Staphylococcus aureus* |
| *Brettanomyces claussenii* | | *Campylobacter jejuni* |
| *Brettanomyces custersianus* | | *Yersinia enterocolitica* and *Yersinia pseudotuberculosis* |
| *Brettanomyces custersii* | | *Listeria monocytogenes* |
| *Brettanomyces intermedius* | | *Vibrio cholerae* O1 |
| *Brettanomyces lambicus* | | *Vibrio cholerae* non-O1 |
| *Brettanomyces naardensis* | | *Vibrio parahaemolyticus* and other vibrios |
| | | *Vibrio vulnificus* |
| | | *Clostridium perfringens* |
| | | *Bacillus cereus* |
| | | *Aeromonas hydrophila* and other spp |
| | | *Plesiomonas shigelloides* |
| | | *Shigella* spp |
| | | Miscellaneous enterics |
| | | *Streptococcus* |
| | | *Escherichia coli* |

TABLE 8-continued

Exemplary Inoculating Containers (Tanks) With Microorganism

| Spoilage Yeast | Cultured Yeast | Pathogenic Microorganisms |
|---|---|---|
| | | enterotoxigenic (ETEC) *Escherichia coli* enteropathogenic (EPEC) *Escherichia coli* O157:H7 enterohemorrhagic (EHEC) *Escherichia coli* enteroinvasive (EIEC) |

The tanks are inoculated on multiple surfaces, such as the corners, the weld seams, the bottom and sides of the tanks. After the inoculation and before the UV or chemical disinfection, samples are collected from several interior surfaces of the tanks (as described below). Those samples will be referred to as control samples or no treatment samples.

A UV light source, an American Air and Water UVC lamp 64" in length with an output of 190 microwatts/cm$^2$ at 254 nm (Model GML270) is inserted into a 36" radius tank (see, FIGS. 1-3) and activated for 1 minute and 26 seconds for each 64" interval of the tank. The UV-C lamp is moved down the 36" radius tank until the entire interior surface has been covered by the same intensity (dose) of UV-C light. After each interval of 1 minute and 26 seconds the UV lamp will be lowered by 64". In order to kill 100% of *Saccharomyces* sp. Yeast, 17,600 microwatt/cm$^2$ is needed (The timing of 1 minute and 26 seconds was based on achieving 17,600 microwatt/cm$^2$ at a distance of 36").

A UV light source, an American Air and water UVC lamp 64" in length with an output of 190 microwatts/cm$^2$ at 254 nm (Model GML270) is inserted into a 60" radius tank (see, FIGS. 1-3) and activated for 3 minute and 41 seconds for each 64" interval of the tank. The UV-C lamp is moved down the 60" radius tank until the entire interior surface has been covered by the same intensity (dose) of UV-C light. After each interval of 3 minute and 41 seconds the lamp will be lowered by 64" In order to kill 100% of *Saccharomyces* sp. Yeast, 17,600 microwatt/cm$^2$ is needed (The timing of 3 minute and 41 seconds was based on achieving 17,600 microwatt/cm$^2$ at a distance of 60").

The other 36" and 60" tanks, which have been comparably inoculated, are cleaned using the standard sodium hydroxide and citric acid solutions.

In a separate series of experiments, following inoculation, the tanks are sterilized/disinfected at different time intervals simulating alcoholic beverage production protocols (e.g., the time between tanks being emptied and then refilled).

ii. Collecting Samples from an Interior Surface of a Container

After completing the UV disinfection or the chemical disinfection as described above, the interior surfaces of the tanks are wiped using, e.g., Fellowes Surface Cleaning Wipes (STRATUS Inc., Amarillo, Tex.), which are pre-moisten antistatic wipes. Prior to the sampling, a sheet of original wipe cloth is cut to one forth size (48 cm$^2$) using sterilized scissors, placed into sterile whirl pack bags, and placed under a UV lamp for disinfection. Several areas of the tanks are wiped back and forth over the entire surface area of approximately 10 cm$^2$ using several vertical strokes, then folded with the fresh side of the wipe exposed, and several horizontal strokes were made over the same area with the other side of the wipe. After the sampling, the wipes are placed in 10 mL of phosphate buffer saline plus 0.01%

Tween-80 (PBST) in 50-mL tubes. Types of sampling areas are recorded after the sampling.

iii. Microbial Assays

Collected wipe samples are assayed with culture methods to measure viable microorganisms. Selective agars, i.e. Tryptic(ase) Soy Agar (TSA) for mesophilic bacteria and thermophilic actinomycetes, Mannitol Salt Agar (MSA) for *Staphylococcus*, CHROMagar for methicillin resistant *Staphylococcus aureus* (MRSA) and Malt Extract Agar (MEA) for total fungi are used.

The log reduction of each inoculated microorganism species is recorded. Experiments are repeated to obtain statistically significant results.

iv. Pulsed UV Light

In a different series of experiments, the experiments described in i. to iii. of above, are repeated using a pulsed UV light. Xenon, SteriPulse-XL and Model RS-3000M will be used. As shown in FIG. 10, 11, or 16 one pulsed UV lamp will be mounted on laterally adjustable arms or mounts that allow the pulsed UV lamp to be brought within the optimal distance of 1.25" of the surface to be sterilized. The pulsed UV lamp uses an elliptical window and has a footprint of 16"×1". The pulsed UV lamp will be rotated at speed such that the footprint is exposed for a duration of 1 second on the surface being sterilized. For the tank with a 36" radius that means that the rate of rotation will be 0.277 rpm. After a 16" interval of the tank has been exposed to the pulsed UV, the device will be lowered by 16" and the rotation will be repeated. This will be repeated in 16" interval until the entire surface of the vessel has been exposed.

v. Closed Top Container

In a different series of experiments, the experiments described in i. to iv. of above, are repeated using a closed top fermentation vessel. Essentially, the only difference will be that instead of supporting the UV device by a bracket from the top of the fermentation vessel, the UV device will be mounted on a tripod and inserted through a hatch at the base of the fermentation vessel.

vi. Pressure Washing at Various Times

In a different series of experiments, the experiments described in i. to v. of above, are repeated by performing the pressure washing after various times following the inoculation. In this series of experiments it is also determined what, if any, effect the presence of water droplets will have on the log reduction. This is done by employing the UV device at various times following the pressure washing.

The first set of experiments involves inoculating the tanks and pressure washing them at different time intervals following inoculation, such as 24 hours, 48 hours, 72 hours and 144 hours. The pressure washing is then immediately followed by a UV sterilization cycle. This is done to determine whether the time bacteria and yeast are allowed to grow prior to pressure washing affects the final duration of the sterilization cycle.

Another set of experiments will not vary the time between inoculation and pressure washing, but rather the time between pressure washing and UV sterilization. The objective will be to determine the effects of varying amounts of water on the inner surface of the tank and its effect on the duration of the sterilization cycle and log reduction. In this set of experiments, the UV sterilization cycle can be applied at 0 minutes following the pressure washing, 15 minutes following the pressure washing and in continually increasing 15 minute intervals following the pressure washing until the tank is completely dry.

vii. Dry Interior Surface

In a different series of experiments, the experiments described in i. to vi. of above, are repeated by including the step of allowing the interior surface of the tanks to dry after performing the pressure washing.

Example 2

Calculating Killing of Microorganisms

The following provides the steps to calculate the time needed to kill a desired microorganism using compositions and methods of the present invention. The required Energy Dosage of UV Radiation (UV Dose) in $\mu Ws/cm^2$ needed for kill factor is provided herein in Tables 1-5. To determine the intensity of UV on a surface at various distances from a germicidal UV lamp one multiplies the radiant energy (shown in microwatts per square centimeter at one meter) by the intensity factor as shown in the Table 9 below.

TABLE 9

| Intensity Factor (American Ultraviolet Company, Lebanon, IN 46052, USA | | | | | | | | | |
|---|---|---|---|---|---|---|---|---|---|
| Distance from UV Lamp | 2" | 3" | 4" | 6" | 8" | 10" | 12" | 14" | 18" | 24" |
| Intensity Factor | 32.3 | 22.8 | 18.6 | 12.9 | 9.85 | 7.94 | 6.48 | 5.35 | 3.6 | 2.33 |
| Distance from UV Lamp | 36" | 39.37" (1 meter) | | 48" | 60" | 80" | 100" | 120" | | |
| Intensity Factor | 1.22 | 1.0 | | 0.681 | 0.452 | 0256 | 0.169 | 0.115 | | |

Using a UV lamp with an output of 190 microwatts/cm² at 254 nm (at a distance of 1 meter), placed within a fermentation vessel 36" from the interior surface, the following calculations are used for achieving 99% killing of *Saccharomyces cerevisiae* (13,200 microwatt seconds/cm² required; see Table 5). Step 1: 13,200 microwatt seconds/cm²/190 microwatts/cm²=69.47 seconds. Step 2: The intensity factor at 36" is 1.22 (see Table 9), therefore 69.47 seconds/1.22=56.96 seconds.

Using a lamp with an output of 190 microwatts/cm² at 254 nm (at a distance of 1 meter), placed within a fermentation vessel 60" from the interior surface, the following calculations are used for achieving 99% killing of *Shigella dysentery* (4,200 microwatt seconds/cm² required; see Table 2): Step 1. 4,200 microwatt seconds/cm²/190 microwatts/cm²=22.10 seconds. Step 2: The intensity factor at 60" is 0.452 (see Table 9), therefore 22.10 seconds/0.452=48.90 seconds.

Using a lamp with an output of 190 microwatts/cm² at 254 nm (at a distance of 1 meter), placed within a fermentation vessel 60" from the interior surface, the following calculations are used for achieving 99% killing of *Sarcina lutea* (26,400 microwatt seconds/cm² required; see Table 2): Step 1. 26,400 microwatt seconds/cm²/190 microwatts/

$cm^2$=138.94 seconds. Step 2: The intensity factor at 60" is 0.452 (see Table 9), therefore 138.94 seconds/0.452=307.40 seconds.

Since *Sarcina lutea* is one of the most UV resistant bacteria (more resistant than known species of yeast), a fermentation vessel where the UV source was 60" away from the internal surface could be left on for about 307.40 seconds at each sterilization interval within the vessel to ensure all yeast (known) and pathogenic microorganisms are killed.

Example 3

Inhibiting the Growth of *Bacillus Subtilis*

To determine the effectiveness of a method of the present invention and efficacy of a UV device of the present invention for the sanitization of a stainless steel tank used in the wine making process, the killing/growth arrest of *Bacillus subtilis* (American Type Culture Collection, ATCC Number 82TM; designations: AMC [ATCC 8037, NRS 315]) was investigated. *Bacillus subtilis* forms spores, thereby making it a more UV resistant microorganism than microorganisms that do not form spores. In this experiment 30" SE UV-C lamps (Steril-Aire) were used. Three identical UV lamps were placed in a mount and put in a spiral configuration with each UV lamp set at a 15 degrees angle.

Two coupons (per time point) were spiked with a *Bacillus subtilus* suspension to give a final concentration of $9.6 \times 10^6$ CFU (colony forming units)/coupon for the first three time points. The fourth (25 minute) time point was inoculated with a suspension of $1.3 \times 10^7$ CFU/coupon (since it was tested on a different day) and allowed to air dry inside a biological safety cabinet. The coupons were allowed to dry and attached to the inside of stainless steel tank. Then the coupons were exposed to the UV light at a distance of 60" from the UV light source for four all four (4) time points: 30 seconds, 5 minutes, 15 minutes and 25 minutes. After each exposure time was performed, the coupons were swabbed in order to perform the recovery process. Two additional stainless steel coupons were spiked to be used as positive controls.

UV readings to measure the UV-C exposure at various time points were done using a General UV512C Digital UV-C Meter (radiometer). Table 10 below provides the actual UV readings recorded for each exposure time:

TABLE 10

UV Readings per Time Point and Interval.

| 30 Seconds Time Point | | 5 Minutes Time Point | | 15 Minutes Time Point | | 25 Minutes Time Point | |
|---|---|---|---|---|---|---|---|
| Seconds | uW | Minutes | uW | Minutes | uW | Minutes | uW |
| 5 | 42 | 0.5 | 135 | 1 | 243 | 3 | 200 |
| 10 | 54 | 1 | 202 | 2 | 225 | 6 | 179 |
| 15 | 69 | 1.5 | 206 | 3 | 212 | 9 | 174 |
| 20 | 87 | 2 | 204 | 4 | 198 | 12 | 167 |
| 25 | 109 | 2.5 | 202 | 5 | 186 | 15 | 162 |
| 30 | 135 | 3 | 198 | 6 | 177 | 18 | 159 |
| | | 3.5 | 195 | 7 | 176 | 21 | 162 |
| | | 4 | 192 | 8 | 181 | 24 | 169 |
| | | 4.5 | 190 | 9 | 175 | | |
| | | 5 | 184 | 10 | 172 | | |
| | | | | 11 | 171 | | |
| | | | | 12 | 171 | | |
| | | | | 13 | 171 | | |
| | | | | 14 | 170 | | |
| | | | | 15 | 168 | | |

The recovery of *Bacillus subtilis* from the coupons after 30 seconds exposure to the UV light was $5.3 \times 10^5$ CFU/ml. After 5 minutes exposure to the UV light, the recovery of *Bacillus subtilis* was reduced to $1.4 \times 10^3$ CFU/ml. After 15 minutes exposure to the UV light, the recovery of *Bacillus subtilis* was further reduced to $1.5 \times 10^1$ CFU/ml. Finally, after 25 minutes exposure to the UV light, no microorganisms were recovered. The recovery positive control had a count of $6.4 \times 10^5$ CFU/ml for the first three time points and $8.1 \times 10^5$ CFU/ml for the fourth time point.

Table 11 below summarizes the results of the above experiment and provides the log reduction results based on calculations from *Bacillus subtilis* recovery from test coupon vs. positive control.

TABLE 11

Inhibiting the growth of *Bacillus subtilis*.

| Exposure Time | Concentration *Bacillus subtilis* Recovered (CFU/ml) | Log Reduction |
|---|---|---|
| 30 seconds | $5.3 \times 10^5$ | 0.1 |
| 5 minutes | $1.4 \times 10^3$ | 2.7 |
| 15 minutes | $1.5 \times 10^1$ | 4.6 |
| 25 minutes | 0 | 5.9 |

The results of this experiment demonstrated that the UV light source tested was effective in reducing the *Bacillus subtilis* microorganism population by about 3 logs at an exposure time of 5 minutes, by about 5 logs at an exposure time of 15 minutes and by about 6 logs at exposure time of 25 minutes.

One of skill in the art will appreciate that in view of the experiments described above, a lower UV dose will be required to kill or inhibit the growth of other microorganisms that do not produce spores. Thus, by having demonstrated that one of the most UV-resistant microorganisms can be efficiently killed or growth inhibited using a method of the present invention, one of skill in the art will appreciate that the methods of the present invention in combination with the UV devices of the present invention are useful to kill or growth inhibit other microorganism that might be present in a fermentation container, more specifically on a surface of a fermentation container Example 4

Sanitization of a Room

The following provides an exemplary procedure for UV sterilization of a room, in particular, an operating room, a clean room (ISO 1-9), a nursing home, or a kitchen (commercial or residential). The UV device for sanitizing the room will be fixed to the ceiling of, for example, a 20 ft by 20 ft room. The UV device is allowed to determine the dimensions of the room and program a sanitization cycle. The room has all of the standard equipment and features of an operating room (OR), a clean room (ISO 1-9), a nursing home, or a kitchen (commercial or residential). Radiometers and plates pre inoculated with pathogenic microorganisms (such as but not limited to: *Streptococcus* and *Pseudomonas*, and foodborne bacteria such as *Shigella, Campylobacter*, and *Salmonella*) are placed throughout the room at varying distances from the UV device to determine the UV-C intensity level attained in addition to the log reduction of microorganisms. Furthermore, swab tests are taken at those locations in addition to swabbing objects of different material composition, such as polymers, metals, papers, and fabrics. This is to determine log reductions on objects of different material. Areas of potential shading are also tested in a similar fashion in order to determine the effects of reflected light on log reductions and UV-C intensity.

These experiments are repeated in each room type, however with multiple UV devices in the room. One UV device is fixed to the ceiling, one to each wall. The UV devices are allowed to scan the respective room and communicate with one another, and program a sanitization cycle.

In some embodiments the UV device will communicate with a surface reading radar unit that will enable it to detect relative distances of objects in the room, material type and will program a sanitization cycle based on the nature of the material and the positioning of the objects and room size.

Example 5

Using UV Device UV55

The UV device UV55 has been extensively tested on 55 gallon wine drums having a 2" Tri-Clover™ fitting located on the side (see below, Examples 6, 7). The UV device UV55 is particularly well suited for use on any small container from about 15 gallon kegs to about 550 gallon Porta tanks. In addition, it has also been tested on oak barrels (see Examples 6). The UV device UV55 comprises an 18" SE lamp manufactured by Steril-Aire. As tests demonstrated, at least a 5 log reduction of microorganism growth was observed when the UV device UV55 was tested in a 55 gallon drum after 3 minutes of activation (i.e., exposure of UV radiation onto the interior surface of the container, which was spiked with microorganisms). Using UV device UV55 the following applications have been proven successful: 3 minutes of exposure for 15 gallon kegs, 6 minutes for a 55 gallon drum, 12 minutes for a Porta tank or oak barrel. Among others, testing was performed with *Pseudomonas aeruginosa*, a gram negative bacterium similar to many of the herein mentioned microbes potentially harmful to wine production.

The following provides a more detailed user guide for using UV device UV55. UV device UV55 is plugged in. The user will want to make sure that the central sleeve tightening knob 86 on the side of the metal sleeve attachment ring 95 is loosened prior to use so that the central sleeve 12 can slide downwardly and upwardly easily. For storage and protection of the UV lamp 5, the central sleeve 12 is pulled into its most upward position so that the UV lamp fully retracts beyond the position of the base plate 10. The on/off or reset button 85 at the handle cap 92 is set to an on/reset position. To turn off the UV device UV55, the on/off or reset button 85 is pressed downwards. To turn on the UV device UV55, the on/off or reset button 85 is twisted clockwise.

The user places UV device UV55 on top of a container 4 so that the housing 2 is positioned on top of an opening within the container 4. The opening on top of the container is at least wide enough to allow the insertion of the UV lamp 5. If the opening of the container is wider than the base plate 10 of the UV device, the user is advised to use an additional protective shield and cover the opening of the container (but leave an opening wide enough to allow insertion of the UV lamp 5) to not get exposed to UV irradiation during the sterilization process. The protective shield may have any shape or form or size—as long as it provides an opening through which a UV lamp 5 can be inserted and prevents exposure to UV irradiation.

Once the housing 2 is positioned on top of the opening of the container 4 and the central sleeve knob 86 is loosened, a user can lower the UV lamp 5 into the container by allowing the central sleeve 12 to move downwardly. A user may conveniently control this downward movement by holding on to the handle 91 or hanging hook 84. As the central sleeve is lowered, the optical switch 98 is activated. In addition, an audible beep will sound to indicate that a sterilization cycle has started and LED lights behind the translucent plastic ring 87 will blink. Minutes of the sterilization cycle will be indicated by a specific number of blinks. Minute one is indicated by one blink, minute two is indicated by two blinks, minute tree is indicated by three blinks., etc.

Using UV device UV55 a standard keg can be sterilized in about three minutes. Using UV device UV55 a standard drum can be sterilized in about six minutes. At 12 minutes of use, an audible beep will sound alerting the user to the amount of time which has elapsed. The UV lamp 5 will remain on until switched off (see above).

UV device UV55 will be automatically reset as the user moves the central sleeve 12 upwardly and the optical switch 98 moves upwardly out of the housing 2. The sterilization cycle of another container may be done.

Example 6

UV Sanitation of a Wooden Barrel Using UV Device UV55

A study was performed to determine the efficacy of UV device UV55 for the sanitization of wood barrel tanks used in the wine making process. The study was performed by inoculating the interior surface of wood barrel coupons (in triplicate) with a suspension of *Pseudomonas aeruginosa*. The coupons were then exposed to UV light according to Table 12.

Details of this study were as follows: Three coupons (per time point) were spiked with the *Pseudomonas aeruginosa* suspension to give a final concentration of $1.9 \times 10^7$ CFU/coupon. The coupons were placed at three different locations within the tank and exposed to the UV light (UV55) for five (5) time points: 2 minutes, 4 minutes, 6 minutes, 8 minutes, and 12 minutes. After each exposure time was performed, the coupons were immersed into 10 ml Tryptic Soy Broth to perform the enumeration/recovery process. Three additional stainless steel coupons were spiked as above and used as positive controls (no exposure to UV light).

The result of this study is shown in Table 12.

TABLE 12

Growth inhibition (log reduction) of *Pseudomonas aeruginosa* after exposure to UV light (UV device UV55).

| Exposure Time (minutes) | Concentration of *Pseudomonas aeruginosa* recoverd (CFU/coupon) | Log Reduction |
| --- | --- | --- |
| 2 | $1.3 \times 10^5$ | 2.2 |
| 4 | $1.5 \times 10^5$ | 2.1 |
| 6 | $1.1 \times 10^5$ | 2.2 |
| 8 | $9.1 \times 10^4$ | 2.3 |
| 12 | $1.4 \times 10^3$ | 4.1 |

Based on this test, it can be concluded that the UV light source tested was effective in reducing the *Pseudomonas aeruginosa* population by about 4.1 logs at an exposure time of 12 minutes.

Example 7

A Comparative Study: UV Sanitation Using UV55 vs. Chemical Cleaning

A study was performed to determine the efficacy of UV device UV55 for the sanitization of stainless steel tanks used in the wine making process versus a solution of sodium carbonate peroxyhydrate at a concentration of 1.56 g/L. The study was performed by inoculating the interior surface of stainless steel coupons (in triplicate) with a suspension of *Pseudomonas aeruginosa*. The coupons were then exposed to either UV light or to the chemical solution according to Table 13.

Details of UV Sanitation were as follows: Three coupons (per time point) were spiked with the *Pseudomonas aeruginosa* suspension to give a final concentration of $1.5 \times 10^8$ CFU/coupon. The coupons were placed at three different locations within the tank and exposed to the UV light (UV55) for four (4) time points: 2 minutes, 4 minutes, 6 minutes, and 8 minutes. After each exposure time was performed, the coupons were immersed into 100 ml Tryptic Soy Broth to perform the enumeration/recovery process. Three additional stainless steel coupons were spiked as above and used as positive controls (no exposure to UV light).

Details of Carbonate Solution Cleaning were as follows: Three coupons were spiked with the *Pseudomonas aeruginosa* suspension to give a final concentration of $1.5 \times 10^8$ CFU/coupon. The coupons were then immersed into 100 ml of sodium carbonate peroxyhydrate solution at a concentration of 1.56 g/L and then into 100 ml Tryptic Soy Broth to perform the enumeration/recovery process. The same positive control and suspension was used for both studies.

The result of this study is shown in Table 13.

TABLE 13

Growth inhibition (log reduction) of *Pseudomonas aeruginosa* after exposure to UV light (UV device UV55) and Treatment with sodium carbonate peroxyhydrate solution.

| UV55 Exposure Time (minutes) | Concentration of *Pseudomonas aeruginosa* recoverd (CFU/coupon) | Log Reduction |
| --- | --- | --- |
| 2 | $1.8 \times 10^3$ | 4.9 |
| 4 | $1.2 \times 10^3$ | 5.1 |
| 6 | $8.3 \times 10^2$ | 5.3 |
| 8 | $<1 \times 10^3$ | >5.2 |
| Sodium Carbonate Solution | $3 \times 10^6$ | 1.7 |

Based on this test, it can be concluded that the UV light source tested was effective in reducing growth of the *Pseudomonas aeruginosa* population by >5.2 logs at an exposure time of 8 minutes. The sodium carbonate solution used as a rinse was effective in reducing growth of the *Pseudomonas aeruginosa* population by about 1.7 log.

What is claimed is:

1. An ultraviolet (UV) device for UV sterilization of an interior surface of a container, the UV device comprising:
   (i) a germicidal UV light source comprising a lamp;
   (ii) a central sleeve comprising a central sleeve upper end and a central sleeve lower end;
   (iii) a housing configured to house the germicidal UV light source and comprising an interior, a housing upper end and a housing lower end and further configured so that the central sleeve can be moved downwardly and upwardly through the interior of the housing permitting movably and inwardly insertion of the germicidal UV light source through an opening of a container into the container and retrieval of the germicidal UV light source from the container into the housing;
   (iv) a means for controlling the movably and inwardly insertion of the germicidal UV light source into the container and positioning of the germicidal UV light source at a predetermined position within the container; and
   (v) a base plate configured to position the UV device on or at the opening of the container;
   wherein the UV light source is attached to the central sleeve lower end;
   wherein the central sleeve is configured to protrude outside of the housing upper end;
   wherein the central sleeve comprises a first cavity and a detachable plate;
   wherein the detachable plate is mounted on top of the first cavity; and
   wherein the detachable plate is configured to be removable upon moving the central sleeve to a position protruding outside of the housing upper end.

2. The UV device according to claim 1, wherein (iv) is a central sleeve tightening knob.

3. The UV device according to claim 1, wherein (iv) is an interface controlling electronically the positioning of the germicidal UV light source at a desired position within the container.

4. The UV device according to claim 1, wherein (iv) is a motorized unit.

5. The UV device according to claim 1, wherein the first cavity is configured to house a component selected from the group consisting of a circuit board, an AC/DC power converter, a power supply, a wire, and a connector.

6. The UV device according to claim 1, wherein the central sleeve further comprises a second cavity and wherein second cavity is configured to house a component different from the component housed in the first cavity and selected from the group consisting of a circuit board, an AC/DC power converter, a power supply, a wire, and a connector.

7. The UV device according to claim 1, wherein (v) is configured to position the UV device on top of a container and wherein the germicidal UV light source is inserted downwardly into the container.

8. The UV device according to claim 1, wherein (v) is configured to position the UV device beneath a container and wherein the germicidal UV light source is inserted upwardly into the container.

9. The UV device according to claim 1, wherein the lamp is selected from the group consisting of a low pressure mercury lamp, a medium pressure mercury lamp, a high pressure mercury lamp, an ultra-high pressure mercury lamp, a low pressure short arc xenon lamp, a medium pressure short arc xenon lamp, a high pressure short arc xenon lamp, an ultra- high pressure short arc xenon lamp, a low pressure long arc xenon lamp, a medium pressure long arc xenon lamp, a high pressure long arc xenon lamp, an ultra-high pressure long arc xenon lamp, a low pressure metal halide lamp, a medium pressure metal halide lamp, a high pressure metal halide lamp, an ultra-high pressure metal halide lamp, a tungsten halogen lamp, a quartz halogen lamp, a quartz iodine lamp, a sodium lamp, and an incandescent lamp.

10. The UV device according to claim 1, wherein the germicidal UV light source is a UV-C light source.

11. The UV device according to claim 1, wherein (v) has a configuration selected from the group consisting of a tripod configuration, a circular configuration, an oval configuration, a rectangular configuration, and a hexagonal configuration.

12. The UV device according to claim 1, further comprising:
   (vi) an interface providing at least one functional button for a function selected from the group of functions consisting of activating the UV device, deactivating the UV device, releasing the germicidal UV light source from the housing, setting a time for performing a sterilization cycle, providing time remaining for completing the UV sterilization of the container, and providing time elapsed for UV sterilization of the container.

13. The UV device according to claim 1, wherein the germicidal UV light source comprises a plurality of UV lamps arranged in a UV lamp cluster.

14. The UV device according to claim 1, further comprising:
(vi) a reflector partially surrounding the germicidal UV light source.

15. The UV light device according to claim 1, further comprising:
(vi) a rangefinder.

16. A system comprising:
(i) a UV device according to claim 1; and
(ii) a container.

17. The system according to claim 16, wherein the container is selected from the group consisting of a container for fermenting an alcoholic beverage and a container for storing or transporting a dairy product, a liquid dairy, a liquid dairy composition or a dry dairy composition.

18. The system according to claim 17, wherein the alcoholic beverage is selected from the group consisting of beer, wine, gin, vodka, and whisky.

19. The system according to claim 16, wherein the container is a container for water, milk, coffee, tea, juice, or a carbonated beverage.

20. The system according to claim 16, wherein the container is selected from the group consisting of a vat, a silo, a tub, a basket, a case, a box, a barrel, a storage bin, a container for a biological fluid, a beverage container, and an aquarium.

21. The system according to claim 20, wherein the container for the biological fluid is selected from the group consisting of a container for blood, a container for a blood product, a container for a fermentation product, a container for a cell culture product, and a container for a biotechnology product.

22. The system according to claim 16, wherein an interior surface of the container comprises etched aluminum, foil aluminum, polished aluminum, chromium, glass, nickel, silver, stainless steel, tri-plated steel, water paint, white cotton, white oil paint, white paper, white porcelain or white wall plaster.

23. The system according to claim 16, wherein the container is made of stainless steel, wood, plastic, concrete, a polymer, or glass.

24. The system according to claim 16, wherein the container is selected from the group consisting of a container comprising an interior surface on which a microorganism is present, a container comprising an opening at the top of the container, a container comprising an opening at the bottom of the container, a container comprising an opening at the side of the container, and a container comprising a material selected from the group consisting of wood, plastic, concrete, polymer, etched aluminum, foil aluminum, polished aluminum, chromium, glass, nickel, silver, stainless steel, tri-plated steel, water paint, white cotton, white oil paint, white paper, white porcelain, and white wall plaster.

25. The system according to claim 16, wherein the container comprises an interior surface comprising a liquid layer.

26. The system according to claim 25, wherein the liquid layer comprises a liquid selected from the group consisting of apple juice, beer, liquid sugar, milk, vinegar, water, and wine.

27. A method for UV sterilization of an interior surface of a container, the method comprising the steps of:
(a) movably and inwardly inserting through an opening of a container the germicidal UV light source of the UV device of claim 1; and
(b) activating the germicidal UV light source;
whereby the interior surface of the container is sterilized.

28. The method according to claim 27, wherein the container is selected from the group consisting of a container for fermenting an alcoholic beverage and a container for storing or transporting a dairy product, a liquid dairy, a liquid dairy composition or a dry dairy composition.

29. The method according to claim 28, wherein the alcoholic beverage is selected from the group consisting of beer, wine, gin, vodka, and whisky.

30. The method according to claim 27, wherein one or more species of microorganisms is present on the interior surface of the container and wherein the activation of the germicidal UV light source results in inhibiting the growth of the one or more species of microorganisms, and wherein the one or more species of microorganisms is selected from the group consisting of *Candida, Kloeckera, Hanseniaspora, Zygosaccharomyces, Schizosaccharomyces, Torulaspora, Brettanomyces, Saccharomycodes, Pichia, Williopsis, Pediococcus, Lactobacillus*, and *Oenococcus*.

31. The method according to claim 27, wherein the container is a container for water, milk, coffee, tea, juice, or a carbonated beverage.

32. The method according to claim 27, wherein the container is selected from the group consisting of a vat, a silo, a tub, a basket, a case, a box, a barrel, a storage bin, a container for a biological fluid, a beverage container, and an aquarium.

33. The method according to claim 32, wherein the container for the biological fluid is selected from the group consisting of a container for blood, a container for a blood product, a container for a fermentation product, a container for a cell culture product, and a container for a biotechnology product.

34. The method according to claim 27, wherein the interior surface of the container comprises etched aluminum, foil aluminum, polished aluminum, chromium, glass, nickel, silver, stainless steel, tri-plated steel, water paint, white cotton, white oil paint, white paper, white porcelain or white wall plaster.

35. The method according to claim 27, wherein the container is made of stainless steel, wood, plastic, concrete, a polymer, or glass.

36. The method according to claim 27, wherein the container is selected from the group consisting of a container comprising an interior surface on which a microorganism is present, a container comprising an opening at the top of the container, a container comprising an opening at the bottom of the container, a container comprising an opening at the side of the container, and a container comprising a material selected from the group consisting of wood, plastic, concrete, polymer, etched aluminum, foil aluminum, polished aluminum, chromium, glass, nickel, silver, stainless steel, tri-plated steel, water paint, white cotton, white oil paint, white paper, white porcelain, and white wall plaster.

37. The method according to claim 27, wherein the interior surface of the container comprises a liquid layer.

38. The method according to claim 37, wherein the liquid layer comprises a liquid selected from the group consisting of apple juice, beer, liquid sugar, milk, vinegar, water, and wine.

* * * * *